US009107417B2

(12) United States Patent
Broglie et al.

(10) Patent No.: US 9,107,417 B2
(45) Date of Patent: Aug. 18, 2015

(54) COMPOSITIONS AND METHODS TO CONTROL INSECT PESTS

(71) Applicant: Pioneer Hi-Bred International, Johnston, IA (US)

(72) Inventors: Karen E. Broglie, Landenberg, PA (US); Mani Muthalagi, Hockessin, DE (US); Kevin Kriss, Wilmington, DE (US); Albert L. Lu, Newark, DE (US); James K. Presnail, Des Moines, IA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 13/791,567

(22) Filed: Mar. 8, 2013

(65) Prior Publication Data

US 2013/0177539 A1 Jul. 11, 2013

Related U.S. Application Data

(63) Continuation of application No. 12/868,994, filed on Aug. 26, 2010, now abandoned.

(51) Int. Cl.

| | |
|---|---|
| ***A01N 57/16*** | (2006.01) |
| ***A01N 63/00*** | (2006.01) |
| ***C12N 15/113*** | (2010.01) |
| ***C12N 15/63*** | (2006.01) |
| ***A01N 65/38*** | (2009.01) |
| ***A01N 65/20*** | (2009.01) |
| ***A01N 65/12*** | (2009.01) |
| ***A01N 65/44*** | (2009.01) |
| ***C12N 15/82*** | (2006.01) |

(52) U.S. Cl.

CPC ................ *A01N 57/16* (2013.01); *A01N 63/00* (2013.01); *A01N 65/20* (2013.01); *A01N 65/44* (2013.01); *C12N 15/113* (2013.01); *C12N 15/8218* (2013.01); *C12N 15/8286* (2013.01); *C12N 2310/531* (2013.01)

(58) Field of Classification Search

None

See application file for complete search history.

(56) References Cited

U.S. PATENT DOCUMENTS

| | | | | |
|---|---|---|---|---|
| 7,612,194 | B2 * | 11/2009 | Andersen et al. ............ | 536/24.5 |
| 2004/0187170 | A1 | 9/2004 | Plaetinck et al. | |
| 2006/0272049 | A1 | 11/2006 | Waterhouse et al. | |
| 2007/0050860 | A1 | 3/2007 | Andersen et al. | |
| 2012/0164205 | A1 | 6/2012 | Baum et al. | |

FOREIGN PATENT DOCUMENTS

| | | | |
|---|---|---|---|
| WO | 2005110068 | A2 | 11/2005 |
| WO | 2007035650 | A2 | 3/2007 |

OTHER PUBLICATIONS

Baum et al (Nature Biotechnology, 25(11), pp. 1322-1326, 2007).*
Yan et al (Plant Physiology, 141, pp. 1508-1518, 2006).*
Thomas et al (Plant Journal, 25, pp. 417-425, 2001).*
Bird et al (Biotechnology and Genetic Engineering Reviews, 9, pp. 207-227, 1991).*
Baum et al, "Control of coleopteran insect pests through RNA interference," Nature Biotechnology, vol. 25 No. 11, (Nov. 1997), pp. 1322-1326 and 1 page of Supplementary Tables and 15 pages of Supplementary Figures.
International Search Report for International Application No. PCT/US2010/046762 completed Nov. 9, 2010.
International Search Report for International Application No. PCT/US2010/0467 completed Jan. 20, 2011.
Written Opinion for International Application No. PCT/US2008/087954 completed Jan. 20, 2011.

* cited by examiner

*Primary Examiner* — Anne Kubelik
*Assistant Examiner* — Stephen Uyeno
(74) *Attorney, Agent, or Firm* — Pioneer Hi-Bred, Int'l

(57) ABSTRACT

Methods and compositions are provided which employ a silencing element that, when ingested by a pest, such as a Coleopteran plant pest or a *Diabrotica* plant pest, decrease the expression of a target sequence in the pest. In specific embodiments, the decrease in expression of the target sequence controls the pest and thereby the methods and compositions are capable of limiting damage to a plant. The present invention provides various target polynucleotides set forth in any one of SEQ ID NOS: 1-236 or active variants and fragments thereof, wherein a decrease in expression of one or more the sequences in the target pest controls the pest (i.e., has insecticidal activity). Further provided are silencing elements which when ingested by the pest decrease the level of the target polypeptide and thereby control the pest. In specific embodiment, the pest is *D. virgifera virgifera, D. barberi, D. speciosa*, or *D. undecimpunctata howardi*. Plants, plant part, bacteria and other host cells comprising the silencing elements or an active variant or fragment thereof of the invention are also provided.

29 Claims, 2 Drawing Sheets

T0 Test of first RNAi candidates in SFX germplasm

Missing Rows 440

Means Comparisons

Comparisons for all pairs using Tukey-Kramer HSD

| Construct | Gene | # events | Priority | Grouping | mean |
|---|---|---|---|---|---|
| Control | | 6 | | A | 2.16 |
| PHP41121 | SEQ ID NO: 8 RIBOSOMAL PROTEIN S10E | 1 | 17 | AB | 1 |
| PHP41134 | SEQ ID NO: 26 RIBOSOMAL PROTEIN | 7 | 29 | B | 0.89 |
| PHP41127 | SEQ ID NO: 17 27kD PROTEINASE | 22 | 44 | B | 0.81 |
| PHP41130 | SEQ ID NO: 28 Nucleoplasmin-like | 4 | 12 | B | 0.75 |
| PHP41118 | SEQ ID NO: 10 NO HITS | 8 | 26 | B | 0.72 |

COMPOSITIONS AND METHODS TO CONTROL INSECT PESTS

CROSS-REFERENCE TO RELATED APPLICATIONS

This application is a continuation of U.S. Utility application Ser. No. 12/868,994, filed on Aug. 26, 2010, which claims the benefit of U.S. Provisional Application No. 61/330,484, filed on May 3, 2010 and U.S. Provisional Application No. 61/237,880, filed Aug. 28, 2009, the contents of which are herein incorporated by reference in their entirety.

FIELD OF THE INVENTION

The present invention relates generally to methods of molecular biology and gene silencing to control pests.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 391924SEQLIST.txt, a creation date of Aug. 25, 2010 and a size of 306 Kb. The sequence listing filed via EFS-Web is part of the specification and is hereby incorporated in its entirety by reference herein.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including Lepidoptera, Diptera, Coleoptera, Hemiptera, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life. Sci.* 59(3):417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences. Thus, there is an immediate need for alternative methods to control pests.

BRIEF SUMMARY OF THE INVENTION

Methods and compositions are provided which employ a silencing element that, when ingested by a pest, such as Coleopteran plant pest including a *Diabrotica* plant pest, is capable of decreasing the expression of a target sequence in the pest. In specific embodiments, the decrease in expression of the target sequence controls the pest and thereby the methods and compositions are capable of limiting damage to a plant. The present invention provides various target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236 or active variants or fragments thereof, wherein a decrease in expression of one or more the sequences in the target pest controls the pest (i.e., has insecticidal activity). Further provided are silencing elements, which when ingested by the pest, decrease the level of expression of one or more of the target polynucleotides. Plants, plant parts, plant cells, bacteria and other host cells comprising the silencing elements or an active variant or fragment thereof are also provided.

In another embodiment, a method for controlling a pest, such as a Coleopteran plant pest or a *Diabrotica* plant pest, is provided. The method comprises feeding to a pest a composition comprising a silencing element, wherein the silencing element, when ingested by the pest, reduces the level of a target sequence in the pest and thereby controls the pest. Further provided are methods to protect a plant from a pest. Such methods comprise introducing into the plant or plant part a silencing element of the invention. When the plant expressing the silencing element is ingested by the pest, the level of the target sequence is decreased and the pest is controlled.

DETAILED DESCRIPTION OF THE INVENTION

Figure 1:
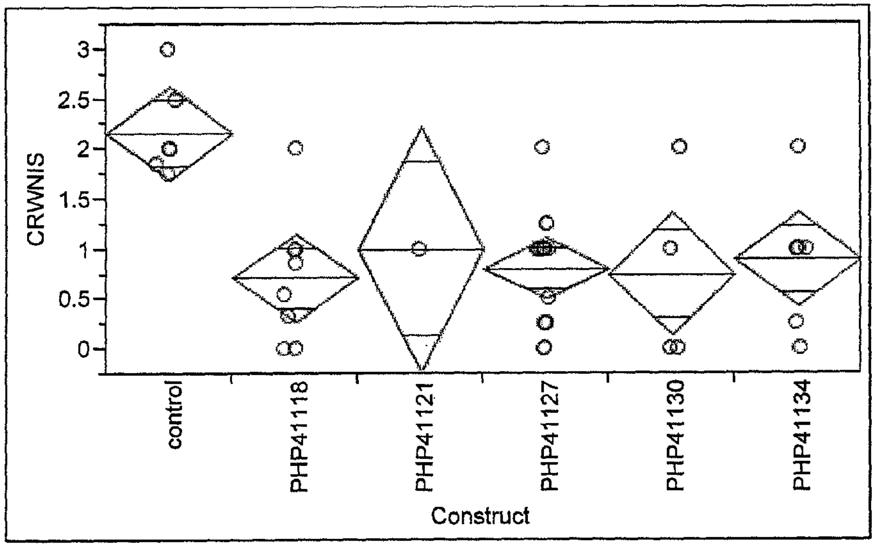
FIG. 1 shows a corn rootworm whole plant assay. The data demonstrates that expression of SEQ ID NO: 8 (clone idvlc.pk001.e9.f; SEQ ID NO: 26 (clone idvlc.pk003.p13.f); SEQ ID NO:17 (clone idvlc.pk003.f9.f); SEQ ID NO:28 (clone idvlc.pk004.d17.p); and SEQ ID NO:10 (clone idvlc.pk001.n1.f) as a hairpin in a maize plant produces a maize plant, which when ingested by corn root worm, has insecticidal activity. CRWNIS refers to corn root worm nodal injury score.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Frequently, RNAi discovery methods rely on evaluation of known classes of sensitive genes (transcription factors, housekeeping genes etc.). In contrast, the target polynucleotide set forth herein were identified based solely on high throughput screens of all singletons and representatives of all gene clusters from a cDNA library of neonate western corn rootworms. This screen allowed for the discovery of many novel sequences, many of which have extremely low or no homology to known sequences. This method provided the advantage of having no built in bias to genes that are frequently highly conserved across taxa. As a result, many novel targets for RNAi as well as known genes not previously shown to be sensitive to RNAi have been identified.

As such, methods and compositions are provided which employ a silencing element that, when ingested by a pest, such as a Coleopteran plant pest or a *Diabrotica* plant pest, is capable of decreasing the expression of a target sequence in the pest. In specific embodiments, the decrease in expression of the target sequence controls the pest and thereby the methods and compositions are capable of limiting damage to a plant or plant part. The present invention provides target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, or 236, or active variants and fragments thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. Silencing elements designed in view of these target polynucleotides are provided which, when ingested by the pest, decrease the expression of one or more of the target sequences and thereby controls the pest (i.e., has insecticidal activity).

As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

Reducing the level of expression of the target polynucleotide or the polypeptide encoded thereby, in the pest results in the suppression, control, and/or killing the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to control pests, particularly, Coleopteran plant pest or a *Diabrotica* plant pest.

Assays that measure the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also Baum et al. (2007) *Nature Biotech* 11:1322-1326 and WO 2007/035650 which proved both whole plant feeding assays and corn root feeding assays. Both of these references are herein incorporated by reference in their entirety. See, also the examples below.

The invention is drawn to compositions and methods for protecting plants from a plant pest, such as Coleopteran plant pests or *Diabrotica* plant pests or inducing resistance in a plant to a plant pest, such as Coleopteran plant pests or *Diabrotica* plant pests. As used herein "Coleopteran plant pest" is used to refer to any member of the Coleoptera order.

As used herein, the term "*Diabrotica* plant pest" is used to refer to any member of the *Diabrotica* genus. Accordingly, the compositions and methods are also useful in protecting plants against any *Diabrotica* plant pest including, for example, *Diabrotica adelpha; Diabrotica amecameca; Diabrotica balteata; Diabrotica barberi; Diabrotica biannularis; Diabrotica cristata; Diabrotica decempunctata; Diabrotica dissimilis; Diabrotica lemniscata; Diabrotica limitata* (including, for example, *Diabrotica limitata quindecimpuncata*); *Diabrotica longicornis; Diabrotica nummularis; Diabrotica porracea; Diabrotica scutellata; Diabrotica sexmaculata; Diabrotica speciosa* (including, for example, *Diabrotica speciosa speciosa*); *Diabrotica tibialis; Diabrotica undecimpunctata* (including, for example, *Diabrotica undecimpunctata duodecimnotata; Diabrotica undecimpunctata howardi* (spotted cucumber beetle); *Diabrotica undecimpunctata undecimpunctata* (western spotted cucumber beetle)); *Diabrotica virgifera* (including, for example, *Diabrotica virgifera virgifera* (western corn rootworm) and *Diabrotica virgifera zeae* (Mexican corn rootworm)); *Diabrotica viridula; Diabrotica wartensis; Diabrotica* sp. JJG335; *Diabrotica* sp. JJG336; *Diabrotica* sp. JJG341; *Diabrotica* sp. JJG356; *Diabrotica* sp. JJG362; and, *Diabrotica* sp. JJG365.

In specific embodiments, the *Diabrotica* plant pest comprises *D. virgifera virgifera, D. barberi, D. speciosa* or *D. undecimpunctata* howardi.

II. Target Sequences

As used herein, a "target sequence" or "target polynucleotide" comprises any sequence in the pest that one desires to reduce the level of expression. In specific embodiments, decreasing the level of the target sequence in the pest controls the pest. For instance, the target sequence can be essential for growth and development. While the target sequence can be expressed in any tissue of the pest, in specific embodiments, the sequences targeted for suppression in the pest are expressed in cells of the gut tissue of the pest, cells in the midgut of the pest, and cells lining the gut lumen or the midgut. Such target sequences can be involved in, for example, gut cell metabolism, growth or differentiation. Non-limiting examples of target sequences of the invention include a polynucleotide set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, or 236 or variants and fragments thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. As exemplified elsewhere herein, decreasing the level of expression of one or more of these target sequences in a Coleopteran plant pest or a *Diabrotica* plant pest controls the pest.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprise one or more silencing elements to the same or different target polynucleotides. The silencing element can be produced in vivo (i.e., in a host cell such as a plant or microorganism) or in vitro.

In specific embodiments, the target sequence is not endogenous to the plant. In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a siRNA, a amiRNA, a miRNA, or a hairpin suppression element. Non-limiting examples of silencing elements that can be employed to decrease expression of these target Coleopteran plant pest sequences or *Diabrotica* plant pest sequences comprise fragments and variants of the sense or antisense sequence or consists of the sense or antisense sequence of the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236 or a biologically active variant or fragment thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. The silencing element can further comprise additional sequences that advantageously effect transcription and/or the stability of a resulting transcript. For example, the silencing elements can comprise at least one thymine residue at the 3' end. This can aid in stabilization. Thus, the silencing elements can have at least 1, 2, 3, 4, 5, 6, 7, 8, 9, 10 or more thymine residues at the 3' end. As discussed in further detail below, enhancer suppressor elements can also be employed in conjunction with the silencing elements disclosed herein.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

i. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 16, 17, 18, 19, 20, 22, 25, 30, 50, 100, 150, 200, 250, 300, 350, 400, 450, 500, 600, 700, 900, 1000, 1100, 1200, 1300 nucleotides or longer of the target polynucleotides set forth in any of SEQ ID NO:1-106. In other embodiments, the sense suppression element can be, for example, about 15-25, 19-35, 19-50, 25-100, 100-150, 150-200, 200-250, 250-300, 300-350, 350-400, 450-500, 500-550, 550-600, 600-650, 650-700, 700-750, 750-800, 800-850, 850-900, 900-950, 950-1000, 1000-1050, 1050-1100, 1100-1200, 1200-1300, 1300-1400, 1400-1500, 1500-1600, 1600-1700, 1700-1800 nucleotides or longer of the target polynucleotides set forth in any of SEQ ID NO:1-236.

ii. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 16, 17, 18, 19, 20, 22, 25, 50, 100, 200, 300, 400, 450 nucleotides or greater of the sequence set forth in any of SEQ ID NO:1-236 may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference.

iii. Double Stranded RNA Suppression Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. In the context of the present invention, the dsRNA is capable of reducing or eliminating the level or expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional dsRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In another embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 19, 18, 17, 16, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 475, 450, 425, 400, 375, 350, 325, 300, 250, 225, 200, 175, 150, 125, 100, 75, 60, 50, 40, 30, 25, 22, 20, 19, 18, 17, 16, or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 10 to about 20 nucleotides, about 19 to about 50 nucleotides, about 50 nucleotides to about 100 nucleotides, about 100 nucleotides to about 150 nucleotides, about 100 nucleotides to about 300 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides, about 600 nt, about 700 nt, about 800 nt, about 900 nt, about 1000 nt, about 1100 nt, about 1200 nt, 1300 nt, 1400 nt, 1500 nt, 1600 nt, 1700 nt, 1800 nt, 1900 nt, 2000 nt or longer. In other embodiments, the length of the first and/or the third segment comprises at least 10-19 nucleotides, 10-20 nucleotides; 19-35 nucleotides, 20-35 nucleotides; 30-45 nucleotides; 40-50 nucleotides; 50-100 nucleotides; 100-300 nucleotides; about 500-700 nucleotides; about 700-900 nucleotides; about 900-1100 nucleotides; about 1300-1500 nucleotides; about 1500-1700 nucleotides; about 1700-1900 nucleotides; about 1900-2100 nucleotides; about 2100-2300 nucleotides; or about 2300-2500 nucleotides. See, for example, International Publication No. WO 0200904. In non-limiting examples the first stem of the hairpin comprises nucleotides 1-380 of SEQ ID NO: 45; nucleotides 1-266 of SEQ ID NO:50; nucleotides 1-675 of SEQ ID NO:37; or nucleotides 1-132 of SEQ ID NO: 40 or active variants and fragments thereof. In specific embodiments, the first and the third segment comprise at least 20 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 19-35 nucleotides, about 20-35 nucleotides, about 25-50 nucleotides, about 19 to 75 nucleotides, about 20 to 75 nucleotides, about 40-90 nucleotides about 15-100 nucleotides 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides or longer. In other embodiments, the length of the first and/or the third segment comprises at least 10-20 nucleotides, at least 10-19 nucleotides, 20-35 nucleotides, 30-45 nucleotides, 40-50 nucleotides, 50-100 nucleotides, or about 100-300 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129: 1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments, a domain of the silencing element shares sufficient homology to at least about 15, 16, 17, 18, 19, 20, 22, 25 or 30 consecutive nucleotides from about nucleotides 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem.* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4):16499-16506 and Mette et al. (2000) *EMBO J.* 19(19):5194-5201.

In other embodiments, the dsRNA can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). miRNAs are regulatory agents comprising about 19 ribonucleotides which are highly efficient at inhibiting the expression of target polynucleotides. See, for example Javier et al. (2003) *Nature* 425: 257-263, herein incorporated by reference. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

When expressing an miRNA, it is recognized that various forms of an miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA is present in a duplex, the two strands being referred to as the miRNA (the strand that will eventually basepair with the target) and miRNA*. The pre-miRNA is a substrate for a form of dicer that removes the miRNA/miRNA*duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) *Genes & Development* 18:2237-2242 and Guo et al. (2005) *Plant Cell* 17:1376-1386).

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, US Application Publication 2007-0130653, entitled "Methods and Compositions for Gene Silencing", herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins that retain biological activity. Thus, fragments of a nucleotide sequence may range from at least about 10, about 15, about 19 nucleotides, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide employed in the invention. Alternatively, fragments of a nucleotide sequence may range from 1-50, 25-75, 75-125, 50-100, 125-175, 175-225, 100-150, 100-300, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-

1700, 1700-1800, 1800-1900, 1900-2000 of any one of SEQ ID NO: 1-236. Methods to assay for the activity of a desired silencing element are described elsewhere herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. A variant of a polynucleotide that is useful as a silencing element will retain the ability to reduce expression of the target polynucleotide and, in some embodiments, thereby control a pest of interest. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotide, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A method is further provided for identifying a silencing element from the target polynucleotides set froth in SEQ ID NO:1-236. Such methods comprise obtaining a candidate fragment of any one of SEQ ID NO:1-236 which is of sufficient length to act as a silencing element and thereby reduce the expression of the target polynucleotide and/or control a desired pest; expressing said candidate polynucleotide fragment in an appropriate expression cassette to produce a candidate silencing element and determining is said candidate polynucleotide fragment has the activity of a silencing element and thereby reduce the expression of the target polynucleotide and/or controls a desired pest. Methods of identifying such candidate fragments based on the desired pathway for suppression are known. For example, various bioinformatics programs can be employed to identify the region of the target polynucleotides that could be exploited to generate a silencing element. See, for example, Elbahir et al. (2001) *Genes and Development* 15:188-200, Schwartz et al. (2003) *Cell* 115:199-208, Khvorova et al. (2003) *Cell* 115:209-216. See also, siRNA at Whitehead (jura.wi.mit.edu/bioc/siRNAext/) which calculates the binding energies for both sense and antisense siRNAs. See, also genscript.com/ssl-bin/app/rnai?op=known; Block-iT™ RNAi designer from Invitrogen and GenScript siRNA Construct Builder.

V. DNA Constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element or in specific embodiments employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. In other embodiment, the double stranded RNA is expressed from a suppression cassette. Such a cassette can comprise two convergent promoters that drive transcription of an operably linked silencing element. "Convergent promoters" refers to promoters that are oriented on either terminus of the operably linked silencing element such that each promoter drives transcription of the silencing element in opposite directions, yielding two transcripts. In such embodiments, the convergent promoters allow for the transcription of the sense and anti-sense strand and thus allow for the formation of a dsRNA.

The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes*(Kiyokawa et al. (1994) *Plant Physiology* 104:801-02; Pandolfini et al. (2003) *BioMedCentral (BMC) Biotechnology* 3:7, (website designated as: biomedcentral.com/1472-6750/3/7); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or Commelina yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from *Arabidopsis* shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultr1; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Chemy promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11):1779-86), Rice (RSs1) (Shi, T. Wang et al. (1994). *J. Exp. Bot.* 45(274): 623-631) and maize sucrose synthese −1 promoters (Yang., N-S. et al. (1990) *PNAS* 87:4144-4148), PP2 promoter from pumpkin Guo, H. et al. (2004) *Transgenic Research* 13:559-566), At SUC2 promoter (Truernit, E. et al. (1995) *Planta* 196(3):564-70., At SAM-1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as f3-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon, pp.* 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising the silencing element can be provided as an external composition such as a spray or powder to the plant, plant part, seed, a pest, or an area of cultivation. In another example, a plant is transformed with a DNA construct or expression cassette for expression of at least one silencing element. In either composition, the silencing element, when ingested by an insect, can reduce the level of a target pest sequence and thereby control the pest (i.e., a Coleopteran plant pest including a *Diabrotica* plant pest, such as, *D. virgifera virgifera, D. barberi,* or *D. undecimpunctata* howardi). It is recognized that the composition can comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition. Various insecticidal formulations can also be found in, for example, US Publications 2008/0275115, 2008/0242174, 2008/0027143, 2005/0042245, and 2004/0127520, each of which is herein incorporated by reference.

It is recognized that the polynucleotides comprising sequences encoding the silencing element can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*.

A number of ways are available for introducing the polynucleotide comprising the silencing element into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory Manual* (3rd ed.; Cold Spring Harbor Laboratory Press, Plainview, N.Y.); Davis et al. (1980) *Advanced Bacterial Genetics* (Cold Spring Harbor Laboratory, Cold Spring Harbor, N.Y.); and the references cited therein. Suitable host cells include the prokaryotes and the lower eukaryotes, such as fungi.

Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element can be in a suitable form for direct application or as a concentrate of primary composition that requires dilution with a suitable quantity of water or other dilutant before application.

The compositions (including the transformed microorganisms) can be applied to the environment of an insect pest (such as a Coleoptera plant pest or a *Diabrotica* plant pest) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

In one embodiment, the methods of the invention involve introducing a polynucleotide into a plant. "Introducing" is intended to mean presenting to the plant the polynucleotide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. Nos. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), *macadamia* (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

VIII. Methods of Use

The methods of the invention comprise methods for controlling a pest (i.e., a Coleopteran plant pest, including a *Diabrotica* plant pest, such as, *D. virgifera virgifera, D. barberi*, or *D. undecimpunctata* howardi). The method comprises feeding to a pest a composition comprising a silencing element of the invention, wherein said silencing element, when ingested by a pest (i.e., a Coleopteran plant pest including a *Diabrotica* plant pest, such as, *D. virgifera virgifera, D. barberi*, or *D. undecimpunctata* howardi), reduces the level of a target polynucleotide of the pest and thereby controls the pest. The pest can be fed the silencing element in a variety of ways. For example, in one embodiment, the polynucleotide comprising the silencing element is introduced into a plant. As the Coleopteran plant pest or *Diabrotica* plant pest feeds on the plant or part thereof expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In specific embodiments, the silencing element is expressed in the roots, stalk or stem, leaf including pedicel, xylem and phloem, fruit or reproductive tissue, silk, flowers and all parts therein or any combination thereof.

In another method, a composition comprising at least one silencing element of the invention is applied to a plant. In such embodiments, the silencing element can be formulated in an agronomically suitable and/or environmentally acceptable carrier, which is preferably, suitable for dispersal in fields. In addition, the carrier can also include compounds that increase the half life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) Gene 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262: 1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, U.S. application Ser. No. 12/351,093, entitled "Compositions and Methods for the Suppression of Target Polynucleotides", filed Jan. 9, 2009 and herein incorporated by reference in its entirety.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element. Thus, in specific embodiments, the suppressor enhancer element comprises a polynucleotide set forth in SEQ ID NO: 1-236 or an active variant or fragment thereof.

It is recognized that multiple suppressor enhancer elements from the same target sequence or from different target sequences, or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the invention have an improved loading of RNAi into the phloem of the plant than would be observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell, or phloem when compared to an appropriate control. In other embodiments, the increase in the level of RNAi in the plant, plant part, plant cell, or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Methods to assay for an increase in the level of RNAi are discussed elsewhere herein.

The following examples are offered by way of illustration and not by way of limitation.

EXPERIMENTAL

Example 1

In Vitro Transcript dsRNA Screening Method

A cDNA library was produced from neonate western corn rootworm larvae by standard methods. A selected cDNA clone containing an expressed sequence tag is amplified in a PCR using universal primers to the plasmid backbone and flanking the EST insert. The universal primers also contain T7 RNA polymerase sites. 1 ul of the PCR reaction is used as the template for an in vitro transcription (IVT) reaction to produce long double stranded RNAs. Following enzymatic digestion and removal of the DNA template and single stranded RNA, the IVT reaction products are incorporated into artificial insect diet as described below.

Insect Bioassays 2.5 ul of the IVT reaction are added to a given well of a 96 well microtiter plate. 25 ul of molten lowmelt Western corn rootworm diet are added to the sample and shaken on an orbital shaker to mix the sample and diet. Once the diet has solidified, neonate rootworms are added to the well. An average of 5 neonates is added to each well. After the plate is infested, the plate is sealed with mylar and a single hole in punched in the mylar over each well to allow air exchange. 4 replicate wells are produced for each sample. The assay is scored for activity 7 days post infestation. The possible scores are dead, severely stunted (little or now growth but alive), stunted (growth to second instar but not equivalent to controls), or no activity. Samples demonstrating mortality or severe stunting were advanced to confirmation. Primary assays and confirmation assays were performed with the southern corn rootworm.

Following confirmation, a simple dose response assay was performed with both southern and western corn rootworms. Samples for dose response assays were produced in the same manner with the following modification; samples were further purified using column purification prior to enzymatic treatment. Samples were also normalized to 0.5 ug/ul and all samples were evaluated by gel electrophoresis. Dose response assays were performed with the following rates; 50, 25, 12, 6, 3, and 1.5 ppm

Example 2

Sequences Having Insecticidal Activity

DNA sequences which encode double stranded RNAs which were shown to have insecticidal activity against corn rootworms using the assay described in Example 1 are set forth below. Non-limiting examples of target polynucleotides are set forth below in Table 1.

TABLE 1

SEQ ID NO: 1
>iwm2c.pk005.e1.fis1
SEQ ID NO: 2
>iwm2c.pk004.b13.fis1
SEQ ID NO: 3
>iwm2s.pk003.o11.fis1
SEQ ID NO: 4
>iwm2c.pk002.e24.fis1
SEQ ID NO: 5
>iwm2c.pk002.e24.fis1
SEQ ID NO: 6
>iwm2c.pk011.n17.fis1

TABLE 1-continued

SEQ ID NO: 7
>idv1c.pk001.d14.f.fis1
SEQ ID NO: 8
>idv1c.pk001.e9.f.fis1
SEQ ID NO: 9
>idv1c.pk001.m5.f.fis1
SEQ ID NO: 10
>idv1c.pk001.n1.f.fis1
SEQ ID NO: 11
>idv1c.pk002.c5.f.fis1
SEQ ID NO: 12
>idv1c.pk002.f20.f.fis1
SEQ ID NO: 13
>idv1c.pk002.j17.f.fis1
SEQ ID NO: 14
>idv1c.pk002.n13.f.fis1
SEQ ID NO: 15
>idv1c.pk003.d6.f.fis1
SEQ ID NO: 16
>idv1c.pk003.f8.f.fis1
SEQ ID NO: 17
>idv1c.pk003.f9.f.fis1
SEQ ID NO: 18
>idv1c.pk003.j4.f.fis1
SEQ ID NO: 19
>idv1c.pk003.j6.f.fis1
SEQ ID NO: 20
>idv1c.pk003.j20.f.fis1
SEQ ID NO: 21
>idv1c.pk003.l1.f.fis1
SEQ ID NO: 22
>idv1c.pk003.m1.f.fis1
SEQ ID NO: 23
>idv1c.pk003.m10.f.fis1
SEQ ID NO: 24
>idv1c.pk003.o13.f.fis1
SEQ ID NO: 25
>idv1c.pk003.o22.f.fis1
SEQ ID NO: 26
>idv1c.pk003.p13.f.fis1
SEQ ID NO: 27
>idv1c.pk004.b12.f.fis1
SEQ ID NO: 28
>idv1c.pk004.d17.f.fis1
SEQ ID NO: 29
>idv1c.pk004.f20.f.fis1
SEQ ID NO: 30
>idv1c.pk004.k5.f.fis1
SEQ ID NO: 31
>idv1c.pk004.l15.f.fis1
SEQ ID NO: 32
>idv1c.pk004.n6.f.fis1
SEQ ID NO: 33
>idv1c.pk004.o4.f.fis1
SEQ ID NO: 34
>idv1c.pk004.o9.f.fis1
SEQ ID NO: 35
>idv1c.pk004.p1.f.fis1
SEQ ID NO: 36
>idv1c.pk013.a15.f.fis1
SEQ ID NO: 37
>idv1c.pk013.b11.f.fis1
SEQ ID NO: 38
>idv1c.pk013.c21.f.fis1
SEQ ID NO: 39
>idv1c.pk013.d22.f.fis1
SEQ ID NO: 40
>idv1c.pk013.h1.f.fis1
SEQ ID NO: 41
>idv1c.pk013.h14.f.fis1
SEQ ID NO: 42
>idv1c.pk013.k1.f.fis1
SEQ ID NO: 43
>idv1c.pk014.a19.f.fis1
SEQ ID NO: 44
>idv1c.pk014.b9.f.fis1
SEQ ID NO: 45
>idv1c.pk014.b17.f.fis1
SEQ ID NO: 46
>idv1c.pk014.c14.f.fis1

TABLE 1-continued

| |
|---|
| SEQ ID NO: 47 |
| >idv1c.pk014.d11.f.fis1 |
| SEQ ID NO: 48 |
| >idv1c.pk014.f3.f.fis1 |
| SEQ ID NO: 49 |
| >idv1c.pk014.j2.f.fis1 |
| SEQ ID NO: 50 |
| >idv1c.pk014.k23.f.fis1 |
| SEQ ID NO: 51 |
| >idv1c.pk014.m5.f.fis1 |
| SEQ ID NO: 52 |
| >idv1c.pk014.m13.f.fis1 |
| SEQ ID NO: 53 |
| >idv1c.pk014.n16.f.fis1 |
| SEQ ID NO: 54 |
| >idv1c.pk014.n23.f.fis1 |
| SEQ ID NO: 55 |
| >idv1c.pk014.o1.f.fis1 |
| SEQ ID NO: 56 |
| >idv1c.pk015.a16.f.fis1 |
| SEQ ID NO: 57 |
| >idv1c.pk015.b8.f.fis1 |
| SEQ ID NO: 58 |
| >idv1c.pk015.g10.f.fis1 |
| SEQ ID NO: 59 |
| >idv1c.pk015.l13.f.fis1 |
| SEQ ID NO: 60 |
| >idv1c.pk015.n19.f.fis1 |
| SEQ ID NO: 61 |
| >idv1c.pk015.p2.f.fis1 |
| SEQ ID NO: 62 |
| >idv1c.pk016.a9.f.fis1 |
| SEQ ID NO: 63 |
| >idv1c.pk016.f12.f.fis1 |
| SEQ ID NO: 64 |
| >idv1c.pk016.f21.f.fis1 |
| SEQ ID NO: 65 |
| >idv1c.pk016.h15.f.fis1 |
| SEQ ID NO: 66 |
| >idv1c.pk016.h19.f.fis1 |
| SEQ ID NO: 67 |
| >idv1c.pk016.j12.f.fis1 |
| SEQ ID NO: 68 |
| >idv1c.pk016.j15.f.fis1 |
| SEQ ID NO: 69 |
| >idv1c.pk016.k9.f.fis1 |
| SEQ ID NO: 70 |
| >idv1c.pk016.p18.f.fis1 |
| SEQ ID NO: 71 |
| >idv1c.pk017.c3.f.fis1 |
| SEQ ID NO: 72 |
| >idv1c.pk017.d14.f.fis1 |
| SEQ ID NO: 73 |
| >idv1c.pk017.e22.f.fis1 |
| SEQ ID NO: 74 |
| >idv1c.pk017.f1.f.fis1 |
| SEQ ID NO: 75 |
| >idv1c.pk017.h14.f.fis1 |
| SEQ ID NO: 76 |
| >idv1c.pk017.n19.f.fis1 |
| SEQ ID NO: 77 |
| >idv1c.pk017.p2.f.fis1 |
| SEQ ID NO: 78 |
| >idv1c.pk018.a5.f.fis1 |
| SEQ ID NO: 79 |
| >idv1c.pk018.c11.f.fis1 |
| SEQ ID NO: 80 |
| >idv1c.pk018.d5.f.fis1 |
| SEQ ID NO: 81 |
| >idv1c.pk018.d14.f.fis1 |
| SEQ ID NO: 82 |
| >idv1c.pk018.e10.f.fis1 |
| SEQ ID NO: 83 |
| >idv1c.pk018.e20.f.fis1 |
| SEQ ID NO: 84 |
| >idv1c.pk018.f19.f.fis1 |
| SEQ ID NO: 85 |
| >idv1c.pk018.f22.f.fis1 |
| SEQ ID NO: 86 |
| >idv1c.pk018.g20.f.fis1 |

TABLE 1-continued

| |
|---|
| SEQ ID NO: 87 |
| >idv1c.pk018.h21.f.fis1 |
| SEQ ID NO: 88 |
| >idv1c.pk018.m5.f.fis1 |
| SEQ ID NO: 89 |
| >idv1c.pk019.c4.f.fis1 |
| SEQ ID NO: 90 |
| >idv1c.pk019.i5.f.fis1 |
| SEQ ID NO: 91 |
| >idv1c.pk019.k3.f.fis1 |
| SEQ ID NO: 92 |
| >idv1c.pk019.l7.f.fis1 |
| SEQ ID NO: 93 |
| >idv1c.pk020.a8.f.fis1 |
| SEQ ID NO: 94 |
| >idv1c.pk020.b11.f.fis1 |
| SEQ ID NO: 95 |
| >idv1c.pk020.g17.f.fis1 |
| SEQ ID NO: 96 |
| >idv1c.pk020.i7.f.fis1 |
| SEQ ID NO: 97 |
| >idv1c.pk020.i24.f.fis1 |
| SEQ ID NO: 98 |
| >idv1c.pk020.k19.f.fis1 |
| SEQ ID NO: 99 |
| >idv1c.pk020.l3.f.fis1 |
| SEQ ID NO: 100 |
| >idv1c.pk020.p23.f.fis1 |
| SEQ ID NO: 101 |
| >idv1c.pk021.c21.f.fis1 |
| SEQ ID NO: 102 |
| >idv1c.pk021.d22.f.fis1 |
| SEQ ID NO: 103 |
| >idv1c.pk021.g16.f.fis1 |
| SEQ ID NO: 104 |
| >idv1c.pk021.h12.f.fis1 |
| SEQ ID NO: 105 |
| >idv1c.pk021.m20.f.fis1 |
| SEQ ID NO: 106 |
| >idv1c.pk004.j11.f.fis1 |
| SEQ ID NO: 107 |
| >idv1c.pk001.o20.f |
| SEQ ID NO: 108 |
| >idv1c.pk002.a20.f |
| SEQ ID NO: 109 |
| >idv1c.pk002.c15.f |
| SEQ ID NO: 110 |
| >idv1c.pk002.i21.f |
| SEQ ID NO: 111 |
| >idv1c.pk024.b23.f |
| SEQ ID NO: 112 |
| >idv1c.pk024.e1.f |
| SEQ ID NO: 113 |
| >idv1c.pk024.e24.f |
| SEQ ID NO: 114 |
| >idv1c.pk024.k17.f |
| SEQ ID NO: 115 |
| >idv1c.pk024.m13.f |
| SEQ ID NO: 116 |
| >idv1c.pk024.n1.f |
| SEQ ID NO: 117 |
| >idv1c.pk024.o3.f |
| SEQ ID NO: 118 |
| >idv1c.pk025.a4.f |
| SEQ ID NO: 119 |
| >idv1c.pk025.c5.f |
| SEQ ID NO: 120 |
| >idv1c.pk025.c23.f |
| SEQ ID NO: 121 |
| >idv1c.pk025.d18.f |
| SEQ ID NO: 122 |
| >idv1c.pk025.d20.f |
| SEQ ID NO: 123 |
| >idv1c.pk025.f24.f |
| SEQ ID NO: 124 |
| >idv1c.pk025.j20.f |
| SEQ ID NO: 125 |
| >idv1c.pk025.l10.f |
| SEQ ID NO: 126 |
| >idv1c.pk026.a16.f |

TABLE 1-continued

| |
|---|
| SEQ ID NO: 127 |
| >idv1c.pk026.b23.f |
| SEQ ID NO: 128 |
| >idv1c.pk026.d22.f |
| SEQ ID NO: 129 |
| >idv1c.pk026.e6.f |
| SEQ ID NO: 130 |
| >idv1c.pk026.g12.f |
| SEQ ID NO: 131 |
| >idv1c.pk026.h15.f |
| SEQ ID NO: 132 |
| >idv1c.pk026.i12.f |
| SEQ ID NO: 133 |
| >idv1c.pk026.j18.f |
| SEQ ID NO: 134 |
| >idv1c.pk026.k13.f |
| SEQ ID NO: 135 |
| >idv1c.pk027.b21.f |
| SEQ ID NO: 136 |
| >idv1c.pk027.c7.f |
| SEQ ID NO: 137 |
| >idv1c.pk027.k4.f |
| SEQ ID NO: 138 |
| >idv1c.pk027.p21.f |
| SEQ ID NO: 139 |
| >idv1c.pk028.b7.f |
| SEQ ID NO: 140 |
| >idv1c.pk028.c22.f |
| SEQ ID NO: 141 |
| >idv1c.pk028.h6.f |
| SEQ ID NO: 142 |
| >idv1c.pk028.i16.f |
| SEQ ID NO: 143 |
| >idv1c.pk028.m11.f |
| SEQ ID NO: 144 |
| >idv1c.pk028.o18.f |
| SEQ ID NO: 145 |
| >idv1c.pk029.a17.f |
| SEQ ID NO: 146 |
| >idv1c.pk029.d16.f |
| SEQ ID NO: 147 |
| >idv1c.pk029.i22.f |
| SEQ ID NO: 148 |
| >idv1c.pk029.j20.f |
| SEQ ID NO: 149 |
| >idv1c.pk029.k11.f |
| SEQ ID NO: 150 |
| >idv1c.pk029.l22.f |
| SEQ ID NO: 151 |
| >idv1c.pk030.e10.f |
| SEQ ID NO: 152 |
| >idv1c.pk030.e21.f |
| SEQ ID NO: 153 |
| >idv1c.pk030.h13.f |
| SEQ ID NO: 154 |
| >idv1c.pk030.h23.f |
| SEQ ID NO: 155 |
| >idv1c.pk030.l9.f |
| SEQ ID NO: 156 |
| >idv1c.pk030.m22.f |
| SEQ ID NO: 157 |
| >idv1c.pk030.o7.f |
| SEQ ID NO: 158 |
| >idv1c.pk031.a11.f |
| SEQ ID NO: 159 |
| >idv1c.pk031.e16.f |
| SEQ ID NO: 160 |
| >idv1c.pk031.g2.f |
| SEQ ID NO: 161 |
| >idv1c.pk031.g22.f |
| SEQ ID NO: 162 |
| >idv1c.pk031.i13.f |
| SEQ ID NO: 163 |
| >idv1c.pk031.m3.f |
| SEQ ID NO: 164 |
| >idv1c.pk032.b4.f |
| SEQ ID NO: 165 |
| >idv1c.pk032.e16.f |
| SEQ ID NO: 166 |
| >idv1c.pk032.f14.f |

TABLE 1-continued

| |
|---|
| SEQ ID NO: 167 |
| >idv1c.pk032.m9.f |
| SEQ ID NO: 168 |
| >idv1c.pk033.a15.f |
| SEQ ID NO: 169 |
| >idv1c.pk033.b14.f |
| SEQ ID NO: 170 |
| >idv1c.pk033.m3.f |
| SEQ ID NO: 171 |
| >idv1c.pk033.n10.f |
| SEQ ID NO: 172 |
| >idv1c.pk033.n18.f |
| SEQ ID NO: 173 |
| >idv1c.pk034.e8.f |
| SEQ ID NO: 174 |
| >idv1c.pk034.p24.f |
| SEQ ID NO: 175 |
| >idv1c.pk035.f21.f |
| SEQ ID NO: 176 |
| >idv1c.pk035.g1.f |
| SEQ ID NO: 177 |
| >idv1c.pk035.h19.f |
| SEQ ID NO: 178 |
| >idv1c.pk035.j4.f |
| SEQ ID NO: 179 |
| >idv1c.pk035.m1.f |
| SEQ ID NO: 180 |
| >idv1c.pk035.o13.f |
| SEQ ID NO: 181 |
| >idv1c.pk036.a14.f |
| SEQ ID NO: 182 |
| >idv1c.pk036.e18.f |
| SEQ ID NO: 183 |
| >idv1c.pk036.f4.f |
| SEQ ID NO: 184 |
| >idv1c.pk036.f9.f |
| SEQ ID NO: 185 |
| >idv1c.pk036.i17.f |
| SEQ ID NO: 186 |
| >idv1c.pk036.i20.f |
| SEQ ID NO: 187 |
| >idv1c.pk036.k23.f |
| SEQ ID NO: 188 |
| >idv1c.pk034.k22.f |
| SEQ ID NO: 189 |
| >idv1c.pk002.c7.f |
| SEQ ID NO: 190 |
| >idv1c.pk002.f18.f |
| SEQ ID NO: 191 |
| >idv1c.pk002.i23.f |
| SEQ ID NO: 192 |
| >idv1c.pk002.j24.f |
| SEQ ID NO: 193 |
| >idv1c.pk002.m16.f |
| SEQ ID NO: 194 |
| >idv1c.pk002.n13.f |
| SEQ ID NO: 195 |
| >idv1c.pk024.c7.f |
| SEQ ID NO: 196 |
| >idv1c.pk024.j15.f |
| SEQ ID NO: 197 |
| >idv1c.pk025.b17.f |
| SEQ ID NO: 198 |
| >idv1c.pk025.f3.f |
| SEQ ID NO: 199 |
| >idv1c.pk025.i8.f |
| SEQ ID NO: 200 |
| >idv1c.pk025.l17.f |
| SEQ ID NO: 201 |
| >idv1c.pk025.o24.f |
| SEQ ID NO: 202 |
| >idv1c.pk025.p9.f |
| SEQ ID NO: 203 |
| >idv1c.pk026.f20.f |
| SEQ ID NO: 204 |
| >idv1c.pk026.p8.f |
| SEQ ID NO: 205 |
| >idv1c.pk026.p22.f |
| SEQ ID NO: 206 |
| >idv1c.pk027.a14.f |

TABLE 1-continued

| |
|---|
| SEQ ID NO: 207 |
| >idv1c.pk027.g7.f |
| SEQ ID NO: 208 |
| >idv1c.pk027.k23.f |
| SEQ ID NO: 209 |
| >idv1c.pk028.b17.f |
| SEQ ID NO: 210 |
| >idv1c.pk028.f11.f |
| SEQ ID NO: 211 |
| >idv1c.pk029.c3.f |
| SEQ ID NO: 212 |
| >idv1c.pk029.f5.f |
| SEQ ID NO: 213 |
| >idv1c.pk029.j4.f |
| SEQ ID NO: 214 |
| >idv1c.pk030.b23.f |
| SEQ ID NO: 215 |
| >idv1c.pk030.f9.f |
| SEQ ID NO: 216 |
| >idv1c.pk030.g11.f |
| SEQ ID NO: 217 |
| >idv1c.pk031.c20.f |
| SEQ ID NO: 218 |
| >idv1c.pk031.d1.f |
| SEQ ID NO: 219 |
| >idv1c.pk031.j1.f |
| SEQ ID NO: 220 |
| >idv1c.pk031.j6.f |
| SEQ ID NO: 221 |
| >idv1c.pk031.p16.f |
| SEQ ID NO: 222 |
| >idv1c.pk032.a16.f |
| SEQ ID NO: 223 |
| >idv1c.pk032.f11.f |
| SEQ ID NO: 224 |
| >idv1c.pk032.i21.f |
| SEQ ID NO: 225 |
| >idv1c.pk032.n18.f |
| SEQ ID NO: 226 |
| >idv1c.pk032.p5.f |
| SEQ ID NO: 227 |
| >idv1c.pk033.d24.f |
| SEQ ID NO: 228 |
| >idv1c.pk033.j21.f |
| SEQ ID NO: 229 |
| >idv1c.pk033.o9.f |
| SEQ ID NO: 230 |
| >idv1c.pk033.p15.f |
| SEQ ID NO: 231 |
| >idv1c.pk033.p16.f |
| SEQ ID NO: 232 |
| >idv1c.pk034.i2.f |
| SEQ ID NO: 233 |
| >idv1c.pk034.j6.f |
| SEQ ID NO: 234 |
| >idv1c.pk035.i17.f |
| SEQ ID NO: 235 |
| >idv1c.pk035.k18.f |
| SEQ ID NO: 236 |
| >idv1c.pk036.i19.f |
| SEQ ID NO: 237 |
| Construct expressing SEQ ID NO: 8 as a hairpin RNA. The construct comprises: UBI1ZM promoter 5'UTR and $1^{st}$ intron operably linked to SEQ ID NO: 8 operably linked to the ADH1 intron operably linked to the complement of SEQ ID NO: 8. |
| SEQ ID NO: 238 |
| Construct expressing SEQ ID NO: 26 as a hairpin RNA. The construct comprises: UBI1ZM promoter 5'UTR and $1^{st}$ intron operably linked to SEQ ID NO: 26 operably linked to the ADH1 intron operably linked to the complement of SEQ ID NO: 26. |
| SEQ ID NO: 239 |
| Construct expressing SEQ ID NO: 17 as a hairpin RNA. The construct comprises: UBI1ZM promoter 5'UTR and $1^{st}$ intron operably linked to SEQ ID NO: 17 operably linked to the ADH1 intron operably linked to the complement of SEQ ID NO: 17. |
| SEQ ID NO: 240 |
| Construct expressing SEQ ID NO: 28 as a hairpin RNA. The construct comprises: UBI1ZM promoter 5'UTR and $1^{st}$ intron operably linked to SEQ ID NO: 28 operably linked to the ADH1 intron operably linked to the complement of SEQ ID NO: 28. |

TABLE 1-continued

| |
|---|
| SEQ ID NO: 241 |
| Construct expressing SEQ ID NO: 28 as a hairpin RNA. The construct comprises: UBI1ZM promoter 5'UTR and $1^{st}$ intron operably linked to SEQ ID NO: 28 operably linked to the ADH1 intron operably linked to the complement of SEQ ID NO: 28. |
| SEQ ID NO: 242 |
| Construct expressing SEQ ID NO: 13 as a hairpin RNA. The construct comprises: UBI1ZM promoter 5'UTR and $1^{st}$ intron operably linked to SEQ ID NO: 13 operably linked to the ADH1 intron operably linked to the complement of SEQ ID NO: 13. |
| SEQ ID NO: 243 |
| Construct expressing SEQ ID NO: 40 as a hairpin RNA. The construct comprises: UBI1ZM promoter 5'UTR and $1^{st}$ intron operably linked to SEQ ID NO: 40 operably linked to the ADH1 intron operably linked to the complement of SEQ ID NO: 40. |
| SEQ ID NO: 244 |
| Construct expressing SEQ ID NO: 72 as a hairpin RNA. The construct comprises: UBI1ZM promoter 5'UTR and $1^{st}$ intron operably linked to SEQ ID NO: 72 operably linked to the ADH1 intron operably linked to the complement of SEQ ID NO: 72. |
| SEQ ID NO: 245 |
| Construct expressing SEQ ID NO: 73 as a hairpin RNA. The construct comprises: UBI1ZM promoter 5'UTR and $1^{st}$ intron operably linked to SEQ ID NO: 73 operably linked to the ADH1 intron operably linked to the complement of SEQ ID NO: 73 |
| SEQ ID NO: 246 |
| Construct expressing SEQ ID NO: 15 as a hairpin RNA. The construct comprises: UBI1ZM promoter 5'UTR and $1^{st}$ intron operably linked to SEQ ID NO: 15 operably linked to the ADH1 intron operably linked to the complement of SEQ ID NO: 15. |
| SEQ ID NO: 247 |
| Construct expressing SEQ ID NO: 18 as a hairpin RNA. The construct comprises: UBI1ZM promoter 5'UTR and $1^{st}$ intron operably linked to SEQ ID NO: 18 operably linked to the ADH1 intron operably linked to the complement of SEQ ID NO: 18. |
| SEQ ID NO: 248 |
| Construct expressing nt 1-380 of SEQ ID NO: 45 as a hairpin RNA. The construct comprises: UBI1ZM promoter 5'UTR and $1^{st}$ intron operably linked to nt 1-380 of SEQ ID NO: 45 operably linked to the ADH1 intron operably linked to the complement of nt 1-380 of SEQ ID NO: 45. |
| SEQ ID NO: 249 |
| Construct expressing nt 1-675 of SEQ ID NO: 37 as a hairpin RNA. The construct comprises: UBI1ZM promoter 5'UTR and $1^{st}$ intron operably linked to nt 1-675 of SEQ ID NO: 37 operably linked to the ADH1 intron operably linked to the complement of nt 1-675 of SEQ ID NO: 37. |
| SEQ ID NO: 250 |
| Construct expressing SEQ ID NO: 29 as a hairpin RNA. The construct comprises: UBI1ZM promoter 5'UTR and $1^{st}$ intron operably linked to SEQ ID NO: 29 operably linked to the ADH1 intron operably linked to the complement of SEQ ID NO: 29. |
| SEQ ID NO: 251 |
| Construct expressing nt 1-266 of SEQ ID NO: 50 as a hairpin RNA. The construct comprises: UBI1ZM promoter 5'UTR and $1^{st}$ intron operably linked to nt 1-266 of SEQ ID NO: 50 operably linked to the ADH1 intron operably linked to the complement of 1-266 of SEQ ID NO: 50. |
| SEQ ID NO: 252 |
| Construct expressing nt 16-585 of SEQ ID NO: 47 as a hairpin RNA. The construct comprises: UBI1ZM promoter 5'UTR and $1^{st}$ intron operably linked to nt 16-585 of SEQ ID NO: 47 operably linked to the ADH1 intron operably linked to the complement of nt 16-585 of SEQ ID NO: 47. |

Example 3

Transformation of Maize

Immature maize embryos from greenhouse donor plants are bombarded with a plasmid containing the silencing element of the invention operably linked to either a tissue specific, tissue selective, or constitutive promoter and the selectable marker gene PAT (Wohlleben et al. (1988) Gene 70:25-37), which confers resistance to the herbicide Bialaphos. In one embodiment, the constructs will express a long double stranded RNA of the target sequence set forth in table 1. Such a construct can be linked to the dMMB promoter. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the silencing element of interest operably linked to either the tissue specific, tissue selective, or constitutive promoter is made. This plasmid DNA plus plasmid DNA containing a PAT selectable marker is precipitated onto 1.1 μm (average diameter) tungsten pellets using a $CaCl_2$ precipitation procedure as follows: 100 μA prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity.

Plants are monitored and scored for the appropriate marker, such as the control of a Coleoptera plant pest, such as a *Diabrotica* plant pest and have insecticidal activity. For example, $R_0$ plant roots are fed to western corn rootworm larvae (VCR, *Diabrotica virgifera*). Transgenic corn roots are handed-off in Petri dishes with MSOD medium containing antibiotics and glyphosate for in vitro selection. Two WCR larvae are infested per root in each dish with a fine tip paintbrush. The dishes are sealed with Parafilm to prevent the larvae from escaping. The assays are placed into a 27° C., 60% RH Percival incubator incomplete darkness. Contamination and larval quality are monitored. After six days of feeding on root tissue, the larvae are transferred to WCR diet in a 96 well plate. The larvae are allowed to feed on the diet for eight days making the full assay fourteen days long. Larval mass and survivorship are recorded for analysis. A one-way ANOVA analysis and a Dunnett's test is performed on the larval mass data to look for statistical significance compared to an untransformed negative control. WCR larvae stunting is measured after feeding on two events and compared to growth of larvae fed on negative control plants.

In other assays, transgenic corn plants ($R_0$) generated are planted into 10-inch pots containing Metromix after reaching an appropriate size. When plants reach the V4 growth stage, approximately 1000 Western corn rootworm (WCR, *Diabrotica virgifera*) eggs are infested into the root zone. Non-transgenic corn of the same genotype is infested at a similar growth stage to serve as a negative control. Eggs are pre-incubated so hatch occurs within 24 hours of infestation. Larvae are allowed to feed on the root systems for 3 weeks. Plants are removed from the soil and washed so that the roots can be evaluated for larval feeding. Root damage is rated using a Node Injury Scale (NIS) to score the level of damage where a 0 indicates no damage, a 1 indicates that one node of roots is pruned to within 1.5 inches, a 2 indicates that 2 nodes are pruned, while a 3 indicates that 3 nodes are pruned. Because the plants being used for evaluation are directly out of tissue culture after transformation and because transformation events are unique, only a single plant is evaluated per event at this time. The plants in the assay that present signs or symptoms of larval feeding indicate that a successful infestation is obtained. Negative control plant roofs are moderately to severely damaged averaging whereas roots of the transgenic plants provide substantial control of larval feeding, with about 0.2 or less on the Node Injury Scale.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-1$H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-1$H_2O$ following adjustment to pH 5.8 with KOH); 3.0 g/l Gelrite (added after bringing to volume with D-1$H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l glycine brought to volume with polished D-1$H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-1$H_2O$ after adjusting to pH 5.6); 3.0 g/l Gelrite (added after bringing to volume with D-1$H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l glycine brought to volume with polished D-1$H_2O$), 0.1 g/l myo-inositol, and 40.0 g/l sucrose (brought to volume with polished D-1$H_2O$ after adjusting pH to 5.6); and 6 g/l bacto-agar (added after bringing to volume with polished D-1$H_2O$), sterilized and cooled to 60° C.

Example 4

*Agrobacterium*-Mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Such as a construct can, for example, express a long double stranded RNA of the target sequence set forth in table 1. Such a construct can be linked to the dMMB promoter. Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants. Assays for insecticidal activity can be performed as described above in Example, 5.

Example 5

Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 μE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the examples above by the method of particle gun bombardment (Klein et al. (1987) *Nature,* 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB 196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the silencing element of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing silencing element of interest are cut from the agarose gel. DNA is purified from the agarose using the GELase digesting enzyme following the manufacturer's protocol.

A 50 μl aliquot of sterile distilled water containing 3 mg of gold particles (3 mg gold) is added to 5 μl of a 1 μg/μl DNA solution (either intact plasmid or DNA fragment prepared as described above), 50 μl 2.5M $CaCl_2$ and 20 μl of 0.1 M spermidine. The mixture is shaken 3 min on level 3 of a vortex shaker and spun for 10 sec in a bench microfuge. After a wash with 400 μl 100% ethanol the pellet is suspended by sonication in 40 μl of 100% ethanol. Five μl of DNA suspension is dispensed to each flying disk of the Biolistic PDS 1000/HE instrument disk. Each 5 μl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB 166, for 1-2 weeks. Clusters are then subcultured to medium SB103 for 3 weeks. During this period, individual embryos can be removed from the clusters and screened for the appropriate marker or the ability of the plant, when injected with the silencing elements, to control the Coleopteran plant pest or the *Diabrotica* plant pest.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2 SO 4 | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 solid medium (per liter) comprises: 1 pkg. MS salts (Gibco/BRL—Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat#21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide

Example 6

Expression of Silencing Elements in Maize

The silencing elements set forth in SEQ ID NO: 8, 26, 17, 28 and 10 were expressed in a maize plant as hairpins and the plant was tested for insecticidal activity against corn root worms. The sequences set forth in SEQ ID NO: 8, 26, 17, 28 and 10 were engineered to be expressed as a hairpin. The constructs comprised the following components: the maize ubiquitin promoter/5'UTR/1$^{st}$ intron operably linked SEQ ID NO:8, 26, 17, 28 or 10:: ADH1 intron:: complement of SEQ ID NO:8, 26, 17, 28 and 10. Plasmids PHP41121, PHP41134, PHP41127, PHP41130, PHP41118 were generated as summarized below in Table 2.

TABLE 2

| SEQ ID NO of silencing element | SEQ ID NO of construct w/promoter and silencing element | Clone name of silencing element | Sequence homology of the silencing element | Plasmid name |
|---|---|---|---|---|
| 8 | 237 | idvlc.pk001.e9.f | Ribosomal protein s10E | PHP41121 |
| 26 | 238 | idvlc.ph003.p13.f | Ribosomal protein | PHP41134 |
| 17 | 239 | idvlc.pk003.f9.f | 27 kD proteinase | PHP41127 |
| 28 | 240 | idvlc.pk004.d17.f | *Tribolium* | PHP41130 |
| 10 | 241 | idvlc.pk001.n1.f | No hits | PHP41118 |

Maize plants were transformed with Plasmids PHP41121, PHP41134, PHP41127, PHP41130, PHP41118 and plants expressing the silencing elements denoted in Table 2 were transplanted from 272V plates into greenhouse flats containing Fafard Superfine potting mix. Approximately 10 to 14 days after transplant, plants (now at growth stage V2-V3) were transplanted into treepots containing Fafard Superfine potting mix. At 14 days post greenhouse send date, plants were infested with 100 eggs of western corn root worms (WCRW)/plant. For later sets, a second infestation of 100 eggs WCRW/plant was done 14 days after the first infestation and scoring was at 14 days after the second infestation. 21 days post infestation, plants were scored using CRWNIS. Those plants with a score of <0.5 are transplanted into large pots containing SB300 for seed. As shown in FIG. 1, each of SEQ ID NO: 8, 26, 17, 28 and 10 had insecticidal activity.

Example 7

Insect Bioassays 2.5 ul of an in-vitro transcription reaction which synthesized one of the sequences set forth in SEQ ID NO: 107-236 were added to a given well of a 96 well microtiter plate. 25 ul of molten lowmelt western corn rootworm diet were added to the sample and shaken on an orbital shaker to mix the sample and diet. Once the diet had solidified, neonate rootworms were added to the well. An average of 5 neonates were added to each well. After the plate was infested, the plate was sealed with mylar and a single hole was punched in the mylar over each well to allow air exchange. 4 replicate wells were produced for each sample. The assay was scored for activity 7 days post infestation. Table 3 provides insecticidal bioassay data employing the southern corn rootworm. The possible scores are dead (D), severely stunted (SS; little or no growth but alive), stunted (S; growth to second instar but not equivalent to controls), contaminated (c), or no activity.

Following confirmation, a simple dose response assay was performed with both southern and western corn rootworms. See, Tables 4 and 5 below. Samples for dose response assays were produced in the same manner described above with the following modification: samples were further purified using column purification prior to enzymatic treatment. Samples were also normalized to 0.5 ug/ul and all samples were evaluated by gel electrophoresis. Dose response assays were performed with the following rates: crude, 0.5, 0.25, 0.125 ppm, and 0.125 dilutions (equivalent to 51, 25, 12.5 and 6 ppm).

TABLE 3

Insecticidal Bioassay Data Against Southern Corn Root Worm

| Clone name | | | | | |
|---|---|---|---|---|---|
| idv1c.pk001.o20.f | S | S | S | S | S |
| idv1c.pk002.a20.f | S | S | S | S | S |
| idv1c.pk002.c7.f | SS | SS | SS | SS | SS |
| idv1c.pk002.c15.f | S | S | S | S | S |
| idv1c.pk002.f18.f | SS | SS | S | SS | SS |
| idv1c.pk002.i21.f | S | S | S | S | S |
| idv1c.pk002.i23.f | SS | SS | SS | SS | SS |
| idv1c.pk002.j24.f | SS | SS | SS | SS | SS |
| idv1c.pk002.m16.f | SS | SS | SS | SS | SS |
| idv1c.pk002.n13.f | SS | SS | SS | SS | SS |
| idv1c.pk024.b23.f | S | S | S | S | S |
| idv1c.pk024.c7.f | SS | SS | D | SS | SS |
| idv1c.pk024.e1.f | S | S | S | S | S |
| idv1c.pk024.e24.f | S | S | S | S | S |
| idv1c.pk024.j15.f | SS | SS | SS | SS | SS |
| idv1c.pk024.k17.f | S | S | S | S | S |
| idv1c.pk024.m13.f | S | S | S | S | S |
| idv1c.pk024.n1.f | S | S | S | S | S |
| idv1c.pk024.o3.f | S | S | S | S | S |
| idv1c.pk025.a4.f | S | S | S | S | S |
| idv1c.pk025.b17.f | SS | SS | SS | SS | SS |
| idv1c.pk025.c5.f | S | S | S | S | S |
| idv1c.pk025.c23.f | S | SS | S | S | S |
| idv1c.pk025.d18.f | S | S | S | S | S |
| idv1c.pk025.d20.f | S | S | S | S | S |
| idv1c.pk025.f3.f | SS | SS | SS | SS | SS |
| idv1c.pk025.f24.f | S | S | S | S | S |
| idv1c.pk025.i8.f | SS | SS | SS | S | SS |
| idv1c.pk025.j20.f | S | S | S | S | S |
| idv1c.pk025.l10.f | S | S | S | S | S |
| idv1c.pk025.l17.f | SS | S | SS | SS | SS |

TABLE 3-continued

Insecticidal Bioassay Data Against Southern Corn Root Worm

| Clone name | | | | | |
|---|---|---|---|---|---|
| idv1c.pk025.o24.f | SS | SS | SS | SS | SS |
| idv1c.pk025.p9.f | SS | SS | S | SS | SS |
| idv1c.pk026.a16.f | S | S | S | S | S |
| idv1c.pk026.b23.f | S | S | S | S | S |
| idv1c.pk026.d22.f | S | S | S | S | S |
| idv1c.pk026.e6.f | S | S | S | S | S |
| idv1c.pk026.f20.f | SS | SS | SS | SS | SS |
| idv1c.pk026.g12.f | S | S | S | S | S |
| idv1c.pk026.h15.f | S | S | S | S | S |
| idv1c.pk026.i12.f | S | S | S | S | S |
| idv1c.pk026.j18.f | S | S | S | S | S |
| idv1c.pk026.k13.f | S | S | S | S | S |
| idv1c.pk026.p8.f | SS | SS | S | S | SS |
| idv1c.pk026.p22.f | SS | SS | SS | SS | SS |
| idv1c.pk027.a14.f | SS | SS | SS | SS | SS |
| idv1c.pk027.b21.f | S | S | S | S | S |
| idv1c.pk027.c7.f | S | S | S | S | S |
| idv1c.pk027.g7.f | SS | SS | SS | SS | SS |
| idv1c.pk027.k4.f | S | S | S | S | S |
| idv1c.pk027.k23.f | SS | SS | SS | SS | SS |
| idv1c.pk027.p21.f | S | S | S | S | S |
| idv1c.pk028.b7.f | S | S | S | S | S |
| idv1c.pk028.b17.f | S | SS | SS | S | SS |
| idv1c.pk028.c22.f | S | S | S | S | S |
| idv1c.pk028.f11.f | SS | SS | SS | SS | SS |
| idv1c.pk028.h6.f | S | S | S | S | S |
| idv1c.pk028.i16.f | S | S | S | S | S |
| idv1c.pk028.m11.f | S | S | S | S | S |
| idv1c.pk028.o18.f | S | S | S | S | S |
| idv1c.pk029.a17.f | S | S | S | S | S |
| idv1c.pk029.c3.f | SS | SS | SS | SS | SS |
| idv1c.pk029.d16.f | S | S | S | S | S |
| idv1c.pk029.f5.f | SS | SS | SS | S | SS |
| idv1c.pk029.i22.f | S | S | S | S | S |
| idv1c.pk029.j4.f | SS | SS | SS | SS | SS |
| idv1c.pk029.j20.f | S | S | S | S | S |
| idv1c.pk029.k11.f | S | S | S | S | S |
| idv1c.pk029.l22.f | S | S | S | S | S |
| idv1c.pk030.b23.f | SS | SS | SS | SS | SS |
| idv1c.pk030.e10.f | S | S | S | S | S |
| idv1c.pk030.e21.f | S | S | S | S | S |
| idv1c.pk030.f9.f | SS | SS | SS | SS | SS |
| idv1c.pk030.g11.f | SS | SS | SS | SS | SS |
| idv1c.pk030.h13.f | S | S | S | S | S |
| idv1c.pk030.h23.f | S | S | S | S | S |
| idv1c.pk030.l9.f | S | S | S | S | S |
| idv1c.pk030.m22.f | S | S | S | S | S |
| idv1c.pk030.o7.f | S | S | S | S | S |
| idv1c.pk031.a11.f | S | S | S | S | S |
| idv1c.pk031.c20.f | SS | SS | SS | SS | SS |
| idv1c.pk031.d1.f | SS | SS | SS | SS | SS |
| idv1c.pk031.e16.f | S | S | S | S | S |
| idv1c.pk031.g2.f | S | S | S | S | S |
| idv1c.pk031.g22.f | S | S | S | S | S |
| idv1c.pk031.i13.f | S | S | S | S | S |
| idv1c.pk031.j1.f | SS | SS | SS | SS | SS |
| idv1c.pk031.j6.f | SS | SS | SS | SS | SS |
| idv1c.pk031.m3.f | S | S | S | S | S |
| idv1c.pk031.p16.f | SS | SS | SS | SS | SS |
| idv1c.pk032.a16.f | SS | SS | SS | SS | SS |
| idv1c.pk032.b4.f | S | S | S | S | S |
| idv1c.pk032.e16.f | S | S | S | S | S |
| idv1c.pk032.f11.f | SS | SS | SS | SS | SS |
| idv1c.pk032.f14.f | S | S | S | S | S |
| idv1c.pk032.i21.f | SS | SS | SS | SS | SS |
| idv1c.pk032.m9.f | S | S | S | S | S |
| idv1c.pk032.n18.f | SS | SS | SS | SS | SS |
| idv1c.pk032.p5.f | SS | SS | SS | SS | SS |
| idv1c.pk033.a15.f | S | S | S | S | S |
| idv1c.pk033.b14.f | S | S | S | S | S |
| idv1c.pk033.d24.f | SS | SS | SS | SS | SS |
| idv1c.pk033.j21.f | SS | SS | SS | SS | SS |
| idv1c.pk033.m3.f | S | S | S | S | S |
| idv1c.pk033.n10.f | S | S | S | S | S |
| idv1c.pk033.n18.f | S | S | S | S | S |
| idv1c.pk033.o9.f | SS | SS | SS | SS | SS |

TABLE 3-continued

Insecticidal Bioassay Data Against Southern Corn Root Worm

| Clone name | | | | | |
|---|---|---|---|---|---|
| idv1c.pk033.p15.f | SS | SS | SS | SS | SS |
| idv1c.pk033.p16.f | SS | SS | SS | SS | SS |
| idv1c.pk034.e8.f | S | S | S | S | S |
| idv1c.pk034.i2.f | SS | SS | SS | SS | SS |
| idv1c.pk034.j6.f | SS | SS | SS | SS | SS |
| idv1c.pk034.p24.f | S | S | S | S | S |
| idv1c.pk035.f21.f | S | S | S | S | S |
| idv1c.pk035.g1.f | S | S | S | S | S |
| idv1c.pk035.h19.f | S | S | S | S | S |
| idv1c.pk035.i17.f | SS | SS | SS | SS | SS |
| idv1c.pk035.j4.f | S | S | S | S | S |
| idv1c.pk035.k18.f | SS | SS | SS | SS | SS |
| idv1c.pk035.m1.f | S | S | S | S | S |
| idv1c.pk035.o13.f | S | S | S | S | S |
| idv1c.pk036.a14.f | S | S | S | S | S |
| idv1c.pk036.e18.f | S | S | S | S | S |
| idv1c.pk036.f4.f | S | S | S | S | S |
| idv1c.pk036.f9.f | S | S | S | S | S |
| idv1c.pk036.i17.f | S | S | S | S | S |
| idv1c.pk036.i19.f | SS | SS | SS | SS | SS |
| idv1c.pk036.i20.f | S | S | S | S | S |
| idv1c.pk036.k23.f | S | S | S | S | S |

*columns in Table 3 represent replicate wells 1, 2, 3, and 4 and the average.

TABLE 4

Insect Bioassays Against Southern and Western Corn Root Worm.

| | | SCRW | | | | WCRW | | | | SCRW 2 | | | |
|---|---|---|---|---|---|---|---|---|---|---|---|---|---|
| Clone name | Seq id | Crude | 0.5 | 0.25 | 0.125 | Crude | 0.5 | 0.25 | 0.125 | Crude | 0.5 | 0.25 | 0.125 |
| idv1c.pk034.k22.f | DNA directed polymerase | SS | S | S | S | D | D | S | S | SS | S | S | S |
| idv1c.pk002.c7.f | regulatory; prolactin; binding element | SS | S | N | N | S | S | N | N | SS | N | N | N |
| idv1c.pk002.f18.f | cadherin like | S | N | N | N | S | N | N | N | S | N | N | N |
| idv1c.pk002.i23.f | mitochondrial NADH dehydrogenase Fe—S protein | S | N | N | N | S | S | S | S | S | S | N | N |
| idv1c.pk002.j24.f | Human DNA sequence from clone RP5-858M22 | S | S | N | N | N | N | N | N | S | S | N | N |
| idv1c.pk002.m16.f | conserved hypothetical protein | SS | N | N | N | SS | N | N | N | SS | S | N | N |
| idv1c.pk002.n13.f | 16s ribosomal RNA gene | S | N | N | N | SS | SS | N | N | S | S | N | N |
| idv1c.pk024.c7.f | conserved hypothetical protein | SS | S | N | N | SS | SS | N | N | SS | S | N | N |
| idv1c.pk024.j15.f | | SS | N | N | N | N | N | N | N | SS | N | N | N |
| idv1c.pk025.b17.f | cadherin like | SS | S | N | N | SS | SS | S | N | SS | S | N | N |
| idv1c.pk025.f3.f | alpha tubulin | SS | SS | S | S | SS | SS | N | N | SS | SS | S | S |
| idv1c.pk025.i8.f | chromaffin granule amine transporter | SS | S | S | S | SS | SS | SS | S | SS | S | N | S |
| idv1c.pk025.l17.f | Cytochrome b561 domain-containing protein 2 | S | S | N | N | S | S | N | N | S | S | N | N |
| idv1c.pk025.o24.f | ATP-dependent RNA helicase | N | N | N | N | SS | S | N | N | S | N | N | N |
| idv1c.pk025.p9.f | conserved insect hypothetical protein | S | N | N | N | N | N | N | N | S | N | N | N |
| idv1c.pk026.f20.f | NADH-ubiquinone oxidoreductase 24 kDa subunit | S | S | N | N | SS | N | N | N | S | S | N | N |
| idv1c.pk026.p8.f | Sec61 gamma subunit alpha | SS | N | N | N | SS | SS | S | S | SS | S | S | N |
| idv1c.pk026.p22.f | no hits | S | N | N | N | SS | S | N | N | S | N | N | N |
| idv1c.pk027.a14.f | conserved insect sequence | S | N | N | N | N | N | N | N | S | N | N | N |
| idv1c.pk027.g7.f | conserved hypothetical protein | SS | SS | S | S | S | S | S | S | SS | SS | S | S |
| idv1c.pk027.k23.f | low homology to zebrafish sequence | SS | N | N | N | SS | S | S | S | SS | N | N | N |
| idv1c.pk028.b17.f | highly similar to conserved drosophila sequence | SS | S | N | N | SS | SS | SS | SS | SS | S | N | N |
| idv1c.pk028.f11.f | | S | S | N | N | S | N | N | N | S | S | N | N |
| idv1c.pk029.c3.f | dynein heavy chain of insects | SS | N | N | N | S | S | S | S | SS | N | N | N |
| idv1c.pk029.f5.f | COP9 complex homolog subunit 6 | SS | S | N | N | SS | SS | SS | SS | SS | S | N | N |
| idv1c.pk029.j4.f | acyl-coa dehydrogenase | S | S | S | S | SS | SS | S | S | S | S | S | S |

TABLE 4-continued

Insect Bioassays Against Southern and Western Corn Root Worm.

| Clone name | Seq id | SCRW | | | | WCRW | | | | SCRW 2 | | | |
| --- | --- | --- | --- | --- | --- | --- | --- | --- | --- | --- | --- | --- | --- |
| | | Crude | 0.5 | 0.25 | 0.125 | Crude | 0.5 | 0.25 | 0.125 | Crude | 0.5 | 0.25 | 0.125 |
| idv1c.pk030.b23.f | Lancl1 protein [*Tribolium castaneum*] | SS | S | N | N | SS | SS | SS | S | SS | S | S | N |
| idv1c.pk030.f9.f | no hits | S | N | N | N | S | N | N | N | S | S | S | N |
| idv1c.pk030.g11.f | aspartate aminotransferase | SS | SS | S | S | SS | N | N | N | SS | SS | S | S |
| idv1c.pk031.c20.f | low-density lipoprotein receptor, | SS | S | N | N | SS | SS | N | N | SS | S | N | N |
| idv1c.pk031.d1.f | chaperonin | SS | S | S | N | SS | SS | SS | S | SS | S | S | N |
| idv1c.pk031.j1.f | 1,4-dihydroxy-2-naphthoate octaprenyltransferase | S | N | N | N | N | N | N | N | S | N | N | N |
| idv1c.pk031.j6.f | no hits | S | N | N | N | SS | SS | SS | N | S | N | N | N |
| idv1c.pk031.p16.f | ribosomal protein S12 | S | S | S | S | SS | SS | SS | SS | S | S | S | S |
| idv1c.pk032.a16.f | DEAD box ATP-dependent RNA helicase | S | S | S | S | SS | SS | N | N | S | S | S | S |
| idv1c.pk032.f11.f | ribosomal protein L4e | SS | SS | SS | S | SS | SS | SS | N | SS | SS | SS | S |
| idv1c.pk032.i21.f | conserved hypothetical protein | SS | S | S | S | SS | SS | S | N | SS | S | S | S |
| idv1c.pk032.n18.f | similar to pol-like protein | S | S | S | S | SS | SS | S | S | SS | S | S | S |
| idv1c.pk032.p5.f | no hits | S | S | S | S | SS | SS | S | N | S | S | S | S |
| idv1c.pk033.d24.f | sodium pump alpha subunit; | SS | S | N | N | N | N | N | N | SS | SS | S | N |
| idv1c.pk033.j21.f | proteasome subunit alpha type 6 | SS | S | S | N | SS | SS | SS | S | SS | S | S | N |
| idv1c.pk033.o9.f | similar to Uncharacterized protein ZK1236.4 [*Acyrthosiphon pisum*] | S | S | S | N | S | S | N | N | S | S | S | N |
| idv1c.pk033.p15.f | ribosomal protein L35Ae | SS | SS | S | N | S | S | N | N | SS | SS | SS | N |
| idv1c.pk033.p16.f | similar to ribosomal protein L10Ae | S | S | S | S | S | S | S | S | S | S | S | S |
| idv1c.pk034.i2.f | cadherin-like gene conserved | S | N | N | N | SS | SS | SS | N | SS | S | N | N |
| idv1c.pk034.j6.f | hypothetical protein | SS | S | N | N | S | S | S | N | SS | S | S | N |
| idv1c.pk035.i17.f | ryanodine receptor-like protein [*Tribolium castaneum*] | N | N | N | N | SS | SS | N | N | S | N | N | N |
| idv1c.pk035.k18.f | conserved hypothetical protein | S | N | N | N | SS | S | N | N | S | N | N | N |
| idv1c.pk036.i19.f | predicted protein | SS | S | N | N | SS | S | S | N | SS | SS | SS | S |

TABLE 5

Insect Bioassays Against Southern and Western Corn Root Worm.

| Clone name | 1° assay result | 1st Confirmation | 2nd Confirmation | SCRW dose response #1 | | | | SCRW does response #2 | | | |
| --- | --- | --- | --- | --- | --- | --- | --- | --- | --- | --- | --- |
| | | | | Crude | 0.5 | 0.25 | 0.125 | Crude | 0.5 | 0.25 | 0.125 |
| idv1c.pk001.o20.f | S | SS | SS | S | N | N | N | S | N | N | N |
| idv1c.pk002.a20.f | S | SS | SS | S | N | N | N | N | N | N | N |
| idv1c.pk002.c15.f | S | S | N | SS | S | N | N | SS | SS | S | N |
| idv1c.pk002.i21.f | S | SS | SS | SS | S | N | N | SS | S | S | S |
| idv1c.pk024.b23.f | S | SS | SS | SS | N | N | N | S | S | N | N |
| idv1c.pk024.e1.f | S | S | S | S | S | N | N | S | S | N | N |
| idv1c.pk024.e24.f | S | S | S | S | S | N | N | S | N | N | N |

TABLE 5-continued

Insect Bioassays Against Southern and Western Corn Root Worm.

| | 1° assay | 1st | 2nd | SCRW dose response #1 | | | | SCRW does response #2 | | | |
|---|---|---|---|---|---|---|---|---|---|---|---|
| Clone name | result | Confirmation | Confirmation | Crude | 0.5 | 0.25 | 0.125 | Crude | 0.5 | 0.25 | 0.125 |
| idv1c.pk024.k17.f | S | S | S | SS | N | N | N | SS | SS | N | N |
| idv1c.pk024.m13.f | S | S | S | S | N | N | N | S | S | N | N |
| idv1c.pk024.n1.f | S | S | S | S | S | S | S | S | S | N | N |
| idv1c.pk024.o3.f | S | SS | SS | S | S | S | S | N | N | N | N |
| idv1c.pk025.a4.f | S | SS | S | S | S | N | N | S | N | N | N |
| idv1c.pk025.c5.f | S | N | N | N | N | N | N | S | N | N | N |
| idv1c.pk025.c23.f | S | N | N | S | N | N | N | S | N | N | N |
| idv1c.pk025.d18.f | S | S | N | SS | SS | N | N | SS | SS | S | N |
| idv1c.pk025.d20.f | S | S | S | S | S | S | S | S | S | N | N |
| idv1c.pk025.f24.f | S | SS | SS | S | S | S | S | S | S | S | N |
| idv1c.pk025.j20.f | S | SS | SS | S | N | N | N | S | S | N | N |
| idv1c.pk025.l10.f | S | S | S | S | N | N | N | S | N | N | N |
| idv1c.pk026.a16.f | S | SS | SS | S | N | N | N | S | N | N | N |
| idv1c.pk026.b23.f | S | S | S | S | N | N | N | S | N | N | N |
| idv1c.pk026.d22.f | S | S | S | N | N | N | N | N | N | N | N |
| idv1c.pk026.e6.f | S | S | S | S | S | N | N | S | S | N | N |
| idv1c.pk026.g12.f | S | S | S | SS | S | N | N | SS | SS | N | N |
| idv1c.pk026.h15.f | S | N | N | S | N | N | N | N | N | N | N |
| idv1c.pk026.i12.f | S | N | N | N | N | N | N | N | N | N | N |
| idv1c.pk026.j18.f | S | S | N | S | S | N | N | SS | N | N | N |
| idv1c.pk026.k13.f | S | SS | SS | S | S | S | S | S | S | S | N |
| idv1c.pk027.b21.f | S | N | N | S | N | N | N | N | N | N | N |
| idv1c.pk027.c7.f | S | N | N | N | N | N | N | N | N | N | N |
| idv1c.pk027.k4.f | S | SS | SS | SS | N | N | N | SS | S | N | N |
| idv1c.pk027.p21.f | S | SS | SS | SS | S | N | N | SS | S | N | N |
| idv1c.pk028.b7.f | S | SS | SS | S | N | N | N | N | N | N | N |
| idv1c.pk028.c22.f | S | SS | SS | SS | N | N | N | SS | S | N | N |
| idv1c.pk028.h6.f | S | SS | SS | SS | N | N | N | SS | N | N | N |
| idv1c.pk028.i16.f | S | N | N | S | N | N | N | S | N | N | N |
| idv1c.pk028.m11.f | S | N | N | S | N | N | N | S | N | N | N |
| idv1c.pk028.o18.f | S | S | SS | S | S | S | S | S | S | S | N |
| idv1c.pk029.a17.f | S | S | S | S | S | S | S | S | N | N | N |
| idv1c.pk029.d16.f | S | S | S | S | S | S | S | S | S | S | S |
| idv1c.pk029.i22.f | S | S | S | SS | SS | S | S | SS | SS | S | N |
| idv1c.pk029.j20.f | S | S | S | SS | SS | S | S | SS | S | S | S |
| idv1c.pk029.k11.f | S | N | N | SS | S | S | N | SS | S | S | S |
| idv1c.pk029.l22.f | S | S | SS | S | S | N | N | S | N | N | N |
| idv1c.pk030.e10.f | S | S | S | SS | S | S | S | SS | S | S | S |
| idv1c.pk030.e21.f | S | S | S | SS | S | S | S | SS | SS | S | S |
| idv1c.pk030.h13.f | S | S | S | S | S | S | S | SS | S | S | S |
| idv1c.pk030.h23.f | S | SS | S | SS | SS | S | S | SS | S | S | N |
| idv1c.pk030.l9.f | S | N | N | S | N | N | N | S | S | N | N |
| idv1c.pk030.m22.f | S | N | N | S | N | N | N | S | N | N | N |
| idv1c.pk030.o7.f | S | S | SS | SS | S | N | N | SS | S | N | N |
| idv1c.pk031.a11.f | S | S | S | SS | S | S | S | SS | S | S | S |
| idv1c.pk031.e16.f | S | S | S | S | N | N | N | N | N | N | N |
| idv1c.pk031.g2.f | S | SS | SS | SS | S | S | N | SS | S | S | N |
| idv1c.pk031.g22.f | S | S | S | SS | N | N | N | SS | S | N | N |
| idv1c.pk031.i13.f | S | SS | SS | SS | S | S | S | SS | N | N | N |
| idv1c.pk031.m3.f | S | S | S | SS | S | S | N | SS | S | S | N |
| idv1c.pk032.b4.f | S | S | S | SS | S | N | N | SS | S | N | N |
| idv1c.pk032.e16.f | S | S | S | S | S | S | S | S | S | N | N |
| idv1c.pk032.f14.f | S | N | N | S | N | N | N | S | N | N | N |
| idv1c.pk032.m9.f | S | SS | SS | SS | N | N | N | SS | S | N | N |
| idv1c.pk033.a15.f | S | N | N | N | N | N | N | S | N | N | N |
| idv1c.pk033.b14.f | S | N | N | S | N | N | N | S | N | N | N |
| idv1c.pk033.m3.f | S | S | S | SS | N | N | N | SS | N | N | N |
| idv1c.pk033.n10.f | S | SS | SS | S | S | S | S | S | S | N | N |
| idv1c.pk033.n18.f | S | SS | SS | S | N | N | N | S | N | N | N |
| idv1c.pk034.e8.f | S | S | S | S | N | N | N | S | N | N | N |
| idv1c.pk034.p24.f | S | S | N | S | S | S | N | S | N | N | N |
| idv1c.pk035.f21.f | S | S | S | S | S | S | S | S | S | S | N |
| idv1c.pk035.g1.f | S | S | N | S | N | N | N | S | N | N | N |
| idv1c.pk035.h19.f | S | SS | SS | S | N | N | N | N | N | N | N |
| idv1c.pk035.j4.f | S | SS | SS | SS | S | S | S | SS | SS | S | S |
| idv1c.pk035.m1.f | S | S | S | S | S | S | S | S | S | S | N |
| idv1c.pk035.o13.f | S | S | S | S | N | N | S | S | N | N | N |
| idv1c.pk036.a14.f | S | S | N | SS | S | S | N | SS | S | S | N |

TABLE 5-continued

Insect Bioassays Against Southern and Western Corn Root Worm.

| Clone name | 1° assay result | 1st Confirmation | 2nd Confirmation | SCRW dose response #1 Crude | 0.5 | 0.25 | 0.125 | SCRW does response #2 Crude | 0.5 | 0.25 | 0.125 |
|---|---|---|---|---|---|---|---|---|---|---|---|
| idv1c.pk036.e18.f | S | S | S | S | S | S | N | S | S | S | N |
| idv1c.pk036.f4.f | S | S | S | S | S | S | S | S | S | N | N |
| idv1c.pk036.f9.f | S | S | S | SS | S | S | S | SS | S | S | N |
| idv1c.pk036.i17.f | S | S | S | S | S | S | S | S | S | S | N |
| idv1c.pk036.i20.f | S | S | S | SS | SS | N | N | SS | SS | S | N |
| idv1c.pk036.k23.f | S | S | S | S | S | N | N | S | S | S | N |

Example 8

Expression of Silencing Elements in Maize

The silencing elements set forth in SEQ ID NO: 13, 40, 72 and 73 were expressed in a maize plant as hairpins and the plants were tested for insecticidal activity against corn root worms. The sequences set forth in SEQ ID NO: 13, 40, 72 and 73 were engineered to be expressed as a hairpin. The constructs comprised the following components: the maize ubiquitin promoter/5'UTR/0 intron operably linked to one of SEQ ID NO: 13, 40, 72 and 73::the ADH1 intron:: complement of the corresponding SEQ ID NO. Plasmids PHP41136, PHP41567, PHP41992, PHP42000 were generated as summarized below in Table 6. PHP19288 was a control plasmid which lacked a silencing element.

TABLE 6

| SEQ ID NO of silencing element | SEQ ID NO of construct w/ promoter and silencing element | Clone name of silencing element | Plasmid name |
|---|---|---|---|
| 13 | 242 | idv1c.pk002.j17.f | PHP41136 |
| 40 | 243 | idv1c.pk013.h1.f | PHP41567 |
| 72 | 244 | idv1c.pk017.d14.f | PHP41992 |
| 73 | 245 | idv1c.pk017.e22.f | PHP42000 |

Maize plants were transformed with plasmids PHP41136, PHP41567, PHP41992, PHP42000, and PHP19288 (control lacking silencing element) and plants expressing the silencing elements denoted in Table 6 were transplanted from 272V plates into greenhouse flats containing Fafard Superfine potting mix. Plants were infected (100 eggs per plant) 14 days post greenhouse send date and a second infestation (150 eggs per plant) was performed 14 days later. The scoring for insecticidal activity was done 14 days later (28 days post first infection). Each of SEQ ID NO: 13, 40, 72 and 73 had insecticidal activity in this assay.

Figure 2:
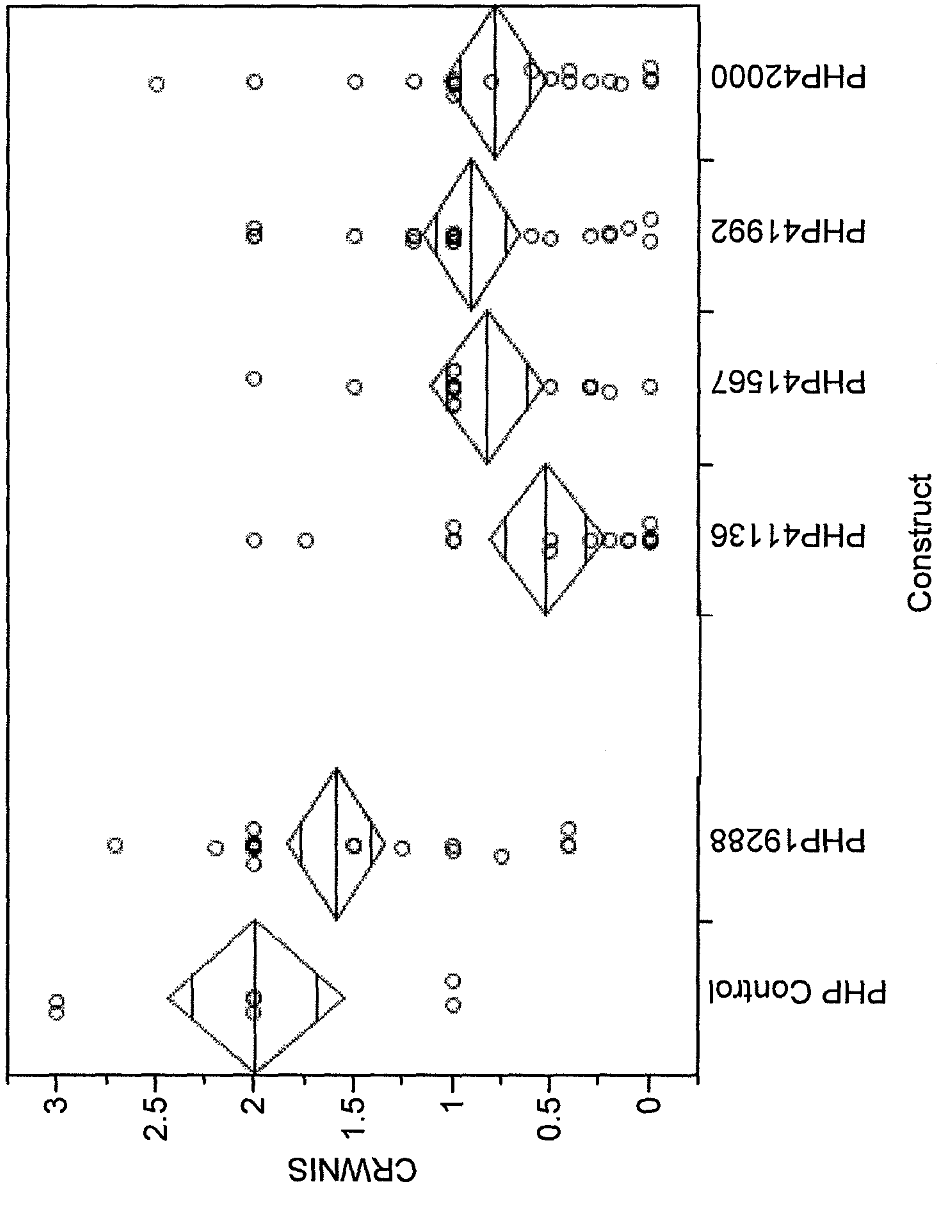
FIG. 2 shows a corn rootworm whole plant assay. The data demonstrates that expression of SEQ ID NO: 13 (clone idvlc.pk002.j171); SEQ ID NO: 40 (clone idvlc.pk013.h1.f); SEQ ID NO:72 (clone idvlc.pk017.d14.f); and SEQ ID NO:73 (clone idvlc.pk017.e22.f) as a hairpin in a maize plant produces a maize plant, which when ingested by corn root worm, has insecticidal activity. CRWNIS refers to corn root worm nodal injury score. PHP19288 is a control plasmid lacking the silencing element.

As shown in FIG. 2, significant efficacy was shown with the PHP41136, PHP41567, PHP41992, and PHP42000 constructs. No significant difference between PHP41136 and the PHP positive control was seen. Table 7 provides a summary of the data shown in FIG. 2.

TABLE 7

Oneway Anova
Summary of Fit

| | |
|---|---|
| Rsquare | 0.440885 |
| Adj Rsquare | 0.412145 |
| Root Mean Square Error | 0.654125 |
| Mean of Response | 1.270885 |
| Observations (or Sum Wgts) | 226 |

Analysis of Variance

| Source | DF | Sum of Squares | Mean Square | F Ratio | Prob >F |
|---|---|---|---|---|---|
| Construct | 11 | 72.20360 | 6.56396 | 15.3407 | <.0001* |
| Error | 214 | 91.56622 | 0.42788 | | |
| C. Total | 225 | 163.76982 | | | |

Means for Oneway Anova

| Level | Number | Mean | Std Error | Lower 95% | Upper 95% |
|---|---|---|---|---|---|
| PHP Control | 20 | 1.96000 | 0.14627 | 1.672 | 2.2483 |
| PHP19288 | 22 | 1.59545 | 0.13946 | 1.321 | 1.8703 |
| PHP41136 | 16 | 0.52813 | 0.16353 | 0.206 | 0.8505 |
| PHP41567 | 17 | 0.82941 | 0.15865 | 0.517 | 1.1421 |
| PHP41992 | 23 | 0.91304 | 0.13639 | 0.644 | 1.1819 |
| PHP42000 | 21 | 0.78810 | 0.14274 | 0.507 | 1.0695 |

Std Error uses a pooled estimate of error variance

Example 9

Insect Bioassays 2.5 ul of an in-vitro transcription reaction which synthesized one of the sequences set forth in SEQ ID NO: 13, 40, 72 and 73 was added to a given well of a 96 well microtiter plate. 25 ul of molten lowmelt western corn rootworm diet were added to the sample and shaken on an orbital shaker to mix the sample and diet. Once the diet solidified, neonate rootworms were added to the well. An average of 5 neonates was added to each well. After the plate was infested, the plate was sealed with mylar and a single hole was punched in the mylar over each well to allow air exchange. 4 replicate wells were produced for each sample. The assay was scored for activity 7 days post infestation. Dose response assays were performed with the following rates: 50, 25, 12.5, 6.5, 3.2, and 1.5 ppm. Table 8 provides insecticidal bioassay data employing the southern corn rootworm. The possible scores are dead (D), severely stunted (SS; little or no growth but alive), stunted (S; growth to second instar but not equivalent to controls), contaminated (c), or no activity.

TABLE 8

Comparison of T0 activity and dsRNA assay results

| | SCRW | | | | | | WCRW | | | | | | | |
|---|---|---|---|---|---|---|---|---|---|---|---|---|---|---|
| | | | | | | | | | | eqiuvalent to 5 ng/cm2 | | | | |
| Gene id | 50 ppm | 25 ppm | 12.5 ppm | 6.5 ppm | 3.2 ppm | 1.5 ppm | 50 ppm | 25 ppm | 12.5 ppm | 6.5 ppm | 3.2 ppm | 1.5 ppm | PHP# | $T_0$Gene testing results |
| Proteosome subunit alpha type 3 | SS | SS | SS | | | | SS | SS | SS | SS | SS | SS | 41136 | good |
| Low homology to sea urchin reverse transcriptase | N | N | N | N | N | N | SS | SS | SS | SS | SS | SS | 41129 | poor |
| Mosquito conserved hypo. Prot. | SS | SS | SS | SS | SS | SS | SS | SS | SS | SS | SS | SS | 41124 | poor |
| Syntaxin | ss | ss | ss | N | N | N | N | N | N | N | N | N | 41558 | poor |
| Ribosomal protein L27E | SS | SS | SS | SS | SS | SS | S | S | N | N | N | N | 41567 | good |
| No hits | SS | SS | S | N | N | N | S | N | N | N | N | N | 41549 | poor |
| Proteosome beta subunit | SS | SS | SS | SS | SS | SS | S | S | S | S | N | N | 41999 | poor |
| Cadherin like | S | S | S | S | S | S | SS | SS | SS | SS | S | S | 41992 | good |
| Ribosome biogenesis regulatory homolog | S | S | N | N | N | N | SS | SS | SS | SS | S | S | 42000 | good |

Example 10

Expression of Silencing Elements in Maize

The silencing elements set forth in the various SEQ ID NOs denoted in Table 9 were expressed in a maize plant (via the FASTcorn highthoughput screening methods) as hairpins and the various plants were tested for insecticidal activity against corn root worms. The sequences set forth in the SEQ ID NOs denoted in Table 9 were engineered to be expressed as a hairpin. The constructs comprised the following components: the maize ubiquitin promoter/5'UTR/$1^{st}$ intron operably linked SEQ ID NO set forth in Table 9:: ADH1 intron:: complement of the SEQ ID NO: set forth in Table 9. The various plasmids having these silencing expression constructs were generated as summarized below in Table 9.

TABLE 9

| Row Labels | SEQ ID NO making up one stem of the hairpin | Clone name of silencing element | SEQ ID NO of full length expression vector | Pass | Weak pass | # tested | % rtPCR (+) | % actives of rtPCR + | Diet assay activity |
|---|---|---|---|---|---|---|---|---|---|
| PHP44742 | nt 1-380 of SEQ ID NO: 45 | idv1c.pk014.b17.f | 248 | 100.0% | 0.0% | 19 | 90 | 100 | s |
| PHP44107 | 8 | idv1c.pk001.e9.f | 237 | 94.7% | 0.0% | 19 | 95 | 100 | ss |
| PHP44118 | 15 | idv1c.pk003.d6.f | 246 | 55.0% | 10.0% | 20 | 70 | 100 | s |
| PHP44747 | nt 1-266 of SEQ ID NO: 50 | idv1c.pk014.k23.f | 251 | 40.0% | 13.3% | 15 | 67 | 50 | ss |
| PHP44116 | 18 | idv1c.pk003.j4.f | 247 | 31.6% | 10.5% | 19 | 25 | 100 | ss |
| PHP44109 | 29 | idv1c.pk004.f20.f | 250 | 30.0% | 10.0% | 20 | 58 | 63 | SS |
| PHP44750 | nt 1-675 of SEQ ID NO: 37 | idv1c.pk013.b11.f | 249 | 30.0% | 0.0% | 10 | 50 | 33 | s |
| PHP44119 | 9 | idv1c.pk001.m5.f | | 26.3% | 0.0% | 19 | No data | No data | ss |
| PHP44117 | 14 | idv1c.pk002.n13.f | | 26.3% | 5.3% | 19 | 0 | 0 | s |
| PHP44744 | nt 1-132 of SEQ ID NO: 40 | idv1c.pk013.h1.f | 243 | 21.1% | 5.3% | 19 | 68 | 38 | s |
| PHP44748 | nt 16-585 of SEQ ID NO: 47 | idv1c.pk014.d11.f | 252 | 17.6% | 5.9% | 17 | 83 | 25 | s |
| PHP44211 | 54 | idv1c.pk014.n23.f | | 15.0% | 0.0% | 20 | No data | No data | s |
| PHP44208 | 32 | idv1c.pk004.n6.f | | 12.5% | 25.0% | 8 | No data | No data | s |
| PHP45641 | 92 | idv1c.pk019.l7.f | | 12.5% | 0.0% | 8 | 50 | 12 | s |
| PHP44115 | 12 | idv1c.pk002.f20.f | | 10.0% | 10.0% | 20 | No data | No data | ss |
| PHP44122 | 27 | idv1c.pk004.b12.f | | 10.0% | 0.0% | 20 | No data | No data | ss |
| PHP44120 | 25 | idv1c.pk003.o22.f | | 10.0% | 15.0% | 20 | No data | No data | s |

TABLE 9-continued

| Row Labels | SEQ ID NO making up one stem of the hairpin | Clone name of silencing element | SEQ ID NO of full length expression vector | Pass | Weak pass | # tested | % rtPCR (+) | % actives of rtPCR + | Diet assay activity |
|---|---|---|---|---|---|---|---|---|---|
| PHP44121 | 21 | idv1c.pk003.l1.f | | 10.0% | 5.0% | 20 | No data | No data | s |
| PHP44746 | 46 | idv1c.pk014.c14.f | | 9.1% | 18.2% | 11 | 40 | 25 | s |
| PHP44976 | 66 | idv1c.pk016.h19.f | | 7.7% | 0.0% | 13 | 92 | 8 | ss |
| PHP44213 | 23 | idv1c.pk003.m10.f | | 5.6% | 0.0% | 18 | No data | No data | s |
| PHP44113 | 26 | idv1c.pk003.p13.f | | 5.3% | 5.3% | 19 | No data | No data | ss |
| PHP44114 | 24 | idv1c.pk003.o13.f | | 5.3% | 5.3% | 19 | No data | No data | s |
| PHP44745 | 33 | idv1c.pk004.o4.f | | 5.3% | 0.0% | 19 | 76 | 0 | s |
| PHP44210 | 11 | idv1c.pk002.c5.f | | 5.0% | 0.0% | 20 | No data | No data | ss |
| PHP44106 | 10 | idv1c.pk001.n1.f | | 5.0% | 15.0% | 20 | No data | No data | s |
| PHP44112 | 28 | idv1c.pk004.d17.f | | 0.0% | 0.0% | 17 | No data | No data | ss |
| PHP44216 | 20 | idv1c.pk003.j20.f | | 0.0% | 0.0% | 12 | No data | No data | ss |
| PHP44220 | 13 | idv1c.pk002.j17.f | | 0.0% | 0.0% | 20 | No data | No data | ss |
| PHP44209 | 56 | idv1c.pk015.a16.f | | 0.0% | 0.0% | 14 | No data | No data | s* |
| PHP44212 | 38 | idv1c.pk013.c21.f | | 0.0% | 0.0% | 20 | No data | No data | s* |
| PHP44215 | 39 | idv1c.pk013.d22.f | | 0.0% | 0.0% | 18 | No data | No data | s* |
| PHP44217 | 53 | idv1c.pk014.n16.f | | 0.0% | 0.0% | 13 | No data | No data | s* |
| PHP44221 | 48 | idv1c.pk014.f3.f | | 0.0% | 0.0% | 10 | No data | No data | s* |
| PHP44743 | 48 | idv1c.pk013.k1.f | | 0.0% | 0.0% | 20 | 37 | 0 | s* |
| PHP44756 | 49 | idv1c.pk014.j2.f | | 0.0% | 0.0% | 20 | 0 | 0 | s* |
| PHP44757 | 61 | idv1c.pk015.p2.f | | 0.0% | 0.0% | 20 | 80 | 0 | s* |
| PHP44975 | 65 | idv1c.pk016.h15.f | | 0.0% | 0.0% | 5 | 31 | 0 | s* |
| PHP44977 | 68 | idv1c.pk016.j15.f | | 0.0% | 0.0% | 6 | 30 | 0 | s* |
| PHP44982 | 75 | idv1c.pk017.h14.f | | 0.0% | 0.0% | 11 | 55 | 0 | s* |
| PHP44989 | 84 | idv1c.pk018.f19.f | | 0.0% | 0.0% | 9 | 45 | 0 | s* |
| PHP44991 | 87 | idv1c.pk018.h21.f | | 0.0% | 0.0% | 12 | 60 | 0 | s* |
| PHP44992 | 91 | idv1c.pk019.k3.f | | 0.0% | 0.0% | 5 | 25 | 0 | s* |
| PHP45629 | 99 | idv1c.pk020.l3.f | | 0.0% | 0.0% | 13 | 80 | 0 | s* |
| PHP45635 | 104 | idv1c.pk021.h12.f | | 0.0% | 0.0% | 6 | 30 | 0 | s* |
| PHP45636 | 98 | idv1c.pk020.k19.f | | 0.0% | 0.0% | 14 | 70 | 0 | s* |
| PHP45638 | 97 | idv1c.pk020.i24.f | | 0.0% | 0.0% | 7 | 35 | 0 | s* |
| PHP45640 | 95 | idv1c.pk020.g17.f | | 0.0% | 0.0% | 15 | 75 | 0 | s* |
| PHP44111 | 17 | idv1c.pk003.f9.f | | 0.0% | 0.0% | 19 | No data | No data | s |
| PHP44204 | 16 | idv1c.pk003.f8.f | | 0.0% | 0.0% | 20 | No data | No data | s |
| PHP44205 | 34 | idv1c.pk004.o9.f | | 0.0% | 0.0% | 13 | No data | No data | s |
| PHP44206 | 43 | idv1c.pk014.a19.f | | 0.0% | 0.0% | 17 | No data | No data | s |
| PHP44207 | 22 | idv1c.pk003.m1.f | | 0.0% | 0.0% | 20 | No data | No data | s |
| PHP44214 | 41 | idv1c.pk013.h14.f | | 0.0% | 0.0% | 18 | No data | No data | s |
| PHP44218 | 19 | idv1c.pk003.j6.f | | 0.0% | 0.0% | 20 | No data | No data | s |
| PHP44219 | 52 | idv1c.pk014.m13.f | | 0.0% | 0.0% | 20 | No data | No data | s |
| PHP44222 | 31 | idv1c.pk004.l15.f | | 0.0% | 5.6% | 18 | No data | No data | s |
| PHP44223 | 36 | idv1c.pk013.a15.f | | 0.0% | 5.3% | 19 | No data | No data | s |
| PHP44739 | 44 | idv1c.pk014.b9.f | | 0.0% | 0.0% | 4 | 0 | No data | s |
| PHP44741 | 51 | idv1c.pk014.m5.f | | 0.0% | 0.0% | 3 | 0 | 0 | s |
| PHP44749 | 57 | idv1c.pk015.b8.f | | 0.0% | 0.0% | 3 | 0 | 0 | s |
| PHP44752 | 60 | idv1c.pk015.n19.f | | 0.0% | 0.0% | 10 | 70 | 0 | s |
| PHP44753 | 71 | idv1c.pk017.c3.f | | 0.0% | 0.0% | 19 | 85 | 0 | s |
| PHP44973 | 59 | idv1c.pk015.l13.f | | no data | no data | 0 | 24 | No data | s* |
| PHP44978 | 69 | idv1c.pk016.k9.f | | no data | no data | 0 | 10 | No data | s* |
| PHP45630 | 102 | idv1c.pk021.d22.f | | no data | no data | 0 | 5 | No data | s* |
| PHP45631 | 105 | idv1c.pk021.m20.f | | no data | no data | 0 | 30 | No data | s* |
| PHP45637 | 96 | idv1c.pk020.i7.f | | no data | no data | 0 | 15 | No data | s* |
| PHP45639 | 94 | idv1c.pk020.b11.f | | no data | no data | 0 | 15 | No data | s* |

Maize plants were transformed with PHP plasmids and plants expressing the silencing elements denoted in Table 9 were transplanted from 272V plates into greenhouse flats containing Fafard Superfine potting mix. Approximately 10 to 14 days after transplant, plants (now at growth stage V2-V3) were transplanted into treepots containing Fafard Superfine potting mix. At 14 days post greenhouse send date, plants were infested with 100 eggs of western corn root worms (WCRW)/plant. For later sets, a second infestation of 100 eggs WCRW/plant was done 14 days after the first infestation and scoring was at 14 days after the second infestation. 21 days post infestation, plants were scored using CRWNIS. Those plants with a score of <0.5 are transplanted into large pots containing SB300 for seed. "Pass" as denoted in Table 9 is a Nodal injury score of 0.2 to 0. "Weak pass" as denoted in Table 9 is a score from >0.2 to 0.75 which was the cut off for advancing an event. "% rtPCR" as denoted in Table 9 is the percent of the 20 events with demonstrated expression of the hairpin as determined by rtPCR. "% actives of rtPCR" as denoted in Table 9 is the percent of rtPCR positives that also passed the CRWNIS test. So this last number could be 100% even if only 10 of 20 events were rtPCR positive if all 10 also passed the CRWNIS test. The "diet assay activity" summarizes the data previously presented herein denoting either stunted (s) or severely stunted (ss) activity when the hairpins mixed with the CRW diet and fed directly to the bugs.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An expression cassette, comprising a heterologous promoter and at least one polynucleotide, wherein said at least one polynucleotide is selected from the group consisting of:

a) the polynucleotide sequence of SEQ ID NO: 234, or the full-length complement thereof;

b) a polynucleotide sequence comprising at least 95% identity to the nucleotide sequence of SEQ ID NO: 234, or the full-length complement thereof; or c) a polynucleotide sequence comprising at least 380 nucleotides of the sequence set forth in SEQ ID NO: 234, and said polynucleotide sequence having at least 320 consecutive nucleotides of SEQ ID NO: 234, or the full-length complement said polynucleotide sequence having at least 320 consecutive nucleotides of SEQ ID NO: 234;

wherein said polynucleotide, or the full-length complement thereof, encodes a silencing element having insecticidal activity against a Coleopteran plant pest.

2. The expression cassette of claim 1, wherein said at least one polynucleotide encodes a silencing element which is expressed as a hairpin RNA.

3. A silencing element produced by an expression cassette comprising a heterologous promoter and at least one polynucleotide, wherein said at least one polynucleotide is selected from the group consisting of:

a) the polynucleotide sequence of SEQ ID NO: 234, or the full-length complement thereof;

b) a polynucleotide sequence comprising at least 95% identity to the nucleotide sequence of SEQ ID NO: 234, or the full-length complement thereof; or c) a polynucleotide sequence comprising at least 380 nucleotides of the sequence set forth in SEQ ID NO:

234, and said polynucleotide sequence having at least 320 consecutive nucleotides of SEQ ID NO: 234, or the full-length complement said polynucleotide sequence having at least 320 consecutive nucleotides of SEQ ID NO: 234;

wherein said polynucleotide, or the full-length complement thereof, encodes a silencing element having insecticidal activity against a Coleopteran plant pest.

4. The expression cassette of claim 1, wherein said at least one polynucleotide is flanked by a first operably linked convergent promoter at one terminus of the silencing element and a second operably linked convergent promoter at the opposing terminus of said at least one polynucleotide, wherein the first and the second convergent promoters drive expression of the silencing element to form a double-stranded RNA (dsRNA).

5. A host cell comprising the expression cassette of claim 1.

6. A plant cell having stably incorporated into its genome an expression cassette comprising a heterologous promoter and at least one polynucleotide, wherein said at least one polynucleotide is selected from the group consisting of:

a) the polynucleotide sequence of SEQ ID NO: 234, or the full-length complement thereof;

b) a polynucleotide sequence comprising at least 95% identity to the nucleotide sequence of SEQ ID NO: 234, or the full-length complement thereof; or c) a polynucleotide sequence comprising at least 380 nucleotides of the sequence set forth in SEQ ID NO: 234, and said polynucleotide sequence having at least 320 consecutive nucleotides of SEQ ID NO: 234, or the full-length complement said polynucleotide sequence having at least 320 consecutive nucleotides of SEQ ID NO: 234;

wherein said polynucleotide, or the full-length complement thereof, encodes a silencing element that, when ingested by a Coleopteran plant pest, reduces the level of a target sequence in said Coleopteran plant pest and thereby controls the Coleopteran plant pest.

7. The plant cell of claim 6, wherein the Coleopteran plant pest is a *Diabrotica* plant pest.

8. The plant cell of claim 6, wherein said silencing element is expressed as a double stranded RNA.

9. The plant cell of claim 6, wherein said silencing element is expressed as a hairpin RNA.

10. The plant cell of claim 6, wherein said at least one polynucleotide is operably linked to said heterologous promoter.

11. The plant cell of claim 6, wherein said plant cell is from a monocot.

12. The plant cell of claim 11, wherein said monocot is maize, barley, millet, wheat or rice.

13. The plant cell of claim 6, wherein said plant cell is from a dicot.

14. The plant cell of claim 13, wherein said plant cell is soybean, canola, alfalfa, sunflower, safflower, tobacco, *Arabidopsis*, or cotton.

15. A plant or plant part comprising the plant cell of claim 6.

16. A transgenic seed comprising the plant cell of claim 6.

17. A method for controlling a Coleopteran plant pest comprising feeding to a Coleopteran plant pest a composition comprising an expression cassette comprising a heterologous promoter and at least one polynucleotide, wherein said at least one polynucleotide is selected from the group consisting of:

a) the polynucleotide sequence of SEQ ID NO: 234, or the full-length complement thereof;

b) a polynucleotide sequence comprising at least 95% identity to the nucleotide sequence of SEQ ID NO: 234, or the full-length complement thereof; or c) a polynucleotide sequence comprising at least 380 nucleotides of the sequence set forth in SEQ ID NO: 234, and said polynucleotide sequence having at least 320 consecutive nucleotides of SEQ ID NO: 234, or the full-length complement said polynucleotide sequence having at least 320 consecutive nucleotides of SEQ ID NO: 234;

wherein said polynucleotide, or the full-length complement thereof, encodes a silencing element having insecticidal activity against a Coleopteran plant pest.

18. The method of claim 17, wherein said Coleopteran plant pest comprises a *Diabrotica* plant pest.

19. The method of claim 18, wherein said *Diabrotica* plant pest comprises *D. virgifera virgifera, D. speciosa, D. barberi*, or *D. undecimpunctata howardi*.

20. The method of claim 17, wherein said composition comprises a plant or plant part having stably incorporated into its genome said at least one polynucleotide comprising said silencing element.

21. The method of claim 17, wherein said silencing element is expressed as a double stranded RNA.

22. The method of claim 17, wherein said silencing element comprises a hairpin RNA.

23. The method of claim 20, wherein said at least one polynucleotide is operably linked to said heterologous promoter.

24. The method of claim 20, wherein said at least one polynucleotide is flanked by a first operably linked convergent promoter at one terminus of the silencing element and a second operably linked convergent promoter at the opposing terminus of said at least one polynucleotide, wherein the first and the second convergent promoters drive expression of the silencing element to form a double stranded RNA (dsRNA).

25. The method of claim 20, wherein said plant is a monocot.

26. The method of claim 25, wherein said monocot is maize, barley, millet, wheat or rice.

27. The method of claim 20, wherein said plant is a dicot.

28. The method of claim 27, wherein said plant is soybean, canola, alfalfa, sunflower, safflower, tobacco, *Arabidopsis*, or cotton.

29. The expression cassette of claim 1, wherein said silencing element is expressed as a double stranded RNA.

* * * * *

SEQUENCE LISTING

```
<160> NUMBER OF SEQ ID NOS: 252

<210> SEQ ID NO 1
<211> LENGTH: 1442
<212> TYPE: DNA
<213> ORGANISM: Diabrotica virgifera virgifera
<220> FEATURE:
<221> NAME/KEY: misc_feature
<222> LOCATION: 189, 190, 191, 192, 193, 194, 195, 196, 197, 198, 199,
      200, 201, 202, 203, 204, 205, 206, 207, 208, 209, 210, 211, 212,
      213, 214, 215, 216, 217, 218, 219, 220, 221, 222, 223, 224,
      225, 226, 227, 228
<223> OTHER INFORMATION: n = A,T,C or G

<400> SEQUENCE: 1

gcacgaggcg tcaagcaagg ccagtcagtg aaaaattacc tgccaaccat cctctgctta     60

caggacagcg tgtacttgat gctcttttcc catgtgtaca gggtggtact actgccattc    120

ccggagcttt cggttgtgga aaaactgtaa tttcacaatc tctttccaaa tattccaact    180

ctgatgtcnn nnnnnnnnnn nnnnnnnnnn nnnnnnnnnn nnnnnnnnct gaagtattga    240

gagatttccc tgaattgact gttgaaattg acgggcacac tgaatctatt atgaaacgta    300

ccgcattggt cgccaacaca tctaacatgc ctgtagctgc tcgtgaagct tctatctata    360

ctggtattac tctttctgaa tacttccgtg atatgggtta caacgtatct atgatggctg    420

actcgacatc acgttgggcc gaagctttga gagaaatttc aggtcgtttg gctgaaatgc    480

ctgccgattc cggttatccg gcttacttag gtgcccgttt ggcttccttc tacgaacgtg    540

ctggtcgcgt taaatgttta ggtaatccag acagagaagg atccgtttca attgtaggag    600

ccgtatcacc tcctggtggt gatttctcag atcctgttac cactgctact cttggtattg    660

tacaggtgtt ctggggtttg gacaagaaac ttgcccaacg taagcacttc ccttcagtag    720

actggcttgg atcatattcc aaatatttaa gagcattgga cgacttttat gacaaaaact    780

tccaagagtt tattcctctt agaaccaaag ttaaggaaat tcttcaggaa gaagatgatc    840

tagccgaaat tgtgcagctg gtaggtaaag catctctggc agaaacggac aaaatcacct    900

tggaaattgc caggcttctt aaagaagatt tcttgcaaca aaactcatac tcttcttatg    960

acagattctg tccattctat aaaactgtcg gtatgttgag aaacatgatc ggtttgtacg   1020

acatggcgag acacgctgta gaatcaaccg cacaatcaga aaataagatc acttggaacg   1080

taataagaga ttcaatgagt ggaattttat atcaacttag cagtatgaaa tttaaggatc   1140

ccgtaaaaga tggtgaagct aaaatcaagg cagattttga tcaattatat gaagatattc   1200

agcaggcctt cagaaactta gaagattaaa tctttttaag gaaattttcc tattttgttc   1260

atcagtgtaa gtttaaaaat atagcgatat ttatcaaaaa gaataataag gcctctatcc   1320

ctcacttctg tgaatattaa tatggccgta ctaaagatag taactaaaga taggttttct   1380

ctttttgat attatcctgt acaaaataaa ttatgtaaat tgttaaaaaa aaaaaaaaaa   1440

aa                                                                  1442

<210> SEQ ID NO 2
<211> LENGTH: 1098
<212> TYPE: DNA
<213> ORGANISM: Diabrotica virgifera virgifera
```

<400> SEQUENCE: 2

```
gcccaacgta agcacttccc ttcagtagac tggcttggat catattccaa atatttaaga     60
gcattggacg acttttatga caaaaacttc caagagttta ttcctcttag aaccaaagtt    120
aaggaaattc ttcaggaaga agatgatcta gccgaaattg tgcagctggt aggtaaagca    180
tctctggcag aaacggacaa aatcaccttg gaaattgcca ggcttcttaa agaagatttc    240
ttgcaacaaa actcatactc ttcttatgac agattctgtc cattctataa aactgtcggt    300
atgttgagaa acatgatcgg tttgtacgac atggcgagac acgctgtaga atcaaccgca    360
caatcagaaa ataagatcac ttggaacgta ataagagatt caatgagtgg aattttatat    420
caacttagca gtatgaaatt taaggatccc gtaaaagatg gtgaagctaa aatcaaggca    480
gattttgatc aattatatga agatattcag caggccttca gaaacttaga agattaaatc    540
tttttaagga aattttccta ttttgttcat cagtgtaagt ttaaaaatat agcgatattt    600
atcaaaaaga ataataaggc ctctatccct cacttctgtg aatattaata tggccgtact    660
aatgatagta actaaagata ggttttctct tttttgatat tatcctgtac aaaataaatt    720
atgtaaattg ttgaatatgt gtatagtttt tttgggtgag ggtacagtgc ttattaaata    780
ctttttaaac atttttcccg ccattccaat tactattaag ttttttcgtt ttaatacttt    840
tttaaatata caggtgctta atatcgttta tattttcagt attacttggt tttcttcatg    900
taaattgttt taaatttttc ttttaccctt ttaatcttgt atattacatt acccaattaa    960
agttaattgt acagattaag ataaacgagt atcttataac atctattaga ttgttagaat   1020
caataaatgt agtgtaattg ttctgttttg aacaaataaa tgcatcatta ttgttgttta   1080
aaaaaaaaaa aaaaaaaa                                                 1098
```

<210> SEQ ID NO 3
<211> LENGTH: 1766
<212> TYPE: DNA
<213> ORGANISM: Diabrotica virgifera virgifera

<400> SEQUENCE: 3

```
tttttatccc gtgagatatt tttgcagtcc ttttaataaa attcttcata attcaccatg     60
aagggctgcg ttttcaacat cgacaacggt tatttggaag gcctgtgtcg tggctttaaa    120
tgtgggatcc tgaaacaatc cgattatttg aatttggtcc agtgtgaaac tcttgaagat    180
ttaaaactgc acttgcaagg cactgactat ggaacttttt tggccaatga accttcacct    240
ttgtcagtat ccgtcatcga ttcaagactt cgagaaaaac tcgtgattga gttccagcac    300
atgcgtaacc aagcagtaga gcctctctcg acatttatgg acttcattac ctacagttac    360
atgatcgaca acataatttt gcttattaca ggaactcttc accagagacc aatcagtgaa    420
ttaatcccta aatgtcaccc tctaggtagc ttcgagcaaa tggaagccat ccacgtagct    480
gctactccag ctgagttata caacgctgta ttggtggaca caccacttgc tccattcttc    540
gttgattgca tcagtgaaca agatttggat gaaatgaaca ttgaaattat cagaaacacc    600
ttatacaaag cttacttgga agcattttat accttctgca aggaaattgg aggtactact    660
gccgatagca tgtgtgaaat tttggctttt gaggcagata gacgtgctat tattattact    720
atcaactcgt ttggcactga attaagcaaa gatgaccgtg ctaagttgta ccctcgctgt    780
ggaagactca accccgatgg tttggctgct ctagtgagag ccgaggacta cgaccaagtt    840
aaagcagttg ctgaatacta cgctgaatat tccaaactgt ttgaaggagc tggcaacaac    900
ccgggagaca aaacattgga agacaaattc tttgaatacg aagtacgtct taacatcaat    960
```

-continued gctttcatgc aacagtttca ctttggggtg ttctactctt acttgaaatt gaaggaacag 1020
gaatgcagaa atattgtatg gattgctgaa tgtgtagctc aaaaacacag ggctaaaatc 1080
gataactaca tcccaatatt ctaaaggaat ttcttgtttg cactattgtt tgcattccat 1140
ttggctcatt tagttcttag tgtcagtaag tggaattatc aaaagtatca gtttttatga 1200
ttcagatgta ctattcagac cttcagacaa atccagttag tacaatgttt tcgtttcaca 1260
tttattatca actacatctt tcagtcgtcc aagattgtta tgaaattaaa tatacattaa 1320
atgtgttgat gttttaacaa tacatagcaa atcctcaaaa agaacaataa aaagactcgc 1380
agtttatttt gaaggaaaat ccattgagta ttaatgtatc ctaaaatatg taatcataaa 1440
attacatggt catatcagtt ttatcgcctt tcagaaattt gctgttacct atccttattg 1500
tttattatat tttttaatga tcggtatgtt tttgatatta ttttagtttt ctggaaataa 1560
tattgcacaa attcttagtt atctgattca acatgtatca atgctttgtt gagtcatatc 1620
ataaatatta ttatgttttc tgtgtataaa gcgtagctag gccaaaatgt tatttctgtt 1680
gtatatgtaa gaataaataa aattatatgt atctgaaaaa aaaaaaaaaa aaaaaaaaaa 1740
aaaaaaaaaa aaaaaaaaaa aaaaaa 1766

<210> SEQ ID NO 4
<211> LENGTH: 1016
<212> TYPE: DNA
<213> ORGANISM: Diabrotica virgifera virgifera

<400> SEQUENCE: 4
gtgacatttg cttcagaact ttgaaactca caacacccac atatggagac ttaaaccatt 60
tggtatccct cacaatgtcc ggtgtaacca cctgtcttag gttcccaggt cagttgaatg 120
ctgatcttag aaaattggct gtcaacatgg ttcccttccc ccgtctccac ttcttcatgc 180
ccggattcgc tccactcacc tcaagaggca gccaacaata cagagcgttg acagttccag 240
agctcacaca gcaaatgttt gatgccaaga acatgatggc ggcttgtgat cccagacacg 300
gaaggtacct tacagtagct gcagtattca gaggtaggat gtcaatgaaa gaagttgacg 360
aacagatgct caacatccag aacaagaaca gcagctactt cgtcgaatgg atccccaaca 420
acgttaaaac agccgtttgt gatatcccac caagaggtct caagatgtct gccactttca 480
tcggcaactc aaccgccatc caagaattgt tcaaacgtat ctccgaacag tttacagcta 540
tgttcaggag gaaagctttc ttgcattggt acaccggaga aggtatggat gaaatggaat 600
tcacggaagc agaatccaac atgaacgact tggtatcaga ataccaacag taccaagaag 660
ccacagctga cgaagatgcc gaattcgacg aagaccagga agccgaagtc gacgagaact 720
aaatttcata cgttaatttt ggatctgaaa tcaaagcttt ataactttta tatttgtctc 780
ctctcctttt attttttatt taagcatgtt ttttgtacag tctctacatt cccgtttgta 840
aatttcgaat acactactta aattattcca agactgactt tttgttgctt gtgtttctgg 900
aatttcagga agtgtttaga tatttaacat gttttgcgaa ctgttttttt atgaataggc 960
attaaaactg ctgccattac ttataaaaaa aaaaaaaaaa aaaaaaaaaa aaaaaa 1016

<210> SEQ ID NO 5
<211> LENGTH: 1016
<212> TYPE: DNA
<213> ORGANISM: Diabrotica virgifera virgifera

<400> SEQUENCE: 5

```
gtgacatttg cttcagaact ttgaaactca caacacccac atatggagac ttaaaccatt     60

tggtatccct cacaatgtcc ggtgtaacca cctgtcttag gttcccaggt cagttgaatg    120

ctgatcttag aaaattggct gtcaacatgg ttcccttccc ccgtctccac ttcttcatgc    180

ccggattcgc tccactcacc tcaagaggca gccaacaata cagagcgttg acagttccag    240

agctcacaca gcaaatgttt gatgccaaga acatgatggc ggcttgtgat cccagacacg    300

gaaggtacct tacagtagct gcagtattca gaggtaggat gtcaatgaaa gaagttgacg    360

aacagatgct caacatccag aacaagaaca gcagctactt cgtcgaatgg atccccaaca    420

acgttaaaac agccgtttgt gatatcccac caagaggtct caagatgtct gccactttca    480

tcggcaactc aaccgccatc caagaattgt tcaaacgtat ctccgaacag tttacagcta    540

tgttcaggag gaaagctttc ttgcattggt acaccggaga aggtatggat gaaatggaat    600

tcacggaagc agaatccaac atgaacgact tggtatcaga ataccaacag taccaagaag    660

ccacagctga cgaagatgcc gaattcgacg aagaccagga agccgaagtc gacgagaact    720

aaatttcata cgttaatttt ggatctgaaa tcaaagcttt ataactttta tatttgtctc    780

ctctcctttt attttttatt taagcatgtt ttttgtacag tctctacatt cccgtttgta    840

aatttcgaat acactactta aattattcca agactgactt tttgttgctt gtgtttctgg    900

aatttcagga agtgtttaga tatttaacat gttttgcgaa ctgttttttt atgaataggc    960

attaaaactg ctgccattac ttataaaaaa aaaaaaaaaa aaaaaaaaaa aaaaaa       1016
```

```
<210> SEQ ID NO 6
<211> LENGTH: 1374
<212> TYPE: DNA
<213> ORGANISM: Diabrotica virgifera virgifera

<400> SEQUENCE: 6

ggacaacttc gtgtttggac agtctggagc tggaaacaac tgggccaagg gacattacac     60

agaaggtgct gaattagttg attcagtatt agatgttgta aggaaagaag ctgaatcatg    120

tgattgttta caaggattcc aactcacaca ctcacttgga ggtggtactg gatcaggtat    180

gggtaccctc cttatctcaa aaatccgtga agaataccca gacagaatta tgaacacata    240

ctcagtagtc ccctcaccca aagtatcaga taccgtagta gaaccataca acgccacact    300

ttcagtacat caattggtag aaaacacaga tgaaacatac tgtattgata atgaagctct    360

ctatgacatt tgcttcagaa ctttgaaact cacaacaccc acatatggag acttaaacca    420

tttggtatcc ctcacaatgt ccggtgtaac cacctgtctt aggttcccag gtcagttgaa    480

tgctgatctt agaaaattgg ctgtcaacat ggttcccttc cccgtctcc acttcttcat    540

gcccggattc gctccactca cctcaagagg cagccaacaa tacagagcgt tgacagttcc    600

agagctcaca cagcaaatgt ttgatgccaa gaacatgatg gcggcttgtg atcccagaca    660

cggaaggtac cttacagtag ctgcagtatt cagaggtagg atgtcaatga aagaagttga    720

cgaacagatg ctcaacatcc agaacaagaa cagcagctac ttcgtcgaat ggatccccaa    780

caacgttaaa acagccgttt gtgatatccc accaagaggt ctcaagatgt ctgccacttt    840

catcggcaac tcaaccgcca tccaagaatt gttcaaacgt atctctgaac agtttacagc    900

tatgttcagg aggaaagctt tcttgcattg gtacaccgga gaaggtatgg atgaaatgga    960

attcacggaa gcagaatcca acatgaacga cttggtatca gaataccaac agtaccaaga   1020

agccacagct gacgaagatg ccgaattcga cgaagaccag gaagccgaag tcgacgagaa   1080

ctaaatttca tacgttaatt ttggatctga aatcaaagct ttataacttt tatatttgtc   1140
```

-continued

```
tcctctcctt ttatttttta tttaagcatg ttttttgtac agtctctaca ttcccgtttg   1200

taaatttcga atacactact taaattattc caagactgac tttttgttgc ttgtgtttct   1260

ggaatttcag gaagtgttta gatatttaac atgttttgcg aactgttttt ttatgaatag   1320

gcattaaaac tgctgccatt acttataaaa aaaaaaaaaa aaaaaaaaaa aaaa         1374


<210> SEQ ID NO 7
<211> LENGTH: 1128
<212> TYPE: DNA
<213> ORGANISM: Diabrotica virgifera virgifera

<400> SEQUENCE: 7

ggggagttca gaatttgtga atagagattg accaaaatga aagcggcttg tattattaca     60

ctattactac ctgttgtatt aagttacaaa gctaacttaa atcctctttc aaatgagttt    120

ataaactata tcaatagcaa gcaaaacaca tgggttgctg gaaagaactt tgatgagaaa    180

ctttcaatcc aagaaataaa aaatttatta ggagcgagaa aaaggagttt aggagatgta    240

aaaggattta tgcacagtga agatattcaa gttccagatt ctttcgatgc aagggaaaac    300

tggaaagact gttcagatgt tatcagcact attgtagacc aatctgcttg tggatcttgc    360

tgggcaatgt ctgcagcatc tgcaatgagt gacagacgat gcatagtcac ccagggaaag    420

cttaaagtgc ctgtttctgc tgaaaattta ttgtcttgtt gcgatgactg tggatttgga    480

tgcgccggag gatatataga tgatgcatgg tcgttttggc aagagaatgg aattactaca    540

ggaggtcttt acggcagcaa ccagggttgt caatcatatt cgcttcaacc ttgtgaacat    600

catacaaatg gtactaaagt gcaatgcagt actttgaact acggcacacc ttcttgcaga    660

agcgatcaat gtgacgatac cgcactaaat tataagtccg agttaactta tgcctcaggt    720

ccagtgaatt actatactac agttcccaat atgcaaaagg aaatattgac aaatggtccg    780

atacaaactc gttttgatgt gtacagcgat ttcttcagtt acaaaagtgg tgtttatcaa    840

catgtcgctg gagattatgt aggaggacat gccgtcagag ttttaggttg gggagtagag    900

aatggagtcg cttattggtt ggctgctaat tcatggaatg aagattgggg agacaaggga    960

ttgtttaaaa taattcgcgg aacaaatgaa tgcagtttcg agaatggtat ggttgcgtca   1020

actccaagag tctaattcta aacaaaatat tggaaatagg cttaattctg gtttatttta   1080

aataaaacac ttgatcccaa aaaaaaaaaa aaaaaaaaaa aaaaaaaa                1128


<210> SEQ ID NO 8
<211> LENGTH: 600
<212> TYPE: DNA
<213> ORGANISM: Diabrotica virgifera virgifera

<400> SEQUENCE: 8

ggggctttct gatttttgac agcttctata gaagtttatc aagatgttga tgccaaaaaa     60

gaatagagta tgtatttacg aatacctctt caaagaggga gtcatggtag ctaaaaaaga    120

ttaccatgcc ccaaaacacc tcgaactaga aactatccct aaccttcaag taattaaggc    180

tttacaatca cttaaatcaa aaggttacgt aaaggaacaa ttcgcctgga ggcattatta    240

ttggtatttg actaactctg gcatcgaata cctccgcaca ttcttacact tacctggaga    300

aattgtccca tctaccttga aacgcccagc aaggacagaa accacccgtc ctagaccagc    360

tgctctcaga tctgagacat ctaaaccttc agaagaccgt gcaggataca gaaggactcc    420

tggaggccct ggagctgaca agaaagctga tgttggtcca ggaactggag atgttgagtt    480
```

caggcaagga ttcggacgtg gacgggcacc acaataaatt tattgataag ttaattttta 540
taaattgatc agccaataaa aagtttggtt aaaaaaaaaa aaaaaaaaaa aaaaaaaaaa 600

<210> SEQ ID NO 9
<211> LENGTH: 1874
<212> TYPE: DNA
<213> ORGANISM: Diabrotica virgifera virgifera

<400> SEQUENCE: 9
tttttttttt tttttttttt ttttttttc tttatttgtc caagtttaat ttacagatca 60
caaataatgc aatgcaagta ataagtcaat tagttattaa aaatacattg atactccaat 120
attagtatat aaaagaaaca aaacatatca aaattattta agtagtggag tccaaataga 180
ctatttcttc ttttgggctt tttctgcagc ttttgtgact tttccggcgc tgggatcttt 240
gaaggcaacg ctcttgatga ctcctactgc aacggtttgc ctcatgtcac ggacagcaaa 300
acgtccaagg ggtgggaatt cttggaatga ttctacacac atgggcttgg tgggtaccaa 360
gttgacaatg gcggcatcac cagatttgat ggctttggga ttttcttcag tggtcttacc 420
agaacgacgg tcaacctttt ctttgccaaa aggatcgata ggccgtgctt tcgcagtccc 480
tatgcatact gaacatcagg atcaagccag cttttgccct tttgctctac gcgaggtttc 540
tgtcctcgct gagctggcct taggacacct gcgttattct ttgacagacg taccgcccca 600
gtcaaactcc ccgcctggca gtgtcctcga atcgaatcag gctggaggta agttgacgct 660
cgaaacgaag cacacggacg ctagccgagt atccgaaagg caagccttat cggaaccacg 720
aaaccgacga acggcacaac gcaacgaaac gtcactccgt gccctcggct caagaatacc 780
gtgacagtcg cagcctcgtg agcgaacgac gcacgcgttt cgccttaccg agtaagtaaa 840
gaaacgatga aagtagtggt atttcaccgg cgatgttgcc atctcccact tatgctacac 900
ctctcatgtc tccttacaat gccagactag agtcaagctc aacagggtct tctttccccg 960
ctaatttttc caagcccgtt cccttggcag tggtttcgct agatagtggg tagggacagt 1020
gggaatctcg ttaatccatt catgcgcgtc actaattaga tgacgaggca tttggctacc 1080
ttaagagagt catagttact cccgccgttt acccgcgctt gcttgaattt cttcactttg 1140
acattcagag cactgggcag aaatcacatt gtgtcaacac ccgctggggc catcgcaatg 1200
ctttgtttta attagacagt cggattcccc tagtccgtgc cagttctgag ctgaccgttg 1260
aatggcggcc gaagaggaca tccaagcacc cgaaagtaac tcagagcctc gcagcaagac 1320
ggttccgcgg gaggccaagg cacgggaccg aactcggatc catgaaaccc aactcgtaag 1380
aattaggctc acttcacctc acccaggccc ggcacgtcag ccatgaccca cttcctcgcc 1440
aagcccgaca cgccccgatc ctcagagcca atccttatcc cgaagttacg gatccaattt 1500
gccgacttcc cttacctaca ttattctatc gactagaggc tcttcacctt ggagacctgc 1560
tgcggatatg ggtacgaacc ggtgcgagcc tccacgtggc cctctcctgg attttcaagg 1620
ttcgaggaga agatccggac accgctgcaa ctgcggtgct cttcgcgttc caaaccatat 1680
ctccctgcta gaggattcca tggaactcga acgcttatac agaaaagaaa actcttcccg 1740
gatctctcga cgacgtctcc aggtcctttt gggttacccc gacgaactct cttgcgaggg 1800
cccgactttt tgacggttcc gctaccgggt tccggaatag gaaccggatt ccctttcgcc 1860
caatgggtgt gccc 1874

<210> SEQ ID NO 10
<211> LENGTH: 816

<212> TYPE: DNA
<213> ORGANISM: Diabrotica virgifera virgifera

<400> SEQUENCE: 10

```
ttttttttt ttttttttt ttttttttt cagagagatt cccatcaacg taaataatca     60
gggtatttat tcacatgtcc ctacgttctt atcatcatgt aaaaggagtt ttgactatac    120
atattttgaa aacatttaaa tggggccctc agaacaacag tggactaagt cacaaattca    180
gcatttttag attaatatat caataaaagc agcaaaatta aatcttccga ttaacaggga    240
cctacacaac ctacctctat atttggctag atgatgctac ataatttgta gctttatctc    300
ataaacataa tgaaaatatg aatgcaaaga ttgcatttat ctcaaaactt agtttttgag    360
cttatgccac tgttgctgat agcctcaaat attaacatgt tgacagacat aacatctata    420
gatgtctaat ttccattgaa acgtctagat gacattttta aaataacgaa ttgtgcatat    480
tcaaactaca tctatagatg catatgaaat atgacatgaa catacattgt cgtcatcaat    540
atgtttacaa aactcattgt ttccatattg acagtctaat tctatacccc gtatctgcaa    600
aaaaacttaa tttccaattt tcgtggcaaa cgactaacaa aacagttatc catctataca    660
caaaactctg atctaaacaa aaaattctag gaacctctaa taccagtcat ctaatacctc    720
gtaactgaat atctttagac ttgataagaa aaaaaaaaca gaaaaaacct acttgacaaa    780
tctcttggca gatacgggct attagaatta gacccc                              816
```

<210> SEQ ID NO 11
<211> LENGTH: 579
<212> TYPE: DNA
<213> ORGANISM: Diabrotica virgifera virgifera

<400> SEQUENCE: 11

```
ggggctttta catcaaaaat ttctttagct gttgtcggtt aaggaacagc ttacaaaatg     60
aaattcaaca aattagtaac cgcttcaaga agcaaaaata ggaaaaggca tttcacagcc    120
ccatcccaca tcagaagaac ccttatgtcc gcacccttgt ctaaagaact tagacaaaag    180
tacaatgtta gcactatgcc aatccgcaag gacgatgaag tacaagttgt aagggggcac    240
tacaaaggct agcaagtagg taaagttgta caagtataca ggaagaaatt cgttatctac    300
attgaaagga tccagagaga aaaagccaat ggagctagtg tatatgtagg aatccaccct    360
tcaaaagttg ttattgttaa acttaaaatg gacaaggaca ggaagaagat cattgacaga    420
agagccaaag gacgtttggc tgctttgggc aaagacaaag gaaaatacac tgaagaatca    480
gctgcctcag ctgtagaaac atcttaagtg taataagtaa tttttaataa taaaataata    540
taaagttcca aaaaaaaaaa aaaaaaaaaa aaaaaaaaa                           579
```

<210> SEQ ID NO 12
<211> LENGTH: 585
<212> TYPE: DNA
<213> ORGANISM: Diabrotica virgifera virgifera

<400> SEQUENCE: 12

```
gggggctggc agtttgctgt cttaatgttg acatttttat atattggaaa aaatgtcgaa     60
agttgaattt aaacaagata tgcccccaca agggggctac aatccaatta actataaaag    120
agttccagcc aaaactttat ttggaggatg ggccttaatc gggggctacc ttggcatgac    180
tgcaggagcg gcgtatttat attatttaaa cgttaaggca gtaaaaaactc gagaacttga    240
attaaagggc gccagcttag cgctgtatcc aatacttatg gctgaaagag accgtgaata    300
```

-continued

```
tatgaagcaa ttaaggagaa atagagatga agaacgtgaa ttaatgaaaa atgttgaagg    360

atggcagacg ggtacatggt atggtgaacc catctacaag actaaagaca aagatactct    420

tattcatccc ctattccatg aatattacat tcacagttct tacaaggact acactgttcg    480

tgcaaacgtt ggtttgatgt cttaaatttt tattctattg taatttagta gcgaaattta    540

aatattaaat tgtaaatatg aaaaaaaaaa aaaaaaaaaa aaaaa                    585
```

```
<210> SEQ ID NO 13
<211> LENGTH: 1043
<212> TYPE: DNA
<213> ORGANISM: Diabrotica virgifera virgifera

<400> SEQUENCE: 13

ggggagtcgt caacatcaat ttcaagtttc aagaaaaagc aaatcactac gacttgccgg     60

attttgtagt agtgttaatt ttgtattaaa aaatcaaaat gagttctatt ggaactgggt    120

acgatttatc agcttcccaa ttctctcctg atggaagagt atttcaagtt gaatatgcaa    180

tgaaagcagt tgaaaatagt ggcaccgtaa taggcctccg aggtacagat ggcattgtat    240

tggctgctga aaagctcatt atgtcaaaat tgcatgaacc aagtacaaat aaacgaattt    300

tcaacattga taaacacata ggaatggcat tttcaggctt aatagctgat gcaaggcaaa    360

tcgttgagat tgctagaaaa gaagcatcaa attatagaca tcaatatggt tcaaatattc    420

ctcttaaata cctaaatgat agagtaagca tgtacatgca tgcatacact ttatacagtg    480

ctgttagacc atttggttgc agtgtcatct tggccagtta tgaagatagt gacccatcta    540

tgtatctgat tgatccatct ggagttagct atggatactt tggatgtgct acaggtaaag    600

caaaacagtc tgcaaagact gaaatagaaa aattgaagat ggggaatcta acatgcaaag    660

aacttgttaa agaagcagcc aaaatcattt atttggtcca tgatgagctg aaggataaga    720

attttgaact ggaactttca tgggtatgca aagatacgaa tggtttacat accaaagtgc    780

ctgaatcagt gtttgctgat gcagaaaaag ctgccaaaca agcaatggaa gcagattcag    840

aatcagatac agaagatatg taataactac atttagtttt taatatttcg ctgatggtgg    900

ctgttcttac aatatttcgt gtgttatgtt catatattat gtaatactgt gagaatttcc    960

atttcaagga taggtttata actttttttt ctaataaata cataacttta tgtcaaaaaa   1020

aaaaaaaaaa aaaaaaaaaa aaa                                            1043
```

```
<210> SEQ ID NO 14
<211> LENGTH: 601
<212> TYPE: DNA
<213> ORGANISM: Diabrotica virgifera virgifera

<400> SEQUENCE: 14

gggataatca ttagtttttt tattgaaagc tggaatgaag ggttggatga aaaaaaaaac     60

tgtctttatt taatttataa agaattttat ttttaagtta aaaagcttaa atttttttaa    120

aagacgagaa gaccctatag agttttataa aattattaat aagttttttt agtattaaat    180

ttatttatat aataaattta tttaattggg gtgattaaaa aataaattta actttttta     240

tattattata ttaattaata attttttgat ccaatttttt tgattataag aataaattac    300

cttagggata acagcgtaat tttattggag agttcaaatc ggtaataaag attgcgacct    360

cgatgttgga ttaaagttta taattggtgt agcagctata ttattaagtc tgttcgactt    420

ttaaaatttt acatgatctg agtttaaacc ggtgtgagcc aggttggttt ctatctttaa    480

tttattaata tattttagta cgaaaggacc aaatatataa aataattttt atatttagat    540
```

```
aaatattaaa aaaaaaaaaa aaaaaaaaag caaaaaaaaa aaaaaaaaaa aaaaaaaaaa    600

a                                                                    601


<210> SEQ ID NO 15
<211> LENGTH: 913
<212> TYPE: DNA
<213> ORGANISM: Diabrotica virgifera virgifera

<400> SEQUENCE: 15

gggggcagtt atttcgactt ttcatgcttg tcataaaata aaattaaaat atatccggcg     60

aggtgttgac tagcggattt ttttagattc aacaatctta ttttataaaa taattagtta    120

aaatgatgca aacagctaat aatgcatatt atcccgatta ttccactgct ccaatgcaac    180

gtcaaattaa cccctatgca gataatggag ggagtgtagt agcaatagca ggtgaagact    240

ttgtaataat tggtgcagat acacgtttga gtactggatt ttccatttat accagagaac    300

aaaacaaact tttcccacta tcaggcacta ctgttttggg ttgtgcagga tgttggtgtg    360

acactctaac attaaccaga atccttaaat ctcgcatgca gatgtaccaa caagagcata    420

acaaaacaat gtctacaact gcatgtgccc agatgttgtc aaccatgctc tactacaaga    480

gattctttcc ttattatata tcaaacattc tagtaggttt agataatgaa ggaaagggct    540

gtgtttacag ctatgatcct attggacatt gtgaaaaagc tacgtataga gcaggtggtt    600

cagctggagc tcttcttcag cctctgttgg acaatcaaat tggacagaag aacatgctta    660

aaacatctgg ggaacctctt agtcaggaga aagctctgtc tacccttaaa gatgtattta    720

tttctgctgc tgaaagagac atctacactg gagatagcgt acttataaat attattacta    780

aagatggagt aaaggaagag tccttccagt tgagacggga ttagaagcaa gtggttttgt    840

ttatattttc ttatgtgtaa ttcaaatata ctttctaaat aaacaaaaaa aaaaaaaaaa    900

aaaaaaaaaa aaa                                                       913


<210> SEQ ID NO 16
<211> LENGTH: 681
<212> TYPE: DNA
<213> ORGANISM: Diabrotica virgifera virgifera

<400> SEQUENCE: 16

ggggatttcg ttggtttaac gattgatagt aactataaat tcaaattaca gatcagatgt     60

atatatatat ataaacacgc aaaaatgctt ggctataaaa tgaaaaatgt aactgcaata    120

ttagatgacg ttatatataa aaataaataa aatctgctgt tgatattgta gttcattagt    180

tttgaaaaat aagcagtact aactttaatc ttgtgccaaa ttagttttat tgttaatatt    240

aatattttca cccaaataag agaaatggat gacgtgcaac tgggtcctgt gagtattagc    300

atgatagaag ataatttata tttaggagga ttggcagctg cgaaaaaattt ggaagtttta    360

aagaagtaca acattactca tattcttacc atagatatat gtccattacc aagaactgta    420

acagaacaaa gaaatttagt taccagattt atacagttgt cagaccaacc aagagaagat    480

ttgctttcat attttgatga aacagattta tttattaatg aaggaaggga gaagggaatt    540

gttttggttc attgttattt tggtgtttct agaagtgcca ctgttgttat tgcccatata    600

atgaaaaaat accagatgag ttactttgag gcatttgata tggtaaaagc tgaaaaaaaa    660

aaaaaaaaaa aaagaaaaaa a                                              681


<210> SEQ ID NO 17
```

<211> LENGTH: 1109
<212> TYPE: DNA
<213> ORGANISM: Diabrotica virgifera virgifera

<400> SEQUENCE: 17
gggggagtag ttgtttttat tgtgagatga tttcgaagtt caccctggtt ttcttggttt 60
gcattgtcgc accagcgata ggtgatccac cagttccaga atggagtgac acttatagcg 120
tagaaggaac tatccatttg ccttatgcag aaatagtaga gcctttccat gcttggtatg 180
atggaaaatc taaaaattcg cgcattgatt actacaatgg gacggctaag acataccaac 240
ttggaggaaa tggaaatggt gtccaactga aagtagttcc attcactaca gaggaggtcc 300
taaaccaaat aacgtgcttc cagatcaatg gaactgaaga cgatccagtg actcctcaat 360
cgattttgcc agatttagaa ggatttgaat atcaaggcat acaggagtat ggagatagag 420
aactagaggt atggtttcta aaaactgtcc agttagaaaa agaaaacgaa tacactctat 480
gggttgtccg agatgagcat ggtaaagcta ttccagttaa atatgatatg agaggataca 540
attcgttatt gggaagccac tacgatcatt actatttgct atacacatcg aagtcttaca 600
ggactcacaa gattgatccc tccgtttttg aagtagaaac taatagtgaa tgcagaagtt 660
ttcctggacc cggaaatcaa catgttcaca tcatgaaccc catggccgaa tacattcgtc 720
ccgaaaaaag tgagcacgtg gactcaagct ttggcgattt tataaataac cacaacaaaa 780
attacgcaga cacaaaagaa cacgttttta gaaaagaggt tttccgtcaa aacgtcaggt 840
tcatcgaatc tgtcaaccga caaaataaag gtaagtgtta tagtagggga gcaaagtagg 900
tgtgctaaat ttgcagtcac tcgagagtta tggcgaccta ttgggttgtg attattaggt 960
cctaaaacca aaaaaagtta agtaaaattt tccatttcca acaatcgttt tttccgatta 1020
tagcgtcatc tatccataat tcgaaaaaat gtctctaata aaagttgctt atttttacga 1080
aaaaaaaaaa aaaaaaaaaa aaaaaaaaa 1109

<210> SEQ ID NO 18
<211> LENGTH: 400
<212> TYPE: DNA
<213> ORGANISM: Diabrotica virgifera virgifera

<400> SEQUENCE: 18
gggggatttt ctctagtttg caggaagcag gaatttcagt aaagaaataa gattaaaatg 60
gcagacaaag tagaaaaggt tgccagacca atgaaattcc cttacacatt cagtgcaaaa 120
attgcacaat tcccaatcaa gcactacttg aagaaccaat ggatctggaa atactatgct 180
atttctcttg tagtatgtct tccagtcttc aactcgatta gtaaactggc caactctcct 240
ggaaacgttg ctaaatgggc agagattcgc agaagagaag ctgctgaaca tcatcactaa 300
gaaaattttt tttatagtaa ttagtctgcc aattgttttg ttctaattta atttctatta 360
aatacatgta gaaaaaaaaa aaaaaaaaaa aaaaaaaaaa 400

<210> SEQ ID NO 19
<211> LENGTH: 800
<212> TYPE: DNA
<213> ORGANISM: Diabrotica virgifera virgifera

<400> SEQUENCE: 19
gggaagcagt ggtatcaacg cagagtggcc attacggccg gggtagttct agcgttctag 60
ttctatagtt gttgtgtagt attttctgtg tagtttgtga tttttcctat tgtgcatttg 120
tatattttat ttatttattt atatatttac gatcagtaag aacattttac ataaattcaa 180
taagcatata gattcgtgta aaaaaatgcc aaagctatcc aaaaaaaatc aaaaaaaagt 240
aggcgctcaa caagactcgt taccgagaaa tgacagaact actgactgta cctcaaattc 300
acattcacat tctggtaatg gtgaaactac ttatcatagc gcaaattcaa attctgttgc 360
tcttgaaagt agttcatcaa atgcccaaat tcaaattagc accatacctc caataaatga 420
taattcttcg ccaaacagct cctttgatca aactgcacct acaagttcaa gtttacctga 480
gggaagagta cactccgaaa gaattaattt tcgtcctaga agagccagtt tggtaacact 540
gagacgtgaa aaagttacag ctttgaggaa gacacataaa aatatgagaa aaaataaagc 600
tgtaacaagt tttaaatctt ttgctcaagc cgaaattcaa catgtatctc ttcccagcca 660
ggagaatttg aaatctcgag gatcaattgt gaatttggtc actaaaagaa aaaacacaaa 720
tgaagaatgt tcatcccatg gctcccttac agaatcagat atgggtaacc aaaaaaaaaa 780
aaaaaaaaaa aaaaaaaaaa 800

<210> SEQ ID NO 20
<211> LENGTH: 1105
<212> TYPE: DNA
<213> ORGANISM: Diabrotica virgifera virgifera

<400> SEQUENCE: 20
gggagccctt atttctccta ttgctatata cgcagctgaa acatggactc tcaaaaaaat 60
caatcgaagt aagatcgaag ccttcgaaat gtaggtctac agaattattg tacccgtgtc 120
caggagagaa cacagaacca acctgtcaat tctgaaagag cttcatataa aagacaaggt 180
attaaaaaaa gtataccgac catacttaaa ttactttggt aaagtaacga ttactatacg 240
aagaggcaaa tcgttacttt gattactctg attacttcgt accaatcgta tcagagcgag 300
taacgactat tgtatctact ttgattactt cgtatcagag cgaataacga ctattgtatc 360
tactttgatt actctgatta cttcgtacca atcgtatcag agcgagtaac aactattgta 420
cctactttga ttattctgat tacttcgtac caatcgtatc agagcgagta acaactattg 480
tcagggccgc gtttaggtca aatgacgccc taggcaattc tctagtagcc gcccttcaaa 540
catgtaccat ttttgcgaaa aaaaacgcaa gcagaatttt ttatttaaat aagaatgtta 600
ttgcacaaat ctcggtgttc ttcaaataat gtttagaaat gtgttaaaaa tattctttat 660
tttacatcag gcgtaatgtt acatattact attataagta tgtttgagcg tttggaactg 720
tgtccaatgc atgcgtttta atgcatgata cgtagaaatt gcctgtttgt agccgcacct 780
acttgttcga ttttaaatga gagatgcatt gaaaacatta ctcaagcact atgtgtttat 840
agctttgttt aacaataaaa aaattaattt ttagcgatgc aaataatcaa aaccggtata 900
atttgacatg cactttcaaa tgcggtaagc agaattgcta ttttattttt taatcaaaag 960
ttattcggat tcaaaaattg caatttttcg atattttgaa agttcaaccg cgtctatctc 1020
gaaaactatg catcctacga aaaaacttta acaacatttt ttgcttagaa tgacccaaaa 1080
aaaaaaaaaa aaaaaaaaaa aaaaa 1105

<210> SEQ ID NO 21
<211> LENGTH: 936
<212> TYPE: DNA
<213> ORGANISM: Diabrotica virgifera virgifera

<400> SEQUENCE: 21
gggggctcat tgtagtagcg ccaggcgcgg aaacgtgagt gctaaaacac agtgatcgta 60

-continued

```
ctagtccaaa acatctttta tatttttcta cttttatatc taattgtata gtttcgttat    120

ttttattact tagaagttta tattttctca tcgttttata cgcttctggt aaggattttt    180

atacattaaa caatattact tgcttgggta agttatgttt tattttgaaa tatagcattg    240

taaccttttt taaatctttt atttttttta ttttttcttt ttctttaaca tactactgat    300

acgctgcaga ggtccatgcg ttttcaattt tttaggatct tttgataact tttttaaaat    360

gtaacacatt tagaaagacc gttgaaaagt tcgccctttt agaccgcgga ggcagtgacg    420

tagctgacag gtccgcaagg cgggggcccc cgacattagg agggataagt agagatctct    480

ctagtcagag ataagtactt actttcgatc ttttcgtaat tacgtactta ctttcgatct    540

tttcgtaatt acctctgttt tccttccatt gcatgtgatc tttgtatata tttcttaata    600

ttttacagaa aacgtaagtg tgtctacaaa atgttttgca tatttgtgta aaattaatca    660

aaatatctta aaaccagtag tcaattaaaa aaatatttaa aaatgttgtg caataaacct    720

tgcggtattt actgaagtgt ttcacacctg tttgaagtta aatatcaagg tttatttttt    780

ggccgggaat ttaaaggttg tggtatattt actttttaca attaataatg ggatcaactg    840

attgggtata tagggtgatc aaattatacc ttgtagttca atatcttcgt tgccagaaga    900

gatgcaggaa aaaaaaaaaa aaaaaaaaaa aaaaaa                              936
```

<210> SEQ ID NO 22
<211> LENGTH: 812
<212> TYPE: DNA
<213> ORGANISM: Diabrotica virgifera virgifera

<400> SEQUENCE: 22

```
gggaaagcac taaaaaatgc aggatacaaa tttgacattg catatacatc tgtccttaca     60

agagctcaga acacacttaa ttcaataatc aaagaaattg gccaagagaa tttggaaact    120

ataaaaactt ggagactcaa tgaaagacat tatggtggcc tcactggctt aaataaagca    180

gaaacagcag caaaatatgg agatgagcag gtagctattt ggcggcgcag ttttgacatt    240

ccacctccac caatggaacc tgaccatgct tattatgata ccattgtaaa agatgcccga    300

tatgctgatg gtcctgcacc agatcagttt cctaaatttg aatccttaaa gctaacaatt    360

gagcgtactt taccctctg gaatgaaact gttgttccac aaattaaggc tggaaaacag    420

atcttaattg cagcacatgg taacagtttg agaggaattg taaagcatct agaccagctt    480

actgatgacc aaattatgca gttgaatttg ccaacaggaa ttccatttgt ctacacatta    540

gatgaaaatt tgaaaccaat aaagagttta gaattcctag gagatccaga aactgtgaaa    600

aaggctatgg aagctgtagc tgcccaagga aaagccaaat aagcattatt tattatttat    660

tgttttaatt tatatcaaaa tcatttattg ttagatattt gatgtgtaat gaataaatgg    720

ttaggctgaa ttgtaaaact cagcagaaat gttatgtgca agacattaaa gcatattctt    780

ctcaaaaaaa aaaaaaaaaa aaaaaaaaaa aa                                  812
```

<210> SEQ ID NO 23
<211> LENGTH: 1127
<212> TYPE: DNA
<213> ORGANISM: Diabrotica virgifera virgifera

<400> SEQUENCE: 23

```
gggggaagta ttctgtagaa aactgataag tatattgctt ttctcattta tttatgtggt     60

taaatagtga gttagtgttg gtcaacgtag atgataacaa ctgaacattg aataaactac    120

aagaataatg ttaagcataa aaattctgtt atgtatgttg ctggcacacc aatctgcggt    180
```

-continued

```
agaagctgta tataatgttg gagttggacg agccgattgc acaggaccat cagcagaaat    240

tacttttatg ggttatgcca aatccggtca gaaaggatgt ggtatccatt taaggcagtt    300

ttcaagagca tttgtgatta aagatgagaa cactctagtt gcatttgtga caattgacac    360

atgtatgatg aaccatcccc taaaacaagc ggtaatagat aaattggatc taaaatatcc    420

caatgtattt actctaaaga atacaattct cagtggaaca cacagtcaca gcacacctgg    480

aggtttcctc aaggatgtaa tgttggacat accaagctcg ggatattgta aagaaacctt    540

taacgcattg gtagcaggaa ttgtaaaatc catagataaa gcatacaaca atcaagttga    600

agcaagaatc ttttacagca ctactacagt aactaataca aacaggaaca gaagtccagc    660

tgcttacctc tataatccag aatcagaaag aaaaaagtaa gtgtaatact agataataat    720

actttaaact ttattaagta taataaaatt aataacgtac aaaatactca aaattaacat    780

ttatttccaa attaccatat aaatataatt ttaataattc tgggactcaa aacattgtaa    840

tttatttttg cttattaata ataataaatt gtacaaataa attctatttg tcactctaaa    900

cacaaataag atgttgctgt tctttacgac agtctcctgg cgactagtgt cataactttt    960

atactcgcat tttaatggcc atcattaata gtggagtcaa tggagttttt acttaggaaa   1020

aaaatcaaac aagagaggac tgtttataac ttcattcaga aatgtatcat aaacaacaca   1080

tcaaaaagtt ctactccaaa aaaaaaaaaa aaaaaaaaaa aaaaaaa                 1127
```

<210> SEQ ID NO 24
<211> LENGTH: 869
<212> TYPE: DNA
<213> ORGANISM: Diabrotica virgifera virgifera

<400> SEQUENCE: 24

```
gggccaatag tcccatgaaa gcagcctacg attattacaa gaaatgttca aagacaggaa     60

attgcttgcc accagtaagc ctccttcctg gcaaccaaaa ggaaggcgaa gttcaactgc    120

aaccaatcga tctcaagaaa aatccatttt taaacggagt ttatgaagcc ggaagttctg    180

ctgacttctc caggtcttcg tctgagacga aatccaatgg agcctctctt gatagtgacg    240

cgtccaatgc gagatttgcg ataactggag ccaacgatga ggacaacgag gtatctccca    300

gccagaggat tccatgcaaa ggtgatggaa aagtgtgcgt gcccaaggac gcttgcgtca    360

atggtgtggt caccaaacat agaggaagcg cattgcagat caaacaaaat aattatctaa    420

gtaaacattc agatccacaa agccaggcgt tgttagaaaa tgtgaattca aaatattact    480

actacacgag aacaaaagga ttattcagga tatgttaccc aaaagaaagg ccgcctactg    540

taaagacata cttgagtcct ttggaaacgc attgtaacaa tgtaaattac tacattcccg    600

atgaaaataa cgataccaag gacttcactg acgatgcttg gacaagatta catatgggac    660

gatccatgat agctctcttt atcatatcgt tcatagctgt ctttgctgcc ttctgcaccg    720

gggtcactgg atgttggaag aggtctccag gaaatattac agccactgca atacttatgc    780

tgctagcatg tttgttgagt gctggtgcta tgggtctatg gcacggagtg gaatattaca    840

aaaaaaaaaa aaaaaaaaaa aaaaaaaaa                                       869
```

<210> SEQ ID NO 25
<211> LENGTH: 569
<212> TYPE: DNA
<213> ORGANISM: Diabrotica virgifera virgifera

<400> SEQUENCE: 25

```
ggggagttcg attccggcag cggacggcga ctctgtgaaa gttgatcgct taaacgtttc     60

tacacgtggt gcacgtgctc cgtaccgaga cgacgacgaa gagaagacgc cggcgtcgcg    120

acgcgagtag acgacaacgt ggttgaacaa gtgtggaagt gccggcatgt tgcactgagt    180

gaagtgacag agttgtgcgc atgtgaggaa aggatgtcaa gggattaaag ggcggcatca    240

tggtgagctg tttaaggtta gtaaattcca tactgctggc gcttgactga gaataatgag    300

taagtgttta atagtgattt aatatagttt cttgaacttt tattcaggaa agattcaagt    360

aaatgtgata cagtaggcgg tactgtagac taaagagaag ctttatttaa attttaggaa    420

atattatttt taatattatt tttttgatag tttttttata gattttaatt atattgaaaa    480

agttgacatg ttgtgtaatg tctggctaat tggctcggcc aaggccatca aattcactca    540

aaaaaaaaaa aaaaaaaaaa aaaaaaaaa                                        569
```

<210> SEQ ID NO 26
<211> LENGTH: 576
<212> TYPE: DNA
<213> ORGANISM: Diabrotica virgifera virgifera

<400> SEQUENCE: 26

```
ggggcttttt cacaatgcag gcaccaacga caaagccaaa aagagatcca atccactctg     60

tccaagtttt tggcagaaag aaatcagcta cagccgtagc ttattgcaaa agaggtagag    120

gagtcttgag ggtaaatggc agacctctca gccaagtgga gcctaaaatg ctccaagaca    180

aacttcaaga acccattctt cttcttggaa aggacaaatt ctctgctgtt gacatcagag    240

ttagagtaaa tggtggtgga catgtttccc aaatttatgc tattagacaa gctatctcaa    300

aggctttggt agcttattac caaaaatatg ttgatgaagc atcaaagaag gaattgaagg    360

atatccttat ccaatatgac cgtaccttgt tggtagccga tcccagacgc tgcgaaccca    420

agaaattcgg tggtccaggt gctcgtgccc gctaccaaaa atcttaccgt taagttcttt    480

tttagattta atgttgtgtt tcttgtatgt attaagatat caacaataaa cacaattttt    540

tcccgcaaaa aaaaaaaaaa aaaaaaaaaa aaaaaa                              576
```

<210> SEQ ID NO 27
<211> LENGTH: 1118
<212> TYPE: DNA
<213> ORGANISM: Diabrotica virgifera virgifera

<400> SEQUENCE: 27

```
ggggcaccaa ttaatccttt ttaattagta cgtgtatacc tataagaaaa atcaataaaa     60

tacatattcg atagttcgct gctgaagtga caggcaaaga gaaaatgaag gtgattcttt    120

gtttactggg ggttgttacc ttagtactga gcactcccgt gtaccaggaa gacttacaga    180

aatattatcc tcaaggatca attccatgcc cattcttcaa gaaagacgcc agttttaatg    240

catcttccga tgatattaaa gtttatttta gaaacaaaga tcatcctgag agttcagtac    300

caatagacat taacgatagt tcggaagtcg atgcgttggg attttcacca aataaagata    360

caatgtttgt tgtccacggc tggcacaacg gtcacgactc gccagtctgc gatgagatat    420

ccaaagctgt cctccagaac gacgacataa acgttttcct aatcgattgg aacaaaatcg    480

ccagcaacct ctacttagta gcttacaaag cagttccagg ggtcggtcaa ttactaggaa    540

cactcattag aaatttggtc aacaacaata aattggattt gaataaagct tctatcgttg    600

gccattcttt gggagctcat gtcgctggat tggccggagc tgaactcaac ggacgggtta    660

gtaacattgt aggtctggac cctgctctac catgcttctc atacaacgat atcagtacaa    720
```

```
gattggaccc ctccgatgca caatacgtcg aggtaataca cacatgcgca ggtttactcg    780

gttttgatgt agatattgga cactcagatt attaccctaa tggcggaaaa gatcaacccg    840

gttgcacttt ggatgttgta ggaatgtgca gacacagtag atcatattac tactatgcgg    900

aatctttaat tagtggagga tttgctgcaa aacaatgtaa ttgctacaaa gattttaaca    960

acaatcaatg taatggagga acatccaata tgggagaata taatatcaac aaaagtgcca   1020

aaggcggata ctacctcaac acaaatagtc agtcaccata tgcccaacat tgatataaat   1080

gtataataga aaaaaaaaaa aaaaaaaaaa aaaaaaa                            1118
```

<210> SEQ ID NO 28
<211> LENGTH: 955
<212> TYPE: DNA
<213> ORGANISM: Diabrotica virgifera virgifera

<400> SEQUENCE: 28

```
ggggattaca aactgaactc aacaacctct tttcatcttc gacccgtttg ccggcgttag     60

cttgtaaaac atttctgtta aaatcacgaa ccatccgtta aaagaaatgg cagatgaata    120

ttttttgct ttaaccctca aaggtaaaaa cagtgaaatc tgggatccag aagcgaaggg    180

agcagaggat taccaagggg gacacaaatt gatcattaaa caagctttgt tgggacccga    240

agcccaagaa ggtgaagtaa atgttgtaca agtagaagct atgacgtgga aagactcagt    300

taaaatccca attgccacac taaaagccgg aggcccaaat aaccaagtat tgttagatct    360

gtcattccca gacccaccag tcacattttc acttatacaa ggtaatggac cagttcacat    420

tgtaggccat catttaattg gtagtccgat ggaagaattc gatgaaatgg atgaattaga    480

agaggaaatg ttggatgatg aagaagggga agaaggagcc gaggaagatg aggatgaaga    540

tgaacccaaa gccaaaaaag caaaatcagc gactaacgcc aagggcaaaa ctcccgtaaa    600

aaacaattca aaggctgcaa agaaataaac aagttcatct aatccccaaa ccacctcctt    660

tgtaatgtta agttagtttt ttaatgtatc tcgggagttg ttatacatcc attaacagat    720

caaccgtaac aatttctctt aaatataagt ataatatttt atgtttcttg acgtcataag    780

attttgtgaa agtttctttt attccaggtg taactcttag ttttaatgtg atcaatattt    840

ttaagctgga aacgtattta tttcctttga aatcatccaa ttttgttgta aatatgcagc    900

cctcattaaa ccattttttg tagcaaaaaa aaaaaaaaaa aaaaaaaaaa aaaaa         955
```

<210> SEQ ID NO 29
<211> LENGTH: 422
<212> TYPE: DNA
<213> ORGANISM: Diabrotica virgifera virgifera

<400> SEQUENCE: 29

```
gggggaaata tatactacaa tgaagttttt aagatcgaca gtgtgctaca ttgccatctt     60

ggcaattctc tttaccctct gtgccgatga ggttgaagga aggagaaaaa ttttgatggg    120

gcgaaaaagc attaccagga catatcttcg tggaaatgct gttcctgcgt atgtgataat    180

aatccttgta ggaattggtc aactcatcct gggagggata ttgtacgttg cattgaggaa    240

gaagatcatt gctgcacctg taacggcatc atatgcagtg gctagacaag aaccataaat    300

tttatttgtc tagaatatta ttttctaaat atgcatcttt tttaaattat tgtctacgta    360

aataataagt ctagaaatat ataaaaattg tcaaaaaaaa aaaaaaaaaa aaaaaaaaaa    420

aa                                                                   422
```

<210> SEQ ID NO 30
<211> LENGTH: 2911
<212> TYPE: DNA
<213> ORGANISM: Diabrotica virgifera virgifera

<400> SEQUENCE: 30
gggggtgcga agctaccatc cgtgggatta tgcctgaacg cctctaaggc cgatcctttt 60
ggcttgaaga gttttcagca agaggtgtca gaaaagttac cacagggata actggcttgt 120
ggcggccaag cgttcatagc gacgtcgctt tttgatcctt cgatgtcggc tcttcctatc 180
attgcgaagc agaattcgcc aagcgttgga ttgttcaccc atagacaggg aacgtgagct 240
gggtttagac cgtcgtgaga caggttagtt ttaccctact gatgactcgt cgttgcgata 300
gtaatcctgc tcagtacgag aggaaccgca ggttcggaca tttggttgac gcacttactc 360
gagcgggtaa tggtgcgaag ctaccatccg tgggattatg cctgaacgcc tcctcaaagt 420
cacaagatga gtgtaacgcc acctacagat ctacacaaga aagaagaacc acgatagcat 480
cgacagacag tggtaatggc cgacgaccgc gacgagggaa ttttaaaata cgaaatgttg 540
taaaaggaga ggcaccaaaa agaagagtag atggttcgaa aaatcaatga aaagctagtt 600
gaacgttcag tttcttttaa aaaagaaagt tttgtagatt ttgaaacaac accgcacaca 660
tcttatggaa aatgtaatgt cactcaagtg caattgaatt tgcctgaata tattggtctc 720
gaagttacaa tcatttcagg tcgttgcgcc aactctgaat ttttattaat aacggtgcat 780
attgatataa ataaaacata aaactaaaat caaatgggta tgagtgagaa aagaatgtga 840
atcggcagtt cataaatctt tctgaaagta ttaaggtctc ttatcttata gataaatgac 900
aaagcacttc tagtgatgca ccgcaaaata aaggtcaacc tcacgctcgg gtaacctgtt 960
ttcaatagcg actagactaa tagtatttgt aaataggaca gttttatgga cttcaaaatg 1020
tgattctaca atttacgcgg atattaatca aaattcggag ttggcgcagt gatgtgagat 1080
tattgtaatt tctaaacgaa tctatttatg taaattttat tgtgtttgag tgacattaca 1140
tcaaccataa gatgtgtgtg gggccctttt ggcgaatttt gccataaaaa aattaatttg 1200
gaggcttttt aactagctcc aagagttgta cagaaagata tgccgctatt aatattgttt 1260
cgcaacaaat agatcatttt gattacttaa aaaaagtaca atgaatcata ctaagttatt 1320
ttttgttgta ctatccgttg caagataatt tggatagtaa atttaaacta attcaactaa 1380
atatattaaa attttcgttc catctacttc cattttcttt tatttttttt tataacgagt 1440
ggatcaacaa aatgagcatt tttttatatt ttaattgtga tttgaaagtg tattttaagt 1500
gggagatgat gatgttcgag tctattaact gtacgttact tatcacaatc tattttgtat 1560
ggattttcat acaaagaact ttagtttgtt gattattatt taataaacta cattttattt 1620
aaaatgtact gtttaacgaa tcatgtaacg atcacgctcc tgcgcagtaa acaaaatatg 1680
ttccaacaaa cagatgatcg ttcatcgcat cgtccttcca attgttccaa caaaaattgt 1740
gatcgtccaa tgacagtgtt gcgacgatca ttttagtact ctgatactat aaaaattgtg 1800
tgttggaaga aacctaatgt aactgcgcca ttttgaactc agatgtttct taggtatgcc 1860
cagggtagta gttcccttaa agaaaaaaaa gtgggaaaat gtttaggttt ctatttatta 1920
acaaatcaca tattggatgg acagtctgca tcttttttttg tcagtataga taaaaaaatcc 1980 tgttcttata atgctaactt gattatcaaa cgactgctaa gccttagatt gaagcctcat 2040
acgcaccaaa ctgcctaatt tagatacaaa attagccaaa ctaaatcttc gaatacccaa 2100
aacacttaaa ttattgccat ccatatgtct agtgtgtaaa gacaaccaga aaaacctgat 2160

-continued

```
tactgatact aggagtgtaa aatataagct gagggccctg acatctgacg agttgatgaa   2220

gaatatatct tcctatagaa actgttaaaa aaacggtaat attaaatgcg aaacacggag   2280

ctacgatgag aagaaaaaat ttggtcctct aaccactaca agaaaggtcc aaaggtgttg   2340

taatatttga tcttatacag tataactcat gatcaaacaa cgtagagagc aaatatgaga   2400

acatcaaatg tatgttaata ttccgttggg gtgagttgac ggaattaatt aaaaataagt   2460

gtaacgacga acagtaatat atttatttat tttgggtgaa caagcggcgt gttttgctta   2520

tatctcgaaa gagggttgat tgttagcgaa ccgaggattt gtctgcatcg tttgcgtgct   2580

gtgtagagac tggcctccgg accaccacct ttatgtcaac tagttttgcg gttttgagat   2640

aatgaccaga aagggccata cattctgcat ctccttttaa gaaccttttt gtattttaag   2700

aagttgacat aacgagtgtg gcactctggg catcgcaatc tattagtgtt tccttgaatg   2760

aaacattaat cacaatctgt ttaaaggata acatttcgtt tctcgaaatc aacggcatat   2820

ggtttgtata tcacatgtgg attttaaatg accaatgccg tttcattttg agaaaagcca   2880

tgaaaaaaaa aaaaaaaaaa aaaaaaaaaa a                                  2911
```

<210> SEQ ID NO 31
<211> LENGTH: 1287
<212> TYPE: DNA
<213> ORGANISM: Diabrotica virgifera virgifera

<400> SEQUENCE: 31

```
gggagacaag aggcagctac tattaacgat acatcgctct ctcgttagtg ttcatatttt     60

acgtgtagtg taacagaaag tgcagttttt tattcaccat gtctaaccgc aacatcccta    120

tcaaaatggg tgacttcagt gttatcgaca cggagtttag cagcatcagg gaaaggttcg    180

acgccgaaat gaggaaaatg gaagaagaaa tgaacaaatt cagatctgaa cttaccagta    240

gggaagcgaa caacttcttc agaagcacaa ccagcatgtc gtacgaatct gaaacggtga    300

ctggtggaaa taagtcttca tcgacgtcca gttcaacgac acagcaaagc agcacaggat    360

cagatttagc ccacagagca ccaagtggtg atgtcagaac atggtacgac gacctcaact    420

ctcccctaat ccaacaggac ggtaacgaaa agagcctaaa attaagattc gacgttagtc    480

agtatgctcc agaagaaatt gtagtcaaaa ctgttgataa taaactcttg gttcacgccg    540

agcacgaaga gaaaacagaa tcaaaatccg tatacagaga atacaatagg gaattcttgc    600

tgcctaaagg aacaaatccc gaacacatca agagctcatt aagtaaagat ggcgtcctca    660

ctgtcgaagc acctctccca gctatcacct caggggaaaa attaattcca atccaacatt    720

aagtaattta aaattccttg taagccttcg aagcgtttat gtccgctagt aaatactcat    780

cgattaatta tttaaaatgt aacaactcat gtgactaaca aaatttttat tttatttcat    840

ttttaaaacc tggcaacgtt gtctggcttg tttaggataa gtcacaaatt tagtgttggc    900

tctaaagtac ttactgtcta cacagcacaa gtcacaaatc gttaaataca ccataaacct    960

catgcatcgt tgccggatgg ttcaaaagct catactattt gtgactatct tcttgatggc   1020

ggtcgtaaac ttgaaggttg attaacatcc tttcacaaag cttaattatg caatgaaaat   1080

aatttttaac aactttattt gtgacaaaaa aattgaagct aatgtaaaat tgtttggtta   1140

aattcttgtg aaggtctatg gttcgatgtt caataaccag caatttcacc gtaggcgtag   1200

tgtaacaaat tgtatcatgt gtaggatatt tacgaataaa ttatttttaa tctcgttaaa   1260

aaaaaaaaaa aaaaaaaaaa aaaaaaa                                       1287
```

<210> SEQ ID NO 32
<211> LENGTH: 560
<212> TYPE: DNA
<213> ORGANISM: Diabrotica virgifera virgifera

<400> SEQUENCE: 32
gggatcacgt gaataaatta caatatttct tcaaaatccc ttgacgcatc cccttgtaca 60
caatactgat aacatggtat tcggtataga tgttatcggt attgtggaca ggggcgcgcg 120
ttaaggtatt ttgaagaaat attgtgattt attcacgtga tcactccgtc tgttaggtag 180
acggagttat tttatgttcg taacaggtag tctgtatttc ttttaaggca aatatttggt 240
ccgtcgttga tctattgttt ctaaaacctg cctggtattc tcccaatact ttttccgaat 300
attgatttag cctttttctt atacagtatg cggcaaaata aacagtacct actgaaatga 360
atattgaaat gtttatgatg atttatatat ctagtataca tgatatagcc ttgcaaactt 420
tattcacgac gacgcatgtt cccgataaac agatgttaaa gatgtcctct ggtcagtgac 480
ggatctacgg ggagggaaaa tgagaaaatt ttttccccta acaaggttca aaaaaaaaaa 540
aaaaaaaaaa aaaaaaaaaa 560

<210> SEQ ID NO 33
<211> LENGTH: 807
<212> TYPE: DNA
<213> ORGANISM: Diabrotica virgifera virgifera

<400> SEQUENCE: 33
gggggacagt tcaatatgga tccactactt tactggttca tatttgttac gttaatatgt 60
acgctaggta ttctaggaag ttacttaatg ttttctataa taagagatag ctgttttaag 120
agaaagaaac aaaaagatac tgtgatggta atatatgaac cagattttca tccagcatgt 180
ctgagtaagt tacagtatga taaacatgat gttgaagatt taacgagaat cgaaagaaat 240
tccaagacgg ggtttagaag actaagtttt caaaatgaag tatttggtaa gcagtttgaa 300
ggattattgg gtgagaaaag acaatctgtt gacaaggaaa gtgatgtgtt tgtatctacc 360
aacactcttg acaaaagcat tacatcaatt acagaagaag atgaagaatc agacgatagt 420
tttgatcgag atactgtcag cgtagacatt gaagtatcag acgaggtaag agaagtttta 480
agaaccgaaa aagaagctaa gaaggtcgag aaagaaatga acaggtttgc aggtggtaca 540
aacgatttac aatattacga aatcaatgag aagtatataa aattaatgat ttctctttgt 600
gatatggaat gcagctccat cgagtgcaga aaacacaaaa acagagtttt aagttacatc 660
gagcaatgtc agaaccaact caaattaaaa tctctgaagt ctaaataatt atttttattt 720
gcttggagat gtaattatta taaatatatt ttaaatataa gtttagtata aacagccaaa 780
aaaaaaaaaa aaaaaaaaaa aaaaaaa 807

<210> SEQ ID NO 34
<211> LENGTH: 981
<212> TYPE: DNA
<213> ORGANISM: Diabrotica virgifera virgifera

<400> SEQUENCE: 34
ggggattcta aacttttcga actaacaaac aagatggcaa ccaaattttt agttctcgcc 60
gcattcattg cagtagctaa agccggttct tatggatcag gtttcggcta cgccgcgcca 120
gctgttgtcg ctcacggatc tcacgatgcc atctctacct actccactgt gcaacatcat 180
gctccagccg tacactccta tgctgctcac gctcccctcg ttcatgctcc agttgcccat 240

```
tcctacgcag ctcctttggt tcaagctcca gtcgctcacg cttacgctgc tcccgttgct    300

cacgttcacg ctgaaccctc tgcaccagcc cattacgact tcgcatatgg agtaagtgac    360

ccccacaccg gagatgctaa gagccaacac gaatctcgtc gtggagatgt tgttcacgga    420

agctactccc tcgtagaatc cgatggaacc aaacgtaccg tagactacac tgctgatcca    480

caccatggat ttaatgctgt tgtacacaaa gaacctaccg tacatgctgt tgctccagtt    540

gttgccaaaa tcgtagtccc agtagcacat gctgctccag tagctcatgc tgcttatgct    600

gctccagcgg ttcatgccgc ttactctgct ccagcagttc atgctgctta ctctgctcca    660

gcagttcatg ccgcttactc tgctccagtt gtccatgctg cccacgctgc cccagttgcc    720

catgctgctt atgctggtcc agttgcccac gccgcttatg cagcaccagc tctacatgga    780

tacgctggct ctgttgctca tggttacgct gctcctttgg ctcatggtca tcatgcttat    840

gctgctcatg ctccagtcct ttcacataac ttgtggtaat tctagaaagg aaaaattgta    900

gattttgtat ataaattatt tatactgctt gcattacaat aaaagattgt ggaaaaaaaa    960

aaaaaaaaaa aaaaaaaaaa a                                              981
```

<210> SEQ ID NO 35
<211> LENGTH: 1160
<212> TYPE: DNA
<213> ORGANISM: Diabrotica virgifera virgifera

<400> SEQUENCE: 35

```
gggagtaaaa ttaaactgca gtgattaaca atgaaagttg ttattatttt cgcttttatc     60

tgcaatattg catttgtagc tcatgtttac ccggaatact taaaacaata tcgctgcaag    120

gcatcttcgg aaaattatag tgaatgcttt ctaaataagc tcagaaatac tctgccctac    180

tacgttaaag gcattcctga attagatata cctccatttg atccgtttac actacctata    240

tacagtcgca atgtaaacat attgggaaac aagattagtg cgactttcaa aaattcgatt    300

gtaactggac taaggaactc tattattcat aatgctaagg ttgatctgaa taacaactat    360

gcagaaataa gcgttactat tccttggttg gatatggcca cagagtatga tatttctggt    420

gaattctttc aatacccact agatgtgaag ggtactttta aaggaaatat aactgacatt    480

caacttttct caaaatctac tctacaaact ttcaaaaata acggtgaaga ttattataaa    540

tttgataaaa taaaccaaaa agtacaaatt ggaggaggcc atattgaaat aacaactaca    600

gataaagatc ttatgccgat agttcaaaca atacaagaat attttaatga gcatcccaga    660

ggcttcttta acttgatatt gccattcaca ttggaatacg cacaagacct actcagagaa    720

tttggcaatg aatatttagc caatcttcct gcttctgaat ggttaccgca gtaaacataa    780

atttgaaaaa aatagtagac ttagtagttt aaacaacata gtttttttagt taaaaaaatt    840

gaccgtagta tttaaataat ataatgacaa taatgttgtt gatgatcagt tgagatatat    900

ctatccgcta ttctatggaa aattccagaa atgcaatgca ttttgaatta tgcccataag    960

tggagtaatt cgttctagca gcatatagcc tacatgttca aatggactga gacccgtatc   1020

ttctgttgac catagcaata catacatttc ctcgtagaac actttttttgt gattattatt   1080

tttactttgt gagtattttg tatatgtgaa ataaaaatat tatattttgc aaaaaaaaaa   1140

aaaaaaaaaa aaaaaaaaaa                                               1160
```

<210> SEQ ID NO 36
<211> LENGTH: 721
<212> TYPE: DNA

<213> ORGANISM: Diabrotica virgifera virgifera

<400> SEQUENCE: 36

```
ggggtcactt taattgtcag taggaactga gtgctagttc aaggtagacg tacgttgacg     60
agcgtgtagc aaagttgttc gtttcggatt ttgtttttcg taggtagatt aatatggatt    120
atagtaagac atggctggga ggcattaaaa aatgcagctt ctgtgcatgt cttccagaaa    180
aatatagcaa tgaatgggtt aaaggcgcct cacgcttctc tgagttacct aggacattct    240
tggtattaat ttttctattt tgcttcaagt aatattgtcc tcatggctta gtggcgggaa    300
gcaagatcat attagtcgcc gtttcgcaaa atgaagcata tttcataaat atctgtgggt    360
ataaagtatt ctccaagcga agctccagaa tgctgcagaa tgcaggagct ttatagccaa    420
gtctgaagtg aatacagagc aatatcatta ataagtcatg ttcttaaatt atttctaaaa    480
attataaaaa ctgtcagagt gatgatgata gccaacttgg atttagaaag gaattaggaa    540
taaaagatgc attatttact tttaatgtga taactcaaaa atgcatggat tatgtttgtg    600
aatctgcatg tttgttactt taatttttaa attgtatttt tttttaaatt ttaaaaagca    660
tttgacaaag taagacatga aatattagtc caaaaaaaaa aaaaaaaaaa aaaaaaaaaa    720
a                                                                    721
```

<210> SEQ ID NO 37
<211> LENGTH: 928
<212> TYPE: DNA
<213> ORGANISM: Diabrotica virgifera virgifera

<400> SEQUENCE: 37

```
ggggtttagt atgtcttaga gcattatggt tactcttcca atcattggat gatcgttctc     60
caatgcggta tcctgtatat taccacttaa tacaaattgc gaaacagaca gaatctgtaa    120
aattagtgtt tcaagatatc aaccatctaa agcaacagtt tgccaattgc cttccgtcta    180
atgaacagct tcaaaagctt tataggcttt tacatgaagt actggttaaa tcaaatcaaa    240
gtgagcaggc tgctttagtg atgattgaac ttcttggtac atacactgac aaaaatgctt    300
ctcatgccag agaagacgcc atccgttgca ttgtatcagc actagctgat cccaacacat    360
tccttcttga tccattgtta tcactaaaac ctgtcagatt tttggagggt gatttaatac    420
atgacctttt aaacatcttt gttagtgaaa atttgtccac ctacctcaag ttttacaatg    480
aacataagga atttgtgagt gcacaaggtt taaatcatga acagaatatg caaaaaatga    540
gactgctttc cttcatgcag cttgctgaga gtaatcctga aatatctttt gatgtcatcg    600
aaaaggagtt acagatgaaa ccagacgaag ttgaaagctt tattattgaa gtattaaaaa    660
ccaagttagt tcgtgcaaga atggatcaat cttcccggaa agtctttgtg tccagcacaa    720
tgcacaggac tttcggaagg gcacaatggc aacaactgcg ggacttactg cactcttgga    780
ggggaaatat aagttctgtt caagacggta tgaagactat cgccgctgct cagctagaac    840
ttatgaacca acaacagtaa tgataatgaa gttttcataa cttttaataa aacgttgaaa    900
aaaaaaaaaa aaaaaaaaaa aaaaaaaa                                       928
```

<210> SEQ ID NO 38
<211> LENGTH: 1339
<212> TYPE: DNA
<213> ORGANISM: Diabrotica virgifera virgifera

<400> SEQUENCE: 38

```
ggggaatata attaattcaa taattagaat tagaaatatc tcgttggaac agttgtagat     60
```

-continued

```
attcataatg gagagtaact tgggttatca aaatgggagt caaagtagag aacaagactt    120

tcaaaaactg tcgcagacca tcggtaccag catacagaaa atatcacaaa atgtgtcttc    180

tatgcagcgg atggtcaatc aaataggaac ccatcaagat tcgcctgaat tgagaaagca    240

attacattcc attcaacact acacccagca gttagtaaag gacacaaatg gatacatcaa    300

agaccttagc catattccac catctctatc acaatccgag cagagacaaa ggaaaatgca    360

gagggagagg cttcaagatg agtacaccag tgcattgaat ttgtttcaaa acgtccagag    420

aagtacagca tacaaagaaa aggagcaggt caataaggct aaggcccagg tgtatggaga    480

accccattta attggatata agtccaagga ccaacaactc atagaactgc aagacaataa    540

ttcgaggcaa atgcaaatgc aagaggagtc aaatctaagg gaattagaag aacaggaaca    600

gtcaataaga cagttggaga gcgacatcaa cgatgtcaac ctaattttca aagaattagg    660

aacccttgtg cacgaacagg gcgaagtgat agacagtatc gaggccaacg tggaaagaac    720

caccgacttc gtcagccaag gtgcccaaca actccgcgaa gctagtacgt tgaaaaacaa    780

agtaagaaga aagaagctga tcatgttgat gatcgctgct ctagttttaa ctatactcat    840

aataataatc gttgtatccg tgaaacgtta aaatagtatt atggtaatga tattaaaaat    900

gtgatgattt aaatgattgt ggtaagtaga taggaaatat tcatgaacta cacatcctta    960

cttattattt tatcttattt ggtgaagctc ccagttcctt aaccctttc ttggcaaacc   1020

gatataaaac tgtgaaaact ctgttttctt tatattcatg cccttctaga attatttaaa   1080

aatttatgaa ataaatattt cacctttaat ttattcctaa gtaccaaatt tgaatgtgtt   1140

acaaatttgt tacgttgcca agaataccat accccttatt accactgatg gtccatgcat   1200

tttctaaggt ttgaaccgat ttctcagaac aaagttaaaa tttcttttat ctgagttcat   1260

gggagtgctc tcgcgtcaca acaccccct atccccatta aattttagga aaaaaaaaaa   1320

aaaaaaaaaa aaaaaaaaa                                               1339
```

<210> SEQ ID NO 39
<211> LENGTH: 533
<212> TYPE: DNA
<213> ORGANISM: Diabrotica virgifera virgifera

<400> SEQUENCE: 39

```
ggggctttta tttccgcttg atagtcaaga aaaggtgtca agatgacatg taaaaggcgc     60

aatggagggc gctccaagca cggccgtggt cacgtaaagc cagttcgatg caccaactgt    120

gctagatgcg ttcccaagga taaggcaatc aagaagttcg tcatcagaaa cattgttgaa    180

gccgccgctg tgagagatat tactgaggca tcagtatatc aagcttacgt tctccccaag    240

ctctatgcga agctccacta ctgtgtatcc tgcgctatcc acagcaaagt tgtgcgtaat    300

agaagcaaaa aggataggag agtcagaact cctccacaga gaaacttccc tggtagggac    360

aatgctagag ttcagcaaca acaacctagg aagtaaactg tttctttagt tttacaataa    420

aatttaagaa aaaataaaaa aaaaaaaaaa aaaaaaaaaa aaaaaaaaaa aaaaaaaaaa    480

aaaaaaaaaa aaaaaaaaaa aagggaaaaa aaaaaaaaaa aaaaaaaaaa aaa           533
```

<210> SEQ ID NO 40
<211> LENGTH: 535
<212> TYPE: DNA
<213> ORGANISM: Diabrotica virgifera virgifera

<400> SEQUENCE: 40

```
ggggcttttt cagcagttgt caaagcactg ccacaatggg taaaataatg aaatcaggaa     60

aagtcgtatt ggtcctcggg ggccgatacg ccggcagaaa agccgtagtc gtcaaaacct    120

acgatgaagg tacatcagat aaacaatacg gacatgcctt agtagctgga attgataggt    180

acccaaggaa aatccacaaa cgcatgggca aaggcaaaat gcacaagagg tccaagatca    240

agccttttat caaagtattg aactacaacc atctcatgcc cactagatac tctgtagatt    300

tggcatcaga cttgaaagtt gtacccaagg acctcaaaga tgccatgaag aggaagaagg    360

ctagattcca gacccgtgtc aaatttgagg aaaggtataa gcaaggaaag aacaaatggt    420

tcttccaaaa attgaggttc taggctgtag atttaatttt ataattgtac actttttatt    480

ttgagaataa aatgtggata aatgcaaaaa aaaaaaaaaa aaaaaaaaaa aaaaa         535
```

<210> SEQ ID NO 41
<211> LENGTH: 788
<212> TYPE: DNA
<213> ORGANISM: Diabrotica virgifera virgifera

<400> SEQUENCE: 41

```
ggggaactgt caaatataac cttaaataat atttatttac gtgtgtgtct tgtttccata     60

gttttagctt tttttctttt aatttaaaaa gatgagtgac gatagtgata actttgaata    120

tgtagacgat gagatagatg ataaaactca caataaacta gtggataacg tttttaaagt    180

taaataaagt tcaacatgtc aaaagtgcac atagaactga agctgccact aaagtgtctg    240

aatttaatct agtaaaatcc ctttcgaata aaaatttagt gcatgttaat gaattaacga    300

gcgttttaaa gggaaggaag tctcttcagc tgtctaataa aattaaatct acaagtaata    360

tcagcaagac attgcctaaa cctctagaaa agccacaagc tgaacgtatt aaacgagctt    420

taaactatga gaaagcgaaa ttaaaattgg atagatggga agctcttgtt caggctaata    480

gatcagctgc acaattatcg ttccctttaa atagtgatga gaaagtaaag gtcattgaga    540

aacgggccat atcttacccc ttatctttca gagttaaatc ggaccttcag aaaaatttgg    600

aaaatataga ttcacaaata gaagagtatc acatagatac agtagaaaag aaagaagatg    660

aagactatcc acttacacta gaagaattaa aggaaaaaaa agaaaagaac tagccaaact    720

tcgtgcacac cagagtttta aagaagcaaa agctagacaa aaaaaaaaaa aaaaaaaaaa    780

aaaaaaaa                                                             788
```

<210> SEQ ID NO 42
<211> LENGTH: 444
<212> TYPE: DNA
<213> ORGANISM: Diabrotica virgifera virgifera

<400> SEQUENCE: 42

```
ggggaacgaa gtggccattt cttacagata attccacatg ccaaccattc ataagataaa     60

gcaaggcatc gtcgtgttct tgttgaaact ctagtagtcg gtatgggccc actatccaat    120

ttccaataat tctaatccaa ccagtaactt tttgtgacac ttctgtatga tctccttgaa    180

tataatcagg gttgttaaca acgcaactga atatttccgt agagggcgct tcaaaaatcc    240

gtagaaatcc gtagtacaaa aatctgacag aaaatgacac ttggcagacc aaaaaaagaa    300

gaagaatgac acttgacata caaaaaaaga agaagaatga cacttgacag accaaaaaaa    360

gaagaataat gacacttgac agaccaaaaa gaagaagaat ggcacttgac acaccaaaaa    420

aaaaaaaaaa aaaaaaaaaa aaaa                                           444
```

<210> SEQ ID NO 43
<211> LENGTH: 472
<212> TYPE: DNA
<213> ORGANISM: Diabrotica virgifera virgifera

<400> SEQUENCE: 43
gaggtttaca tattttcaag ttgtccaaaa atatccacat gtcttcgagg taattgagat 60
ggtagtccag acctttaaaa catttttaaa ttcatttggg tgacatatat atattggtgg 120
aattgaatat gtcaaattta tttattactt caatagtata taagtcttgc agctgttacg 180
tttaaaattt gagtagctta cttaactgtc gtatttgaaa agtgtgttgg tcgaatatgc 240
gcctcgttag ttatttctag ttgctttttg taaatttgga ggatcaaaaa ataaataagc 300
ttatgattaa ttgtttatat gggaggtggg ccgcagttga aatgaaaaaa aataatttta 360
ttaacgtttc gacgcccaaa tcgggtgccg ttgtcaaaat acaaaatatt attaaaataa 420
acaaaagtgt tgttgctaag cgaaaaaaaa aaaaaaaaaa aaaaaaaaaa aa 472

<210> SEQ ID NO 44
<211> LENGTH: 497
<212> TYPE: DNA
<213> ORGANISM: Diabrotica virgifera virgifera

<400> SEQUENCE: 44
ggggcttatt cacaattatt aaaataataa atggatatga ccaattatca gtaagtgaaa 60
cagaattcat tggtataaat ttcatatctg taatccgtct acccgtaaag gaaaccagaa 120
ccaatagtat taatttattt tctgaaatac agggcatgcc tttgtttaca taatatttgc 180
atactaacct ttgaaacgtt attcctgaag atctacattt gcttctgctg ctccaactgc 240
gttgaggaca ggacagacac attttatgca atatgttaat aatactataa aagtatccga 300
attaaaaaaa atattcttaa aaagcacaaa taaaacaaac aacgatcacg ccacacacga 360
caaggccggg caaggtggcc aagatgccaa gatggccgaa gtgaggtcgt tcgttggtcg 420
tttttagtca cgtgatgcca tcgtgatgcc ctctctaagc ggcatgcgaa aaaaaaaaaa 480
aaaaaaaaaa aaaaaaa 497

<210> SEQ ID NO 45
<211> LENGTH: 809
<212> TYPE: DNA
<213> ORGANISM: Diabrotica virgifera virgifera

<400> SEQUENCE: 45
ggggaagtaa ttctgctaaa aattttacac tcctttggat tggaggaaga attacaattt 60
tcattattaa atatctattt gaaaataaat aacaattgca caaggtgtag taaaaaggtg 120
ggtcatgaat aaaataaaat attctgggaa taaaaatagt tccattgaac ctaagttacc 180
ttagtacaaa ggtgcacata aaaaaagtta taactctttg agcttataaa ataaaaatcg 240
agaatatcga aaaatattag aggttaaaat gggcatttga cattattatg gtaggaaaat 300
ctttaaaaaa atagtagtga aattttcaca gccgataaaa attttatagg ggctttattc 360
ccttaacctc cccccccccc aaacctttat gtacgttcca gttaaattat tatttagtcc 420
tggaggggga tgtgtcacca acacgatatt ttttttcctt atttctctga actaattgtg 480
ataccattag ttaaacacaa tatttctaaa acttttttgc tgactatttt gtcgatgaac 540
cagttgttat atgcggcttt ttttcacatg ttatgagagg ttattaaaat tattgttaaa 600
ttatttattt gtagttaaat gtgtaagcca gttcccacat tcaaacctgt cagaggtgag 660
ctaagatatt ggttggcgac aatgtttgtg gacatcaggg ccggttttgt ggtttttgag 720
cgccccgggc aaaataaaat ttgtcgccca ttcatacaag aatatacaaa tttactccga 780
aaaaaaaaaa aaaaaaaaaa aaaaaaaaa 809

<210> SEQ ID NO 46
<211> LENGTH: 1728
<212> TYPE: DNA
<213> ORGANISM: Diabrotica virgifera virgifera

<400> SEQUENCE: 46
ggggagtaaa gaataattcg gtgtttaccc ttattaagtg aagttttttt actacgaagt 60
gtactgtgtg ggagacaaaa aaaaacatga agaatctgtt gttcttgttt gggtttatca 120
gtattttatc agtattgcta gccgcagatg ttcgcctggt agacttagat ccaccagaag 180
ctcaacagca aatagaacaa caggaccagt ctcttcacta tgcgccaaaa gtagaatcaa 240
atgttcccgc agtaagatat ttgggaaacg aacctcacaa tgttctggaa gatatttact 300
tagctagaca gtatcacgga caagacggaa taggaggata cctttatgga tacaacatcc 360
cagatattgc caaaactgag aaaaaagttg ctggtggaga tttaagaggg gcgtacaatt 420
acattaatga tgatggggcc gaaatcaagg tcgaatattg ggacgatgga actggattcc 480
atcaaatcga taatgttcct aaaatcttac ccaagccaat tgaagagtct ccggaagtta 540
aagctgaaaa ggataagttt ctagcaagat ggcatgaaga ggccgagaga aatcaacgtc 600
cagttgcttc cccctatgat gctgatggta attacgctag cggaccatta tcgctccagg 660
gacaagctga atttaagaaa atgtttgaaa atcaaccccc aaggtcagta ctaccaacaa 720
cctagctcta gttctggagt ttaccagcaa aacggacaat atcaacccgc tggacaatac 780
caacaaactg gacaatacca acaaactgga cagtaccaac aacctggaca gtaccaacaa 840
cctggacagt atcatcaatc tggtcaaatt aaacaagttc aacaaccagg accccttcaa 900
caaggtcaat attatcaatc atctaaatcg caatcttctg gtcagcacca acaacctggt 960
caataccaac caactgatca ataccaacaa actggtcaat accaacaacc aggtcaacaa 1020
gtttctgttc agcaattaac caatcctaat caaatcgatt acactggagc atacagtgaa 1080
agccaaaact cttacgcaaa cccaactcca aacaaaccat ctggtcaata cacgccagtt 1140
gcttcaagct ccaaccagta cagccaacaa ggaggatatc aacagcctgg acaacaccaa 1200
caaggtgcat atcaacaaag tggaacaaat cagcaaccag gatcatacca acaaggtgca 1260
taccagcaga gtggagcaaa tcaacaacca ggatcatacc aacagggtgg tcaataccac 1320
caatctggac agtaccagcc ctccgataac tcaaaatcaa accaagttga taattccggt 1380
gattacgata aaagctggga caacgagggc caatatgata aaaaatacga tgaagaagaa 1440
ggctccactg ggcccccaaa gggattcttc tataagtttg attaccctgt aggaaaaatt 1500
gttcagaaag gagaaatcgc tagagttgga gatctgaaaa atgcgtatag tcaaaataaa 1560
gctgcgtacg aatcccaagt aagttcaggc cactcgggtt cagctgcttc ccaaagcagt 1620
tactcatatg gttcttaact ttaagctgtg ataatgtatt ttatagattt ttaggagaat 1680
aaaaaatata ttactttcaa aaaaaaaaaa aaaaaaaaaa aaaaaaaa 1728

<210> SEQ ID NO 47
<211> LENGTH: 962
<212> TYPE: DNA
<213> ORGANISM: Diabrotica virgifera virgifera

<400> SEQUENCE: 47

```
gggacggttt tacgtgggaa cagcccaaaa cactacaact aaactgacaa ccttccgtaa     60
caatatttta gaaatctttt attgacgcac tagatgcctc cttctagatt ttaagtttag    120
aaaaaacttc tgtgattggc gctctgaacc ttgagaccga cgcgattttt tgcctctctg    180
aatcggaaac attctacaga gcaaagtatc gcgtactaac aagtaactgt cgcaaaacgt    240
gcccacagat tcccgatata gaccacagtg gcgtttcaag cgttactgca attcagtgtg    300
agtcaaacgt tcagtttcaa gttagatatt actcgcacat tgtgttgtgt ttaagagaaa    360
aaataatttg gaaaagagca tttctataaa cactccggac tgtattggga atggtggtca    420
tccatgcatg aaaagttctt gcaaaaacaa tatttatata ttatgtattt tatacaactc    480
atcagtgttc actggttgta aattatattt tattctaatt ttttaaccta caactctaca    540
ttccttgtta ttttaaaata atcgtcaaat taacatagaa tttgcaagaa acatgtacaa    600
tgggcattta agatctgctg ccgtttgata tagaattccc ttagtgttaa ttttattgat    660
ttgattttgt aaactgtaga tgaataatta ttgtagatga tagtttgaat gtatagattt    720
tattgtacct atgtaattta ttatgagagg ataaaacgat ctatatgttg tatacaattg    780
atttaagtaa gtttggtaga tgtattgtcc aatgtagatc gtaaaatttg gtgtaatttt    840
ttatagcata gtttattttt taaataaccc aactgatact ctattgctct attcaaattg    900
tgcttttttt gtctaagaaa taaaatagtt gtgaaaaaaa aaaaaaaaaa aaaaaaaaaa    960
aa                                                                   962
```

<210> SEQ ID NO 48
<211> LENGTH: 1146
<212> TYPE: DNA
<213> ORGANISM: Diabrotica virgifera virgifera

<400> SEQUENCE: 48

```
ggggattggt gttcaagtca agtcaagttt gttgagtaaa atcaaactag tttgacttga     60
tgcatctcta atatctgcca taaattgaag gactccagta ttcaatccga atatgtttca    120
acgtaaatgt aaattctaca tgacaaaaac tcagttctta atagatggac acaacatttc    180
agcgaacatc taaatattaa cgatattgaa gaaggttaca acatagaaaa tcaacaaaat    240
ctacatcatc aactacacac tgaagaccca acaagagaag aagtatcaac tgccatccta    300
aaactcaaag acaataaagc cctgaatctg ttctgatctg tataaaaagg tggtgatcat    360
ttgcagcaat ccataaatta atagtactga tatggcagaa tgaactggat ccagaaaagg    420
gaataatacg tccgttgcat aaaaaaggtg atcaactgga ttgtaagaac tatataggca    480
ttactctact agcatctacg tataaaatct tcggcaatgt attgtttgaa agactgaaac    540
ttttcacaaa ggatattgtt ggtcaatatc aatgcggatt cactgctgga aagtcaacta    600
tacatcaaat tcaagcacat agacagattc tagaaaagtc aatagaatat aacatagata    660
cccaccatct cttcgtcgac ttcaaagcag cctatgacag tgttaaaaga actgcattat    720
ataatgcaat gattgacttt gggatcccac cgaatttggt taagttgacc caactaacaa    780
tgcaaaatgt aagctcgtgc gttagaattc aaggagaaaa ctggacattc tttgacatta    840
ataatggtct aaggtctaag acagggggac gcgctggcgt gtctcctctt taatattcct    900
tggaaaaggc agtgagaaaa ttaaatatta gaatgaatgg aagtattttt aatagatcga    960
cgcaaattct cgcattcgct gacgatatag ttatagtggg cagaagtgtg agagacatgg   1020
tgcagtattt taaaagactt gcggacgcgg caagtgaatt aggacttgtg atacacgagg   1080
```

aaaaaaacaa atatatgttg gtttctaaaa actcccgaaa aaaaaaaaaa aaaaaaaaaa 1140
aaaaaa 1146

<210> SEQ ID NO 49
<211> LENGTH: 630
<212> TYPE: DNA
<213> ORGANISM: Diabrotica virgifera virgifera

<400> SEQUENCE: 49
ggggagtcag tgttgcgatc gtccagcagt cttccaaaaa ttgacgtgtt ttctggaata 60
aacaatatgt gattgagtgc tttttaacct taaaaatcaa aaagtttctt gtgatagtga 120
agtgaaatac ttaaaataat agacaatgtt tgcgaacgga caggtagtag gtgatggtac 180
ctgggacctt cgggtttttg tcacagatct acaaacggag aggttgattc gcgtaaaagg 240
agatgtccac attggcggag tgatgttgag gctggtcgag gacctagaaa tttcaatgga 300
ttggtctgac catgcgcttt ggtggcccga taaaaatata tggctgacaa gaacaagatc 360
tactctcgac caatgcggag tccacgcaga tgccttactt cattttactc caatgcacaa 420
aattctcagg ctacaattac ccgatcttag gtatttggat atgcgggttg acttttcaat 480
caaaactttc tccgctgtag ctcaactttg caaagattta ggcttaaggc acccagaaga 540
attgtctctt tcgaagccac tggaacccaa tcatttaaaa tacaattata aagacctgcc 600
aaaaaaaaaa aaaaaaaaaa aaaaaaaaaa 630

<210> SEQ ID NO 50
<211> LENGTH: 293
<212> TYPE: DNA
<213> ORGANISM: Diabrotica virgifera virgifera

<400> SEQUENCE: 50
attggtcaac agaaaactaa tagaagaaga taacttaaca aatttaattt ataaaatacc 60
tagggtaaat ttagtgggcg caaacaaacg gacattggca actataaatg aaggcatacg 120
agtaatggta cgactgggca agaatatgta tgcactacaa tgtgtaataa tgccaaacat 180
gtcacatgac atgatagtag gagtggacga attggcagaa aaacatgtag tggtagattt 240
taaaaataat acgatgaaac taacagaaaa aaaaaaaaaa aaaaaaaaaa aaa 293

<210> SEQ ID NO 51
<211> LENGTH: 1508
<212> TYPE: DNA
<213> ORGANISM: Diabrotica virgifera virgifera

<400> SEQUENCE: 51
gggtagcaga gaagaggaaa ttgtatctga tgtggtttat gaaaaaagtt gacggtgtag 60
gggttgaaaa tctcggttaa atgacacatg gcgattgaca caattaggac ttctctgctt 120
ctctttaact atttctaagt cttcatacag gtccaatttt aggaagtttt tttgtgaaat 180
attatgtaat aacgagacat cttctgggat attaagggta tgtttgtttt ttacaagatg 240
ttgagagaaa gtagaagtgt tttctctttt ggtgtgctct aaggagcgtg aagataagga 300
tctacaggtc ctacctatat atgtagcgtc acaatcagaa cattgtaatc tatacacacc 360
actacgatcc atgtagttga tagggtcttt ggaattggta agacactgtc ccagattgtt 420
gggcactttg aaagaaatat gagtattatc aactgctctt ttaagaatat atctaatgtc 480
tccagaaaga cgttcatgaa gatatggtaa ggaagcatat gagggtttga aggtcaagtc 540
tctagggaaa gcagtctctc tcaagactct aaggtgtctc ttttgaataa gtttgtagac 600

-continued

```
aatattagga tcgtaaccgt tgttgaacgc tatttgacga agaatattaa gttctttatc    660

atagtttgat ggtgataaag gaatagtttc aagtcaggaa tagaatcaaa aataattagt    720

aatatgtagt taacatctgc acttgaaccg ttttatcagt aacatttatt aacaccatgt    780

accgattcaa gtacattttt ttaataattg aaaaaaagga aggatatagt aagagtaata    840

atatacccttt atgtttttat caccttatag taaattgtac actagacaaa ttttagttta    900

atgactccta gaatttataa aactcaaaca actttgaagc tgattatctc agaactacca    960

aaactgcact taaacgcttt tacgtgtggc cccctcaatt gtaaaaccaa aatgttaatg   1020

cgggctgaat ccccgcgaca aatgaatcag aagatagtcc attctttaaa atttagagca   1080

aaaaccgtga aagaatggac taagagctca aagagtgcgg caatcactcc tttaggagtg   1140

tagatgccat gatgatgatg ataccttgta taaaggattt taattatttt tgtgattaat   1200

tgtacacagt cgataaaaag aaagagtata aatgcctttt aaatatatta aattttactt   1260

ttccatgaaa ctttagtgtt tcaatatcta atcatgaaaa gttcaagtgt cttcaacaga   1320

atattaactt tcagatttgt aatagttttg ggattaatta ttgtattgga gattcgaatt   1380

taataattct tatccacctt accgttaccg tccagtccgt ctgctgctac tcctattgtg   1440

ataaaagtat aaattggcaa actttatttt tcatctacaa aaaaaaaaaa aaaaaaaaaa   1500

aaaaaaaa                                                             1508
```

<210> SEQ ID NO 52
<211> LENGTH: 631
<212> TYPE: DNA
<213> ORGANISM: Diabrotica virgifera virgifera

<400> SEQUENCE: 52

```
ggggaaaaag ttattttttg ataaatttcg aactgtattt gaaaattgat tctatataat     60

aaatacataa aaagattggt tttaaataaa aatggcacac aatattaaaa aactgagtgt    120

ttcaatgagt aaagcgggaa tgccatttcc agtacctaca aagattatta gatttgttag    180

gaaaggttgt actaatagac ccttttttcca catagtagtt gcagatgcta gatcagatca    240

acacgaccct tcaatagaac aacttggaac tcatgatcct ttcccaaatg aacacaatga    300

aagattaaca tccttaaact tcgaaagaat tcgatattgg ttatcgcatg gagcgattgc    360

aacaaatcct gttcttgaat tattaggtct tgcaggattc tatcctattc accccaggag    420

ttatatgact gcttggagaa acagggaaaa ggcaaaacaa gcttctgaag ctgctgaaca    480

gaccaaagag gagaaaagtt aataacatgt catttacttc tgtgttgtgt gtacatttta    540

gtatgtttaa gtagctataa gtctattatt ttgtaaaaag tcattataaa catataaacg    600

caaaaaaaaa aaaaaaaaaa aaaaaaaaaa a                                   631
```

<210> SEQ ID NO 53
<211> LENGTH: 114
<212> TYPE: DNA
<213> ORGANISM: Diabrotica virgifera virgifera

<400> SEQUENCE: 53

```
ggggatttta taaatctgtt aaacaatgag ttggtcagca taagctccaa agtgttgtag     60

caatacagaa tgagtttaaa tatctaaaaa aaaaaaaaaa aaaaaaaaaa aaaa          114
```

<210> SEQ ID NO 54
<211> LENGTH: 597
<212> TYPE: DNA

-continued

<213> ORGANISM: Diabrotica virgifera virgifera

<400> SEQUENCE: 54

```
ggggtctttt ctcagtgaag ccatcttggc aaacgttagt aacgtgaaat aaaacttaaa     60
tttttcaaa atgggtcgta tgcacgcacc aggaaaaggt attgcccagt cggcattgcc    120
atacagaagg agtgtaccaa catggttgaa agtcacacca gaagaagtaa aagaccatat    180
ttttaaactt ggcaagaaag gcttgactcc atcacaaatt ggtgttatcc tcagggattc    240
atatggtgtt gcccaagtaa ggtttgtttc tggaaacaaa atcttgcgta tcatgaaagc    300
tatgggtctt gcccctgatc taccagaaga tttgtactac cttatcaaga aggcagtagc    360
tatccgcaaa catttagaac gtaacagaaa agacaaggac agcaaattcc gtttgatttt    420
ggtagaatca cgtatccacc gtttggctag gtactacaaa accaagagcg tattggcacc    480
caactggaag tacgaatcaa gcacagcatc tgctttggtc gcttaaattg tgcttttatg    540
ttaagtttat aaaataaaaa tttctattaa aaaaaaaaaa aaaaaaaaaa aaaaaaa      597
```

<210> SEQ ID NO 55
<211> LENGTH: 543
<212> TYPE: DNA
<213> ORGANISM: Diabrotica virgifera virgifera

<400> SEQUENCE: 55

```
ggggcctttt taacgaaaaa tcgtgtgtaa aggtagcaca cgaataatca tcttttaatt     60
ttccctataa tcctttcagg atggcaatca gaccagttta ccgtcctcaa atcatcaaaa    120
agaggacaaa gaagttcatc aggcatcagt ccgatagata tggtaaactt aagagaaact    180
ggcgtaaacc aaagggtatt gacaacagag tcagaaggcg tttcaaggga caatatttga    240
tgccaaatat tggttatggt tccaattcta agactaggca tatgctacca acaggtttca    300
gaaaagtttt ggtacacaat gtaaaagaac ttgaagttct ccttatgcaa aaccgtaaat    360
attgtgcaga aattgcacat ggagtttcgt caaagaaacg caaggatatt gtagaacgtg    420
ctcagcaatt gagtattagg gtcacaaatg gaaatgctag gttacgtagc caagaaaatg    480
aataagctat tattttgttt aataaaaaat agcaaaaaaa aaaaaaaaaa aaaaaaaaaa    540
aaa                                                                 543
```

<210> SEQ ID NO 56
<211> LENGTH: 1023
<212> TYPE: DNA
<213> ORGANISM: Diabrotica virgifera virgifera

<400> SEQUENCE: 56

```
ggggattcag tatattggga tttattaaag agatttctag cccagtgaga agaaattcaa     60
gaaagtggcg aggttcgagg gaaaattttt ttctgccgtc aataattttt tttctagttc    120
acccttggtg aaccaaatta aggacttagt tactaaacaa gtaagttcgt cagataccga    180
aatgtcacag aaagaaagtg aatctgtgga tgctacatca cctcctccaa tgctaattga    240
aaccactgag aaatccgatg gagtcccttc cagatcacca tctgatgaaa ttagtaaact    300
aagaccagag gaccgctcaa gaaatcagag cttttctatc agaaatatgc aggtgtccag    360
gagccaaatg aaggaataca gagaagcctt tagactgttc gacaaagacg gtgatggcag    420
tataacaaaa gaagaattag gcaaggtgat gaggtcgtta ggacaattcg ctcgcactga    480
agagcttaaa caaatgcttc aagaaataga tatcgatggt gatggtaatg ttagttttga    540
agaattcgta gatatagctt ggtcagcaag ctcagggcgt gatcccgatc acactatgtc    600
```

-continued

```
tttggaggaa gaagaaaaag agctaagaga tgccttccgt gtatttgata aacacaacag     660

aggatatatt gtctcgtcag atctccgagc cgttttgcat tgtcttggag aagacttatc     720

tgatgaagaa attgaagaaa tgattaaaga agttgatgta gacggagatg gacgaataga     780

cttttatgaa ttcgttaatg ctttgggtga accaggcaat gaggatagct acgatgatga     840

cgacgatgat tacttatcat tttataacta gaaaacatta agatatatgg tttttatgta     900

cctgtgtttc cagagaactt catccataat caaataagct gcctaataaa caattaacct     960

aattataaag tttaaatata cctatgcctg ctacaaaaaa aaaaaaaaaa aaaaaaaaaa    1020

aaa                                                                  1023
```

<210> SEQ ID NO 57
<211> LENGTH: 1179
<212> TYPE: DNA
<213> ORGANISM: Diabrotica virgifera virgifera

<400> SEQUENCE: 57

```
ggggctttat aatttgtcgt tgaaaaagat agggctccaa agtcctattg ccaacaaaaa      60

aacaacgcaa gacattaaac aacttttttc aagcccatct gtatttaaaa aaacagtgca     120

aaatgtttct gtgggactgg tttacgggaa tgctgggata tctaggattg tggaagaaac     180

ctggaaaact attattctta ggactggata acgcaggcaa aactaccctt ctacatatgc     240

tcaaggatga cagactggcc cagcatcttc ccacgttaca tcccacatca gaggagcttt     300

ccattggtaa catgaggttt acgacgttcg atttgggggg ccacgagcag gctaggagag     360

tgtggaggga ctactttcca gcagtcgatg ccatagtgtt ccttgttgat gccaacgaca     420

gctcaagatt tgtagaaagc caggaacagc taaatgccct cctctcagac gaaactctat     480

caaactgtcc aatacttatc ttaggtaata aaattgatct cccaggtgct gcttcggaag     540

atgaattacg aactagattc ggcttgtttg gccaaaccac aggcaaaggc aaagtagcca     600

gaaatgatct acccggtagg cctctagaac tatttatgtg ctctatactc aaaagacaag     660

gttatggaga aggtttccgt tggttggcac aatatatcga ttaattatgt atttttccat     720

ttcgttctgt cattgagtta ggatattaat gtttgaggaa ctattggcaa cactgcaact     780

acctgattca tttcagatct taggtacttt acataaatat ctaaatatag atgttggcaa     840

tgtaattttg aacaacagta tatacattca atgtaaatta tatattttta gttaagttac     900

cttcttaaat ggtgtttgag tggctatggt actgaaatag tttgactttt tgtgttcttc     960

gataactaaa aatgatttct tgtggaaagt tacactcaga attacatagt taacttcttt    1020

atcagcagtt gttgtcaaga tttccatttt gagacgattg ttttgtaaat taggtgggaa    1080

tttttaaaat gttggactgt tttttaacat gcctttctca acttttgtta caaataatgt    1140

tttgtccaca aaaaaaaaaa aaaaaaaaaa aaaaaaaaa                           1179
```

<210> SEQ ID NO 58
<211> LENGTH: 453
<212> TYPE: DNA
<213> ORGANISM: Diabrotica virgifera virgifera

<400> SEQUENCE: 58

```
gggggaagtt cgtggtggta ttgtccgtat ccgcctgaca ttcctgccgg cttttcaatt      60

gttttccgag ttcgcgaata cattacgtgg agtggtcgtg gatttgaaaa gttttgcgtg     120

ttttaaattt tgtgagtgaa cttcgcggcg acgatacagt tggactgtgc cgctaattgt     180
```

```
tgataactgg agataacggc tttgtaataa agtggtgaca gggatctctt cgggacgctg    240

aggaaggtat ttcaatcttg gttttgtcac tttttgaatt tcatagtaat catttttaat    300

cgagttatga aaccttgaaa tggccatttt cgcatttttc aaatttttaa taactcgaca    360

acagtcaatt ttagagaaaa attacaaggg accttttttg ctcagaatga cccaagttat    420

ccgaaaaaaa aaaaaaaaaa aaaaaaaaaa aaa                                 453
```

<210> SEQ ID NO 59
<211> LENGTH: 532
<212> TYPE: DNA
<213> ORGANISM: Diabrotica virgifera virgifera

<400> SEQUENCE: 59

```
ggggagtggc aagtttcata tctgtgaatt tgttgtttgt tacattttct ccggcattac     60

agataatcgt tatgaagaag ttccccttag tgctgacatt tgttgcattt ctgtggattt    120

gggaggctaa tggatttacc gcagaacaaa taaatgaaat tcgtagtatt tgtagtgaag    180

aattaaaaaa aattccacgt caaaaaggtg atatgggttt tccgggaatt ccgggtgtac    240

cagctccacc atcttttggg gcaatcggac ctccaggaaa aactatatat ggtctcccag    300

gagcacccgg aatacccggt ccaatgggag ctcccggtgc ggcaggacta cccggattgc    360

caggagttaa aggtgatgta ggttcctgta gcagaaaata atttggaagt tctgagtgaa    420

aatttaaaac tattcttact tttgacatat tatgtagata tttgctgttg tatcatccaa    480

ataagtatca ttagaacata caaaaaaaaa aaaaaaaaaa aaaaaaaaaa aa            532
```

<210> SEQ ID NO 60
<211> LENGTH: 707
<212> TYPE: DNA
<213> ORGANISM: Diabrotica virgifera virgifera

<400> SEQUENCE: 60

```
ggggacagtc accactcgac ccagtcaaca taagcatcat gaactcttac agtgtggtat     60

ttgcgtttgc attggccgct gttgttgtag ccgaaccacc ttctggctac aactacaacc    120

ggcccagcgg gggtggcggc atctccttcg ggggaagcag cctctccttg gggggtggac    180

tgtccggcgg tggtggatac acggctgtat cgtctggtgg tcaaactagc gaaggagctt    240

ccgtagaccc acagcttctc gaacaagtcc gtcaaattct gctcaaagaa gaacagagct    300

cttccagcgg cggtggtcat ggtggtggtg gtggataccc aggaccatct tcccaatacg    360

gtgctccatc tcctcaatac ggagtaccca gctaccaata ccgcgtcgtt ggaatcgatc    420

tagagggaat caaacaagcc atccaagttg cccagtacaa ccaaatctca cagggaccaa    480

gctttggagg ataccccagc ggacctagtt cgataccatc cgggtcttac ggagcccctt    540

actaaggctc tagaactgat ttcagtgtga ataccatctt ttaccatctc agacgggtca    600

tgatgcattc aataccatca agtttcaacc ataccatcaa aagttgaatg tttgtataaa    660

gctttcgtag gttattcaaa aaaaaaaaaa aaaaaaaaaa aaaaaaa                  707
```

<210> SEQ ID NO 61
<211> LENGTH: 715
<212> TYPE: DNA
<213> ORGANISM: Diabrotica virgifera virgifera

<400> SEQUENCE: 61

```
gggacaactg tcaaatattt aactcccaac ataacctgta acctgtgtaa gatcttgatt     60

gaccaaaaaa atacaaaaat ggtcaaggct tccgagacag ggggcgtgaa gcccatgtcg    120
```

```
atagcaggtc gctttataaa cgaacgagaa cgtttactag gaatgacagc tgcagaacga    180

gactttcgca aacagtggct aaaagaccaa gaattgtccc attctgagcc gaaaaatgtc    240

cctgaaatgt ataaagctac ccataatcca atcaggaggc tctacagatt tcctctggat    300

accttaggta aaatgttgga gcctgttttg ggattacaga gtgcttctag agtgagatac    360

ttcaccggaa aatttctttt ggctgttgca ggtgcttacg ccttgaccta ctatgttaaa    420

tacaatacca atgactggac acgtaagaac ggaatgagaa tactcaagtc taacatatca    480

gtacatgaag gtgacccagg ctatcctaga gtatctcaaa ggagtaaacc atcagattat    540

ggtgatcgag gattcaatga taacaaatta aacttgtaat atatttatat gaaaatattt    600

agtgttcgtt ttaggatcat ttatttgttg cttgcaaatt ttaaccataa catctttgta    660

taataaagtg caagaactat tgtaagaaaa aaaaaaaaaa aaaaaaaaaa aaaaa         715
```

<210> SEQ ID NO 62
<211> LENGTH: 1242
<212> TYPE: DNA
<213> ORGANISM: Diabrotica virgifera virgifera

<400> SEQUENCE: 62

```
ggggacataa aatctacaag atctacagta gatacagtgt ttcgtactac aatgataaaa     60

aacaatcttt caaagagatg ttacaagaag tgctcttaaa attatgggaa ggtctagtca    120

aaaacgaagg ctcgcaaccc acccaaaaag gcaccctgta ttcgtaagac ctacgataga    180

cttcactcaa gaagaaacga ttctacagaa cctcattcca caaattcgag aagacattct    240

gaatgaatct ttagtttacc agaagaacac gccaacagtt agaggacatg tcgaaaacct    300

tattaatgat acagtcggag atcttaagcc aaaatttctc aactgtgctt taatagcgat    360

atacgcctac aagtatttta aacaggatca caccgaagaa gagttggtca aggctgggat    420

tttgggctgg tgctacaaat tgcaagacct cgccatgatt atcgttgatg acatactgga    480

tgaatcaaaa attcgttaca ataaacctcc cttgtatagg gtagtgggaa taaaacaagc    540

tatcctagac tctataattt tagaatcagc cgctaacttc ctagttttaa aatatttttc    600

tgatcacaag catttagtta aaatccaaaa ggatctcatc ctaaacatag cgacaactac    660

gatttcacag aaacaagagc tgttaaagta tgaaatagac gaattggaag tttttgaaaa    720

tttgattaag tcttttccgc ttttaataca tgctgttaca tctgcggtgt atttggctgg    780

tatcgatgat ccaaagatcc aatccatagt gaagaagttt tgcgtggata ttgctatatt    840

tggaaaaaga tatgatgact ttacagtatt tctagaccca aaaactattg gggaaaagga    900

caacacagat atcgttagtt ttaagataac atggatggcc atccaagtct ccaaaatggg    960

aagcccccaa cagaaaaaga ctttcatgaa acactacggt cactcagatc ctgaatcagt   1020

tgctatcatt tttgatatat acagggaact caatttagtt gaacatttcg ataaatatat   1080

gatggaattt tacgacgaca tgcttacaca aattcagaac ttgcctcctc aactgccaaa   1140

agaatttttc tataatatac tagactgtgc tgtagcaaat aagatgtatg cttaataaat   1200

ttaaattatg tcgaaaaaaa aaaaaaaaaa aaaaaaaaaa aa                      1242
```

<210> SEQ ID NO 63
<211> LENGTH: 1950
<212> TYPE: DNA
<213> ORGANISM: Diabrotica virgifera virgifera

<400> SEQUENCE: 63

```
ttttttttt ttttttttt ttttttttc gcttagcaac aacactttag tttattttag      60
taatattttg tattttgaca acggcacccg atttgggcgt cgaaacgtta ataaaattat   120
ttttttcatt ttaattgtgg cttatttccc atataaataa ttaatcataa aaatgccaca   180
aggaaatagc ttcagaacaa cataaagaaa cgattgttgg aaatggaaaa ttaaattaaa   240
aatggaaagt ccccactaaa atggaaaatt ttactttact tttttggtg ttaggaccta    300
cccttcacaa tccaataggt ccccaaagcg ctcgagtgac tgcacattta gcatactttg   360
ctcccccacc attattgata gtcaagaaga gtattacaaa atgtgtatgc atacatatta   420
aaaaaaaaat actacgtacc aaagaaatca cgaagaagtg aaaagcaaca gtaatatcat   480
tctcaaaata agtttatcat ccacctttag ccctaaacat agattattat cgaactcatt   540
tagaatttag aatacatatt atgtaaaata aaaaaaccag tataataata aataatacat   600
tttactagtg aaagaacacc aatttgctgt tggtagtatg taattgttta ggaagatctg   660
tgtgttggag tggtttcttt ttgcacaaga acattcataa ataactcaac gggtcatcaa   720
tatgccatcg tggagaatta acagataagg aaaatcaatt tgcaaagcat acaaatcagt   780
caatgttaac ttacaggaca cgatgtgata ctcatatgtt cggttcttct acccactctt   840
ttttcacggc agaagtatgg tcagtaccgt attcagattg caaagttact tacagtacgt   900
aaatccttca ggtggacaag ttacgtactg tataacataa atatatttta aaaaggtgca   960
tttttaagaa aaataaaata tttgaatcac cctattggta aaaagtaaca atatgggtct  1020
atgaagacag aataataact taattgtgta tcatatatat tcaaaacctg taaacgagct  1080
ttttatagta taacgtatta tcaatttgtt ttaaattctt tttatagtat aacgtattat  1140
caatttgttt taaattctta gaagattaca aggattccat ataaaaaatg aagatatcaa  1200
acaagtggac aaaataaaat acttaggagt ctggatcacg gaagctttaa atccgaaatc  1260
agaaattcga tcaagaatag agcaatcaag agcagccttt ttgaatatga ggaaatttct  1320
gagtaaccaa agattcaatc tgcaaatccg atatcggatg gtaacgtgtt atatccactc  1380
tattcttctt tacggtgtcg aagcttggac tgttaatgct gacttaatga gaaagctgga  1440
agcttctgag atgtggcttt ttaggagaat attgaaaata ccatggaaaa actgtttagt  1500
tttgaaatta gtttttaaat aaaaaatatt ttaaaaatta aagacaaatt attaactcat  1560
taatcataaa ctttgttttt gatttattta tggacagcct tgctacaaaa ttccctcatt  1620
ccattcattc taacagctct attgcaccaa aaactcatac tcgaacagaa gcttcaacta  1680
acacaggtta gcgcagttgg caatatggtt gttagcatta aggggcatta accttcaaat  1740
tgacaactca tttcgactga cacaaacgtc aaaatgtgac aatgtgatag ctaaatattt  1800
tggaacacat acatagaaat gataagtagg agttattaca gctgattatg aagggtacaa  1860
ttggaagggg tcctagtgga ctacaaatat cctggctgaa aaacattcgc gactggacca  1920
ggttaaacac acagacgttt ttcagagccc                                    1950
```

<210> SEQ ID NO 64
<211> LENGTH: 776
<212> TYPE: DNA
<213> ORGANISM: Diabrotica virgifera virgifera

<400> SEQUENCE: 64

```
gggtacacat aacctataaa aaaaacatta atttgattta ttttgaagtg tatatgttgc    60
agttcaagtt gattctcagt tggagttgac tccaactagt tggagtcaac tccaactgaa   120
atgagcagta aaagttgatt ttaaaaattt aaatcaactt ttactagttg gagttgactc   180
```

-continued

```
ttcctggatc gattcagtaa atgttgatta tacgagaatc gcaagtgcat ttttgatgag    240
tgtgcgtttc tttgtttgga ccgtttcaac tacttattag tatggcctgt aacgtcgccc    300
ccgttgggtg aattattctg attcgatttt ttgcacaaac ttactcaaag aaatacatcc    360
gtataacaat ccttataaca aatacacagg gtgtcacgcg gtagcgcggt cgaaaaattg    420
tttaaccaat ttttgttgac caaattcaca aaaataattt ttatctactc tatctcattt    480
atgtaaatca gcggttctca atctgtggta catgtaccac tggtggtaca aatcattatt    540
tgcggtcctg ccaaagacaa accattttca tttccaataa tgacacgagc cgtctcaccg    600
tgcctcggag agcacgttac accgtcggtc cccctgggct agtgtacatc gacactagtt    660
acttgaaaca gggttaaaga tgtaattggc gccggaactg tccgaaaggc aaaaatgcca    720
tacgatatca tatattatga aagtcggaaa aaaaaaaaaa aaaaaaaaaa aaaaaa        776
```

<210> SEQ ID NO 65
<211> LENGTH: 1191
<212> TYPE: DNA
<213> ORGANISM: Diabrotica virgifera virgifera

<400> SEQUENCE: 65

```
ggggacaagt tttttggat ccatcaagtg ttttcaaaat ggctacacac ctagacgtgg      60
ataaaattat tacaaaactc acctccaaag aggttcggga gagcaagaaa atcaaactaa    120
taagcatatc tgaatctgat ataaaagcgt tatgtttcaa gtctatgagc acatttatgt    180
cacaacccat gctgctcgag ctagaagcac caatcaaagt ttgcggtgat atacatggac    240
aatttctcga tttgttaaaa ctgtttggat ttggtggttt tccccccgac tcaaattact    300
tattcctcgg agactatgta gatagggggga aacagtctgt agaagtcata tgcttattgt    360
tagcatacaa aattaaatac ccgaaaatt tcttcttact gcgaggtaat catgaagcat    420
ccgcagtatg taagatatac ggattttttg atgaatgcaa aagaagatat agcactaaaa    480
tatttaaact atttaccgat gtttttaaca cattgccggt ggctgccatc atagacgaca    540
aaattttctg ctgccatgga ggcttgagcc cagatctctt acatatagga caaattcgaa    600
atattcagcg tcctattgac attcctattc aaggtttact ctgtgattta ttgtggtctg    660
atcccagtac cgagcctggt tggacggaaa atgacagagg agtgtcattc tcatttggtc    720
cagatgttat taataagttt ttaaggaaac atgactttga tttaatttgc agaggtcatc    780
aggttgttga agacggctat gaattcttcg ctcagagaaa attaataacg atattttcgg    840
ctccaaatta ttgtggtaca tttgacaacg ctggagcgct tatgtcaata aatgaaaatc    900
ttttgtgttc atttcagatt ttggagccaa caaaacatat tgaaaaaaag aagtgattta    960
aaaagtgaat tagatttatt tatggatatt aatttaagta ctaagtagtt acttattgac   1020
tgttatttaa aaacagaatc acgtaaagta acaaattaaa aaaaaaaatg taaagtattc   1080
tgctcgttac atgctttaca tgttatttgc atgacctttt acgaaattct gttcatagtt   1140
gttaatagat aataaagatg caaaaaaaaa aaaaaaaaaa aaaaaaaaaa a            1191
```

<210> SEQ ID NO 66
<211> LENGTH: 854
<212> TYPE: DNA
<213> ORGANISM: Diabrotica virgifera virgifera

<400> SEQUENCE: 66

```
ttttttttt ttttttttt ttttttttt atagtgtaaa actgattttt ttattttaat      60
```

atataccaaa acataccaaa gcttaaaaaa taatcaatta accttcataa aatttgggca 120
attcatttcc taaaacaact cttcgttcaa taccagcttc agtgatgatc cccagtctga 180
ctacacctcc tgaagaacca tctcttgaca tggcaagtgc caatgtattt gtgacaaact 240
tcacacattc ttccttgctc atattgggct tgaagttggc atctacgtaa ccataaacat 300
aactggaacc tgatcctccg attgacactt cttgtctaac acacatccca ccaattggta 360
tggaatatac ttgtccgcct ttctttttat cccaacctgc taccagtata ccagccatta 420
gcgaatctct ataattgtag caaagttctt ggaaaatggc ggcacctact tgtactttgg 480
gttcttcacc aagttccata ccatgaaaat taagatgata agcaacaatg tctgcaattg 540
cttgtgtatc tgctgcagat cctgaacgac aacagtatat atggtcagtg actttggtga 600
gtttgtctgc tacccggttt gcaatgtagg ccccagtagt tgtgcgagaa tctgctccta 660
taacaacgcc tccatcaaac tccgcggcca taatagaggt tcctgtactg tgagcggcat 720
ctctccaatc attaggacca gtcattgcac catactcagt cataagaggc attttttaca 780
agtttaatga aaagaataca agcttagaaa aattacactt gtaatcctgc aatgcaatat 840
tttgccagtc cccc 854

<210> SEQ ID NO 67
<211> LENGTH: 1162
<212> TYPE: DNA
<213> ORGANISM: Diabrotica virgifera virgifera

<400> SEQUENCE: 67 ttttttttt ttttttttt tttttttatt ataactattt atattttagt taatacatct 60
taaatacaca gtacacatta tatacaacta ttaattcaga tttttttcta tccagtcaac 120
aaaagtagta actctggtgt agacaccggg atatcccttt tcagcgcatc taaatccata 180
ggaaaccact ccaatcagat aatatcttat aaattcacca tcaaacttgc cccaaattaa 240
tggacctcct gaatctcctt gacatgcatc ttggcggcca tccgcccgtc ctgcacatag 300
agttctctcg tcaattgttg ctttagcccc aaaggcggca gcgcattttg atgtgtcaac 360
tactggaatc tgggctattt ggagggccga acttgaaggt ccattataat atgtggctcc 420
ccaaccagca actacagctg catattttac aaaactttgt tttctgaaat tatcgtcaat 480
tggtagacat acaggccata cccaaggatt ggtgggggct ctttccaaag taagaattgc 540
gatatcactg gtgtatttca cgggactgta gtcttcgtga actttagctt tgatcaatgg 600
tatatcttct ggttctgctc catcattagg attgtttaaa tctaagtctc ctaaacgagc 660
gacatataag tctttcttgt tgtgtacaca gtgagcagct gtgagaatat gtctttctgt 720
aatgagtgtt ccgccacaca accatcttgg ctttgaaggg tccctgctat ttctataacc 780
caaattaaca atgaatggta cctcatgtaa tttggctgga attccaccta caactctaaa 840
gtttgttaca ttactaacac cacatttctc gttatttaaa acggcaccaa tgatttttgt 900
atcggttgct ggttgtgtag gttctggttc tggttctggt tctgtattgt ctgttgggca 960
acaaacatat actacagctc caaatttaca tgttgaacgt tgcagatatt ggcgcgtttc 1020
ctgattattg cttcttgttt taagcaaatt gagcatgtat ttacattcgt atatactttg 1080
acaaattcca tattcattcc tagctgtgta acagggctca ccttcttcaa cagccgcgtg 1140
agcaacacta aacaaaatcc cc 1162

<210> SEQ ID NO 68
<211> LENGTH: 1186

<212> TYPE: DNA
<213> ORGANISM: Diabrotica virgifera virgifera

<400> SEQUENCE: 68
ggggcaaact gtaagttatt atattttgca cgattgaaag acatttacta ttagcaaaaa 60
tgtctaaaga ccgggaattg cagatgggga tgcgatgtgt gaagtacatg atttttgtgg 120
cgaattttat gttcatgtta gttggattgt tgctgatatc aattggatat accattaagg 180
ctatctacac cgatttcgat gctttcctta gcagccatag ctacaaagca tccgacttag 240
ctatagctgt tgggttcgtc attctagtgg ttgctttgtt tggttgtgca ggagcaatta 300
aagaaagtgt tctactggtt aatctatacg ctttactact tcttgtaata gttatcctgg 360
aattgaccgt aagtatcatt gcttacaaat ccaggagtca cttggaagaa acactttctc 420
aggatatgtg gattagtatg gagtattaca tagccgatac tggatatatt tgggatgcaa 480
cacaatactc gttgcactgc tgtggagtac atggtccaaa cgactgggac agatttaaca 540
gttcagacta caatctcaca gtcatttata gttcacaaga cgactcaaca agttcagact 600
tgccacaaat aaattaccca ggagtttacc aagtaccaga gagctgctgc agaaatacca 660
aatgccaaag tatcgcttct ctttacatga gaggttgctt accgaaaatc cactatataa 720
tctcgcaaag tgctcttctg cttggagttg gggctatgtg cataacattc attcagcttc 780
tcggtgctac atttgcccat cttctggcca gatctattag aaaacttaaa acacagattg 840
aagtggaaag atcaataaga agacaacaac tgtacgagtc gcttgcgaaa tctaacacac 900
aagagaaagt tagtccagtc ctatacgtgg cagagtcttc tgaagcttaa gaattcgtcg 960
tgtgttatat ataaaaataa tgatttaaat atagatttaa atatagatta aaccattgtc 1020
catttcatta cactcatgta tattgtgtta gtgtttacag ataagttata atatatacct 1080
tttctgtttt tgtgtattct ttactaggtc tatgtatgta gattctttaa atgttaaata 1140
tagaataatt ttaactgaaa aaaaaaaaaa aaaaaaaaaa aaaaaa 1186

<210> SEQ ID NO 69
<211> LENGTH: 1002
<212> TYPE: DNA
<213> ORGANISM: Diabrotica virgifera virgifera

<400> SEQUENCE: 69
tttttttttt tttttttttt tttttttttt ctttaataaa tagtatattt tgtaaatttt 60
tttatcttac ataatacaaa aaatatatac attagtttta tttatgtttt atttatattt 120
caattattat tctaattctt cttcttaaca tcgtcacctt ctggattttg gtgttttgta 180
aacgttagga atacctgttc tagactactt tgtcccaaag aatagtcttc aatattcaga 240
tcacttcgct tagctctttc taatatacca aacatagtgg accatgccat ggaagtgtcg 300
gttatataat aatacaatag ttcttgatgt ttctctctaa gatgagcata aggaaattta 360
tctttgatat acttctccag tgactctgta tctgcatgta ccagaccacc gctctctggc 420
aatttcttta gttttatggt taaggtgtat ccctccgcaa atttgttttt aagatgctgt 480
gtggatccaa gacatttgaa attgccgttc accataatgg ctattcgagt gcacaaagct 540
tcacattctt ccatgctgtg agaagttaaa acgatgcact tgccgttgtc tcgaattttg 600
cataatgaat cccacaggta acgtttcgtt gctggatcca tacctgttgt aggttcgtcc 660
aaaaatagta ctggcggatc ccctatcaac gacaaaacag tacttaactt cctcttattt 720
ccaccgctca tctctttaac tttcttgtcc aaatgacgat gaaaatcgaa gtctcgagac 780

```
aagaaattcg caattctttg ggttctttta aactctattc ctctgagtag gcagtacatg    840

ataattgttt ctcttgctgt catatcatcc agcaaagcgt cgaattgagg acagtagccg    900

atgtttcgtt gtacttgctt cagttgcgtt tttacactct ttccttcgat ccatgtatca    960

ccgtaagata cagtttcatc tccgctcatc attttaaatc cc                      1002
```

<210> SEQ ID NO 70
<211> LENGTH: 1322
<212> TYPE: DNA
<213> ORGANISM: Diabrotica virgifera virgifera

<400> SEQUENCE: 70

```
gggtatatga ccacattgtc aactattaga aagattctgt tgccaaaaat aattctagac     60

ttttagtagg tataatactg ttgtaaggta ttacaataca tagggtacta ctactgcttc    120

ttcttgtagt tccttatctt atcggaggtt ggcgatccgt accttattga cggctgctct    180

gaaaatatct actgagctgc aatctgcaat tataccactc tcttaggttt cttagccagg    240

atatttaatc ttttatctta tccttaattt taccttgcat tttactacaa cacaggtact    300

aaaatgtgta taccaaattg gatagtttct ttctgaggtg ttactctata tattactgtt    360

gaaatatagt ataaatatgg acatcttccg aaaacaacta gacagaatat gtatactaaa    420

ctcacagtaa agatgcacga gaaataaaca aaccaagaca cgtttaatgt tacgaggagc    480

actcccgaat cctgatttac atctatctat ctaattagcc tctttcggtc catctttgga    540

aatgaacctg aagaaaccca atcctttttc attattctct gtctgtcgct atagtcatcc    600

acctagagcc cacgtgcttc ttgatatcat ctgtccatct catttggggc ttttttctgc    660

ttagtttata ttcccatggt ctccaattta taagaatttt gttcaatcga tcttctttgt    720

gtcttatatt gtgtccggca aatctccatt tcaattttgc aacttcttgt ctaacatccc    780

taacttttgt tttcactctt acccactcgt ttcttttttt tatccattaa accttgatta    840

cacgtaacga gtattgtagc gagacagtgt tctcggccgg gtgcttgttt ggtataaaca    900

tactaacgag tacttggccg agcactcgac ccagtcatat ggcgagacag tcactcggat    960

cttgttatac atatttacta agccgagtct tcgacctccc actcttcaat cgtatactcg   1020

ccaatccact gggtatgtgt aaacaacact cgctgtgtaa ctgtacatgt taccattacc   1080

acttcatcag aggagacgac ttgtgttaat caatgttatt tgggattctc aaaaatagct   1140

aacaaatgga actcagatag gacaataaag tgtagtttaa ttctacagat aagtcacacc   1200

cgtgcttatg aaattataaa tatttggagt ataaaaataa acaaaaacgt gatgcagcat   1260

ttaaatattg ttggttttaa aacttaagga gtaaaaaaaa aaaaaaaaaa aaaaaaaaaa   1320

aa                                                                  1322
```

<210> SEQ ID NO 71
<211> LENGTH: 761
<212> TYPE: DNA
<213> ORGANISM: Diabrotica virgifera virgifera

<400> SEQUENCE: 71

```
gggggacata tggtgacata actcattcaa aatccataaa aaagtttcaa aatgagttta     60

ggagttcgta aaatattttc agtaggctca aaattagtaa gaccaagtgt ccagattgtt    120

ggtcaaagat gttgctctag cggctctaaa gatggatatt tctatgtaaa cgacaaagaa    180

cccagtatgg agtttggggc tatcacagat cgtgctgccc aaacaatgtt ctttactgaa    240

ttattcagag gatttggtgt tactttggct cacattttca aagaaccagc aactataaac    300
```

```
tatccctttg aaaagggacc tctcagtcct agattcagag gtgagcatgc cttgagaagg    360
taccccctctg gtgaagaacg ttgcatcgcc tgcaagttgt gtgaggccat ctgtcctgcc    420
caggcaatca caattgaagc agaagaacgc gcagatggct ctagaagaac cactaggtat    480
gatattgaca tgacaaaatg tatttactgt ggtttttgcc aagaggcttg tccagtcgat    540
gctatagtag aaggtcccaa ctttgagttc tctactgaga ctcatgaaga acttctctat    600
aataaagaaa agttattaaa caatggcgac aaatgggagt ctgaaatagc cagtaatatt    660
catgctgacc atttatatcg ttgaaaatat atagaaaatt gtaaaaagtt gtagaatata    720
tcttattaaa caaaaaaaaa aaaaaaaaaa aaaaaaaaaa a                        761
```

<210> SEQ ID NO 72
<211> LENGTH: 2041
<212> TYPE: DNA
<213> ORGANISM: Diabrotica virgifera virgifera

<400> SEQUENCE: 72

```
ttttttttt ttttttttt ttttttttt gataacgatt tctaaagtgg aaatcgaaat     60
gtcaaaaaaa cttaatttca aagtaaagtt atggctcatt ccaaataaaa aacagtaaat    120
ttcattgtgt atataatttt gtaatgtttt tgtattcaat caaaccaaaa ataaaccact    180
aacaaaaaaa atagagtctt ttaccacctt ctccattaaa ggagattact tcactacaca    240
aatgctgatg gatgtggcga tgattgaaat gctcgaaacc gctacttgac caaatacgtg    300
tcgtttggtg ggtaaagctc gtaatcccga attacggaat attggaaacc aattattaac    360
aagatgcttt gatacatcac agagctatgc taaatagttg ctaatgttat tcagcaataa    420
cattatcgat gggatgactg aggtcgatat taccattgct taaacacagt attgaaaaat    480
ttgtttcata cattatttaa atagtaataa ttaaattgta taataatata cagtgatgag    540
cacgctcctc ctccttctcc tcctcagtcg tttcctcatt tctgagtgtc gtgattccct    600
ataatacgat caactatctc tttccgtcgg cttctgtcct gagcttccct catggattca    660
gagaatgttt ttccactggc ttcctgtact tggtccgtcc atcgagcagg tgagcgacct    720
ctacttctgc gctcttcaac cttttccgaa attataagtc tctccagatt atcatcactt    780
cttgcaatat ggccgaaaaa ttttaaggcg gtggagaggc aagtagagga aagtcgagtc    840
tgaatattaa gctcttggaa gattgagtga tttgttctct gttccgtcca tgagatccga    900
agcattcttc tccagcacca catttcaaag gcgtcaatcc tttttctgtc gtccgatttc    960
attgtccatg tttcggatcc ctaattaaat atgggaaaaa ttaatgcacg tactaatctt   1020
attttggtgt tcttcgacaa ggagcgatct ttccagattt tcgataatcg actcatagcg   1080
tttttggcaa tgcctattct cctacgtatt tctgtttcac aacatcctgt attactgatg   1140
taggatccta gataatcgaa ctcgttaacc acttcaaact ggtctaaggc ccgtgttgtc   1200
tgaagtgaat ttaaatattg ttattaagta tattcaaatg ggaaataagc cacaatttta   1260
cctaaaaatg attttattaa cgtttcgacg cccaagtcgg gtgtcgttct caaaatacaa   1320
aataatacta aataaacaaa aatggtgttg cctagtaaaa aattcttcca ataatttatt   1380
taatctgact catttatatc ggcaattcag acacgtatta tacattttaa agtagacgac   1440
tttaaaatga tattgccaat attgatgagt tgcgttcctg ggactatgaa tttaaatatt   1500
ctactatcat aatttttgtt ttttgtttat tgatcttgag accacatcta ttgctttcgg   1560
cttccactag ctgcagcaga ctggacattt cttcttcgga tgcagttatt aatggtgtat   1620
```

```
catctgcata tctgagattt gagatcttct ttcctgcgat agaaataccg ccattccatt   1680

tgtcgagtgc ttttctcatt atatattccc catataataa ccatagcgcg ctaataaaca   1740

cctatatatt tctatttcta tatctatcta tctatccttt tttcagccaa cgtctgcagt   1800

ccttcctgtt ctaccattct ccatctttaa cgtctcgtct ttccatggct tcgtacactt   1860

catccctcca cgatattcgg ggtctacctc ttcttctctt tcctattggg ctccaatccg   1920

taatctttga tatccacctt gtatgatctg ctcttctcac atgtccatac caaattgaac   1980

gtttttcttc gatgtagttg attatgtctt gttctagtgc cattcttcgt tttatctccc   2040

c                                                                   2041
```

<210> SEQ ID NO 73
<211> LENGTH: 523
<212> TYPE: DNA
<213> ORGANISM: Diabrotica virgifera virgifera

<400> SEQUENCE: 73

```
gggggtgtag ctttccgcag caaaaagata ggtggttagg cattattttc taaaaaccac     60

atggatgaat tgttggcaaa ttcagcccta gaggctgaaa aatttaagcc aaccgtagta    120

aataagctta ttgatctaaa ttatgactta ggaagccttt tagcacaaga cacaaatgaa    180

tttgatacaa atttattaag gaggcagaag gaagattatt tgcttaattt agctagagat    240

aacacccaat tactattaaa tcaaatatgg gacttaacta cagaacgcct agaagaagct    300

attgtagtga aattaccact tcaaataact ttattaccta ggatgaaacc actacctaag    360

cccaaacctt taacaaagtg ggaacagttt gccaaaacga aaggtataca gaaaaagaaa    420

aaatccaagt tatcatggga ccagcaactc aaaaagtggg taccctaata tggatttaag    480

cgagcacaag ctgaaaaaaa aaaaaaaaaa aaaaaaaaaa aaa                      523
```

<210> SEQ ID NO 74
<211> LENGTH: 473
<212> TYPE: DNA
<213> ORGANISM: Diabrotica virgifera virgifera

<400> SEQUENCE: 74

```
gggaaagtga attcactaac tatttgagta atttaaatgt caattgacct tagtttacca     60

gagctgccta tattacaccc aaggattacc gttgtgggag tgggtggtgc tggtggaaat    120

gctgtgaata acatgatcca atccaatttg caaggagtaa attttgttgt agcaaatacc    180

gatgctcaag cgttagagaa gtcattatgc gataaaaaaa ttcaactggg tattaactta    240

accaagggtc ttggtgctgg tgccttgcct gatgttggca aaggtgcagc agaagaatca    300

atcgatgaaa ttatggagca tataaaagat agtcatatgc ttttcatcac agcaggaatg    360

ggcggtggta ctggaaccgg tgcagcaccg gtaattgcaa aagcagccag agaagcaaga    420

gccgcagtta aggatagagc gccaaaaaaa aaaaaaaaaa aaaaaaaaaa aaa           473
```

<210> SEQ ID NO 75
<211> LENGTH: 409
<212> TYPE: DNA
<213> ORGANISM: Diabrotica virgifera virgifera

<400> SEQUENCE: 75

```
gggagaaatg gttactttga acaagattta gtactaccaa atgttagtgt atatattatt     60

ctgcacgcat taacaattta tggattttat agaataacta ctactgaagt taaggggtca    120

gccatattat tcagtacttt tattggcatg ttggcaatat taggggtcac agctggagcc    180
```

-continued catcgtcttt gggctcatag aacttacaaa gcaaaactgc cattacgagt atttttaatg 240
ttgttgcaga cagcggccct tcagaatgat cttttcattt gggttagaga tcacagaatg 300
caccacaaat atacagacac caatgctgat cctcacaact cgaacagagg attcttcttt 360
tgtcatgttg gatggctatc aaaaaaaaaa aaaaaaaaaa aaaaaaaaa 409

<210> SEQ ID NO 76
<211> LENGTH: 1532
<212> TYPE: DNA
<213> ORGANISM: Diabrotica virgifera virgifera

<400> SEQUENCE: 76
ggggaagaaa cgtcaattga atcaactaga cggtgatgtg ttcagtaatt gaatgtaaaa 60
tttaaaataa tgttgaaatt aatcaccttc atattcataa tagtgaccgt caatgcagca 120
gaaagaatca acaataattt aatttataaa aatgtggata gaaccataga tttaacgtca 180
cagttagtaa aaatcaccag caccataact cttgaaaatg ccggcgcaga ccctatcaag 240
aattttctac tggcggagca accaaattta gttggacaga tagcatttaa aggtgccaaa 300
gactctgcca agcaagattt aaacgtctta acagcccaag tagaaaacca gagcgataag 360
agattccaca aagttatctt gaggcagaat ttggaaccgg gccgtactgc aacagtggtg 420
gttgaagaaa tactcattaa aagtttaatt ccatatccac atagtatttc ccagaaagag 480
aagcagttag tgaggtattt tggtaatcat tatatttata caccatacac agtggttaaa 540
caaaaaactg atgttacatt aagctctaga agtattgaaa attattctaa attgaaacca 600
gttactcaga cagatagtac aatacattat ggaccatatg gagaaattgc accttttgct 660
gtggatgaac tgatagttca ttacgaaaac aatgctccat tttgacagt tgtccatcta 720 gatagaacaa ttgaaatatc tcactggggt aacattgcag tggaagagca aattgaaatt 780
aaacacacag gagctacatt aaaggggcca ttttcgagat atgattacca aagagacact 840
agtagtacac atcacagtat taaatcatac actactgttt taccagccac tgctcatagc 900
atttattaca gagacagcaa tggcaacatt tctacttcag ctgtaaaaca ccgtaaggat 960
tggatagaac ttgaactgag accaagattc ccactttttg gaggttggca aagttcttat 1020
actctcggct acagtgtccc cagttaccag taccttttca aggctgaaaa tggagataat 1080
gtattagcta tgaggctcat tgaccatgtt tttgacgata tgtatgttga agaagttgtt 1140
actaacgtag ttcttcctgt tggagtcact gatatcaaaa ttcgaccacc ctatgatgtg 1200
gagagactat cagatgatgt tacttacaaa tatttggata accttgggcg taaagttata 1260
agactgaaaa agagggacct gattgaacaa cacattcaag atttggaaat tacctataaa 1320
tggcaaccac gattgttgtt acatgagcct ttgctgttat cgttggcact ctttattttg 1380
tttgtagctg taattatctg ggtccgattg gacttttcac ttgcagtgcc tgagcacagc 1440
aaaagagaat aactttttgt acatctatat taacattttt tgttaaataa attatgagat 1500
tgaaaaaaaa aaaaaaaaaa aaaaaaaaaa aa 1532

<210> SEQ ID NO 77
<211> LENGTH: 107
<212> TYPE: DNA
<213> ORGANISM: Diabrotica virgifera virgifera

<400> SEQUENCE: 77
ggggatgact tcaatctttg gctatcgagg gccaacgagg aagaacgaga aagaggtggt 60
aaccatggtg acgtaagaaa aaaaaaaaaa aaaaaaaaaa aaaaaaa 107

<210> SEQ ID NO 78
<211> LENGTH: 985
<212> TYPE: DNA
<213> ORGANISM: Diabrotica virgifera virgifera

<400> SEQUENCE: 78
ggggattgaa aggtggtacc gggactgggt gagaggctag ctagatacat acctacctca 60
tgtctctttt taactaactc ttcttgtatg tgtacgctat tttaaggctt tatgcgcaca 120
ttgatatctt gtagtgctat tataggattt tgtttatttt tcattaaaaa tgggtagaag 180
acaaaataaa taccaagatg tatccgagga tctaccggaa agaggacctg tggagagtct 240
gatctactgg cgtgatccca agaaatctgg tccagtcttt ggaggagtcc tcgtagttct 300
actcgctctc acatatttct ctctaatcag tgtggtagcg tacgtttcac tcatcgccct 360
cggcgtcact ttagctttta ggatttacaa aagtattgta caagctgttc aaaagactgg 420
tgatggacat ccattcaaag aatatctgga acttagaaga ttattcttgg tcgaagattt 480
ggtagattcc atcaaattcg cagtattgtt atggactctt acctatgtgg gagcgtggtt 540
caacggaatg actctaatta ttctcgcttg ggtcgccctc ttcactcttc caaaagttta 600
cgaagtgaat aagactcaaa tcgatgccaa tttggagatt gttcggacaa aattggctga 660
aattacttca aagataaagg cagcaatacc gatgggcaag aaagccgaag aaaagaagga 720
acaatagatt taacaacatc tatcagacta tattactata catatattaa tttattgttg 780
tttctttatt ccattaaacg ttcttatgta atgtttctaa atataattag tgtacatata 840
taagatgtta ttttaatgtt tttttatttg aattttttga tgttatttat ttcttgtaat 900
acatagagtc gaagaagaat atagaattta acataataaa tgtgttgcag agaaataaaa 960
aaaaaaaaaa aaaaaaaaaa aaaaa 985

<210> SEQ ID NO 79
<211> LENGTH: 1829
<212> TYPE: DNA
<213> ORGANISM: Diabrotica virgifera virgifera

<400> SEQUENCE: 79
gggggtatat atcaatgata ttacatatcg acctacgttt cacttaatgt tttgatttga 60
cttgtttgca aataaatcat gacgtttgtg caaagatata atggaacagc tatgaaataa 120
ctaaaccaca ttcaaatagc aaattcccaa ctaaactcct ggacaaaatt aacgcaccac 180
tttaattaat ctaaatattt acaatatgaa cacaaaataa aactaagtta cactggaata 240
ataataataa acacctacaa ataagtccaa catgacttta tcatgacctt aatttgcctt 300
atgtttcttt aaaaatttgt ttttgccgga aatgcgtaaa taagctagca taactctaaa 360
ttgcaaaaag aaaaaaatca gtaaagtaac acaataaatt gcatctgggt caacaataat 420
accgtgtagg cccacctaca cggagactgc atttatgcgt caaagcatgc ttgatatcaa 480
atgttcaaca aaagcttgcg gaatattctc ccattcttca ataacggcct caatgagttg 540
gttgtgattg acaatagggg gtctacaact tctaatcttt ttttgagata gttcgataga 600
tgctctatag attgatgtcc ggactgttag gtggccactc taataataga atatcaatat 660
catgtaggta accaataaac tgtcgagcca catgaggacg agcgttgtct tgcatgaata 720
aaaaattagg tccaagaaac ggagcaaaaa gcattacatt ttcgacaata atgttgtcta 780
agtaataatg ggcattcata gacctcgtac gtatggggac caactccata cgagcttaaa 840
aacaaattcc ccccaaaaca ttttagagcc accaccaaag gtagtttagg agagatattg 900
cagctggcaa acctttctcc tcgccttcgc cagacttcgc cagcttttag gcgttgtaca 960
ggacttatat tatacataca cgtaaaattt tctttttatt aataatatag tgaaatgcat 1020
aatatatagt tattttggga taaattagga ttaattattt ttaatacaat tagtaaatta 1080
ggtctagttt ttcgtaatat tcatttcaag aagcatttac ttgacaagtt acttgatatt 1140
ttaactactg ttacatttta tttttttga aaataaatga actttgattt aaatacctag 1200
atagaacttt taaaaagtgt ttacgatttt tatttacata ataactattt ttaactcaat 1260
gcgagtacat atatacataa atctattttt aacttgaacg gatcaaaatg ttatatcagg 1320
cttttatttg gcataaagta tattacattg tggttacctg accctgaaat tacgagtcag 1380
aaatacatac atcaggaatt tgctgaatag agttttacgc attacataag acataaaaaa 1440
tgactgaaat tacacactag gaaaggtgaa ttagaattta atggaattac gataatgaag 1500
aattttgaga atatattgaa ataatattat tgaaaatata agaaacgaca aacaaatcaa 1560
cgttttaaag aagaagaaag gaaaatacaa acatgatgga caagaataag tttcacggaa 1620
aatatgagtt ccgatattat gggaccgatg aatcaagatt tagagaattt tttacaaagg 1680
acaagacaaa gagaagaatc ctaaaaagga aaataaaaaa aaaaacatga agataacaaa 1740
gaaaataaaa ttatttatgt acaaggatat acaagaattt ttatacaatg attttaagaa 1800
aaaaaaaaaa aaaaaaaaaa aaaaaaaaa 1829

<210> SEQ ID NO 80
<211> LENGTH: 1307
<212> TYPE: DNA
<213> ORGANISM: Diabrotica virgifera virgifera

<400> SEQUENCE: 80
gggaataaaa aatttatttt atttatattt ttatttattt taaaataata aaatattttt 60
tagtaaaagt aaagaaaaat tttatttaat gatagttaat tagtattgtg agagaatatt 120
ttatttttat aaaagaaaaa tttatttttt gtaccttgtg tatcagggat tattaattaa 180
taattatata tttattattt tcgaatttaa aagagctaaa aaaattaaaa tttttattgt 240
aaaataaata ttttaaataa tttttttgta atgaaatgtt attcgttttt aaatatatct 300
aattttttaa gaaataaatt aaatttattt attaacaata tatttataat taaatatttt 360
tatattatta atattaaata tttttaggga tgagcttaaa aataaaattt tattaaaatt 420
taatttttaa ataaaaatta ggattaaaaa ttttcatatt ttaaaatatg ttattattta 480
tttttatata ttattatttt tatttttta taatttttta ttaaaatata aatttaaatt 540
atttaaattt agtaatgatg ataatattag tattaaaaaa ttgtatattt agtaaaaata 600
tataggttta ataaaggaat tcggcaacat ttttttcacc tgtttattaa aaacatgtct 660
ttttgtatta aatataaagt ctcgcctgcc cactgattaa tttgaatggc cgcggtattt 720
tgaccgtgct aaggtagcat aatcattagt ttttttttatt gaaagctgga atgaagggtt 780
ggatgaaaaa aaaactgtct ttatttaatt tataaagaat tttattttta agttaaaaag 840
cttaaatttt tttaaaagac gagaagaccc tatagagttt tataaaatta ttaataagtt 900
tttttagtat taaatttatt tatataataa atttatttaa ttggggtgat taaaaaataa 960
atttaacttt ttttatatta ttatattaat taataatttt ttgatccaat tttttttgatt 1020 ataagaataa attaccttag ggataacagc gtaattttat tggagagttc aaatcgataa 1080

-continued

```
taaagattgc gacctcgatg ttggattaaa gtttataatt ggtgtagcag ctatattatt   1140

aagtctgttc gacttttaaa attttacatg atctgagttt aaaccggtgt gagccaggtt   1200

ggtttctatc tttaatttat taatatattt tagtacgaaa ggaccaaata tataaaataa   1260

tttttatatt tagacaaaaa aaaaaaaaaa aaaaaaaaaa aaaaaaa                 1307
```

<210> SEQ ID NO 81
<211> LENGTH: 730
<212> TYPE: DNA
<213> ORGANISM: Diabrotica virgifera virgifera

<400> SEQUENCE: 81

```
ggggattctt ttgtgaatgt ttgcttcgcg ttctcccgtt taccgttccg tgttgacacc     60

gtagaatatt gactgatctg tagtttgaat tattttttaa aaacaatgat gtgttcatga    120

actattttct ttgttaatgt gtaaatgttg caacaagctg atctaaaata gagagcaatg    180

gaatctgcga tggaacagtg cgagaccaag cctttggaaa ctctatcaag tacattaaag    240

atgtttgaca cttttaaatc tacggaagaa gaccatgaat cagacgagga aagctttcat    300

cttccgttat taggatgtga tgatgaagcg gaaaacggca tggaaatatc tgaactaaac    360

gaagaagatg aagatgccat actaaataag ttcgacacac gcgatgaagg aatggacgtg    420

gatgaatgca gcaacaaaaa agacagcgat gtttctaaaa acaatgttgt agatgaagtt    480

aaacttagtg aagaagaggc aaagctagat ggtatagata atttaaataa agataatcgg    540

atagataatt taaatggaga tgatgaatta ttaggaaata atgagatttt agaagataaa    600

acaacagaaa gtacccctga tgataccgaa aataaaatcg aaaatgaaat aaatgaaact    660

gagcctggtt gtgaagaaga ctcaaaagag accaatatta ccaaaaaaaa aaaaaaaaaa    720

aaaaaaaaaa                                                           730
```

<210> SEQ ID NO 82
<211> LENGTH: 1761
<212> TYPE: DNA
<213> ORGANISM: Diabrotica virgifera virgifera

<400> SEQUENCE: 82

```
ggggagtgaa tgagctttca ttcgtttcgg cgagggatta gattttgtac tcgtgaattg     60

ggtcaggtta tttggcgcca tgaatcttct tggaaaagct ctcgtttttg tattgatggg    120

taagtacaca ggaaaattgc taaagaaaat tttgagcgtt cggttgggag ttgttagact    180

gaaaatatta aacagcttac atagcaacac ttacacgact ataactatta ttttaagctt    240

tttataaatc cttaaaaacg ttcaaacata aaataaaata ttggtattga taacggtata    300

ttatattttg catttttttgc tttaagctaa ttgatggaaa tagtatccat atgttttagt   360

cttttaatgc cctattatac ctgttgcata actttatata atttagaaat atcttatcgt    420

gatcattttc tgtttaatcc tgtccaggga ataaaatttt tcttgggact ttcaataatg    480

caggtatctg acaacttttt tagttatgta ttgtagaccg atagaaagaa aacctgcctt    540

gtatcctgtc gagtgttcgg agctgccttt taattattac tattaacaat ttagtgcaaa    600

aaacgcgatt ttttttcgat tttaacacta aattaaaaaa atagattttc cagaatattg    660

aaaaagcttc aaaatggaga ttttttaaag tgaaaatctt tttttgacag atacttgcat    720

tatttatttg cttgtttccc tttagtaatc accttaatat gaaatttaaa aaaacttatt    780

ttttgacgtt gttttgcaac attttcattc acctttataa aaatgttgtt tagctcttta    840

cttttaactg ccgaattttg ttgcatgttt tgttgaattt tgattgtttt gtgtgaaaat    900
```

-continued ttgaaacata aacgggcttt tgaatttgat gactgctggt gaagtaggta ttgagactta 960
gtttcttatt ttacacatag ctattaacaa tattggtatt gaatgataga taaaagtttt 1020
tctttttacc acagtcagat tttttataca agtgtactat tttgacggta tacaccacag 1080
tgacggtata caccatttta ccacagttag attttttata caagtgtact attttgacgg 1140
tacacatgtt catataggta tcatctttct tcttagcttt ctatagtcca tgtatgggca 1200
tggcctcctc taactgattc catcaatctg tatcctaagc aacttacttt caatttgttc 1260
tggctattgt cagagataac tagaagaaga atccgaataa cttcggcagc agtatgaaga 1320
ctgggtgttg tgttgaaaaa caaacagata tcagtataaa gaaaatgata ttcaacaact 1380
agttgtattc tgccagttat gatctatgga gcggaaacta cgacacttac agagttatca 1440
gccaacagat taaaaacacc acgcagggcc ttgaaacgag ctatgtctgt gagagaacat 1500
aatatatgaa atgaggacgt gaaaagcagg gcgaatgtgc aagatgtaat tggaagaact 1560
gcccatatga actggaactg ggtaggacac ttggcatggc aaaacaacga aaggtgaacg 1620
agaaacattg tactttggag accacgcgag ttcattcaga gtagtagaag aagaccagaa 1680
aaatactggc tagacgacat caaagcaaaa gtgggagaca ctggcaccaa caaaaaaaaa 1740
aaaaaaaaaa aaaaaaaaaa a 1761

<210> SEQ ID NO 83
<211> LENGTH: 557
<212> TYPE: DNA
<213> ORGANISM: Diabrotica virgifera virgifera

<400> SEQUENCE: 83
ggggaggtat tctgagtttg ggtattttaa attgataaag tagctagtta agtaagaaga 60
caaaatgtat aaagtagctg ttttagtttg cttccttatt gcagcaataa atgctagccc 120
atacggaact tatgggcatc aggataaaca tgtccaacca gttcctcatg ttcctgacca 180
tccccacggc tcccatggcc atgaggaaca cggcggatat ggtcctcatc atggtggtca 240
ccaagattat acgcacggtt ctcatggtca tgaggaacac ggcgaacatg gttctcacca 300
cggtggtcac caagattata cgtacggttc tcatggtcat gagcaacacg gcgaacatgg 360
ttcacaccat ggtggtcaac atcccggtgc atacggtcct catggtcatg agcaagagca 420
ccaacatgag tctcaccata cgtacggtgg acacgcatat taataattgt tataatgtaa 480
catgtttgac tgttctttaa atttaaataa ataataatat aaattgcaaa aaaaaaaaaa 540
aaaaaaaaaa aaaaaaa 557

<210> SEQ ID NO 84
<211> LENGTH: 486
<212> TYPE: DNA
<213> ORGANISM: Diabrotica virgifera virgifera

<400> SEQUENCE: 84
gggataagaa attggaatta agcccaaatt ctctcgaaac aatttttgtc gtaacattat 60
gctgtaataa ctgttgaaaa gtaatggtgg aaattcggta tttttagata tttatattaa 120
ataataattc gtaggtgaat gcaagttatt atctagaaaa tttgaaggta acaatatagt 180
ttcattagaa tcatttcagt aactcttttc gcaatttttg tcttaaaaat aattgagaaa 240
cgctgtaggg ttaaaaattt aagttacaag aagttagatt ttaggtgtag gcttaatgtt 300
ttgttttaaa tactgctctg gatggtgcag tgaagatgaa cgtaaaaaga aagtaagccc 360

-continued aaattctcaa ttgaaaaatt tttactttca tattcgctgt ggcattgagt tgatgtgaag 420
aaatggtgga aataaaattt ataattgtat atatacaaaa aaaaaaaaaa aaaaaaaaaa 480
aaaaaa 486

<210> SEQ ID NO 85
<211> LENGTH: 492
<212> TYPE: DNA
<213> ORGANISM: Diabrotica virgifera virgifera

<400> SEQUENCE: 85
ggggattttt tagacatttt gatattttgt cggtatacac gtttcgtgtc tcaagactta 60
aaaatgcgtt acgtggctgc ttacttattg gccgttttgg gcggcaaagc ctctcccaat 120
gctgcagatc ttgaaaaaat cttgggatct gtaggtgttg aagctgaagg agaaagagta 180
aagaaagtca tcagcgagct cagtggcaag tctgttgaag aactcattgc tcaaggtcgt 240
gaaaagttga gctccatgcc agttggtggt ggtgccccag ctgctgccgg aggtgccgct 300
gctgctgctc cagctgctga agaaaagaaa gaggccaaga aggaagaaaa gaaggttgaa 360
tctgaatcag aagacgacga catgggcttt gctctattcg actagactca ttagttgtaa 420
gatcaacctt gttttgtacc ttaatatata ttttttaagt caaaaaaaaa aaaaaaaaaa 480
aaaaaaaaaa aa 492

<210> SEQ ID NO 86
<211> LENGTH: 444
<212> TYPE: DNA
<213> ORGANISM: Diabrotica virgifera virgifera

<400> SEQUENCE: 86
gggagcactg ataaaaaaga tggtgtcgtc acttcgctta acatgaaatt ctgtctattt 60
taatatagaa gtctatggga agaacctgga caagagatta tgtccagcag tgaattaaaa 120
tgaccatatt aattactgac agttttttta agaaatgttt ttttagtagt agtgtttata 180
atttaaatgt ctttggtgtt tggaaattgg cctacacatt gtcccatgta cctatgtgaa 240
acccacgata aaaaatatcc catatgtttt tgtacaaatt acaactgtag ctataattct 300
tctatttgac tgatcacatc ctttgacata aagaaaaaac ttaaccttga ttatgatcta 360
ttcttaaacg aagcaacatt atttatttat acctatcgct tcttatagtc ttacaaaaaa 420
aaaaaaaaaa aaaaaaaaaa aaaa 444

<210> SEQ ID NO 87
<211> LENGTH: 340
<212> TYPE: DNA
<213> ORGANISM: Diabrotica virgifera virgifera

<400> SEQUENCE: 87
gggcattcac aaaattaggc ataacgtata tgttactagg tctcaaattg cacctaaatt 60
tcctaaaaac attagtgaat tccatacgtt attaaattct gaagaaataa aaactaatag 120
ggggaacgtt ttcttataaa aaatgacgat aataatcaga tcatgttctc gtgtgaaagc 180
aattttttgg atttaagaca aatatcgaca ttttatattg acggcacttt tgaatactgt 240
ctaagacagc gattctcaat ctgtggtaca tgtacaactg gtggtacaat tcattacttg 300
cggtggtaca caaaaaaaaa aaaaaaaaaa aaaaaaaaaa 340

<210> SEQ ID NO 88
<211> LENGTH: 1447

<212> TYPE: DNA
<213> ORGANISM: Diabrotica virgifera virgifera

<400> SEQUENCE: 88
tttttttttt tttttttttt tttttttttt cttagtacta gataggattt atttatctgc 60
ccagttacaa aatagttata gtaagtaaat ataacaaata ataaataatt ataaggtgtt 120
ataagatctt aaaagtctgt ctggcagtta caaccacggt cgcatattat ttaagaactg 180
caaagatgta aacacagtac aaacaacatg aaaaatagct tattaggtat gaattgatta 240
aatagcttag aagcacttgc ggtggacaat tcctgggccg gattcgtcgt attcttgttt 300
ggagatccac atctgttgga aggtggagag ggaggccaag atggatccac cgatccagac 360
ggagtatttc ctttctgggg gagcgatgat cttgatcttg atggtggatg gagcaagggc 420
ggtgatttcc ttttgcattc tgtcggcaat acctgggtac atggtggtac ctccggagag 480
aacagtgttg gcgtacaagt ccttacggat atcaacgtcg cacttcatga tggagttgta 540
tacggtttcg tggataccgc aagattccat acccaagaag gaaggttgga agagggcttc 600
tgggcaacgg aatctttcgt taccaatggt gatgacttgt ccatcaggca attcgtagct 660
cttttcgagg gaggtggaag cagcagcggt ggccatttcc tgttcgaagt cgagggcgac 720
atagcagagt ttttctttga tgtcacggac aatttccctt tcagcggtgg tggtgaatga 780
gtaacctctt tcagtaagaa tcttcatgag gtagtcggtc aagtcacgac cggccaagtc 840
caaacggagg atggcgtggg gaagagcgta accttcgtag attgggacgg tgtgggtgac 900
accatctccg gagtccaata caataccagt ggtacgacca gaagcgtaca aggagagtac 960
ggcttggatg gctacataca tggcgggtgt gttgaaggtt tcaaacatga tttgggtcat 1020
cttttctctg tttgccttgg ggttgagtgg agcttcagtg aggaggactg ggtgttcttc 1080
tggagctaca cggagttcat tgtagaaggt gtgatgccag attttttcca tatcatccca 1140
gttggtgatg ataccgtgtt caatggggta tttcaatgtg aggatacctc ttttgctttg 1200
ggcttcatct cctacgtatg agtctttttg tcccatacca accatgacac cttgatgcct 1260
tgggcgaccg acgattgagg ggaagacggc acggggtgcg tcatctccgg cgaatccagc 1320
tttgcacata ccggatccat tgtcaacgac aagagccgca acatcgtcgt cacacatgtt 1380
gtcttttgtg gttgatcact gctcactaga cagaaaaaca cagctaataa gcttgaatgc 1440
gaccccc 1447

<210> SEQ ID NO 89
<211> LENGTH: 1444
<212> TYPE: DNA
<213> ORGANISM: Diabrotica virgifera virgifera

<400> SEQUENCE: 89
gggagtcgca ttcaagctta ttagctgtgt ttttctgtct agtgagcagt gatcaaccac 60
aaaagacaac atgtgtgacg acgatgttgc ggctcttgtc gttgacaatg gatccggtat 120
gtgcaaagct ggattcgccg gagatgacgc accccgtgcc gtcttcccct caatcgtcgg 180
tcgcccaagg catcaaggtg tcatggttgg tatgggacaa aaagactcat acgtaggaga 240
tgaagcccaa agcaaaagag gtatcctcac attgaaatac cccattgaac acggtatcat 300
caccaactgg gatgatatgg aaaaaatctg gcatcacacc ttctacaatg aactccgtgt 360
agctccagaa gaacacccag tcctcctcac tgaagctcca ctcaacccca aggcaaacag 420
agaaaagatg acccaaatca tgtttgaaac cttcaacaca cccgccatgt atgtagccat 480

-continued

```
ccaagccgta ctctccttgt acgcttctgg tcgtaccact ggtattgtat tggactccgg    540

agatggtgtc acccacaccg tcccaatcta cgaaggttac gctcttcccc acgccatcct    600

ccgtttggac ttggccggtc gtgacttgac cgactacctc atgaagattc ttactgaaag    660

aggttactca ttcaccacca ccgctgaaag ggaaatcgtc cgtgacatca aagaaaaact    720

ctgctatgtc gccctcgact tcgaacagga aatggccacc gctgctgctt ccacctccct    780

cgaaaagagc tacgaattgc ctgatggaca agtcatcacc attggtaacg aaagattccg    840

ttgcccagaa gccctcttcc aaccttcctt cttgggtatg gaatcttgcg gtatccacga    900

aaccgtatac aactccatca tgaagtgcga cgttgatatc cgtaaggact tgtacgccaa    960

cactgttctc tccggaggta ccaccatgta cccaggtatt gccgacagaa tgcaaaagga   1020

aatcaccgcc cttgctccat ccaccatcaa gatcaggatc atcgctcccc cagaaaggaa   1080

atattccgtc tggatcggtg gatccatctt ggcctccctc tccaccttcc aacagatgtg   1140

gatctccaaa caagaatacg acgaatccgg cccaggaatt gtccaccgca agtgcttcta   1200

agctatttaa tcaattcata cctaataagc tatttttcat gttgtttgta ctgtgtttac   1260

atctttgcag ttcttaaata atatgcgacc gtggttgtaa ctgccagaca gacttttaag   1320

atcttataac accttataat tatttattat ttgttatatt tacttactat aactattttg   1380

taactgggca ggtaaataaa tcctatctag tacgcaaaaa aaaaaaaaaa aaaaaaaaaa   1440

aaaa                                                                1444
```

<210> SEQ ID NO 90
<211> LENGTH: 993
<212> TYPE: DNA
<213> ORGANISM: Diabrotica virgifera virgifera

<400> SEQUENCE: 90

```
ggggagttcc tgtctagttt tgttgctgaa tgttatactc gtagaattga ttgaatcgaa     60

aaaaatattt aaaatgaaat ttaaattttc cgctgatgat gtaattgctg agaaaagaac    120

aacacaagga aatataaatc ttattaaacg atggctgttt gcagccgatg aaaaatatgt    180

accatctaaa ttatcagatg aattcatagt tctgtttcta ttgtcttgta acaatgacat    240

tgatgtgact aaaaagacta ttactgccta ctataaatta aggaaagacg cacctgaact    300

gtttgatgac agaacttccg agagagaaga tattcagaaa gccttaaaca cactgagaat    360

ggtaagcata ccaaatcgga cagacgaaaa ctatcaagta gtgtatctta gtctaaaaga    420

tacagatagc agtaactttg aactgaatcc cgttatgaaa gcctcattaa tgctaataga    480

tatagaacac cacaatagcc caccagatgg agttatgttt ctagctgata tgaaagggtt    540

cgggttttta cacgcgttta aattgaatcc aatctcgtta aagaaatatt tcaattatct    600

tggagaagga ataccaactc agttcaaagg aatgcattta atgaacggaa attatttcgt    660

ggatcaattg ttgagcattc ttaaggtgtt tatggcttca gaccttataa agagggtaat    720

catccatcaa gtaggctgga atccggaaga agcattccca aaaaaatgtt taccaaaaga    780

acttggagga gacctagaat cagaagacgt actttgtgaa cggacattac cgctgttcaa    840

ggatcgggaa tatttttgga aggcggaaga ggaactaagg aaaagtgtac ttaaataaaa    900

atgcgttaca tgtaatagta ttaaggaatt acaattattt ttggaataaa tatttatagt    960

gccaaaaaaa aaaaaaaaaa aaaaaaaaaa aaa                                 993
```

<210> SEQ ID NO 91
<211> LENGTH: 989

<212> TYPE: DNA
<213> ORGANISM: Diabrotica virgifera virgifera

<400> SEQUENCE: 91

```
ttttttttt ttttttttt ttttttttt ctccttccgt attaaatcga tcagttcttt     60

agctctcctt actttttctt cccctgacag ttctgcttct gcctcttctt tagtgtctgt   120

agtttctttt tctgttttaa cttcttcaga ttctgtatct actttaactt ctttatcctc   180

cttattttcc tcggctaccg taacttcttt acctttcgta ctttctgcgt tctcttcttt   240

tgctggttct tcttcttttg ctggttctgt atgcgtttct gacggactcg gttgctcttc   300

ggggggttta tcttcggatg atttttcaat ttctgtttcg gaggggctca attcttcttc   360

ggggggactt tcttcggacg tattcagagc attattatca ctttcgactc gtggtgtctc   420

accagcttgt tcatgtgcca ggaagttttc tgattcagct gaaatagaat gaactggggc   480

tgtactgaat cctgccctgt tcaagacatc atccacttta gcagaaactg tttctaaatt   540

agtacttcct gtaatgatat ctaaaggaac acccttctga ccaataaaat atatcgaggg   600

tacactcggt tctttataaa tttcgctaaa ctgctggtga gctgtagagc ccgcaattac   660

tttgatagct acaaagtgat cttgttccag tttttctcca aggtcgccat tattgatgag   720

gtctgttatt ttttgtgact tttcgtcagt accttcaata tacactacaa aaacggctcc   780

tttcgattta gaaaaagcaa ccgcatcggc tatttctcca ctgtaccact tcattttaaa   840

aaaaaataag ttagtttaga cttttacaac aataaaatac tagcagactt ctaacaatta   900

aaaaagtaca catcagttat cgcaactaca aacacaaaat acaattttaa acgtcaccgt   960

caccggtcac aatctgtcat gtactcccc                                     989
```

<210> SEQ ID NO 92
<211> LENGTH: 817
<212> TYPE: DNA
<213> ORGANISM: Diabrotica virgifera virgifera

<400> SEQUENCE: 92

```
ggggatggcc ttttccggtt cacgccgtcg ttcagcaaga gcttgcgatt tttatttttg    60

aaaaatagag agtattctct aatatttaag gacagcatgg aagacgattg ggctgtggat   120

aatcagagtg gtggagttgt cgccccaaaa attgcagaac tacctgaaat taagttgttc   180

gctagatgga actgcgatga tgtccaagtt tcagacatgt ccccttcagga ctacattgca   240

gtgaaagaaa aaaatgcaaa gtatttaccc aattcagctg gtagatatgc tgcaaaaggg   300

ttccgtaaag cacaatgccc aatcgttgag aggttaacaa actctctaat gatgcatgga   360

cgtaacaatg gtaaaaaatt gatggctgtc agaattgtta aacatgcttt tgaaattatc   420

catttactaa ctggagaaaa tccattacag attttagttt ctgctattat caattcagga   480

cctagagaag attctactcg tattggtaga gctggtactg taagaagaca agctgttgat   540

gtgtcaccct tgagaagggt taaccaagca atttggttgc tctgcacagg tgctagggaa   600

gcagcattcc gtaatattaa aactattgct gaatgtttgg ctgatgaatt aatcaatgct   660

gccaagggat catcaaattc atatgctatc aaaaagaagg atgaacttga acgtgtagcc   720

aaatccaacc gttaaattta tttctcattt tatattttat ttccaataat aaatatggat   780

aaaacacaaa aaaaaaaaaa aaaaaaaaaa aaaaaaa                            817
```

<210> SEQ ID NO 93
<211> LENGTH: 1186
<212> TYPE: DNA

<213> ORGANISM: Diabrotica virgifera virgifera

<400> SEQUENCE: 93

```
ttttttttt ttttttttt tttttttttc gcaatgcgga gacaaattta taaaaagagg 60
acttgtgcaa aatattgctg aacatgtcaa aagaaccaac agaaattgtg ccatccactc 120
cctatattaa ccaaaacagc agtacaaaga aattaacgtt tatttaaata atatctaagg 180
atttttctta ataaaatgac aacacagtgt caaatctata agcgctaata tattttataa 240
ctttttctaa gtttggaccc aaaagtgtat actgtaaatg tttatgttta tatacagtgt 300
gtcatttaaa gtagaaacat ccctgtaaca tttgaaatcc ttaaacattt caagagtttt 360
tttaataccg tgtgtttact tttaaattag atatagatag gaatacatcc aatacatggc 420
aacactgctt cctcgtttcc cacacctgag tcgcgccaat tgactcagtc attcgtcgat 480
tctacagtag caatgcaact tattctcata aaaaatgttg ccgattttag cgattccttt 540
agtctcctat ccctaatcga aaactaaacg tatggtaaag taataaaaga ggtaattcgg 600
gacaacattt aaagggttca tttaaagtac catatcataa tcatcatcat cagcctgttt 660
taaatccagt gcaggacata agcctctcct gtttgtatcc agaggccgtg cctctcctgt 720
acggttttgt gtagtatgga tccaattttt cgttatcttt catcatcttc caatcgtgta 780
ggtggtcttc ctctctttcg gttatctgtt cttggtatcc attcagttaa cttgcgtgtt 840
caccttctat ctttcatcct tgccatgtgg ccagtccatc tccattttag tctgcaagct 900
ctctccacaa aatctgtaac tctagttttg tttcgtagat cttcatttgt gatcttgtct 960
tttattttta ctcctatcat tgaacgattc atttttcttg tgctattctt agttttaaag 1020
cattcttttt gcagacagag tttctggatc ataggtcatt actggcagaa cagactgatc 1080
gaagactttt actctttaga ttaatcggta cattgctgcc tttaaatacg tttttaacag 1140
ctccatatgc tgcccatcca tgtgctattc ttcttgatac atcccc 1186
```

<210> SEQ ID NO 94
<211> LENGTH: 1033
<212> TYPE: DNA
<213> ORGANISM: Diabrotica virgifera virgifera

<400> SEQUENCE: 94

```
ttttttttt ttttttttt ttttttttg cgtagtctga cattgcgacc aggttttgta 60
gacgtcttga actattttg ttattttta attgttgaaa tctaaataga gcggattgaa 120
tattatcatt tactaccctg tgacaataat attattattg tcacaaaaca gtaaacaata 180
atattctcat tccaatgttc gaacaacaat gaatgttaat atagaccagg actaatctgt 240
aaaaattcgg atggcattaa aatttttgca gataaagtta ggtgacacct ttagtaataa 300
taattgaccc atgctccctc tcaaacataa ccggaacatt aataaaaaat caaaatattt 360
aaaaattcag aaaaagatcc attttttct gctttctttg cttatagctt taaaacggtt 420
cgttctggaa caaatccgta cagaaacaaa acagagacaa ttgaatcatg tatgatgtac 480
gaccggtcaa aaatgtctta aggtattacc ttttctgcaa aatagcaata aacacaaaat 540
aagggggcaa aacacgcgtg ttgttattca atgtctctta accactttgg tggcagttag 600
aaccttagta atccgcttag aaaattctta tagcttagtt aaatggtcta ccaaatttca 660
ctaaaatcga cctaacagat tctgcataat aaatttgcaa tataaatgtt tttaaaaaag 720
ttcaaatttc aaaatctttc tgaacaaaaa gtagacaatt tagtagttgg ctaatttttc 780
cacatacaaa aaggcactcc acccatctaa tacaccccac agcatcaaaa tcggaccatc 840
```

taaggggcct cagcaatgtt tcaaaaatac taacaacttt ccggctcata aacaaatagc 900
tttgtttaat aataaaaaaa taataatttt tagcaacgca aataattaat accggtatag 960
tttgacttaa tcttttaaat gctgtcagca gaattgctat tttatttttt aatcaaaagt 1020
tatcctcgtt ccc 1033

<210> SEQ ID NO 95
<211> LENGTH: 551
<212> TYPE: DNA
<213> ORGANISM: Diabrotica virgifera virgifera

<400> SEQUENCE: 95
ggggacatta atttcaagcc taggttctgg agaatattaa ttaacatttc ctgcggtatt 60
gttggatgaa cattagataa gagaagacgt tccgatggag tgactaatct acgtgttaga 120
agtacttcat tatttatttt tatggatcct accttattta gaaagtcatc aactacagct 180
ttacttgaaa gataaacgca tactcggtta ttagagattc ttgatgaata aataatattt 240
tctggttgga cgagtggtcc tagttgcaaa agataatctt gcaattttgc gccattaatt 300
gaactgaaga tgatggcttg ttctttcact ggtaattttg gagtagtttg ttgagatgca 360
atagtagagt acattagagt gttttgagaa gtggtaggag tttccattgt tgataaagta 420
ttattcatca tttaatgtta cttgaacgat ttattataaa catatttagt tagggttata 480
atatgtatgt tgtgactggc tgaatcacta atgtgtatgc caaaaaaaaa aaaaaaaaaa 540
aaaaaaaaaa a 551

<210> SEQ ID NO 96
<211> LENGTH: 1050
<212> TYPE: DNA
<213> ORGANISM: Diabrotica virgifera virgifera

<400> SEQUENCE: 96
ggggagaatt tatgaatata ggtaagcctt aatacactaa tttaagagtt taataattgt 60
atattatttt caaaaatgtt ttaagtgtgt gactttgtag agatattgtt ctgtgatctg 120
agcaggtttt gcacttgact ttttgagaat tgctacaaag gtcgattgca gcaattgtca 180
ggcgattgtg gaagtctgat atgataaatt aggagttcaa ccattacata aatatcatct 240
tcatcaatga gttttaataa ttcgatgtgc acatcttctg gtccagtaac tttgctatct 300
ttagtgttct tgatgacata gatgacttct tctcgtaata atggtggttg atatcctcta 360
tggtttctag tgacagtttt tctctttcct cattaattaa ttcttgaatg taattgatcc 420
agtgacacat tctctccaat tatatcagta ataattcatc atataacaat tcatcatatt 480
tccttcatca tttttgatgt tatttctatt aaaaatgtcc gtacctacat tatcctcctc 540
ctcctcccct atcctttatc cttcgtaagg atgtggtgac gttatggtat ttgacgaatg 600
gtttctatcc attcttctct ctcttgggcg cggtgtgctg cctcagacag agagtaaccg 660
gtggcgcatt ttatttggtc tgaccatcgg agtggctatc ttcctcgagt tcttttaccc 720
tctaccttgc cttcaaccac caacctctcc atgccttctc ttcgtctggt aatgtgtcca 780
aagtacctca atatattttg gttgatgatg gtggtaagcc tagtgttgat gtcgagttct 840
gataatattg agatatttgt gcgatgtgct acattatcca tattacactt aattaaatgc 900
acttttaaaa catttttttt tataataatt atgtaggtcg tttttttaat ttatcattaa 960
gctctaatca agttgagaga agccgaacct cagctatgta tctaatatta tacagtatgg 1020

-continued

```
tacaaaaaaa aaaaaaaaaa aaaaaaaaaa                                    1050


<210> SEQ ID NO 97
<211> LENGTH: 1391
<212> TYPE: DNA
<213> ORGANISM: Diabrotica virgifera virgifera

<400> SEQUENCE: 97

gggggaaaaa atgtttggat acaatgtatg tatacaagtg ggctttgatg atgtgttatt     60

gtgttttaag tgctaaaaat attttttat attatgttca caaaaaaaag catgtgtgtt    120

ggtgacattg ttaatcctcc tgtcagttaa gtcctttatt catcttaaac aataaacttt    180

taaaacatga gcttcaaaaa agagcataaa tgattattat tttaatgctt ttcaaaatgg    240

ggttttagat gtacacgata tatattatgt tttgcataaa tgatactttt attatatttt    300

tattatttgg tcttacttta ttgtagttat ttttttgata ttttttgtt cttactttgt    360

tattttttg tagattgtta atttgcaact aaacgatcta cttataatag cgttagtaca    420

aattaacaaa acgaaaccta atatctacca cgagttactc ggttaagacc atacagaaat    480

aaataaattg cttaattgca attaaaacag ccgtcaaaaa tgataagaaa attaagaaaa    540

acaatatttt ttctaataat aaagtaataa aggcagtttt tgtttttatt ctattcagag    600

ttggaccacc atctccatat agctatttca gcatcccatg catctttagt gaagctatgc    660

agtcacaact ctgaagcgaa tattaacaac cctgaatatt taagggaaac catcgcgata    720

caatgattcc accttttgag acgcaatcta gcgacatctc tcgcaaaacg aggaaaacaa    780

cgaaaagccc tagatacaaa gtttactact ttttaaacaa ttagaataat tgaaataaaa    840

atataataaa caatatttta aatccacgaa tttcgttaat aaactgcttt ctggctgcat    900

cctgtatatc tggctattta tatttagctt aatatttttt ctcttttaat atttggttca    960

agatatagag tgtttagaaa caaaattaca ctaagggcgc tcgcaaacac agccacttgt   1020

ggccgccacc ggtggcagtg ctgactgagg tttgtatgta ttttaaatgg attcggccca   1080

cacactatgt ttccggtgat cttcgagcga caagccacga caagctatgg cggtggccgt   1140

ttctggctac atgaagtcgg tggcgatcac aaaacagcca ttcgtccaga gagagaaaga   1200

gttaaaacaa catcataaga aagagcttgg atacaaaaat aggctaccag aatatatgaa   1260

ataaatagtc ggtctgttta gccatgaaga ggaaatggat gaagaacaac tacggaaaca   1320

aactgtaact cctaacttca aaattaaaac accatgtatt gaaaaaaaaa aaaaaaaaaa   1380

aaaaaaaaaa a                                                        1391


<210> SEQ ID NO 98
<211> LENGTH: 515
<212> TYPE: DNA
<213> ORGANISM: Diabrotica virgifera virgifera

<400> SEQUENCE: 98

ggggcttact tacctgtaaa cgaatcattc ggtttcactg ctgatttacg ttccaacact     60

ggaggtcagg ccttcccaca atcagtcttc gatcactggc aaatcttacc tggtggccca    120

atggaaccca gtaccaaacc ctatggaatt gtgcaggaca cacgtaaaag aaagggtctt    180

aaagaaggac ttccagacct ggcacaatat ctggataaat tataaacaac taagaaactt    240

aatttatgta cagattattt aataaaatta tttcaattta ctcaacggtt tttatagtta    300

attgtatttt tgatattttt attctgataa gttttcagtt ctctcaaatt gatggcaaca    360

ctagaaatga aataaactaa ataatctgac taatatttta tgtttgctat atatattttt    420
```

gttaacagtc cagatatttg tatatttatt aatttgacat caaaagtaaa tctgatgaaa 480
cattgaaaaa aaaaaaaaaa aaaaaaaaaa aaaaa 515

<210> SEQ ID NO 99
<211> LENGTH: 580
<212> TYPE: DNA
<213> ORGANISM: Diabrotica virgifera virgifera

<400> SEQUENCE: 99
ggggatgtta tacattactg aatattgttt gcttaagtaa taataataat acaaaagagt 60
catcatgaag ttcttggttt tcagcttggt ctttgctgtt tactatgcaa atgcagctat 120
tactcccgaa caagctgaga agatcaaaag tttccacaaa gaatgtcttc cagaatccgg 180
agttaatccc gaattggttc aaaaggcaag acaaggagat ttcgccaatg acgacaagct 240
aaaagcacat atcttctgcg tctccaagaa gatcggtttc caaaacgatg ccggtgaaat 300
tcaagtggaa gttctcaaag ccaaagtggg tgctgcctta gaagatccag ctcttgctgc 360
ccaattgatc ggcacctgtg ctaagcaaca agcaaatgga cccgaaacag cctttgaaac 420
cataaaatgc tatcacgaaa agacaccaat tcatcttagt attatttaaa tattttgatt 480
ttgttataat ataaaaaact tctttttgaa gagttgttat aaaataaatt ttttatcatt 540
atatgtacag aaaaaaaaaa aaaaaaaaaa aaaaaaaaaa 580

<210> SEQ ID NO 100
<211> LENGTH: 913
<212> TYPE: DNA
<213> ORGANISM: Diabrotica virgifera virgifera

<400> SEQUENCE: 100
ggggagtgtc aacaatgatt tatagcagat atctgtggat tgtgtgtgta gtgttatcac 60
tattttatca gacaaattgt gaatgcccta aaatatatac tcgcaatgaa tggagcgctc 120
gaaaagcatt aagtaccaga ccgttaagag aagatcctcc accatatgtg gttgtccatc 180
attcggccac tcgctcatgt ttttcagttg aagattgttc aaaacttgta aaaagcatcc 240
aagattacca tatagatcac aatggatggg atgatattgg ttacaacttt ttgattggtg 300
gtgatggaac tatatacgaa ggtagaggat atggtttaca tggtgcgcat tctattccat 360
acaacgcaag aagcttaggg gtttgccttt taggaagttt taaagatacg aatcctccta 420
atgtacaact gaaagcattg gaagactttt tgtcttgtgc agcagctgat cacaaaatta 480
ttgcagatta tcaccttatc ggacatcggc aagctgataa aacagaatgt cccggggatc 540
gagtgcatgc agttatcgaa aaatggcctc attttgaagc caatccacaa gatgcttccc 600
caaagaaact gtaaacatag cgaagttacc ttttctctta tggaataaac acctctctat 660
cgcaatgttt ttagattaca attattaata catgtaaata tttaaaagac tgtatatcta 720
ctcatacttt aaagatgtgc gaaaatatat cactatcttt aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaa 913

<210> SEQ ID NO 101
<211> LENGTH: 569
<212> TYPE: DNA
<213> ORGANISM: Diabrotica virgifera virgifera

<400> SEQUENCE: 101
ggggaggcgg tcgacatgtt tttttttttt tttttttttt ttttacattt atccacattt 60
tattctcaaa ataaaaagtg tacaattata aaattaaatc tacagcctag aacctcaatt 120
tttggaagaa ccatttgttc tttccttgct tataccttcc ctcaaatttg acacgggtct 180
ggaatctagc cttcttcctc ttcatggcat ctttgaggtc cttgggtaca actttcaagt 240
ctgatgccaa atctacagag tatctagtgg gcatgagatg gttgtagttc aatactttga 300
taaaaggctt gatcttggac ctcttgtgca ttttgccttt gcccatgcgt ttgtggattt 360
tccttgggta cctatcaatt ccagctacta aggcatgtcc gtattgttta tctgatgtac 420
cttcatcgta ggttttgacg actacggctt ttcggccggc gtatcggccc ccgaggacca 480
atacgacttt tcctgatttc attattttac ccattgtggc agtgctttga caactgctga 540
aaaaaaaaaa aaaaaaaaaa aaaaaaaaa 569

<210> SEQ ID NO 102
<211> LENGTH: 1350
<212> TYPE: DNA
<213> ORGANISM: Diabrotica virgifera virgifera

<400> SEQUENCE: 102
tttttttttt tttttttttt tttttttttt gaactaaaaa tgaaaataca tttttgggct 60
acgtaatatt cctatcagct cttttacagc tggaatgttg tatgtgctgc tcattattac 120
tgcgttcagc ggtttttat tcttgtcaat ttaatacatg atatttaaaa aaaaaaagta 180
tatttacaaa ccttagggtt ttggaaaata atatgtacag tagatattac tctatgggca 240
gtaagttgcc atatatgaaa gtcatggata tttacaatat ctggaaagtg attcaataac 300
tggatcttca gtgtgtcgat gtctatcgtg tcaggcacag tctgtagaag aatcaggcag 360
ctttctttca tatatggata acttaagaac attatcaaag ttgaagatat tatcgccatg 420
ataggatcta tatattttgc agtatctttg tcagtaaaat atactaggag agcgcatatt 480
acaaccaaaa tacaaccgtt tacatctctg gccatttccc aaaatccctg cctttgtttt 540
tgatggccga tcataggatg gatagttttg cttctggata atcgtcttgc gccttgctgc 600
aaagactggt caactactat tttacttaaa actacatttc cgctttctgt tacataaaga 660
aaacttcctt ggtggaatgt atatccacca atcaacaggt agcatactcc gttgagtaat 720
aaaccacatg ctcctaaaca taaaacagat atggaatgat gcatctcgtc atgatggtcg 780
atatgaacca atgtctgaca tgcttcaaca aaaatagaaa aacttaacga agctaagaac 840
acacaacata ttaacataaa tatgacatca gttctggccc agccaaatgt attttttagc 900
ttcttttctt ggttggacct ggttacggac gctttcgtct tcttatggtc atggcacttg 960
gccgggttgg atgttaactc ttctcctata ctttcgcttt cgcttggtgc ctttttcatt 1020
tcgaatactt gtttcggagt atcttttcca tacttaatag ttaaaataca tcctcccaat 1080
gccataatat tacacaaagt gtggtaagag tccattaata gtgtcagagc atgagtgggg 1140
tgacttacaa ttagttctaa taagaaaaag gcgatggtca agcctagtac cacgtacagc 1200
tgaaaaggtt gcatccttct tacccattct ttcattgcca tggttgaact attcagagca 1260
cacgtctgaa cgctaggaat atcttaattg aatattttcc actgaacact gcaactatac 1320
tgtagaaact gtcaggtgtc gactgtcccc 1350

<210> SEQ ID NO 103
<211> LENGTH: 991

<212> TYPE: DNA
<213> ORGANISM: Diabrotica virgifera virgifera

<400> SEQUENCE: 103
tttttttttt tttttttttt ttttttttc ttaattacaa atatttacta attttcttat 60
tattatcagt caaattacaa aacaaattct atttttgctc atcaatgggc ttaaagtgat 120
ttagtaaatt tacggtccaa tctccttcaa cccctttttgt aaattctctg ataaatctat 180
agttgcaaat cgaaattttt tgttgatatt caggtagcat tcccatattt aagggaggtt 240
cttcacctct agatctcatt ccagctaaac ctttcaaaga atggtaaacc atggttattt 300
cgacgaatcg tttttgttct ttgccttctt cttcgttaaa tataacacca acctgatatg 360
gaaatgaaaa atatatgtca tctacactag ttgctatctg ctccctttga ctcatggaca 420
tcatagatat tgctttttgt agactaccga taatgtcatt tgttactaga ccgtctaatg 480
atttaatatc accttcagac aatttatgtg atactacctc cactgctttt ttagaagcac 540
ttacaaaatc tggaagatta aattcttgat ctaaataggg cctaatgata aaggtagcaa 600
gaataaaatt tcttatagtt ttaaataaag aaggccaaac aaatatggga gagtctggca 660
gtaatggagg taatttgttt gaaggagaac ttggatcatc tgaataccat cttctttgat 720
taaggcctga atttaaggat ttgttattta aaaaatatga aggctgcttg gtacaaaaac 780
ttgcatgttt acataagaaa tgatttgtta ttgtactatt aaatttacac aaatttaaat 840
tactataatt tcgcacattt ctgaacaaaa cgttaatatt cattttatca ttttaatata 900
aatcaacaaa gtcaaaagta ctaaaatatt ctaaaatttt agatttttta ggttctgtcc 960
tgtcacggtt ctgtcctgtc acctactccc c 991

<210> SEQ ID NO 104
<211> LENGTH: 445
<212> TYPE: DNA
<213> ORGANISM: Diabrotica virgifera virgifera
<400> SEQUENCE: 104
ggggagtatt cacttgatct tcaaggtaga ttaacgcaag tagaaatcta aaacatgtct 60
ggacgtggta agggaggcaa agttaaggga aaagcaaagt cccgatcaaa tcgtgctggt 120
ttacaatttc ctgtaggtcg tattcatcgt ttattgagaa aaggaaatta tgccgaaaga 180
gttggtgctg gagctcctgt atacttggca gctgttatgg aatatttagc tgctgaagtt 240
ttggaattgg caggaaatgc agctagagat aacaaaaaga cccgtataat tcctagacat 300
ttacaattgg ccataagaaa tgacgaggaa ttgaacaaat tactgtcagg agttaccatc 360
gcccaaggtg gagtattgcc taatatacaa gcagtacttt tacctaaaaa gacccaaaaa 420
aaaaaaaaaa aaaaaaaaaa aaaaa 445

<210> SEQ ID NO 105
<211> LENGTH: 2235
<212> TYPE: DNA
<213> ORGANISM: Diabrotica virgifera virgifera
<400> SEQUENCE: 105
ggggcagtgc tttagaggcc acgaagcaat ttctaggata gacgaacgac gctcgcgacg 60
acgcgctgcg acgcacacga caaaaaaata cacaatacga caccacgcgc catttgcca 120
ttttctgtgt gtgcagtgaa gtgaagtgct actaaaatct tcaaaattca acccttctaa 180
gaaggccgat ttcatgtgtt ctatatcgaa gtaaaagagc aatagcatgg gagtggcaga 240

-continued

```
ggatttcgct cccagcttca cgcaaaagcc tcaattgagg caggaggacg atggaaacaa    300

actcattttc gaatgccagt tactggctgc tccgaaaccg gaaatcgaat ggtttcgaag    360

cgatatacca ctttcagaag acagtaggac taattttaaa attcaatcca taggcaccaa    420

caaattttta gtagtactcg aattagatga tgttattgaa accgacgctg gcctttacaa    480

ggtcaaagcg aaaaatacca tgggggaaat agcagcctcc atcaatctca acttcagccc    540

catggacgaa ccaaaagaaa aacaaataga cggcctagca cccacttttg cgaagaaacc    600

agctattcgc caagaagatg atggcaaaaa attattattc gaatgtagga tacaggccga    660

tccccgtcca acggtcagtt ggtcccacaa tggcaacgct gttagcgaag gtccacgtca    720

caagttgagg atagataaag atggccattc atattttgcg acccttgaaa taatcgatgt    780

cacggtagag gatgctggca aatacaaggt gaccgcaaaa aatgacttgg gagaaagtaa    840

cgccacaatc agccttaact ttgacagtgg agatagcgct gatggctttg cgccttcttt    900

ccttgagaaa cccaaaatca tacctaatga gagtggcact cttattacta tgaaatgtaa    960

atgcaaagct aaacctaaac ctgacgtcac gtggttccgc ggaaccacag ccgtcaagga   1020

atcttccaaa attaaaatcc agatcgttga tctcgaagaa gacaaattcg aactgtcctt   1080

agaaatcaag gatccatcgg cagctgatgg gggtacttac agatgccatg tgaagaacga   1140

atacggagaa agtaatgcaa atctgaacct aaatatcgaa gcagaaccag aaccagaagg   1200

agaaggacca acgttcgtcg aaaaacccag gataacctct cacgatggag gcaaactcgt   1260

tgtcatggag tgtaaagttc gtgctaatcc taaacccact atagtttggt acagagaaag   1320

caaagaagtc acagaatcat ccaaaattaa gatcagtatt aaacaaacag aagaagatat   1380

atattacgtc aaattggaac tcaatgatcc ggggattgat gactctggct tgtacaaatg   1440

caatataagg aacacacttg gtgaactcaa cgccaacctc accttaaaca tcgagattat   1500

tcctgttatc aaagaaaaac ccaaagttat taaaatcatt aagaagaaaa ctgttattgt   1560

tgaatgtaaa gttctcagca agtttgcacc tgattgtaca tggtttaagg aaagcgatgc   1620

cgttaaagaa gattcaagac atactgttca cgttgaccaa gttaaagacg gcgaatttac   1680

tgttaaactc gaaattaatg aagttgagaa aaaagacaaa ggtatgtaca aattggttgc   1740

taaaaacgaa aagggtgagg caacttcaca agtcgttgaa gtcactgagt tacctccaga   1800

ggagaaaccc aaaggagaca agccgaaact gaccaaacta accaatatcg ttactgacga   1860

aggaaaatca gttgatttta taacttctct caaaatcgaa gacaaaacag tcaaaatcac   1920

atggtacaag aacaccactg tgataaccga atcttcagaa atcaaaatct cttttgatgg   1980

cactgtgacg cgacttagca ttagtaaatg taaagtatca cattccgcta catacaagtg   2040

cgttgccaaa aacgaatttg gcgaagacga aataagcgct acacttaaag taaacgaagc   2100

taaagaggaa gatgaagaag aagaagaatc cgaagaggag gttatcgaag aaaagaaaga   2160

ggaaaagaaa gtagaaaaga aagaagaaaa acaggaaaag aaagcaaaaa aaaaaaaaaa   2220

aaaaaaaaaa aaaaa                                                    2235
```

<210> SEQ ID NO 106
<211> LENGTH: 1148
<212> TYPE: DNA
<213> ORGANISM: Diabrotica virgifera virgifera

<400> SEQUENCE: 106

```
ggggagagta gatagtaagt aagtgaatgt acgttgtgaa tgacggaagc cggtttgtta     60

cagagaggag gatggagtcc aacacgataa cgttgacgag atttttcttg gcggaacaac    120
```

aaaaatttcc agaagccaca ggtgaattga cccagctgct gacttctatt caaacagctg 180
ttaaggttat cagtagcgcc gttagaagag ctggtattac caaattgttt ggtaccgtag 240
gtgaaacaaa tgtacaggga gaagaagtta aaaagttgga cgtattggcc aacgaattat 300
ttatcaatat gcttaagtca tcttatacag tagcattgct tatatctgaa gaaaatgaaa 360
caattttgga ggtagagact gaacaccgag gaaagtatat agtagccttc gatccattag 420
atggttcctc gaatatcgac tgtctggtat cgataggttc aattttcgcc atttacagaa 480
aatccgacaa cacagttcca gccctcgatg acacactaat gtccggaagg aatgtagtag 540
cagccggata tgcgctttat ggcagtgcaa ctatgctggt catatcttct ggatctggtg 600
tgcatggttt catgctggat gccaccatag gagaatttgt tttgactgaa cacaacatgc 660
ggattccgaa aaaaaggaaa aatctactct ataaacgaag ggtactacca cgaatgggat 720
gatgccataa gagaatacgt cgatgccaag aaagatcctt ctaaggggaa agcctatggt 780
gccaggtacg taggttctat ggtcgcagat gttcacagaa ctattaaata tggaggaatc 840
tttttatacc ctgcaacgaa gtcttcccct aagggcaagc ttagactgat gtacgaatgt 900
gttccgatgg cctttttgct cgaccaagca ggaggattag ctactgatgg caagattaat 960
atattagata tcaaacctac taaccaccat cagagaagtc ctatttttct ggggtctata 1020
gaagatgtag aggaggttca aagttatatc aataaacatt gtgaatgtaa aaaataggtt 1080
aagagatttg tttcaataaa gtttattatt agttatacaa aaaaaaaaaa aaaaaaaaaa 1140
aaaaaaaa 1148

<210> SEQ ID NO 107
<211> LENGTH: 574
<212> TYPE: DNA
<213> ORGANISM: Diabrotica virgifera virgifera

<400> SEQUENCE: 107
ggggagttat ttttgattat ttttacgtat attatacagt cttaaagttt ggcttcaccc 60
tgtagtagta gttttcccta attctgacct gttttttttta ttgtttctaa attcccaatt 120
ttgtgtcagt gacacttttc cacaaatctt tttacataaa agaccttatt aacaagaatt 180
tatattaact ataaacgaaa ataagatttt tttctgatac aatgtttgtt gttttgtttc 240
tttttgcaac acgttttatt ctttgctata acttaaaaat gggctattca ttagatacca 300
attttttcat ttaagtccct tttttatttt tcatatcaat gatttgttat tgcgaaaata 360
ttcttagaaa tgaattatat aataaaaaaa acaataaaac taatgttaac cgtcttgatt 420
ttcgcaaaaa tatgggttca tcattttatc tttcggaagg actaaccgaa aaattataca 480
tctactttgc attcggagta ttgtaagaaa aacatgcatt cgttacagta gtaccagcta 540
tacaagagat tcattatgat tcagctctgc gggg 574

<210> SEQ ID NO 108
<211> LENGTH: 725
<212> TYPE: DNA
<213> ORGANISM: Diabrotica virgifera virgifera

<400> SEQUENCE: 108
gggagtgagg cttattgtta acaaactggc aaaaaaataa ttaaaactaa acaaatttga 60
tgaaaaatgt tcataaaagg tatatttcgt tgattgggaa gaatagtatg atatttcaaa 120
aacatcaagt ttacagaaaa gacaattaaa gattgagatg ggttacaaga ttggattact 180

```
taagcaatac aatattaaat atgcttttca tcagaataat taaaacatac agtattaact    240

gacaatatgg gtgttacatc caattcatac accaccccca actcatattt ttcatcccca    300

ttttgagtta taatactttt ctctataaaa attttgtact atttcacaat tataaggtta    360

ttagggacaa taaaacgaaa cagtttaaat gttttattag agtttaaata acaatgaatg    420

aaaaaaatcg cagttatagt acaataacaa tataaaaaaa attaaaaatt tgggcccgcc    480

taaaaaaaaa ggttctacaa gttacaaccg ctacattttt ttttcttttc aaaaagagag    540

agcaggccag ctttcttttt ttcacttatt cccactttct tcttgtaagc ttgttttaga    600

gtaacgtcac gtgctgatgg aagtttgctt tgaagaacgt ttatggtgtt aaattcctgt    660

tctttgtatg acttatatag taggtgacta gggattagat tacatctttt ttcccgattt    720

ttatc                                                                 725
```

<210> SEQ ID NO 109
<211> LENGTH: 725
<212> TYPE: DNA
<213> ORGANISM: Diabrotica virgifera virgifera

<400> SEQUENCE: 109

```
ggggagtgtg ccacgggatc ggattgaggg tgattgtact gtttgtgtag aacattagtt     60

taataaaatg gcagccgtag taaacttgta caattatttt tataacttag cagatcccag    120

agtgaaaaac tggtttatga tggaaaatcc cttcccaact ttaggaataa ttggagtata    180

cctattatta gtcctgcaaa tcctgccaaa ctttatgaaa aataggaaac ccttcgaact    240

aacgaagata attagattat ataatatatt tcaagtagtg gcctgtattg gtataatgta    300

cagtatcctg acgtcaggct ggattcaagg agaatataat attggttgtt ctccaattga    360

ttactccaac aaaccaaatc ccgtcaaact cctgggtgca ttctactggc tctatttgtt    420

aaaaggtgta gaactgatcg agactatatt cttcgctcta cgaaagaaaa acaaccagat    480

aacaggcctc cacatctacc accatggatc tacgttcttt ttggcatgga ttgggtgcaa    540

attcattgga ggtggtatgg cttctattcc tcccttcgtt aactcattca tacatgtact    600

aatgtacaca tattactact tgtcttcttt gggacctgaa tggcaaaaga agctgcaacc    660

atggaaacca aggcttacta tgttgcaaat gatacaattc accctcctca taattcactc    720

tctga                                                                 725
```

<210> SEQ ID NO 110
<211> LENGTH: 508
<212> TYPE: DNA
<213> ORGANISM: Diabrotica virgifera virgifera
<220> FEATURE:
<221> NAME/KEY: misc_feature
<222> LOCATION: 439
<223> OTHER INFORMATION: n = A,T,C or G

<400> SEQUENCE: 110

```
ggggagtgtt acgacgcgaa cggtgccaag cgctgctgta aagttgcgtg cttttctgaa     60

aaaactttcg atttgcgtgc cgcgaaaaag cgagttgtca cagacaattt tgttttgtgg    120

tgaatattcg gcggattgcg taatttgtcg attggttttt ggtgtttttt tgtgtgtgcg    180

acagagtaac tattttattg gattgtgttt tgaagattac tcagctttat cggaacctct    240

gagaggaaag tctagtattc gagcaggtcg aatggagttc ttctacaccg aaaaaaacca    300

gtgaattgtg ttttaaagtg tgcgtttttg tcgatttcca atttcctctg cggcgtataa    360

tttctattgg ctacattatc tatacagttt gtgtttgtgc tttgtaccag atttccaatc    420
```

acttagccat gtttggagng gaataattaa aaggtgagtt tgaatttttt ttacattatc 480
tcttctacaa aaggaacaat agaagctc 508

<210> SEQ ID NO 111
<211> LENGTH: 623
<212> TYPE: DNA
<213> ORGANISM: Diabrotica virgifera virgifera

<400> SEQUENCE: 111
ggggatatca aacgccaaaa gacgtttata aacatattta atgcataaat acatcctact 60
aaactatatt ttccataaaa tctacaataa ataagttata taaactttac acgcccatct 120
gcttcttcca agatgacgtc accatctttt tcactcacaa aaatatcaca atctacaaat 180
caccaaacat ctccaaaata tcggttttat ccaaactatt tctgatattt catatcgtat 240
atttcagtta tcgcaagtgt tgagaacctc aatagcaaaa tagatttgcg ggccttattt 300
ttcacttcaa aatgtctgct aaccagtata ctattagaga gattgtggac tatcagtcta 360
cccataatgc aagtagtgcc gatgacgaaa atgacaccgc atcggacgaa gaacaagtac 420
ccattatgta ccaatacgaa atggtgggcc cattggaaag gacagtaaag cgacgaggcc 480
atcttcctaa agaagcggtt aaaattctaa aaaattggtt atacgaacac agattcaatg 540
catatcctac ggaaattgaa aaacagattt tgtcacaaga aacgaacctg acggttcttc 600
aaatcagcaa ttggtttata aac 623

<210> SEQ ID NO 112
<211> LENGTH: 625
<212> TYPE: DNA
<213> ORGANISM: Diabrotica virgifera virgifera

<400> SEQUENCE: 112
gggtttgttt gaatttttcc gaaacaatgc atgttttcgt tctaattgca ctcccctaca 60
tagttacagg ttattgaagc gctattatag tcgaggcaat aaagcagtaa aaagatcaaa 120
acccgccaaa tttttgcagt tggatgaatc tcaatgaaat attttgcatt cgattcgtaa 180
gagacttagg aaacttcgta aacaaaaatg atgatgaccg aatgtaaatt gcataattga 240
tttgcaaaaa tgtaaacata atgtgtataa gtcgtatttt ataatgaata acgtcataat 300
tgggaggaca aaaactgaaa cgatttacaa tataccgctc caagttgtaa atcctcatag 360
ttaacattgt atttgtgttt gactagatca ttaacgaata cggaaataat caaataaaca 420
acttgtttcg aacatggtaa atgttatgtg taaaattatc attttactta aattttttta 480
aacctaatgt gcatcagcgg tatttttaaa tttataacgt cataattgga gtaaaaaaaa 540
tgcaacatgt taaatataca gcaccaggta gtacaaattt tgtctagacc ttatagacct 600
tatattatag accttagcat agtta 625

<210> SEQ ID NO 113
<211> LENGTH: 664
<212> TYPE: DNA
<213> ORGANISM: Diabrotica virgifera virgifera

<400> SEQUENCE: 113
gaggagttca ctttgggatt gtattcctga atattaaccg gtagtgccag gtgacagtgt 60
ttaattaaat atccagaaaa aatgccaggc ccttcaagac ctctgtggca agtagccgga 120
aagcgtgatc cagaacaaga acgcgaagct caagcatgga tcgaagctgt cacaggaatg 180

-continued

```
aggtttcctc caggagttcc atacgaagat tgtcttaggg acggtattct cctttgcaca    240

ttgatgaacc gtttggcacc tggaatcatc caaaaaatca acacatctgg tggagactat    300

aaaatgatgg ataacttgaa ccaattccaa aaagcttgtg tgaaatacgg tgttcccgat    360

gtagatcttt tccaaacaac tgacctgtgg gacaggaaaa gcatcgtttt agtcacaact    420

accatttttg ctctaggtcg cacctgttac aaacaccctg aatggcgcgg tcctttcttg    480

ggacccagac catctgaaga aaacaggaga gacttcagcg acgaacaatt aagagctggt    540

gaagctatta ttggactcca agctggccaa aacagaggtg ccactcaagc tgggcagaac    600

tttggtgctt ctagaaaaat cattttggga aaataaacaa acattcgaag agacatattg    660

aatc                                                                 664
```

<210> SEQ ID NO 114
<211> LENGTH: 656
<212> TYPE: DNA
<213> ORGANISM: Diabrotica virgifera virgifera

<400> SEQUENCE: 114

```
gggtaagaat gcagcagcta gcaataaggg cgaagtagtc tgcagaagca tttttctttc     60

tagagctcct taaaacatca ttcacgattc attaatacca gttttcattt ttttttaaat    120

atgtagtctt tttattgaaa cattttcaaa tcaaaatttc tagaaaacgg tgtgttttac    180

tgacttaatc aagagtacct tctaatacta gaataccgca caatttaata atccagtgtt    240

agaaatgttt aaaaattaaa gacaaaaaaa ttatccgata aaattacagt tatcctacca    300

aaaacggacg cctacgatcg gtactaggaa ttcacagtag ggcttttcat tcacagaagc    360

tcgaaacaaa tgacaatcga tgaaaagcct tattaatgga atcaatttat ctccgggaga    420

taaacaggca taccagtttt ccatttttca aaatagaagc gttctggagg tattaaagat    480

aactagttat aagacgccaa cgtccaagag ctctagttcc cttaggaagc aatttcgaac    540

tacttgaatt aggttaaaaa caggagagtt tctggacacc ctgtataaga aagacaccag    600

gaatattttc acgaatacga caaccagtgg agctaagagt tgaatctttt gtcacg        656
```

<210> SEQ ID NO 115
<211> LENGTH: 185
<212> TYPE: DNA
<213> ORGANISM: Diabrotica virgifera virgifera

<400> SEQUENCE: 115

```
gggatgtcaa atcataaaaa tcatccttat catttagtag atattagacc atgaccttta     60

ttaggagctt ttagagcaat attaacaata ttaggaataa ttaaatgatt tcatttatat    120

aataataatt tactaataat tggattatta attacaagat taattatata tcaatgatga    180

cgaga                                                                185
```

<210> SEQ ID NO 116
<211> LENGTH: 661
<212> TYPE: DNA
<213> ORGANISM: Diabrotica virgifera virgifera

<400> SEQUENCE: 116

```
ggggaattgt caacctggaa aacgacttgt cgaagtcgca tagtttttat aagtttaaat     60

aaactaaatt aaatataaat acttcgagaa tgcaataatt attattcttt aactagaccc    120

acagcttatt aattagcaga agtagtagca gacttatact aactagcata aggagaaaca    180

tattaacata gcatggcaga cttcatagat tctgaagcag aagaaagtag tgaggaggag    240
```

gaattagatc atagggatcg taaaaaagcc caaaaagcca aagttgtaga tagttcagat 300
gaagatgatg aagatgatga cgaaagactg agagaggaat taaaggattt gattgatgat 360
aatcctattg aagaaagtga tgctgagtct gatgcttcag gaagggaaaa acgtaagaaa 420
tctgacgacg aggatttgga tgatcgactg gaagatgaag attatgattt gcttgaagaa 480
aatttgggtg ttaaagttga aagaaggaaa ttcaagcgac tgcggcgttt tgaagatgaa 540
gaaagtgaag gagaagaaga acatgatcct gaacaagata gggaacaaat tgctatggat 600
atattttcag atgatgacga tgaaagacga tcagaacgaa gtcacaggcc tgccgtcgaa 660
c 661

<210> SEQ ID NO 117
<211> LENGTH: 488
<212> TYPE: DNA
<213> ORGANISM: Diabrotica virgifera virgifera

<400> SEQUENCE: 117
ggggccactt gatttttgt tttagaaaaa ggcacgaaaa tggctggaga ctcagttgat 60
gcttcaaagt taaccggtat gagcaaaatt ttcaatggct ctaccatgag aggaagggca 120
aatgttgcct tagccacata tgccagtgtt ggactcctaa tcgcctattt ctcactgaaa 180
ccatcaaaac ccaaggcacc aaaaaattag tctagtagtc tattccgtaa tgttactcta 240
taactatgta catgtttaat aaaacttaaa atctcaatgc ttaataagtt tttttagata 300
caatgttttt tgtagacata tgtaatgact caataaaatt gatgttgtat acaagggcaa 360
gatgaaaagt tctttgcctg gtagtgaaaa gtgagttttt tattcaaaac atgcctttat 420
ttacagtgca atctcacttt attgtaatat tatttgatat atttttccag taaagagatt 480
ccaccatc 488

<210> SEQ ID NO 118
<211> LENGTH: 616
<212> TYPE: DNA
<213> ORGANISM: Diabrotica virgifera virgifera

<400> SEQUENCE: 118
ggggattgtc aaatagttgt cagcgttaca cagcgaatat tttcctcatc agttcaatat 60
taacaataaa ttgttttgtt gaaattgaaa tcacaaatta ctttataaaa tggtaactct 120
agaagacgtt gaaatgaaaa atgcagacag tcctccagga ttagaagctg gtgatacaaa 180
gaaagatacc gacctacaaa gtgtaataga gattcgtgaa catgcaagac aaatagaaaa 240
atcagtcaca agtaaagaaa accgtttcat cttacgagtt ttacgttgct tgcccaacac 300
tagaaggaag cttaatggac tggtgctgag aagcctcatt actcaaatat atcctgtagc 360
tgaacgtgat gccctcctta gtttcgtcga ggaagcttct ggagaactcg acgccaccca 420
gtcacgagca agatcagctg ttaagtcgcc tgttcccgag gtggatacat atataaatct 480
tttaatacta gtacgtttaa ttgataccaa taagttagtt gaagcagagc gctgttctca 540
agctcttatg aataaaataa ctaaccaaaa cagacgtact atagatcata ttgctgccaa 600
gtgttatttc tatcac 616

<210> SEQ ID NO 119
<211> LENGTH: 609
<212> TYPE: DNA
<213> ORGANISM: Diabrotica virgifera virgifera

<400> SEQUENCE: 119
gggggacaag attttgcaat ggcggatgta gtagacgagg tgattatgga ctctgatgaa 60
aatgaggaaa tactatcaaa aagcccagaa gagatggctg aactcaaaaa ggaaaacggt 120
aaccagttat acaaaaccaa acagtacaga tctgcactcc ctctctatag cgaagccatc 180
aatctttgtc caaatgtagc cccttattat ggaaatagag ctgcctgcta catgatgctt 240
tacaggttta cagaagcttt ggaagatgtc aggaaaagtg tgcagctgga tccagaattc 300
gttaaaggat acatcagaat gttaaagtgt gctatagcaa tgggtgacac cactacagct 360
gattttgcca ttaagaagct tcaggacttg aaagttgacc aacaaacatt tgcaaatgaa 420
ttaaaatcgg ttcagcaatt gaagcagtac gagtcagatg gaaccaaagc gtacgataaa 480
aaagattatc gtttggttgt tttctgtatg gacagatgtc tcgataatgc ccctacttgc 540
taccgataca aaattgccaa agcagaatgc ctcacatatc tcggccgtta ccaagaagct 600
caggaaatt 609

<210> SEQ ID NO 120
<211> LENGTH: 517
<212> TYPE: DNA
<213> ORGANISM: Diabrotica virgifera virgifera

<400> SEQUENCE: 120
ggggtcttga aggtggctcg ttgtagcaga tttgttgaaa accatggaaa tcgttcaaga 60
attatccagc caatatgttc tgtatattcc tgtagcttta gtaatcgttg gagctatttt 120
ggtgttcact tttggtttta aatctgcaga acaaccaccc ttcgacaaat tatcatttga 180
cgatagaaaa tctgctggga aaaagcgtaa aactaaggaa aagaaaccta ctgctaatgg 240
tcacatcagc aatgtagaaa aatctgataa atccccatca aaggactcca agaagtcccc 300
ccagaaagaa gctgttgaag caaaacaaga aaagaaggag aagaaactag acaaacaaaa 360
tgaaaagcct aaaaaacagg aaatcaaaaa gacagaggaa atcaaaaata agaaaaattt 420
aaacaaagtg tcagagaagc cagtagattt tgatgatggc aactgggaga cagtacctct 480
taaatctgat aagaagaaga aagaccaatc gccagtt 517

<210> SEQ ID NO 121
<211> LENGTH: 607
<212> TYPE: DNA
<213> ORGANISM: Diabrotica virgifera virgifera

<400> SEQUENCE: 121
ggggacagcg tgaaatctgt gcgcggacaa aaaaaacttg ttatcgccga tttattataa 60
tttatattta tgaagtgact gtgtcggtac ttaatagctt tatgtatatt gtgtttgttt 120
tcatttaaat tttaaatttc tataccaaag atatgagccg gttgaacata ttcagttttt 180
tgaaaatgct tcaagcattg tgttgtgtac tgggagttac atcagcatct tcagacccag 240
ttatagtctc cagagaagaa tgggggggccc gcgctcctaa aaacatagaa aatatggcga 300
acccagtacc ttacgtcgtt atccaccaca gttatctacc accagcttgt tacaatttaa 360
ccgattgttt caaagccatg cgttggatgc aagaccttca ccaagacacc aacggttggg 420
cggatattgg ctacaacttt ggtgttggcg gagatggtag agcctacgaa ggaaggggat 480
ggtccagagt tggtgctcat gctccctatt acaacagcag aagtattgga atatgtataa 540
ttggagattg gacagttgaa cttccaccag aaaatcagct agcgacagtt catgagctaa 600
tacaaaa 607

<210> SEQ ID NO 122
<211> LENGTH: 590
<212> TYPE: DNA
<213> ORGANISM: Diabrotica virgifera virgifera

<400> SEQUENCE: 122
gggggttgcc caatttgttt caatattgtt ctgattttat ttaaaagcgg cacttaaaca 60
tagtatataa ccatggttga gaacagtaca ttaactatag atgaaaaatt tcacctaata 120
tccagaaacc tgcaggaaat attaggtgaa gatagaatta aagcagtatt gaaagaacgt 180
gatttgaagt tgtattgggg cacagctaca acgggtaaac ctcacattgc ctacttcgtt 240
ccaatgtcca aggtagcaga ctttctcaga gctggtgtag aagttactat tctttttgct 300
gatcttcatg cgtatttgga taatatgaag gcaccctggg aacttctagc gcttagagtt 360
cagtattacg aacattgcat taaagctatg cttcaatcta ttggagttcc tttggacaaa 420
cttaaatttg tgaagggaac agattatgaa ttgtctaaag aatacacact agatgtttac 480
aaaatgactt cagttgttac tgaacatgat gcaaagaagg ctggagctga agttgttaaa 540
caagtagaaa atcctttact aagtggtctt ctatatccta gtttgcaagc 590

<210> SEQ ID NO 123
<211> LENGTH: 103
<212> TYPE: DNA
<213> ORGANISM: Diabrotica virgifera virgifera

<400> SEQUENCE: 123
gactcttacg aactcagata cttccagatt gacagtcaag aagacgatga tgaagaagat 60
aatgaataat ttattcagtt atttttttta ttaaatagat tat 103

<210> SEQ ID NO 124
<211> LENGTH: 381
<212> TYPE: DNA
<213> ORGANISM: Diabrotica virgifera virgifera

<400> SEQUENCE: 124
gggaactata aaatgcggtt acaacgttgt tccagcttag cattctagta tagatttcca 60
tttcagcata tcaagaacga tcacaattta gtgaaagtgt acatgggaat aacaacaact 120
ctatattgaa atattgttta atatttaata tgctaagtaa tattcagtta gaatattatc 180
atggatcatg gatgggtgaa atatcacagt tttaacaaaa aaaaaaagaa tgtgttgtat 240
tttgtacgcg cctaagaagt tatacttcta ttatgtgatt tcaatgaaat aaacatattt 300
taaacagttt atttgtattt tatttaaata ttaaactaat tttaatacct atttcttacc 360
aaatttgttt attaaaatag c 381

<210> SEQ ID NO 125
<211> LENGTH: 627
<212> TYPE: DNA
<213> ORGANISM: Diabrotica virgifera virgifera

<400> SEQUENCE: 125
ggggaacagt ttaattgcta gagttgtata gtcagtgtct ccagttgttt attatcaaac 60
aaaaatgtct ctgacaatga ttggtggtgt aaagatcccc atagtggggc taggaacatg 120
gcaggctacc aatgaagaag aattggaagg tgccgttgag gcagctctgg aaactggata 180
ccgccacata gatactgcat ctgcatacca aaacgagcat gtcatcggca aagttctaaa 240

-continued

```
taaatggttg gcgtctggca aacttaagag agaagatatt ttcattacta ccaagcttcc    300

aatgacacac atccatcccg atctcgtcga aacagctctt aaagaatcct tacagaagct    360

tcagctggac tatgttgatt tgtacttggt gcattctccc atatacatga aatttgttga    420

agctggaaag ccaatggaac ctctacctac tgaccatctg gctgtttgga agaaaatgga    480

agagcaagta gatgcgaaaa gaaccagaac catcggtctc tccaacttca acgtaaacca    540

gatcgacaga atagtgaaga attgtagaat tcaaccagcc aacactcaag tggaactgca    600

cgtttactac cagcagaaaa aacttag                                       627
```

<210> SEQ ID NO 126
<211> LENGTH: 640
<212> TYPE: DNA
<213> ORGANISM: Diabrotica virgifera virgifera

<400> SEQUENCE: 126

```
ggggattgta ttttagtatt ttacaattct ttgaattgca gattatttag cggtttagta     60

caaaaacctg aagtaaattc tataacggaa agtgcttaaa ttttaatggt aaaatgtcca    120

ttctagctta caatggtggt gctatggtgg cgatgaaggg agaaaactgt gtagcaattg    180

cagcagatag gcggtttggt attcaagccc aaacagtagc tacaaatttc caaaaaatct    240

ttgaaatggg accacattta tatgtgggtc ttccaggatt agccacagat acccaaacag    300

ttatggaaaa actccgtttc cgaaaaaact tgtacgaact taaggaaaat cgaaaaatat    360

ctccaaaagt atttgcctct atgatatcaa atatgttgta tgaaaaaaga tttgggccat    420

tttttgtaga acctgtagta gctggacttc tacctaatac ttatgaaccc tttatctgta    480

atatggattt aattggttgt ataaaccaac cttcagactt tgttgttggt ggaacagcgt    540

cagcacagtt gtatggtatg tgtgaagcac tttgggggcc taacctagga cctgaggatc    600

tttttgaaac catctctcaa gctctcatca atgcctttga                          640
```

<210> SEQ ID NO 127
<211> LENGTH: 591
<212> TYPE: DNA
<213> ORGANISM: Diabrotica virgifera virgifera
<220> FEATURE:
<221> NAME/KEY: misc_feature
<222> LOCATION: 156, 241, 244
<223> OTHER INFORMATION: n = A,T,C or G

<400> SEQUENCE: 127

```
gtacattaaa atcgctaaaa acataaaaaa atacaatatg ggtacttgta tgtgataatg     60

ttacctgtta gttactaaat ttaaaacggt tgatattttg tatacttata tttagacatg    120

gcggtaaatg tttattccac gaacgttaca tctganaatc tatcccgtca tgatatgcta    180

gcatgggtga acgaatgttt gcagagtagt tttgcaaaaa ttgaagaatt atgtacaggc    240

nccngcatat tgccagttta tggacatgct ttttcctgga tctgtgcaat taaagagagt    300

taaatttaga accaatttgg aacatgagta catacaaaat ttcaagattc ttcaagctag    360

ttttaagaaa atgcaagtag ataagatcgt ccccatagat agactggtga aaggtagatt    420

ccaggataat tttgagttcc tacagtggtt caagaagttt tttgatgcca attacaaagg    480

gacggactac gatgcgctgg gagcacgtgc cggagagcaa ttggggcaag gaggatctaa    540

cgcccctaga ggtcaatctt tgatgttacg tcggccgaac gcgacgccct c             591
```

<210> SEQ ID NO 128
<211> LENGTH: 614

<212> TYPE: DNA
<213> ORGANISM: Diabrotica virgifera virgifera

<400> SEQUENCE: 128
gggggaggag gttaagttaa acttcgtttg gtttggtttg gttgaccgag tgattttcca 60
gggtggagtt tttttgtgat gctaatttat ttatggccat ttcgcgttct ctgataaatg 120
aactataaag tattaaagca cataaattaa taatctttga ataacttaca ttgatattgc 180
gatcaacaag gtttttctaa acaaatattt agttaaaagt gcacaagttt ttatgcaggt 240
tgtcttgtaa ttgttttcaa ctgcttagag cttctatctc caccatgggc gatcaggttg 300
aaaattcgaa caataaagtg accgaaaatg atccacagcc caacagggac gaaatgataa 360
tggctcagca gaggcaaatt gaacaagagt atattgatgt cctcagaaga ctaaaagata 420
tagataatat tgatgaagcg cttaaagaat tatatagtgt atttaatgat caaggtttct 480
cagattattt ggtggtctac ctcagattgt taaccagtgg ccagttacaa aaggaacacg 540
aattttacag ttgtttcata gaaggtgata gaacggtagc tgatttttgt caccaggaag 600
tagagcctat gtat 614

<210> SEQ ID NO 129
<211> LENGTH: 639
<212> TYPE: DNA
<213> ORGANISM: Diabrotica virgifera virgifera

<400> SEQUENCE: 129
ggggagtcga aaaatatggc agcgtttcta aggcatggcg ttttcaaaac aggacgagtt 60
gtctcttcaa aaaacgtact tttgaggtcc tttgccacga aggctgagaa gaggaaagga 120
atcgacagaa aagttggccc aaaaatagac tccacagctc aatctttagc ttcaaaaggg 180
tttctgaggc aacaaagaga ttattctcca cctgaagatg ttaattccaa gttagaagca 240
atcttccaga ccgtcgtcgg tagttcagat atatctaccg aactcacaga tctgaatcaa 300
aagtttactt tattcatgca gtgtgaacag caactaggcc atagtattcc taattcgtta 360
cttcatcaca tgaaaacatt gaaggacgtt caaatattct ataacatgcc cgtagataca 420
agaacgccac tggaaagaat gaaatccatg gacttgccgg aaaatttaca tgttcagtac 480
gaatataaac gatttaatgc tgatactgat acgatgtttg gaggaaaaac agcattccct 540
aagagttcta caattgttac aggattaaaa tacaaagata agtacaaagg acaaaagcaa 600
ccattacctg atttctagtg ttttttcta gaaaataaa 639

<210> SEQ ID NO 130
<211> LENGTH: 651
<212> TYPE: DNA
<213> ORGANISM: Diabrotica virgifera virgifera

<400> SEQUENCE: 130
ggggatgttt taaaaggcgc tttaagttta agattcacac attgcataaa ataattttat 60
aactaaacta aatcatgggg aagaataaga aagacaagaa aaagggaaaa ggggccgaga 120
aaacaacagc aaaaacagaa aagaaactgt caaacaaaat gaagaaagaa ctgcaagcta 180
agggagagga tgatatagaa tctattttat tacaaattga gaaggaagag aagaaaaggt 240
tgactgttac tgaagctata atcagtccac cttcaagaag attaaatttc acctttatgg 300
cccatccaga aaaagaacag cttattttgt atgggggaga atttttcaat ggacaaaaga 360
cttttgtgta tggtgactta tttttctaca atataccaaa taacaaatgg acagtagtta 420

```
aggctcctaa tggcccaccc cctagatgtg gacatcaaat ggttgtctct tcagcaaata    480

aaggtcaatt atgggtgttt ggaggagagt ttactacacc cacacaatca caattttatc    540

actacagaga tctttgggtc ttccatttag ctactaaaca gtgggaaaaa attactgctc    600

cgaatggacc atcagcgaga agcgggcaca gaatggtatt aataaagaag c             651


<210> SEQ ID NO 131
<211> LENGTH: 652
<212> TYPE: DNA
<213> ORGANISM: Diabrotica virgifera virgifera

<400> SEQUENCE: 131

gggggaccta aatatccaga tattttaaat ccttgctgag caagacaatc ttcaacttca     60

taacattgaa tatttcttaa ttagttatct ggataactgc tgattcaata tcctccagga    120

gtttcatagg acaacacttg tcctcatgaa gtgtaaatca aaagtgatcg atatttaata    180

caccattcta cattcatgaa ccattctaca aaaatttgtc caaattgctc ttctttctta    240

gatatcttca tacattttgt tctcttaatg ttttgtgaaa gttcatatct cttagactta    300

cttctatgat tctatttggc tccccacgtt gggcgccaaa tgttactctt cgccgatgtt    360

accagttttt ctataaggta tgcgaaggta attaactact tttattttct aacaaacgaa    420

agagaataat aataagaaat caaaaaaatc ggagaatcat acactattta ttcttattaa    480

ccaaaattat aaaatttata ttaatcttaa ttgaagatat aaaaaaacca aaagaaaaag    540

gtaaaaagct taaataaagt ttatgcttgc ctctaagaat attcttttca gcgtacacac    600

atattaaaat tcttaaaact atgtaatatt atatttaggt actatttaca ag            652


<210> SEQ ID NO 132
<211> LENGTH: 658
<212> TYPE: DNA
<213> ORGANISM: Diabrotica virgifera virgifera

<400> SEQUENCE: 132

ggggacatta ttattccaag tatctttaag cagtgacatc gagtgttagg cttcaaagat     60

gaaggttttt ctaagtatta gtattggact ttttgtactt tgttcaatag aatcaaggtc    120

tctaaatagc aagctttcta aaaagccaat atttaaagac ttttacggaa agctaaacat    180

agaagtaaga ggaaaccctg gagagccact gatattaact gacttgatta aagcagggaa    240

gctggatgaa gctcagaacc aatcactcgt gcaaggattg gacacagagg ttaaaagtta    300

ttccggctat ttcactgtag ataaaaagca tgattctaat atcttcttct ggtttttccc    360

ttcacaaagt gatcccagtt cggatccggt tgttctatgg ctccaaggag gaccaggatc    420

tacatccatg tttggacttt ttcaagaaaa tggacctctt acagtaaaag atggtgagct    480

gggtattaga ccaacgtctt ggaataggaa tcactcagtt atctacatcg atcagccagc    540

tggaactgga tggagttata ctaacggagg atacgccaag gatcaacata aagtagccac    600

tgatttgtac gaagccttgc agcaattttt caccctcttc tatcaatacc aggagaga      658


<210> SEQ ID NO 133
<211> LENGTH: 638
<212> TYPE: DNA
<213> ORGANISM: Diabrotica virgifera virgifera

<400> SEQUENCE: 133

ggggatattg acattcgaca actttttgg gaggacaggt gaatgttgta gcgtttttca      60

aagtgtaagg tgtttatttt caaaaagttt ataaaataag caatcactat gggtaatgtg    120
```

```
tttgcaaatt tattcaaagg cctctctggc aaaaaggaaa tgaggatatt gatggtagga    180

ctcgatgcag ctggtaaaac cacaatttta tataaactta aattaggaga aattgtaaca    240

actattccaa caattggatt taatgtggag actgtagaat ataagaacat tagttttaca    300

gtatgggatg taggtggtca agataaaatt aggccattgt ggagacacta tttccaaaac    360

acacaaggcc taattttcgt agtagacagt aacgacaggg aacgtatcac tgaggctaaa    420

gatgaattaa tgcgtatgtt ggccgaagat gaacttagag atgccgtact tctcattttc    480

gccaacaaac aagatttgcc caatgcaatg aacgctgcag aaatcaccga caaactcggt    540

ctccattcac tacgcaaccg caactggtac attcaagcta cctgtgcaac tagcggagat    600

ggtctctatg aaggtctgga ctggttgtcc aatcaatt                            638
```

<210> SEQ ID NO 134
<211> LENGTH: 192
<212> TYPE: DNA
<213> ORGANISM: Diabrotica virgifera virgifera

<400> SEQUENCE: 134

```
ggggaaaata cgtcaagctg tcattaatgt cgctatcctt tccttccttt tcctttttaa     60

cttaacacac gtttgcatag gtaggtcaaa atgaccaaag gtacctcaag ttttggtaaa    120

cgtcgcaata agacccacac cctatgcagg aggtgcggta gatcttcata ccacatccaa    180

aagtcacaat gc                                                        192
```

<210> SEQ ID NO 135
<211> LENGTH: 576
<212> TYPE: DNA
<213> ORGANISM: Diabrotica virgifera virgifera

<400> SEQUENCE: 135

```
ggggattttt atttacttta acctaaattt attttagttg atcaacaatt tttttagttt     60

atttgacaaa ctttgtaatt ttaaattatg ccgaactgga atcagatcca ggctcaacta    120

aggcatccag ctaatcctgt agtattcttt gatgtatcag taggaactac agaaatcggt    180

aggatgatat ttgaactttt tgccgatgta gttcccaaaa ccagtgaaaa ttttcgacag    240

ttttgtacag gagaatttag aaaagatgca gtacctcttg gttacaaagg agctagcttt    300

caccgtgtta ttaaagactt tatgatacaa gggggagatt ttgtgaatgg tgatggaacg    360

ggtgtgatga gtatctatgg aggaagtaca tttgccgatg aaaactttag ttttaaaaca    420

tgatacacca ggactgttat ccatggcaaa tagtggaaaa gacacaaatg gttgtcagtt    480

ttttataact tgtgcaaaat gtaattttct tgatggaaaa catgttgttt ttgggagagt    540

tattgatgga cttttagtta tgagaaaaat tgaaaa                              576
```

<210> SEQ ID NO 136
<211> LENGTH: 618
<212> TYPE: DNA
<213> ORGANISM: Diabrotica virgifera virgifera

<400> SEQUENCE: 136

```
ggggaatatt tatttttatt taaacaagtt aactgatagt tattttaaac atttttatat     60

tcagcaacaa tggtgaaggt aaaaaaacaa aaaggcagta tcatctgagc gtgttcatgt    120

taaaaaagaa ccgaaaaaaa tgaacccctt cgaggttcat gtaaataggg aaaaactaca    180

agtgataggc aagaagcaaa agaatgacag aggtcttcca ggtgtctcca gagctaaagc    240
```

-continued

```
catcaaaaaa cgaaaatcta cgttactgga agaatacaag gtacaaaaca aaaacaataa    300

attcgttgac agaagaattg gcgagaaagc tcacatggac agtgaagaaa aagctttggc    360

gaggtataca gctctaaaag taaaggccca taacagaaag agcattttca atcttgcaga    420

tgatgaaatt ttaactcata aaggtcaaac actgaacgaa atagagaaat ttgatgatcc    480

tagatcggat gatgaagact tcgatgatag cgaaacaaag actggaaatt tggagtcaaa    540

ttttatagga gaagcacatt ttggcggagg attatttaca aacacaggaa aagaaggtgc    600

tatgactcac aaagattt                                                  618
```

<210> SEQ ID NO 137
<211> LENGTH: 421
<212> TYPE: DNA
<213> ORGANISM: Diabrotica virgifera virgifera

<400> SEQUENCE: 137

```
ggggtaaaaa cgatgggaaa tgaaatatct ttggataaag aaattattac aggaaatgaa     60

tcaaaaaaat ctgtgtctct gtatcaaaca aattataaat gttatatatg ttctaaatac    120

ttttcagatg aatatatgtt gcgaaggcat attacgacag tgcataatga agaaaaattg    180

tttaagtgtg aagaatgtgg caaaagttta aaaactcgta actcattcag aaagcacatg    240

cgaacacata ccgaagaaga aatgtttgaa tgtaaagtat gttctaaaaa atttagagaa    300

aagtatgtgc acaatgatca tatgcggact catacaggag aaaaccatta tacatgtagc    360

ctttgttcag caacgtttag aaacaggacc ttgctaagaa atcatattgc atcaagtcac    420

g                                                                    421
```

<210> SEQ ID NO 138
<211> LENGTH: 508
<212> TYPE: DNA
<213> ORGANISM: Diabrotica virgifera virgifera

<400> SEQUENCE: 138

```
ggggttcacg aagacaaaaa tcgggtaccc ttcgtcaaag gggcaactga aaggtttgtc     60

tcaagccccg aagaagtatt cgaagctata gaagaaggaa aatctaatag gcacatcgct    120

gtaacaaata tgaacgaaca ttcgtctagg tctcattcag tatttttaat aaatgttaaa    180

caagaaaatt tagaaaacca aaagaaacta tcagggaaac tttatttagt agatttggct    240

ggttccgaaa aagtgtcgaa aacaggcgcc gaaggtactg ttttggacga agctaaaaat    300

attaacaagt ctctgtcggc tttaggaaac gtaattagtg cattagcgga tggtaacaaa    360

actcacattc cttacagaga ctctaaacta accagaatcc ttcaggaatc gctcggagga    420

aacgccagga cgacgatcgt tatttgttgt tctcctgcta gctttaacga atctgaaact    480

aaatcgacgt tagaatttgg taaagagc                                       508
```

<210> SEQ ID NO 139
<211> LENGTH: 517
<212> TYPE: DNA
<213> ORGANISM: Diabrotica virgifera virgifera

<400> SEQUENCE: 139

```
gggtcagccc gatattccca aatttccttg gtacaagtct tgtagggctt ctagaaagta     60

cataacttct attattagag tacgattcgg gcacgcatgt tatccaaagc atttatttaa    120

aatacaggtt ttggataatg ataaatgtga gcattgtgaa gaggaaagtg atttagatca    180

tatatttttt ggttgttcta aaaatacaat ttactcatct aaattaatga atgatttatt    240
```

aaaatgtaaa gtagcaactc cttggaatat actatattta ttatcacttg gttctgcaga 300
tgtataaaac tctttaatta actttttaaa agacagcaaa tcatcattat aattccctta 360
aacattttta attaatgcct ttggtagtta gttgttttag ctgttaagct tagtgttact 420
taataccttt tagttgttat ctttgtttta aacctgtttt gtataacttg ataacttgta 480
ttccttatgt gtctggcagt atgacggtaa gtctaag 517

<210> SEQ ID NO 140
<211> LENGTH: 585
<212> TYPE: DNA
<213> ORGANISM: Diabrotica virgifera virgifera

<400> SEQUENCE: 140
gggggtcggt aaaaagtatg tcaagtaaat gatttatcca atccaaaagt ccaatctgat 60
taaatacttt cctgtttggc tgagttgtga atctggtcga gcagggatta caaggaagaa 120
tagaacacta gttttattct cactatctcg ctactcttat ttcagatgta tcggtcgcca 180
tcgcatgata gaacgcacaa gagatgataa agtttcttcc tacctatagg cttagcgaat 240
acaagtgaac aaagccaaag ttaattaagt aatagatatg attatcagag acagagtacg 300
ttaaaataaa ttgccatgtt accggcggct cacagtggtt ccaaatgctg aaaacgtggt 360
catgagatgt catattctcc ctaaaattgg ataatactta atacaaaaaa agtgataata 420
tggtaagaaa tcagcttcta tggtatgacg gtgtgttgcg ttctcaccac tggcaaagag 480
agtttcatct tcattggtaa gataaaatgg gaaatagtac taaccatgca ttaagatata 540
acgcagaatt tcgactacgt cttctggttt ggcgatttaa acttt 585

<210> SEQ ID NO 141
<211> LENGTH: 383
<212> TYPE: DNA
<213> ORGANISM: Diabrotica virgifera virgifera

<400> SEQUENCE: 141
gggtatatac ggatataaaa atttatattt ttaaatttaa gcggaagttc ggacacaatt 60
ctaactttaa agtgaactcg tttaagatag tgtacacaca agtgttcaat tgttattata 120
acagtgtgac atgtttttga atttgtaccc tttgaatgga gactatggaa tgaagaccgt 180
gatgcttgca gagttgtcag ccattagatt aacacaaaaa tgccacagat gacacccaca 240
aaaaaaagaa tgtgtgtgta ctttgtacgc acgtaagaag ttatacttct attatatgat 300
ttcttaaaaa taaatatact ttaaacagtt tgttttaatt ttttttttta acaccaaact 360
aattttgtgc ttaccgcctc cag 383

<210> SEQ ID NO 142
<211> LENGTH: 616
<212> TYPE: DNA
<213> ORGANISM: Diabrotica virgifera virgifera

<400> SEQUENCE: 142
gggggccata attatatctt aagccaagaa gttaatttta attatgaaaa taattttagt 60
agttttggtg attgtagctg cagctacagc atctacggac gaagaaaaat ggagacaatt 120
taagattacc cacaacagag tatataacaa tattgaagag cataaacatc gatttgaaat 180
ctttaagaaa aatctgattc gtattaaaga gcaaaacgaa aaatacgaaa aaggggaatc 240
aacttttaac ttcggaatca ctcaatttgc agaccttacc gaagaagagt tccttagtcg 300

```
ttttaaactc gctggtagtt ctaagttaag caaaattaat agcaatgtct cttcttctaa    360

aagtagaagt aaaacctccg gtggatcaga tgatttgcca gaacaatatg actgggtccg    420

cactggtgca gtaacatctg taagagatgt tgcagattgt ggtgattgca cagctgaaag    480

cgtggtagcc gcagtagaag gcgctgagtt tataaaaact ggaaatctaa tacagcgaag    540

tcccaagcag ctagaagact gcattccttt taacccagat gaatgttgga tatgttatga    600

gaaggtcctt aattac                                                    616


<210> SEQ ID NO 143
<211> LENGTH: 174
<212> TYPE: DNA
<213> ORGANISM: Diabrotica virgifera virgifera

<400> SEQUENCE: 143

gggttgataa gaacatgttt agttgttaaa gtccctaact ttttttatta cacaacatag     60

gcgaatgaat ggaaagcaga atgttaagaa aatatagcct gaggctatag ttgggtttta    120

atttcaatat tttataaatg ctagaatatt cctcagggtg ttgtgaaagt tgag          174


<210> SEQ ID NO 144
<211> LENGTH: 619
<212> TYPE: DNA
<213> ORGANISM: Diabrotica virgifera virgifera

<400> SEQUENCE: 144

ggggctacta cttcagttca gtgtgtaagt aagagagacg agaattcatg cttttcgtct     60

ctatgtatgt ttggaattgg aatttcatgt gggctgcgac acgacacgat attgctgtgg    120

tggtagggaa aggtgttgac gtttaaagtt cttacagcaa cagtgtggaa tttgtgatta    180

aacggcccaa tgggcgaact tttgtgaaat atcagaactg acaggcaata cttatcaaca    240

atgaagctca gcactcagga aaaacgggaa ttggataaat ttacaaaatt tttggcttta    300

aaatgtactc agatcatcgt acagtccaga cttggagaaa aagtaacaag caactgcaga    360

tcacaaacca caagcacgga ttggttcaac ttgaacatca gtgatctccc ggaagtcctt    420

gcggaaacga aaagagttct caacggcgaa atcctatcct caaatctgcc cttatgtgtc    480

gaaatttctt tgcgtacggt cgagggtgac catatggtcc tcgaaaattg gtgtctgggc    540

atgttgcccg aacaacagtg tgatcctacc acaagaatag tgcatacaat ctataatcgt    600

atggggactc tgctaaaat                                                 619


<210> SEQ ID NO 145
<211> LENGTH: 612
<212> TYPE: DNA
<213> ORGANISM: Diabrotica virgifera virgifera

<400> SEQUENCE: 145

ggggaacatt ttgcgattta taatagtttt gtcagttttg tttattatag atttaaatag     60

attataaatg ggtacattgc ttacatttga ttattttcat taacatatgt attttctaat    120

agtgtggcgc aattatataa ttatcaaaag tacgatttat ttggaaaata gtaaatccaa    180

acaccaaata gcaaagatgc ctcatgaaca tattaaatac acaaattctg tatcttcggt    240

aaataattca gatgaagaag aagatgtgga aagtaagact tctcccatga gctacaaaga    300

acgcaggaga gaagctcata cacaggccga acaaaaaaga cgtgatgcaa ttaaaaaagg    360

atatgataca ttacaagaac tggttccaac ttgccaacag cctgatgttt ctggctacaa    420

attgagtaaa gctactgtct tacaaaaatc catagactat attcagtatc tccaaatgca    480
```

aaagaagaag caagaggagg aacgaaatgc tttaagaaaa gaggtagtag cgttaagaat 540
aatgcagacc aactatgaac aaattgttaa ggcacaacaa tcacaaccgg gacacactgg 600
aactagaatt tc 612

<210> SEQ ID NO 146
<211> LENGTH: 434
<212> TYPE: DNA
<213> ORGANISM: Diabrotica virgifera virgifera

<400> SEQUENCE: 146
gggtaataat aaaataaaat acactgcgaa tctcaacgca aagaaaataa acaacggctg 60
tgaactctga gcggcttgac gaaaacaagt agaatggtgg tgcgtggccg gattatctat 120
caccatcacc accaccacca tgtgattgtg cttgtgctac gacgttgccg gttgcattca 180
aaaggcgcgt aggttcgtag gtattcgacg tattatattt aatatcttag accatggtct 240
aagtttaata taatattatc tccataattt tgtttttggt ttatatactt gtataatata 300
ccttttatgt caacgtaaag gtattaactt tttaggtttg agtacagaaa aatatacaaa 360
atagtaaaat ctcagggggg gccacgaccc ccccctggcc cctctctgcg ggcgcccatg 420
gatggaaaga acac 434

<210> SEQ ID NO 147
<211> LENGTH: 590
<212> TYPE: DNA
<213> ORGANISM: Diabrotica virgifera virgifera

<400> SEQUENCE: 147
gggaagcagt ggtatcaacg cagagtggtc attacggccg ggatattgat acctacgaaa 60
gcctcctgaa ttgtaaaaat ggtcttcgag ggggctgcgc gtcgcatcta agctatttga 120
ttatctgatt ttgttgtacc cacttcatta tttaggattc tgggggctca acaatcctat 180
atgtataatg tagttatgga gcgctgaaaa ctacacctgc atattttagg ccaattgtgg 240
gatgcaacac tctttgtatg aggtatcaga taatcaaata gcttagatgt gacgagaaga 300
caattttcac gatttgggcg cctttcgtag gtataaataa cccatatttc tagtataata 360
tcataataat agaaccagtg gaaattgcta cccacaaagc aaaggcgctc gagtcgtaaa 420
aagtcgaaaa tttattataa cggaaacagc ggatattgat acctacgaaa ggtgccagaa 480
tggtaaaaat ggtcttcgag ggcgccgcgc gtcctcggag cggatattga tacccacgac 540
gaaaggcgct cgaatcctaa aaaatctacg acggcgcaca gtggtccaaa 590

<210> SEQ ID NO 148
<211> LENGTH: 149
<212> TYPE: DNA
<213> ORGANISM: Diabrotica virgifera virgifera

<400> SEQUENCE: 148
ggggtgcggc gcgctccatt tcaaaaatct cctattttca tccgaaaaat attttttata 60
gattctttgg gacattctaa ataaaataag tttcttgaca tttttctcaa aagttaatag 120
ttttcaagtt ataagcgatt gaaaatccg 149

<210> SEQ ID NO 149
<211> LENGTH: 625
<212> TYPE: DNA
<213> ORGANISM: Diabrotica virgifera virgifera
<220> FEATURE:

<221> NAME/KEY: misc_feature
<222> LOCATION: 498, 499, 500
<223> OTHER INFORMATION: n = A,T,C or G

<400> SEQUENCE: 149

```
ggggaagata aaataatttc ctgaaataaa gtattgccgt tgaaaaatat ctacaaaacc     60

actttggggg gtgttcaaaa tggacgtcat tcttcatatt cgctaattgc cggtgaaaaa    120

tattgtctag agttaaaatg gaaacagtaa attcacagtt gttgaccaaa gccataaact    180

ttcatggtca acagctgcag aagttgtggg aaggagaatt tggagaaaat gatttgacaa    240

gaaaaaatgt caaagatttg aattacaatg tgtatagtca acgccagaag aacctatctt    300

ttcaagatag aggtaaacgg ttgaaactcc aacagttttt gataaagaag gctaatttta    360

tctatagttt ggaacccacg aagcaaaaga acaatgagaa agcgattact gaagatatgt    420

atgctgttat gcctcctttt gaaacttaca ccagtgtaga caaacaaaaa agagtggcat    480

tcttcatgga gaatgtgnnn taggtaatct aatcctgggc accattgtga gcagacaaca    540

atcaggaatg atgttgaaag tgttgtgtac tactggaaat ggtaacactt gtttatatgc    600

tgctgatatc aacgtcaagg cattc                                          625
```

<210> SEQ ID NO 150
<211> LENGTH: 594
<212> TYPE: DNA
<213> ORGANISM: Diabrotica virgifera virgifera

<400> SEQUENCE: 150

```
gggggtatg aggatgcagc acaatttgga gcaacagata caagcgagaa accagtccgg     60

tgtgagcgag gatgccctaa aagagttctc catgatgttc aagcacttcg acaaagaaaa    120

atccggaaaa ctcaaccatc aagagttcaa gagttgtcct cgagctcttg gatacgactt    180

acctatggtg gaagaaggcc aacctgatcc agagtttgat gctatactgg atgtagtgga    240

tccgaatagg gatggtcacg tttctctaca ggaatacatg gcctttatga taagcaaaga    300

aactgagaac gtccagagtt ccgaggaaat agaaaaggcg ttcagggcaa taacggcagg    360

agatcgtcca tatgtcacca aagaagaatt atatgccaat cttaccaagg aaatggcgga    420

ctactgcgtg gcgaggatga agccttacgt agagccgaag acagaacggc ccatccaggg    480

cgctttggac tatatcgagt tcacacgcac actttttcaa aattagttag gttaggttcc    540

gcattagtcg cttactcttg ctaaacgtta gatagacagt ataatattat tatt          594
```

<210> SEQ ID NO 151
<211> LENGTH: 627
<212> TYPE: DNA
<213> ORGANISM: Diabrotica virgifera virgifera

<400> SEQUENCE: 151

```
ggggttaagt ttgtaatcga agtcgtttcg ttttcgtttt gtcgtttgta ctttattttg     60

cactttattt gtgataattg ataataaaga caaattaata caaaatggaa acaattttgg    120

aacaacagcg tcgttaccat gaagaaaaag aacgtttaat tgatgccatg gtaaaagaaa    180

tgcttcacaa aaagacaact ttcagagaag caataaactc agaccaccga caaaagtacc    240

tgctggatag atatatggct tcaacagaaa gactaataga tctttatgat gatagagacg    300

gacagcgtaa ggctgaagta gccgctctta cgggccccaa cgagttccaa gaattctaca    360

gtaggttaaa attaatcaaa gacttttaca gaaggcatcc aaacgaaatc agtgttccta    420

tgtcagtgga atttgatgag tttgccaaag ccagggaaaa tcctaacgag gatatggcta    480
```

actttgtaga atttacagat gaggagggct acgggaagta tttggattta catgaatgtt 540
acgaaaagta tataaactta aaaggcatag aaaaggtaga ttacattacc tatttgggta 600
tgtttgacca actatacgat attccga 627

<210> SEQ ID NO 152
<211> LENGTH: 526
<212> TYPE: DNA
<213> ORGANISM: Diabrotica virgifera virgifera

<400> SEQUENCE: 152 gggggcatt gtcttttata aatcgttatc taaaagtttt cagtatgaag gtcgctttac 60
ttttactagt ttttatctgc tttgtaaata ggacctattc ccgaccaaat atttttaaat 120
tcaaagacgc caaacgaatc catgccgtat gtcaagcaaa ctcggaaaca catgtcaacg 180
agtaccttga aaggcttcaa gaatttggca agattgaagt tccaaatatg gcgaagcata 240
cactctgtat gaacattaat gccggactac aatacgaaaa cggtgatatt gcagttgaga 300
gattaagaag cgacttggaa gaagtttcaa acaacgaaaa taaaatcaaa gaaattgttg 360
atacttgtgg tgttcgagcc cctggaagcc ctgaagatgc agctatggct tttggcaaat 420
gtctatgcag tcaatggcct caacatgcag tatgtgtttg cagcacatag tagcagcgaa 480
aaatagtttt tatataaata tatatcaata aataaatttt atcttc 526

<210> SEQ ID NO 153
<211> LENGTH: 601
<212> TYPE: DNA
<213> ORGANISM: Diabrotica virgifera virgifera

<400> SEQUENCE: 153
actttttagt cttacacttt tcaaacaata aaatatatcg ccatgtttat taaaatatat 60
gtataaaaca tatgatgtac aaacatgaaa agtagtcgga accggcaaaa aatttaaaac 120 tttttgttt atttgtgaag cataacgtaa acaattaacg taaaaagtct tatttttaaa 180
aattcttgta gttgatgcac taacaaaaaa tgacatgtga aattatcaac aaaaaaaaaa 240
aagaatctag aaacataaaa ttgtaatatt tttcgatata aaaaaatttg ggaggtacac 300
ccaaattttt caaggtatac accaacaact ccaaaaaaca aaccaaataa gattttgttt 360
aaaatttatc atcaaacttc ggagatatgt ttatatacac atttgtcaaa aaaaaaaacg 420
ataaatcgat atttttgat atattttcgc ttaaacataa aatatttaca catatgattg 480
aagggtttca aaaaaacaaa atgagacttt ctaaattaaa atgaaaaaag tttatgccat 540
aattacaggg gaatagcgct actaaacgtt gcgtataaaa tacttgcagt acatataaaa 600
g 601

<210> SEQ ID NO 154
<211> LENGTH: 95
<212> TYPE: DNA
<213> ORGANISM: Diabrotica virgifera virgifera

<400> SEQUENCE: 154
aatgtgaaag ggcgcacttg atgaaaagga acccccgtaa agtaacatgg actgtcttgt 60
acagacgtaa acataagaag ggtcaggagg aagaa 95

<210> SEQ ID NO 155
<211> LENGTH: 635
<212> TYPE: DNA

<213> ORGANISM: Diabrotica virgifera virgifera

<400> SEQUENCE: 155

```
ggggattctc gcgtcctttt ccccaagaga tcgtgacgaa aataactgtt tgttgaattt     60
ctccaattat ttgtgtaatt ttgccattaa tcgcgtttaa aatggcaacc cgagtgtttg    120
tgggtggtct tacttacaaa attcgcgaac gtgacttaga aaagttcttc agaaagtatg    180
gaagaatcaa ggaggtttcc atgaagaatg gttatgcatt tgtggaattc gacgatcgca    240
gagacgccga cgacgcttgc tatgagctaa acggtaagga cttaatgggg gaaagaatta    300
ctgtagaaag agcccgtggt acgccccgcg gaagtgatca atggcgggga agcggtcgag    360
atagaggtta ttcaggttat agcggtccac gcggtagaaa cgataattct agagctcgtg    420
acaaatatgg gcccccgacg cgtacagaat acagagttat tgttgaaaac ttgtctagcc    480
gttgtagctg gcaagatttg aaggattaca tgcgtaaagc cggtgaggta acctttgctg    540
atgctcataa actagttcca aacgagggag tcgtcgaatt tgtttcatac agcgatatga    600
aaaatgctat tgaaaagctt gatgatactg aaatt                               635
```

<210> SEQ ID NO 156
<211> LENGTH: 599
<212> TYPE: DNA
<213> ORGANISM: Diabrotica virgifera virgifera

<400> SEQUENCE: 156

```
gggggacctt ttctggttgc acctccaagg cttctaaaat ttgcaagcca taacggatgc     60
tgagactaaa aaagatgagg gaattttaca atttataatt cacgtctcat ctgctcagcg    120
cggtaaagtt ccaacgagaa tggttccctt agtactccaa tcagagtaaa catgttaatc    180
aaaaattaat aaccattttc aatttcgttg caacactaca gccgcatcat attctagttc    240
aatcagaggc cgcatcatat tctagttcaa tcagagagtg cagcaagcac ctctaccggt    300
ttcgaaactt attagtctct catcaggagg cacatctgct gctctctctg acccaaccag    360
gacaaaccct ggcgtgcagg tacgcattgc aacgaacgaa atggcaggga tgctctagcg    420
gcaactgcta gcaagagact aagttttcaa actaatagca cataaaataa tatcaaaaaa    480
attactctac atcccaccag attgaaaaca atgagaacct tctctgatta cacatacgag    540
gcttctaaaa tttgcaagcc ataacggatg ctgagactaa agaagatgag ggaattttta    599
```

<210> SEQ ID NO 157
<211> LENGTH: 167
<212> TYPE: DNA
<213> ORGANISM: Diabrotica virgifera virgifera
<220> FEATURE:
<221> NAME/KEY: misc_feature
<222> LOCATION: 85
<223> OTHER INFORMATION: n = A,T,C or G

<400> SEQUENCE: 157

```
agagtacgga atcaagtaga tgaaaagagg cgaatatttc aagcaatatc tgcgaatgtt     60
agttctgaag gtcagagatt gttcntagct atagctaaaa caattagtga ggttaggtgg    120
aacgattcgg aaattgtggt ttttaatcga gatgttataa ttagtcc                  167
```

<210> SEQ ID NO 158
<211> LENGTH: 650
<212> TYPE: DNA
<213> ORGANISM: Diabrotica virgifera virgifera

<400> SEQUENCE: 158

```
ggggaaatat gttagtatgt ggaaattact tgataaataa ataaaatatt gcaaaaagga      60

gcctaaaccg ccattaagaa agacaaaaaa atacacttta ttcaaataaa ctttttatc      120

ccacgcctag attttgtgtc acattggatc tactaaaaat cgattttcta taacaagaaa     180

tcgaacgtga ctgactcggc aacatttcgc gcctatgagt ataaaaatta ttgtttttga     240

tagtataaaa atgtcattgt cagtgtcgaa ttaccgacgc actgttgcct cactgttgaa     300

agttcgcaga actttcgaaa aacaagaata ttgatgacgc gctactgttt actcttaata     360

ttaaatttgt aattctcttt tagcgttcct caataccttc ctctatgctt ggtgtccgct     420

caatttttg ttctagtatg ctggtcattt cttgttttac aatatcacat accatttctt      480

ctctatcaat aataactatt tgctttgtca cccatataat cttgtttaat ctcaatctga     540

tttttcctac aaaaatatgg tctccttgtt gccaatcctt aaatagtgca tgtcttctca     600

gttggttttg agttttggag atattattta caccaattgt aatttcaact                650


<210> SEQ ID NO 159
<211> LENGTH: 584
<212> TYPE: DNA
<213> ORGANISM: Diabrotica virgifera virgifera

<400> SEQUENCE: 159

ccactgaaaa ataaaaaaaa aaactttag taaggggcta ttctggacta cggggcaatt       60

ctggacagtc aaaaaaatgc ctgtccagaa tggccccggt tgacaaatat acttataact     120

ttttttggc tagaacaaaa aacacaacct caagggtcaa taataacaag ccatgtaaca      180

ttttgttaag gtgaaaaaca ttaccattac ttacttggaa atgagtgcag cacagaaagc     240

ttgaccgcta tattttttta acggttttc cacgaaattt tgtttgcgcg ccaaaaggtg      300

aaaatgccca gcgcggacct tccaacagtt atcaaccaac tggctgaatt tctcgcgaaa     360

agttgtgaat atcacgccac ccgcaagtgc aggctttcgg cgcggttgcc acgtttacct     420

gagaaaacgc gttgtccaga attaccccgc atgtccggat taaccccgtt atacggtacg     480

tttttactta aaacttacgt aaaagttttc aaaaattgca tttttgcgtc atatcatttg     540

aattaaattt ttggcatttt tttgaatgaa acattgttta gtaa                      584


<210> SEQ ID NO 160
<211> LENGTH: 508
<212> TYPE: DNA
<213> ORGANISM: Diabrotica virgifera virgifera

<400> SEQUENCE: 160

ggggacattt gaaatttttt ttggagaaga ctggactttg agaaattcag gttagttgag      60

gacaaatttt gcggacttac cttctagtga actagtcaaa ttgtcggtaa ggagtgttct     120

agggcggtac acagtggttc caaatgctga aaacgtggtc atgaggtaaa agagtgtggg     180

tacttatgta caattgtaca gctcccagaa agaatcatgg ccgatgacaa acgctgtcgt     240

cggtcgtaca cccacctaaa ctttagcaga gaggatttct ctcgttggtc atggttcgct     300

ccgggagctg tacacacgta acaagttata cttctttggc gtcattaaaa agtagttttt     360

gattatatta tgtaaataat tacaataaaa taataaaagt actggaaaac gatagtcaaa     420

gttcagttta aatttgaaaa attaaatatt taaatatttt tttatttatg tataaaattc     480

gttaatatac cagaaataaa acgaaaag                                        508


<210> SEQ ID NO 161
```

<211> LENGTH: 644
<212> TYPE: DNA
<213> ORGANISM: Diabrotica virgifera virgifera

<400> SEQUENCE: 161
gggttctgag aaatgttaat tggtttataa caattttttt aaacatttaa agattatgca 60
aaaaactgaa aaatttatat tttgtcgaca aaatattaaa taggcatcac acctttatca 120
tctttctaag tttgatcaat gtctcatgat tattttggtt gttattgcga ctgtaaattg 180
ttaattaaca attgaattgt tgctaaagta ttcgtttcat tttcaccggc ttctgaattt 240
ataatctata ccaagaaaga ttttatttct ccaagctata tactgataaa taattactgg 300
cccaaaaaaa ttatttgaaa attcgagatt ttgttgggga aacccacatt ttccgaggaa 360
aattttcgtc ggagcaaatc gggaaaaaca tgcctctatg tagaattaaa ttggggtgaa 420
tttttatttg agtgtttttg gtgtaaagtt aaaatcttcg gagttataga gcaataattg 480
aaaaaaatac gatttgtcgg cgcaattttg tttataaaaa agtagcacac tatctgcgga 540
cttttcaaac ctatattaat aatatatagg atcttataat tagattccag caataaaatg 600
gctggtaaat aacctttctt tgtacttaac taattagacc agcg 644

<210> SEQ ID NO 162
<211> LENGTH: 659
<212> TYPE: DNA
<213> ORGANISM: Diabrotica virgifera virgifera

<400> SEQUENCE: 162
ggggcgtgta tatgtatata tttttatatt catgtaacgc cttggaaatc tcaatattta 60
attttatttt ataatctctt ggtattaaaa tttttggtat cggaactaat aaaagatagc 120
ggcttataca taattttgtc acgttttatc cttgatacat aacaagggtt ccaaaatctg 180
ccagtttata tcactaggta aaaagtttta gttcgacggt ccttctcact tttgttgtaa 240
aagccgtgaa tacctgtgtt ccagaggcgt gcggtccatg gaagcggggg aagcaccgct 300
tctctattat atacttcgat ataacaaaat atattattaa ctaatattta attatcaaaa 360
attttcccca atcccagtaa tctacatatt attacctagg caataggcat tgaaaaatat 420
taaaaattaa tcgcatagga aggaactcaa tatgcactat gcacacaatt caactattcg 480
gtccacccct gacagaagcg catctcaaaa tcgccgcttg tcatgcagtt gtcctgtata 540
aaaattggtc agggttcaat aaccgcaccc actagtcgcg cgaattttgg taccctgtag 600
aagcgattgt tcgatcgcct tccaagagtg ggatcatctg actgttactg cttctaagg 659

<210> SEQ ID NO 163
<211> LENGTH: 598
<212> TYPE: DNA
<213> ORGANISM: Diabrotica virgifera virgifera

<400> SEQUENCE: 163
gggggaagtt gcgctgtgct gtgagttaca accacgaatc tctcggccag gatgctggca 60
atttggtttt tatttgttgc tgtttcatcc tcaaatcaat ttgtcgttga taccgtgacg 120
gccaatgaag tctggcaagc tcctggttgc cataaagtgg gtcatactag aaaagtcagt 180
attccaaact gcgtagaatt cgtgataaca acaaacgctt gtcgcggatt ttgtgaaagt 240
tgggctatac cgtcattaat aaaaggatcc actatccaac cgataacatc cgttggccaa 300
tgctgcaata taatggagac agaaaatgtg ttagcaaagg ttatgtgcgt tgaaggaatg 360
aaagtattca cgttcaaatc ggccgtcaca tgttcttgtt accactgtaa gaaagattag 420
agcgactgct ggaaaggacc aaggcgagtt tattcaaaat ttatatgtaa catacttaaa 480
gttcattgat tatatttagg cgtaagtaaa aattacaata tactttctta attactgtat 540
atattgtact gactgactga ctgattgtag gaattatgtt cattaaattt tgtttccc 598

<210> SEQ ID NO 164
<211> LENGTH: 410
<212> TYPE: DNA
<213> ORGANISM: Diabrotica virgifera virgifera

<400> SEQUENCE: 164
gggagacagg taatagcaga gataaataga aaaagggtag aataagagaa taatatataa 60
aggtaatgac acacagatag gagaagctat gctctaagtg aataaaatat atcttgaaaa 120
gctagaataa atggaatatg gagagaagta gaaagttgag agatatgtga agaaaattta 180
ttgaaaaagt tacttaaata cgaatgaaga acggtaggag attcatacag aaaacacaga 240
aacagcgtaa aaagactaat aagtgaaaca cagagaataa taattaaatg acagtttgga 300
aaataataat acatagttct gactatgaac tacaagattt aaagaaagga aaaagtcgag 360
gtaatagcac ctatacaaaa aattacagta attacaaata aaagcaacac 410

<210> SEQ ID NO 165
<211> LENGTH: 646
<212> TYPE: DNA
<213> ORGANISM: Diabrotica virgifera virgifera

<400> SEQUENCE: 165
aaaaaatctt tacctaaaat aagagaatca aagaagattt ccccagtaga aatcagtaca 60
tttatcgaag aagaaagatc cgctatatta aaggaaaatg atcatgtcgt tgatagttct 120
tgggtcgtaa tagaagagga agaacttagt tatataccag aagtaatacc acctgtcatt 180
gttgaaccag aaaaaatgga tgcagatact actgaaaaag atgaacctat tcaagttaaa 240
cctgaagata gtttacctga agatcaaatt gaacatacag agtctatcaa aaagccaaga 300
aatcggtcta agtcaaaacg ccaaaaaacc cctaaagaac aggaattgtc tgaaactatt 360
gagcattcgc cacgtgtatt accagctata gctactgtcc aatctaacga acagtttgaa 420
gttaaatcaa ggtcccctag tagaacctac gcatcagttg tgaagtcgca tatagaagga 480
gttactcctg aatacattca gtatacccaa gttattactt ctatcgataa taaaccccag 540
accgttgaaa gcattactga ttcaacagtc gaagaaacta cagaagagat aatatcagaa 600
aaagtagtgg agcaacccac agtgcaagaa ttgcaaacaa cagaga 646

<210> SEQ ID NO 166
<211> LENGTH: 277
<212> TYPE: DNA
<213> ORGANISM: Diabrotica virgifera virgifera

<400> SEQUENCE: 166
gggggcctgg tacttactta tataatgtta agcttcttta aagtaacttt ttctacaacc 60
gtgttaaaaa tgcaattttt agcactccat acgagcgtta aaaatgctac tttaaggcac 120
tagtgcttta aaaaatttaa ggcagtgcag ttcatattga ccgtatacgc tgtgagctcg 180
tacgtagagg ggatgtttac aaattcgcga gcgccagtag tgacaagtcg gtaaacgttt 240
accggaaatt tgacataaat gtcaaagtgg ttaattc 277

<210> SEQ ID NO 167

<211> LENGTH: 659
<212> TYPE: DNA
<213> ORGANISM: Diabrotica virgifera virgifera

<400> SEQUENCE: 167
gggagtgatg aagttttatt cagactggtt attcatccta tattttttt gtaataatta 60 tggcgacatc aaaattaatg gtgtatctga agaaaaagta tcacaatcct gatgtagctt 120
atagagaaat aatcaacatc accacacaat acagaggttt acatccagaa cagagtgtct 180
acaccttcaa cgatggcaca agaatggatc tcattaactt aactggtaca attcctgtgc 240
gttacaaagg caatatttat aatattccaa tttgtatatg gttaattgac acgcatccag 300
agaatgctcc catttgctat gttaaaccga cttccgacat gtccataaaa gtttccatgt 360
ttgtagatca aaatggaaaa gtttatctgc catatttgca cgattgggtg ccgaatgaat 420
cagatttgct aggattaatc caagttatga ttgttacatt tggcgaacaa cctccagtgt 480
ttgctagggc caaagacaat gaatcgtatc cgtcaaattc attcatgcct caaccatctg 540
gtggttacat gcctccgtat cctacccccct acccaccagc atcaggaggt ttcggcgggt 600
accctccata tcctccaacc agcaacaatt ctttccaagg atatccaccc taccttct 659

<210> SEQ ID NO 168
<211> LENGTH: 409
<212> TYPE: DNA
<213> ORGANISM: Diabrotica virgifera virgifera

<400> SEQUENCE: 168
ggggaggtta aggttaaact tatgtcaaat caaattttaa atttgaacat gtggcctgtt 60
atatacacag cactcagaac atatgcaccc tatgtaactc ttcctgttgc tgctcttgta 120
ggagtcatag gttacaatct agaaagttgg atctctaata gatatacacc atacaacaaa 180
tctattaaag aacaacgaga agataggcta ttagttgaag caaaacttaa agaatctgat 240
aaagtagaga agttaaaata taaggctaat attctagaca caaatttatc tccttcctta 300
acttgaacat tagaatggtg cattggtata cacttaaatg ttaaataact ttaataaatt 360
ggagtatgta ttgttttagt tctctatatt aataaaaagt tgtgatatt 409

<210> SEQ ID NO 169
<211> LENGTH: 253
<212> TYPE: DNA
<213> ORGANISM: Diabrotica virgifera virgifera

<400> SEQUENCE: 169
ggggacaaaa tatggagaaa taaaatatcg gaaaagaaat aaaaggcaga atttacaaaa 60
cagtcatcag accaataatg acatacgcgg cagaaatacg acccgacaca gagaggacca 120
aaagattgct cgaaacagag gagatgaaaa ccctaatata atcgacaagc tcatccggaa 180
aagagaatcc aatcgtcttc agcaactagc ttacaattca aacccagtca tcacaccaat 240
ctataggtcc ctc 253

<210> SEQ ID NO 170
<211> LENGTH: 633
<212> TYPE: DNA
<213> ORGANISM: Diabrotica virgifera virgifera

<400> SEQUENCE: 170
ggggaaatac gaatatgaaa acatttcacc acatcaacac gtgaattaat attcgaaaat 60
ggagtacgaa aatacacaac aaaatataaa cttcgtaccg tgtgtaagat gggttaaacg 120

```
aggagtggcc aattcaagcc cagtaaaatt gcaactgtcg aaaaacgagc tggctcaaat    180
tattaatgac accaagatta aattacaaga atccaatgaa aatgaagatg agcctatgga    240
agaaggtgaa acgtctcaaa cagatgagtt tgccttagag gattacgata aagaagacga    300
aaatgaggac actgcaaatg ctttaggaat tggatcattg gcagaactcg ataatgatgc    360
tgcagacaat ttttctgagt cagacgattc tgaaaaagaa gatgataaaa tcaaaccatc    420
tgacaatctc atactagtag gacatgtaga aggggatgca agtctattgg aagtctacat    480
atacaatgaa caagaagagt cattgtatgt tcatcatgat attatgttat catcctttcc    540
tctgtgttta gaaccgctaa actatgaacc gaagatgccc aaaggaaatt attgtgcagt    600
gggatcaatg tcacctgtta tagaggtctg gga                                 633
```

<210> SEQ ID NO 171
<211> LENGTH: 640
<212> TYPE: DNA
<213> ORGANISM: Diabrotica virgifera virgifera

<400> SEQUENCE: 171

```
gggccctgta tatacctcga tggcaataat ggacctgacg gatgtgctat tttttataga     60
aaggacaaat tcgaattact tgaggcacag accaaaattt tggagatatg gaaggttcaa    120
agtaatcagg tcgttctact gacaatctta aagatgaaag aaacaggcca aaaaatctgc    180
gtcaccacaa cccacctcaa ggccaaaaaa ggagctctac tatccactct tcgcaacgaa    240
caaggtaaag atctcctcca gtttgtgaaa gcaaacagcc aggatcttcc tttgattcta    300
gccggagatt tcaacgcaga acctactgaa cctatctact caaccgtact cgacaatcct    360
ctgaagctgg gtagtgctta tgctgactgt gatattgatc ctacgatttc ctcagctgaa    420
agggaacctt cgtacacgac gtggaagatc agaggtgaag gagaggtctg ccataccata    480
gattacgtgt tttattccaa gaataagcta gaactagagg ccgtattaga tatgccgacg    540
ggagaggaaa ttggagagaa cagagtaccc agcttttctt acccatcgga tcacttttcc    600
ttagtgtgtg atttcaaaat aggccatagt taagtttagg                          640
```

<210> SEQ ID NO 172
<211> LENGTH: 651
<212> TYPE: DNA
<213> ORGANISM: Diabrotica virgifera virgifera

<400> SEQUENCE: 172

```
gggggacaaa ttgatgaaag aatgatggtt ggtgcttttt tcaagtctat accaatggca     60
gcttttgcgc actgtagcga tctgaaataa gaaaaaaagt ttttttcgaa ccaccctatt    120
aagcagacaa attaataatt gtatcagaat catttattca ttgggagtta gtaaatatct    180
ctgctcataa tttaaaataa aatatttaaa aaatatcccg ggaagtcttg aagaattctc    240
ggtaatcggg attttcattt tttactgatt tcccgagaaa tttgtcccgg gaatgcagct    300
ctatttgtag gtactctact ggatgattga gaaaaaacaa cactaaaaag cttattgtaa    360
aaagttatga ccgagaaaat aaggccgact taaaagtacc attgggaagc aactgtcaaa    420
aaaaatctaa atgtgctgag agactaaggg ttaattatga tatacagatg tcgttttcct    480
cctcacaact ttttctgttg tccctttggt ctactagctg ataactttgt aggttccttt    540
aaattcatgt gtaactggag tagttgaatt tggtttcact tctctttagt tcatataggt    600
cttgatcatt atcatcattc aatgatgatc ttgatcatca atcagttttg a             651
```

<210> SEQ ID NO 173
<211> LENGTH: 667
<212> TYPE: DNA
<213> ORGANISM: Diabrotica virgifera virgifera

<400> SEQUENCE: 173
ggggcctttt ccaaagtttc atataatttt taagatgagt actgttatta aaatcgtttt 60
aaaatggaac ggaaaagaat ttaatttaga atcatcggaa gatgacactg tatctgattt 120
aaagaaaacc atagaaaatg taacctcagt aaaatgtgga agacaaaagt tgttaaattt 180
aaaatacaaa gggaaaacgc ctgaagatga ttgtactctt ggtcttttga aacttaaacc 240
caactttaaa ctcatgatga tgggttcact tgaagaagac atagcagaag caaatactgc 300
acctgaaaac cttcctgatg ttgtcaatga tttagatata gaggaagagg aagttgccat 360
tgaaaatcag gatgtatatc ttgcaaaagt ggaaaaacgt atcaaagatt ataaaataaa 420
tatgttaaat gatctccggc ctgaaaaaaa gttgctagta ttagatatag attacacact 480
ttttgatcac agatctaccg cccaatctgg agcagaatta atgaggcctt atttacatga 540
gtttttaact acttcttatg aacactatga tattgttatt tggtctgcta caggaatgaa 600
atggatcgag gagaaaatga agctattagg tgtttctacg catcctgatt acaagattgc 660
cttttat 667

<210> SEQ ID NO 174
<211> LENGTH: 623
<212> TYPE: DNA
<213> ORGANISM: Diabrotica virgifera virgifera

<400> SEQUENCE: 174
ggggagtctt gtgaaaaaag tcacagcgct cactggcgtt ttattaagat caaaatgcca 60
tcttcaccgg aggaaacaac ttttcctcaa agactgcagt caagcaacaa cttaggcgaa 120
caaaattcaa aagaccaaat aaaaaaaaat ggttatttcg agcaagattt ggtatggagg 180
aatgtaatta tatatatagt actccattat ctgttaattt ttgcaatatg gagacttttg 240
accggtcaaa tgaagcttgg aacttttatt tttcattgta tttacgctac ggcttctgtc 300
cttggtatca cagctggaaa tcgtcgtctc tgggctcata gaacctacaa agcaaaactg 360
ccattgcgaa tatttttaat gttaatgcaa acaacgacca tccagaataa tatttacgtt 420
tgggccagag accatagact acatcacaaa tacacggaca ctgcagctga tcctcacaac 480
tcgaatagag gattcttctt ctctcacgtt ggatggctat taatgaagaa gaaccctgaa 540
gttaaaaaac aaaggaaaga atattgatat gagcgatgta gcagctgacc ctgtggttca 600
atttcagatc aagtattatg gaa 623

<210> SEQ ID NO 175
<211> LENGTH: 406
<212> TYPE: DNA
<213> ORGANISM: Diabrotica virgifera virgifera

<400> SEQUENCE: 175
gggatatgca gaagacataa ttcttatagg cagatacaag gaaagataaa aacaagcagt 60
aacaatcctg gcaaatcaag tatgggaaag aggtctaaag gttaacgaaa taaaaacaaa 120
atatctactc tgctctagaa gagaagataa aaagacgaga gaaatcaaga tagaaaacta 180
cacttttgaa agggttcaat aatttaaata tttgggagta attgtaaatg gcaaaaataa 240
gaaaagtgaa gaagtaatgg agcgaatact agcaggcaac gaaaatactg gagatatcat 300
aggctaatga aggaccagca cttatccaga aatacaaaac tgaaaatata cagatttgca 360
atcagaccag tatttacata cgcagctgag acaatgtgcc tcacag 406

<210> SEQ ID NO 176
<211> LENGTH: 660
<212> TYPE: DNA
<213> ORGANISM: Diabrotica virgifera virgifera

<400> SEQUENCE: 176 gggggaaga atttgtaggt taagaataaa ctgcatgttt ttgttttaat ttaaattttt 60
gaaagatcag taatacaaaa tggaaacaca ttcatctgaa agttcacaaa aaagaaataa 120
cagaaaaagg aagaagtctt ttctaaaaaa tgcaagaaaa tatgccaaaa aaggacattt 180
tggaagaggt tcccaattgg attctgatac atatcattat ttcgtaaaaa tattagaaac 240
atataaagaa ggttttgata cagatgaaga taaacaagtt tttgctaata atgtgtttgc 300
acaaaccgaa gatcaagaag tgaattgttc ttgtaaccaa gtaggatgca gagttgtgga 360
aatgctatta ccttttgcca atgatgacat attgaagaaa ttcatggttg cctttagtga 420
agatatgagg cctctaatca gtgatagatt tgcaagccat gtattagaat gtcttgtttc 480
ggaaagttgt aaaaggactt taaataacaa agtgccagaa gaatcaagaa cagagtatca 540
gaaatttgct attaaagtta gcaagttctt gttaaacaat ctagaggatt atatttggga 600
tacttatggg aatcatgtta tacgaagttg tcttacacat ttaatacaga tgcctgttga 660

<210> SEQ ID NO 177
<211> LENGTH: 578
<212> TYPE: DNA
<213> ORGANISM: Diabrotica virgifera virgifera
<220> FEATURE:
<221> NAME/KEY: misc_feature
<222> LOCATION: 284
<223> OTHER INFORMATION: n = A,T,C or G

<400> SEQUENCE: 177
ggggcatgct ttgagcgtac agttgaactt ctctacaaat atgtagtacc taaaccacgt 60
gctgactgca ctaaaggcga acaattgatt gttacatttg ctgctggtta cattgcaggt 120
gtattctgtg ctattgtatc acatcctgct gatactgtcg tcagtaaatt gaaccaagaa 180
aagggatcaa ctgctctcga ggctgctaag aaattgggaa tggctggatt atggaaggga 240
ttgactccta ggattgtgat gattggtaca ttaactgctt tgcngtggtt catctatgat 300
gccttcaagg ttgccatgag aatgccacga ccaccaccac cagaaatgcc agaatcatta 360
aagaggaagt tggagggcaa atagagaatt aatttattaa cactaatatg taatttatga 420
ctttatttcc agaaaaacga aatcgcagta tttccattag ttcgttatag ttattgattg 480
tcatcaactt tgcgaatttt gatgttttta agttcatacc agttatgtcc gatattttag 540
attgtaaata gataatcatc aatatacaac tggaactc 578

<210> SEQ ID NO 178
<211> LENGTH: 678
<212> TYPE: DNA
<213> ORGANISM: Diabrotica virgifera virgifera

<400> SEQUENCE: 178
ggggagaatc aaattagaat ataaatttca aatgttttca aattttcaaa tatgaattat 60
taaaataaat agaaatgatt ttgtttaata acttctttct tcgacacgta aataagttaa 120

```
taaaacaagc atactgtaca aatataagta gtttgtcaaa agttgaaaga attaaattcc    180

taaggaaaat ggcccgtcct aacgcaaggg aaaacccggt gataatgaaa ctaaactcac    240

aagaattcca ctctatattc aacgaggaat tgcgaacttt agtatcctta tttaaagagt    300

atggctatga aattcgaatt gcaggtggag cagtaagaga tcttttaatg ggaatgcaac    360

ccaaagattt agattttgcc actacagcta ctccaaccca gatgaaagaa atgttcatat    420

cggaaaatgt tcgaatgata aatgccaatg gagaaaaaca tggcactatc acacccagaa    480

taaatgataa agaaaatttc gaggtaacta ctttaaggat agatgtggta actgacggta    540

ggcatgcaga agtacagttt acaacagatt ggctactaga tgcactgaga agagacttga    600

caatcaattc aatgttccta ggtctggatg gttctgttta tgattacttt tatggacatg    660

atgatcttca aaaacgaa                                                  678
```

<210> SEQ ID NO 179
<211> LENGTH: 647
<212> TYPE: DNA
<213> ORGANISM: Diabrotica virgifera virgifera

<400> SEQUENCE: 179

```
ggggctctgt cattttaaaa tgggtagtgc aagaactctt tttggaattt taggctcaaa     60

acagatatta ctatgttcaa attcccagtt tactactaaa atttcaagaa catttcttca    120

tcaatgcttt agatgtcata aatctctact gctaaatacc tggtcagcta ataatttaac    180

tcaaaattct ttactccata aaagaacgtt tcataagtca cacagtttca atgccgcaag    240

acgggattat tatgaattat taggagtagg taaaaatgct tcaaactctg atattaagaa    300

agcttattac aaattggcca aaaagtatca tccagatgta aataagaatg atccagaagc    360

atctaaaaag tttcaagaag tttctgaagc ctatgaaatt cttggagatg aaaataaaag    420

aaagcaatat gacacttggg gtgcaacagc tgatcaaatg ggaggcatgg gtggtggagg    480

aggccattca aaaggtccac aaggattcag tcagcaatgg caatatcaat caacaattga    540

tccagaagaa ttgtttagga aaattttcgg agatgctttt actcgaggct cttctcattt    600

tgaagatttt gcagaatcaa actatggatt tggcgaagct caagaga                  647
```

<210> SEQ ID NO 180
<211> LENGTH: 204
<212> TYPE: DNA
<213> ORGANISM: Diabrotica virgifera virgifera

<400> SEQUENCE: 180

```
gggttgttag ataaattgaa aaaaaatgta cccacgaata tattacaaca acattacatt     60

ttctcgagaa tgggcgggca tgatgacgta atcgatgatt tttattaaat gataatagga    120

ttcgtgtgat atctcactcg aaagtttatt caatgctcta ttcactaata taaacattta    180

tataattatt tataaagggt gccc                                           204
```

<210> SEQ ID NO 181
<211> LENGTH: 98
<212> TYPE: DNA
<213> ORGANISM: Diabrotica virgifera virgifera
<220> FEATURE:
<221> NAME/KEY: misc_feature
<222> LOCATION: 73
<223> OTHER INFORMATION: n = A,T,C or G

<400> SEQUENCE: 181

```
gtttggacag tctggagctg gaaacaactg ggccaaggga cattacacag aaggtgctga     60
```

attagttgat tcngtattag atgttgtaag gaaagaag 98

<210> SEQ ID NO 182
<211> LENGTH: 174
<212> TYPE: DNA
<213> ORGANISM: Diabrotica virgifera virgifera

<400> SEQUENCE: 182
gtaaaattaa ctacttctgt gaaaacattt atgaaattat gtaagtagtc gtttttatat 60
tatattggta ttaagattat aataatattt ataaattagt attaaaaata gatggatgca 120
acaaaatgta ctcgtacagt gcgctggagt aagtgttagt gttacccccc cccc 174

<210> SEQ ID NO 183
<211> LENGTH: 577
<212> TYPE: DNA
<213> ORGANISM: Diabrotica virgifera virgifera

<400> SEQUENCE: 183
ggggagtagc tgataagcat ggatcataca cctattcaac agttttatag ggatgccaac 60
gtatttatca ctggagggac gggatttatg ggaaaaattc tcgtggaaaa gctgctgagg 120
tcaacggagg tgggaacttt gtatttgctt gtacgagaaa agaaagggaa gcacaaggat 180
gacagaatca cggaaatatt cgacgatgtg gtttttaaaa gacttaaatc agaaaaatcc 240
aaattcagac atcgagtaca agctatatcc ggagacttaa tgctaccgca tttgggatta 300
tcagagtcag atagacagct tttaatttca aaagttaacg taattatcca catgggagca 360
acaatcaaat tcaatgaaag catcatcagt gcattacatg ccaatgtata tagtaccaaa 420
ttagttatag acttagccaa agaaatgaaa catataaaat cgattgttta tgtatccact 480
gcctattcaa attgcacacg aagcgaagta gaggaaaggc tgtatgatcc accgatatcc 540
tatgagaaat cagtagagtt aatagaaaag ttgtcaa 577

<210> SEQ ID NO 184
<211> LENGTH: 473
<212> TYPE: DNA
<213> ORGANISM: Diabrotica virgifera virgifera

<400> SEQUENCE: 184
gggattcctg aagttgattc cgttgtagaa cgatcagaca aaagtcgaag aacagccatg 60
ttgggtagtg tcggcgaaaa aagtgtatgt tcctagagaa aaactcgcag atttttgtgc 120
ttgtgttgtg caatttgtta agtgtttgac ataatttgga ttatgaccgc cgtagcggag 180
aacctcaact ggggcaccga gctctgggac cagtatgaca acttgtccct gcacacgttg 240
aaaggaatag actttttgga aaaatatgga cagtttgtta gggatcgagc tagtatagaa 300
tgtgaatatg ctacaaaatt aaggagacta gtcaaaagtt atcagcctaa gaaaaaggac 360
gaagatgatt accaatttac ttcctgtaag gcatttcgag ccttaatgaa cgaagtaaac 420
gacttggcag gccagcatga gttagttgct gaagatttac aagcgaatgt gat 473

<210> SEQ ID NO 185
<211> LENGTH: 683
<212> TYPE: DNA
<213> ORGANISM: Diabrotica virgifera virgifera

<400> SEQUENCE: 185
ggggggattt tcaaaggtgt ttacaaattc aaattgttta ttacaagttt attacaatga 60

-continued

```
gagtgtatct ttgaaactgg aaatggcata gtccaagaag aaaaaggatt tttgaaaaac    120

gccggtacaa aggaagaagc tcaagtcgct caaggttttt cctcatatac ttcccccgaa    180

ggagtaaaaa tagaactccg gtacatcgca gacgaaaacg gtttccagcc aatcggagac    240

cacctaccga ctccgccacc aatccctgag gctattttac gagcgctaag tgtactgaaa    300

cagttgggta atttgaatga agaccaagaa gaaaataaca acattagatg aagagagagt    360

gtgatcaaat cgttattttg gataagtccc ttcatatttc aaaatggtac catactaact    420

atgaaatact tcaaagaatt aagatctttt taaaatacgt caacacttta gagtaggaaa    480

cagcggtgga acctcgcaaa atgtacacaa gttcggtttt atttttttgc aggaaaatca    540

aggggtgctt ataatgaaac taacattttc ttaaaaaatt tcgcccctga accccccttt    600

ttatcccttt aaagggggta tttgtggttt ttgcgaaacg aggcccttcc tgtatacgtt    660

ttgcaaagaa atgtacttaa tgg                                            683
```

<210> SEQ ID NO 186
<211> LENGTH: 446
<212> TYPE: DNA
<213> ORGANISM: Diabrotica virgifera virgifera

<400> SEQUENCE: 186

```
gggttatttt agtatttgca cgaatctgcc gcacatgggt gcatgtgaag gtgagttgtg     60

catttattac atggtggttg acatagctaa aatgtttaaa atgtttccta aaaaatgttt    120

ttgcgctctt ttcaatggcg gtattaactt ttttaaaaat taatacatac agggtgaaag    180

aattaaaaaa aaaacaacat atttttacat tctaggaaaa acacaacttc tggtaaaccg    240

attcttccgg ttcgacacct tgatcttaca cattaaataa agaacctata taccaaattt    300

ggtttgaata tgacgtctca ataaagaagt tatcgtgcta ttagtcacat atgtatagtc    360

agggccctcg ctacaatatg tgcaaagtgt gaaatgcaca cgggctccgt tctttagggg    420

cgccacaacc gagggtcaaa aagtac                                         446
```

<210> SEQ ID NO 187
<211> LENGTH: 148
<212> TYPE: DNA
<213> ORGANISM: Diabrotica virgifera virgifera

<400> SEQUENCE: 187

```
gggctgttct tcattcttgt tgctttactt aacacatctt caaattacaa agaccggatt     60

tctgtaactt ttgaaacgct catttttacc accgttaaaa atggtttatt ccatttttcc    120

atgttgagat tgttgtttta tctacgtc                                       148
```

<210> SEQ ID NO 188
<211> LENGTH: 517
<212> TYPE: DNA
<213> ORGANISM: Diabrotica virgifera virgifera

<400> SEQUENCE: 188

```
gggggtttcg tttcatcatc atttgttgta atttttgtag taaagcacat taaaaaaaaa     60

atctgtttta aagccatggc tgatgaagaa tttgacgaaa atgatgtagc agatgatttc    120

gatgacgacg tagaggatga taatatcgaa gaactcgaac aacccgagga agatggagat    180

aacatcgata tccttgctcc aggacaagca ggaggtggtg taccaaaaaa caagaggata    240

acaactaaat atatgaccaa atatgagaga gccagagtat taggtactag agccttgcaa    300

atagccatgt gtgccccagt tatggttgaa ctagatggtg aaactgatcc tctgcaaatt    360
```

-continued

```
gccatgaagg aattaaaaca gagaaagatt ccaattatta ttagaagata tttacctgac    420

cattcctatg aagattgggg aatagacgag ctcattatta tagatcacta gattgtaatt    480

tttatgtgga tattatttaa tacataggtt tttataa                             517
```

<210> SEQ ID NO 189
<211> LENGTH: 654
<212> TYPE: DNA
<213> ORGANISM: Diabrotica virgifera virgifera

<400> SEQUENCE: 189

```
ggggacatac gtggaactta gctataagtt gtagttttgt agggtaaatt cgtaggtttt     60

agtgaaagaa aatgtcgtcg aaaagaaaaa gtaaagaaag cataattgct agggtgaatt    120

tcccactata tactcttcag atgttaacgt caaggcatgt aatcgttggt ggtggaggag    180

ggacatccaa aactggtgta cacaatggtt ttgaaatatt tgagattttt catgacggca    240

cacgctttgc agcaaaagaa gtaaccagac acgaaactgg aggcaatgtt gttatgaact    300

gttctgttta cagtgataga aaatattctc ttttggtagc tggacaagaa agtgagtgtc    360

aattgtacaa actgaatcct aaactagtcg aggaagtgga aaatatcggt aataatactc    420

atctcaggca acggaataca aaaaacaaag aagttacaga tgacaacaaa aacgtgacaa    480

aagagttata ttttgatgtt aatgcaatag aaaatgttca aactgacttt aatgggagtg    540

aaccattatc gagggtggta aaaattaatc atgatggtac attattagct acaggtggta    600

cagatggaga tgtacgaata tggaagtttc ctagtatgca acctctattt attc          654
```

<210> SEQ ID NO 190
<211> LENGTH: 433
<212> TYPE: DNA
<213> ORGANISM: Diabrotica virgifera virgifera

<400> SEQUENCE: 190

```
gggccacgtc acaatagaag acgcgtgtaa cggcgggtta acgaactccc ttacattaag     60

agccaatata tggtagaggt acattttcag ggtacaaggt ttctccccat gtaataatct    120

gacgcgctcg agtaactgca aaaatccccg cttgggctcc cctactatat tgaatgtagc    180

aaatatttat tgaaatcttt tattttcaca aaatatttat ttagtattga tattttcaga    240

tagaaaatgt tctgtcagac atactgcata ataatataaa attgaggtat aggctgttga    300

ttatgtactt tagaaaggga ctacaatgtc aaaggtgttt tattgtttca tatagtcaaa    360

gggtccccaa atataaaaaa accgcggagt gctattactt aaagggctac gtttctaagg    420

aaagggtgaa tta                                                       433
```

<210> SEQ ID NO 191
<211> LENGTH: 316
<212> TYPE: DNA
<213> ORGANISM: Diabrotica virgifera virgifera

<400> SEQUENCE: 191

```
tttaatactt cagaaagttg catttcagta tttctttaat ttaattttaa taaaattaat     60

tcacattgta ttcatttaaa tccttagaag caaaaatcca ataatggccc tatcaccatg    120

gttgaagtcc ccttttacag acttaacggg atctctagta aatcaccagt ggtacggaga    180

atgtgctgat atggaattaa aagttttaga ctgtctagat gcctatggat tggacagggg    240

cttaaaaaaa tgtgatgatc tgattgaaga cttcagagag tgtgctttaa aaacaaaaca    300
```

gttcaaaaga atgtac 316

<210> SEQ ID NO 192
<211> LENGTH: 673
<212> TYPE: DNA
<213> ORGANISM: Diabrotica virgifera virgifera
<220> FEATURE:
<221> NAME/KEY: misc_feature
<222> LOCATION: 654
<223> OTHER INFORMATION: n = A,T,C or G

<400> SEQUENCE: 192
gggggagcga cgtggtggcg acgtcagctg attatttcta tttccctatt tctatttctt 60
acccgttttg tagtttataa atttataaaa acaacgaatt tagaatgtag ttttctgtag 120
gtaggaacca taaacataaa aatcatatta tttgattttg ctttttggat gtaaacgtaa 180
aactgaaata cctctacaat aacgatctat ttatacataa atttatttta aaaatcaaat 240
atggaaataa atcgagaagc tagtgaaaaa actgttgaaa taaaagtaga aaacgaagac 300
acctgtgttg gtcccttgga tgctttcaaa attgaaatta cagaagaacc caagagagaa 360
cccagagaac ccgcatacga ggcatttggt tctttagact caaataaatt tctgttaaac 420
actgaagtaa aacaagacga atataaattt gcaccatttc aagaaaagca aagaacagat 480
gaagaaaaat atattataca agttctaact actctatact gaaatcataa tgaagatgca 540
ctagaaataa acaaaccaat atttatttat taagcgcaaa aggccttgta ggcctagggc 600
taaaatgttt acatttctga ttacataaat aatataataa ataacttagt atancttaca 660
taacttataa aag 673

<210> SEQ ID NO 193
<211> LENGTH: 614
<212> TYPE: DNA
<213> ORGANISM: Diabrotica virgifera virgifera

<400> SEQUENCE: 193
ggggtcatca agttcttgtt ttgtctcgag gagttgattc gttttgttgg cagtacattt 60
tataattatt ggagtcggaa tatttaatta atgtgattag aaagtgtata gttttagaac 120
tagccatcac ttacttaaat ttctttaata gactcattgt tttaatatag tttggtcagt 180
tagttaataa agtgtaatta aaaatgagtg accccacaaa tcctactgga ctacctagaa 240
gtttaaatta tgaagcatta aaggctcata taatatcgca caaaataaat tgcggcctat 300
ggttaattag ggtcataggc attctctgct ccatagctta cttcattcca atttttggaa 360
atccttacaa ctactattac aaagtactcc tagcaaatgc agctatcagc gcattgagat 420
tacatcaaag gataggcaga gtgcaattca cgagacaatt tgctgcagaa ttactttcag 480
aagatagttg tcactatctt ttctattcgt tgatattttt atacgtatcg ccagtatcat 540
tggtactcgt accaattatc ctcttctgcg tactccattc agctagttat tcactcacat 600
tgttagatac atta 614

<210> SEQ ID NO 194
<211> LENGTH: 396
<212> TYPE: DNA
<213> ORGANISM: Diabrotica virgifera virgifera

<400> SEQUENCE: 194
gggataatca ttagtttttt tattgaaagc tggaatgaag ggttggatga aaaaaaaaac 60
tgtctttatt taatttataa agaattttat ttttaagtta aaaagcttaa atttttttaa 120

```
aagacgagaa gaccctatag agttttataa aattattaat aagttttttt agtattaaat    180

ttatttatat aataaattta tttaattggg gtgattaaaa aataaattta acttttttta    240

tattattata ttaattaata attttttgat ccaatttttt tgattataag aataaattac    300

cttagggata acagcgtaat tttattggag agttcaaatc ggtaataaag attgcgacct    360

cgatgttgga ttaaagttta taattggtgt agcagc                              396
```

<210> SEQ ID NO 195
<211> LENGTH: 533
<212> TYPE: DNA
<213> ORGANISM: Diabrotica virgifera virgifera

<400> SEQUENCE: 195

```
ggggaggtta taaaatattt gatttttgct ttttgcaacg gggatttttg atttattatt     60

tatttataat tcataggatt tatttgaggg aaaatttgaa aatttggcac agatttgggg    120

atgcctgttg tgttaagtgt tggtagagag taatcagtta ctatttatca tgggaaaagt    180

aaagaaacca aaagcgaaag cgctaggtgc gtttgaatcc aaaaataata gtgctccaat    240

aaaggaatcc atttcagcca actttgattt tagtataaaa caaggaaaat cagttgtggc    300

agatgatgta aaaagtgttc tttcatataa atccattaag tcccataatc caattaacag    360

gattataaag aaaaaagaaa aagtgaattt aaaacgaaag ttactgatga aaaaaattga    420

tttaggcaat gtactaaaga aagaacaaaa gatcagggac aagagaaaaa atacatcact    480

tattggtgac actaatgcac tgcatgatgc tttaccttca ctggattcat tat           533
```

<210> SEQ ID NO 196
<211> LENGTH: 655
<212> TYPE: DNA
<213> ORGANISM: Diabrotica virgifera virgifera

<400> SEQUENCE: 196

```
ggggatttgt aattgagata tctgttggta tgtgttggtt ttctatacac ttgagtctca     60

tatccagtat ccttctttaa gactaaagca tcgaggaaag gcagggtgtt attatattcc    120

ttttccattg taaattttat tgtctctttt atttatttta ttgtctattc tattatctct    180

aacgcgagag ttttagtgtc accgttgcat gtggttgtct ttttgaagac agatcgcatg    240

ctatgatttt tttttgtgac ggatgttctt gagttggggt tgatttcatg tggtcgagtg    300

agctatcttt cagtggagtc gtcccaggaa cgcgactcat aaatgttggc agtatcattt    360

taaagtcttc tactttggaa tgtgtcatat gtatctgaat tgccgatgtg aatgagtcgg    420

attaagtaaa ttattggaag aattttttac taagcaacaa catttttgtt tatattagtg    480

gtattttgta ttttgacagc ggcgcccgat ttgggcgtcg aaacgttagt aaaaatcatt    540

ttttaatgat attgtggttt atttcccatt ctaaatagtt aaaaatgatt tctttgattt    600

gtgtctgatg aataattatt taggtatttt taaatgctac ttaaattata ttttt         655
```

<210> SEQ ID NO 197
<211> LENGTH: 602
<212> TYPE: DNA
<213> ORGANISM: Diabrotica virgifera virgifera

<400> SEQUENCE: 197

```
gggtattcgc tttaaactcc agttttttta aaaactaatc attctaagcc agtcaaactt     60

ctagaatcta ttaataatac ataaataaag aagaataaat aagtccaatg actgaaaaca    120
```

-continued

```
ccgccaactt acattattat gcttccaatt ggatttctct tttttttttc aaaaaaaatat    180

attgattttt taaccgtaac tttttaaatt tttatcttag aaagttcgtt aaataagaat    240

tttgtaggtt tttacaaggt ttataatgct attaacatta aatcctttta aaattctcag    300

tcacaaaaag aggtggcatt gaaagggttg gtaaaggtgg tttttgcgtg atattacaag    360

ttttaattgt caatagctca ctcaattttt gtcgtaaaaa aatttttgca aactaaattc    420

ttgggaatta aataagttac aatttcatat ttaaatattt ttttttcgta tctctgatgc    480

tactctttct attctgaaga aaaggcattt tttaacaaac tacaaaaact cgttattcgc    540

ttttaactca attttttaa aagctgatca ttcgaagccg atcaaacttc tagaacctat    600

ta                                                                    602
```

<210> SEQ ID NO 198
<211> LENGTH: 557
<212> TYPE: DNA
<213> ORGANISM: Diabrotica virgifera virgifera

<400> SEQUENCE: 198

```
gggacatggc ttgctgtatg ttgtacagag gggatgttgt accaaaggat gtaaatgctg     60

ctattgcaac cattaagacc aaacgtacca tccaattcgt agactggtgt ccaactggtt    120

tcaaagtagg tatcaactac caaccaccaa ctgttgtacc tggaggtgat ttggctaaag    180

tacaacgtgc cgtatgcatg ttgtccaaca ctacagctat tgctgaagcc tgggcaagat    240

tggaccacaa attcgatctt atgtatgcca agagagcttt cgtccactgg tatgtaggag    300

agggtatgga agaaggtgaa ttctctgaag ctcgtgaaga tttggctgct ttggagaaag    360

attatgaaga agttggtatg gactccggag aaggtgaggg tgaaggagct gaagaatatt    420

aaatttgatt ccaaacatga caaatcactt gtttttaaga caaaaaattc ctttcaattt    480

ttttacactt tttcattact tttctgtgaa acgattattt aaagtctgat ttaacttaat    540

acagaatttt ttacgag                                                    557
```

<210> SEQ ID NO 199
<211> LENGTH: 630
<212> TYPE: DNA
<213> ORGANISM: Diabrotica virgifera virgifera

<400> SEQUENCE: 199

```
gggagttact cggtattcgg tatcaataat gttattaaca gactcgttta atattttatc     60

agttttctcc tcgacaatga gcagctagta tggtcgttcg gaaatacttg tatataaact    120

ttttgatatt aatggagttg tcctatttct acgcgacttt ctgaacgtgt tagagaatat    180

agttgatcta acatttggta atagtatttt ttagagtgtt tattagtgtg ttcaagatgg    240

ttaactttac gaagagacag tggtcaacgt tgatcgttat tggtattgct gatttttgta    300

acgctgtttg tgtgtcgctg caagctccat tttatccaca agttgccgaa agtaagcatt    360

gcacagcgac ggagtatgga ttggtgtttg gaatttttga atttgttgtg ttcttgatta    420

gtcctatata tggagcaaac ctgaatagaa ttggacctaa actcatgttt aatgttggag    480

gctacactat tggtgtgtgt gctatattgt ttggagctga gacaaaaact gagcatcgga    540

atctgaagct agcggggttt aatgtaagtt ccaataaata attttagaca atagattgta    600

ttttagttga gtgattgctg aataaatagt                                      630
```

<210> SEQ ID NO 200
<211> LENGTH: 615

<212> TYPE: DNA
<213> ORGANISM: Diabrotica virgifera virgifera

<400> SEQUENCE: 200

```
ggggagtgaa aacccctcac cacaacgcac cgacaccgag tatgattcaa cttcaacaag      60

agtgcaacca ttcgatatag aatcacaatc tcatatcgat tttgcaccag taaataatca     120

gaatcagaac aactgtgata gtttagacgc gaaagaaatg agtgcaacga aagaacaaca     180

aagtacattg gggggagccg ataaagtgaa aaaacacaag aaaggccctc gacctccgcc     240

tccccctgga ttaaaagatg atctaacaac aattgcacat gtttctgtgg tgattttcgt     300

agggcttatc ttgtatttat gttttgcacg gccgtttgaa ttcttcacgt ggcatccttt     360

gttgatgtct gtagggtaga tgcttatgat gatagaaggc gttctcttca tatccaaaga     420

aaacccgata ggaagaagac taaacttggg ccgcctttta aaagttcgtt tccattggat     480

agctttaaca ataagttcta ttttagttac gatcggtttc gtaatagtag ttataagcaa     540

aaacaaccac ggcaaggaac attttaaatc cttacatgcg attttcggtc tcataggttt     600

attagggtgt atacc                                                      615
```

<210> SEQ ID NO 201
<211> LENGTH: 587
<212> TYPE: DNA
<213> ORGANISM: Diabrotica virgifera virgifera

<400> SEQUENCE: 201

```
ggggatttta tttttttgaa agtttagtac atgtacatta tatttaaaaa cagtattgtt      60

taaatataaa ataaattctt gacgattgtc agacgtagaa aatgttacaa agtgtaaaaa     120

agtacgatac tattatcaga accattgatg atgatgaaga agttgaagat ttatcagaaa     180

acagtgatga ggaaatagag tttcaaccat ccaaacaaaa aactcgaagt aaggaggatt     240

ttgatacgga atttaatttt gtcagttccg tagaagaata taataaagat gtttggaatg     300

atttgactaa atacgttaaa aggaaagcaa aacaaaaaac tgatgacaaa attaaaaaag     360

tcagaggcac acaagctgat gaggatcaaa caaacactga aaatggtaca aatgatcttg     420

tcgattccga tatatctctt tcagaagatg aactaaaaca tgataggatt aaacttaaag     480

aaaagaaaaa gaaaaaagta aaagctgaca atgatacaga agaatttttt gaagaggttg     540

aattaaattc tggagaaact gttagttttt atcagatgaa tctgtca                   587
```

<210> SEQ ID NO 202
<211> LENGTH: 559
<212> TYPE: DNA
<213> ORGANISM: Diabrotica virgifera virgifera

<400> SEQUENCE: 202

```
ggggacactt cctttcggtc cggctctgca tatcaaaggt gcgaatttag tcattaaatt      60

gccaaatttt ccatttgtat tctctaaatc attcgtttgg taagaagatg gcagacttag     120

atgatttctt tgccaaaaaa gaccgcgaga agtccaaaag tacaaaaaaa tatgctacca     180

ctgaagaagt tgccaagaag ctagaagaca ctgcaaaaaa gactgacaaa ttaaagaaag     240

aacgtgttaa tgagggcgaa gatagtatag ttactgaaca agaccaagac gaatggaagg     300

acttcgagga agaaaagaaa gactacacag ggttaaagat aggaaactta gccatcggtc     360

aaaattcgga aagcagtact acgggagcta aggaaagtac cgaacagcaa caagaagatg     420

agcctggaca agatgtagac aagaaatctg gaccttggaa acgcatcgac gtcggggaag     480
```

-continued

```
cagcggaagt ggagaaagtt gaatataaac cggaaccgat acttcctaat gtatctaaga    540

ctggcactta tataccccc                                                 559


<210> SEQ ID NO 203
<211> LENGTH: 631
<212> TYPE: DNA
<213> ORGANISM: Diabrotica virgifera virgifera

<400> SEQUENCE: 203

gggggattga cgtgaagtta gcagctgcac gcagtgacag ctcagtgttt accgtcagaa     60

aattttaaat taaaagaaat aaaatttaga atatgttgaa attgttcaaa gaaatatctt    120

caagtttggg gaaatctctt accaaaaggg gacttcaaac tacttccact ttacaacatg    180

atagcttatt tgtacatcga gatactcctg aagataatcc agatattgtc tttgaattca    240

ccccggaaaa taaaaagagg gctgaagcta ttctagccat atatccagaa ggccacaaga    300

gggctgcaat gattccatta cttgatttag ctcaaagaca gtatggatgg ttaccaattt    360

ctgctatgca taaagtggct gaaattttaa acttgccaag aatgagggtg tatgaagtag    420

ctactttcta cactatgttt atgaggaaac ccacaggtaa atatcatgtt caaatttgta    480

ctacaactcc ttgctggtta agaggatcag atgagattct ggaagctatt aagaaaaatc    540

ttaagttaga agttggagag acaagcaaag acatgttatg gaccttatct ggggttgaat    600

gtctgggagc atgtgttaat gcccccatgg t                                   631


<210> SEQ ID NO 204
<211> LENGTH: 93
<212> TYPE: DNA
<213> ORGANISM: Diabrotica virgifera virgifera

<400> SEQUENCE: 204

taggattttt cgtaaaacta atccacatcc ccatcaacaa cattatagtg ggatcataaa     60

tatattttc atatttatgt cagttcatac aat                                   93


<210> SEQ ID NO 205
<211> LENGTH: 614
<212> TYPE: DNA
<213> ORGANISM: Diabrotica virgifera virgifera

<400> SEQUENCE: 205

gggaataaaa aatttatttt atttatattt ttatttattt taaaataata aaatattttt     60

tagtaaaagt aaagaaaaat tttatttaat gatagttaat tagtattgtg agagaatatt    120

ttatttttat aaaagaaaaa tttatttttt gtaccttgtg tatcagggat tattaattaa    180

taattatata tttattattt tcgaatttaa aagagctaaa aaattaaaat ttttattgta    240

aaataaatat tttaaataat ttttttgtaa tgaaatgtta ttcgttttta aatatatcta    300

attttttaag aaataaatta aatttattta ttaacaatat atttataatt aaatattttt    360

atattattaa tattaaatat ttttagggat gagcttaaaa ataaaatttt attaaaattt    420

aatttttaaa taaaaattag gattaaaaat tttcatattt taaaatatgt tattatttat    480

ttttatatat tattattttt attttttata aattttttat taaaatataa atttaaatta    540

tttaaattta gtaatgatga taatattagt attaaaaaat tgtatattta gtaaaaatat    600

ataggtttaa taaa                                                      614


<210> SEQ ID NO 206
<211> LENGTH: 621
```

<212> TYPE: DNA
<213> ORGANISM: Diabrotica virgifera virgifera

<400> SEQUENCE: 206

```
ggggcttctc tgtgcatgtt tcaccatttt taataattta aaaacccgct attcgtaatt     60
ttgttggttg tctttacgga ttacttacaa ttttggaaat aaaatgactc ccggccgatc    120
atcaacgact acaaaagtgt ttgtaggaag tttgcctcca gacgctaccc cagaggattt    180
gaagaaactt ttcgagccct acgggaacat tgcagaatgc gacatcgcga acaaatgtgg    240
attcctccac ttggaggatg gcgaattggc aatgaaggcc attgacgaac taaatggtat    300
ggaatttatg ggttccaaaa tttcagtgga aaaggggcga gttaagccgc gaaggagtgg    360
cggtggaccc agaggtggaa gagaacgagg aggcccgtat tcaagagtta tggtggatcc    420
aacggatacg gcgcttctgc cggttacggt cgcgacgccg gtggctacgg cgccgcctat    480
ggagatcgcg cagccgccga tccgtacgct gcagctgatc catacagagg ggcttcagcc    540
ggtggtggct atcaggatag aggtgataga ggatacggtg ggcgacctgc tgagggttat    600
ggaaactcat acgctgctgc a                                              621
```

<210> SEQ ID NO 207
<211> LENGTH: 624
<212> TYPE: DNA
<213> ORGANISM: Diabrotica virgifera virgifera

<400> SEQUENCE: 207

```
gggggagtgt gtggtgagtg tcagttaaac gttaacgtta aacaagtatt ttattacatg     60
gtaacacacg tgttgtagga attcccttta aaaacgatgg atgtccttag tcgtcctgcg    120
gaagaatttg aaaatgacca aacagtggaa actatgtggg ctataaaagc cttcgaacat    180
gccgaagttt actttaacat tttatgttca gttgatccaa aattgctcaa actaacacca    240
gtagacgatt taatctataa agtctttaga gaagaattcc caaaactaga agtcgaagta    300
ataatagaaa atgaattgaa gagcacaaaa gaaaaaagca agtggagacc tttttgtgaa    360
cgatttaaga ccattgcaga agactatagt tatggtactt tactgagagc agatgccaaa    420
gatgattata aagaggagaa caccatatta gttactagga ttcaatttta tgccatcgaa    480
ctggccagga atagggaggg agtcaatgac attctaagga aaaagttctg gcctgaagcc    540
aaggaagaga aagacgatta ggaagtattt aataaatctc agttttttta tacattttag    600
ttatttataa gttttttgta agtc                                           624
```

<210> SEQ ID NO 208
<211> LENGTH: 574
<212> TYPE: DNA
<213> ORGANISM: Diabrotica virgifera virgifera

<400> SEQUENCE: 208

```
ggggagcctt tattttttg tttcgacatg tcgcatgtcg agatcccctg tatatcgggg     60
gccccttta attgatacgt cggtagctac gcctctgctc ataccagacg gaaaagttga    120
tttaagcgct ccgtacctat cttgtttaaa agggtgtgca acaaagtttc gaagccacgg    180
taatccggaa atcacatata tcgaagaact tacgaaattt ggcaactatt acaacagaca    240
atttgttatt tcaagtataa tgcaacatcg gaatcattaa tttgttgctg ttcgtttagt    300
agttttttat aaaaatgggt ttgggaagaa gaaatggtag tagctgttgt agaaaatggc    360
ttataggaac ttgtttgtat atatttgttt tattactatt aatattttta atagtatttg    420
```

ttgtagtccc agtcgttttt aaatatagtg ttggaatcca aagaagtata atatttccgt 480
catgggtaat cgacccgaaa aactattcaa acatcgacca atttgggatc aaaggggtga 540
aaaacttcta cgcgaacttg caagaagatg acaa 574

<210> SEQ ID NO 209
<211> LENGTH: 600
<212> TYPE: DNA
<213> ORGANISM: Diabrotica virgifera virgifera

<400> SEQUENCE: 209
gggggagatg atgagcaacc aaaacaaaac attaacattt taatttaaca cacccatttg 60
attactaata acattttaaa aacggctctt aagacacgat gaattacgta tatctttgta 120
ttcttattgt aatattagtg ttagttaaga aaagtgaagc agtaagatgc tatcaatgcg 180
gatcagatga agatggcaaa tatgaagaca actgtggtgc ctatcaaaaa tttgacaaat 240
tgaatcacat tgccattgaa tgtaatagtg aggaaagtca tatgcctggt tctttttgta 300
tgaaatttac tcaacaaagt cctagaggtt ttatttggga tggcagatgg agacaagtaa 360
taagaagatg tgcatctgta gctgacacgg gagtaacagg agtatgtaac tggggggtgt 420
atgaaaatgg catttactgg gaagaatgtt attgttcaga agatgaatgt aatagtgcac 480
atatgactaa aatatcaata ttttcagtta ttagttttat cattttacca attgtgaggt 540
atatttggaa ctaaaagata tattatctta ttagtttgtt gactaatgaa agtagtcaga 600

<210> SEQ ID NO 210
<211> LENGTH: 574
<212> TYPE: DNA
<213> ORGANISM: Diabrotica virgifera virgifera

<400> SEQUENCE: 210
gggatcccgg tatatacacg acacgatttc taagtttacg ctcaatacac gcgtgaatcg 60
agtcacactc catttgagta tgaccctttt ctagataata ttgaaatatt tctacacctg 120
atgttcttga taagtaagaa agagcattcg aaagcgtaac atttcgagtt tggtagcagc 180
atccgtcgct gaagcaaaca acggatttag tagcaggaga taaatttctt ttgatataat 240
ctatgataat ggaagtgaac tcgtttgctt caacccccacc tgaaccctca tgccatacat 300
agcaatggcc tttgccagtg gataaattat agaagctata gttgtgaaca tttagcttca 360
ttttataata tgcagctgat acttgtaatc ttggtgctgt taatattgcc tgtgcatcca 420
tagtcaaaac aagtttactg ttgtccttac tagcctcttc ttttagtttt tccttttcag 480
cacgagctaa attttttttc tccaaatgct gctgaaactg ttcatcattt attttgccga 540
cagaataccc agtgcaagtg tcgcactgat cttt 574

<210> SEQ ID NO 211
<211> LENGTH: 227
<212> TYPE: DNA
<213> ORGANISM: Diabrotica virgifera virgifera

<400> SEQUENCE: 211
gggacttaga ttttattcat catctcgtta aactgtacaa tgagaaacgg tcagatctgg 60
aggagcaaca gttgcatttg aacgttggtc tgaataagat cgccgaaact gtagaacagg 120
ttgaagaaat gcagaagagt ttggccgtca aatctcagga gccacaggcc aaaaatgaag 180
ctgccaacgc taaactcagg cagatggtga aagatcaaca agaagcc 227

<210> SEQ ID NO 212
<211> LENGTH: 631
<212> TYPE: DNA
<213> ORGANISM: Diabrotica virgifera virgifera

<400> SEQUENCE: 212
ggggattatt tctgattttc gtttgctgct ttgttgtcta tacatattgt aaaaatacag 60
ctaaaaactt ttaaaaatga gcgaagccaa ggaagcaatg gaagttgaag tggaaacagc 120
cccggtggct gaaaattcaa aatcttccat ggaggtaacc acagatacag gcaaaaatgt 180
aatggccccg ggagctgttg gatcaatcac ttgttccctt catcctcttg taataatgaa 240
tgtatcagaa cattggacta gggaaagggc ccaagaagga gctgtgcaac aagtcattgg 300
agctttgatc ggcaaacaaa agggtagaaa tattgaagta atgaactcat ttgagctagt 360
atttacactt ataggaggtg atatagttat tgataaggat tattacaaca tgaaagaaga 420
gcaatttaaa caagtcttca gtgatttaga tttcattggc tggtacacaa caggtgacgc 480
cccaagtgaa atggatatca aggtccacaa gcaaatttgt gaaatcaatg agtctcccat 540
tttattgaag ctcaaccctt atgataaaaa tattgaacat ttaccagtaa acttatagga 600
atctgtgata gacttagtaa atggtgaagc c 631

<210> SEQ ID NO 213
<211> LENGTH: 611
<212> TYPE: DNA
<213> ORGANISM: Diabrotica virgifera virgifera

<400> SEQUENCE: 213
ggggaagaga tgacaatatg gcgtcaaggt attagttgct aggacgtttt atttttcatt 60
cgagagtttt acagtaataa atgagaaagt tgtaccgaaa ttattgtgat ttcgacgtaa 120
tatttctcag tctaactttg gattatgaac attatcacga aagttgatgg agaacatagg 180
cagagacaag aggactatgg agcatctaga atagcagtag agccaattca acacaagcat 240
ggatgacatg gataacatga ggaagaggac tttgttcagc agtggacctt tgaggctgga 300
tgataatgga ctccatcaat gaggatgtaa aggatatcac tttcatgtac tggagtacaa 360
tgtaacattg tgtaggcata atattttact ctttttattt gacaaatatt taccaactcc 420
cttacatggg ggttgactaa tatttgacca cttctgaaaa tctcatttta tgtttttttgc 480 atcaactgta ggcaatttgc tatacaattg caatattgtt tgaacgtcaa tattttgtta 540
aagtaaatta ttatctggtt ttgagtggta tactttttaa atgaattcca aaaattactt 600
tattagccta a 611

<210> SEQ ID NO 214
<211> LENGTH: 569
<212> TYPE: DNA
<213> ORGANISM: Diabrotica virgifera virgifera

<400> SEQUENCE: 214
ggggatttca tttttcattt gtttgtaaac aaatttatgt aaaattgaca gtttgtgcaa 60
aagattatta tattctttgg tttttgtttg gctgaaaatg ttaaaaaatg ttgtattaaa 120
taataaatga atgacattat acctttcttg caaggatttc gtagattgtt tggaacaatg 180
tcccgatcta aagttagata gtttgttaac ccaaaagaag actatagaga atctagtcaa 240
attgtgattc cagtaccaga tataatacaa catttaaatg atactgttgt caaaatagaa 300
agtggtgtta agccagcaga agagaatgct ggagatggaa tttatttagg tactgctggg 360
atagcatata tgttctacca ccttagcaag gttccaacac tttcatcaaa gcaatctcag 420
tatttaagac aagctgtaac ttacctaaat ccggcaataa cagtagcaag ctgcaacaaa 480
acagatagta tcccctcttt catattagga aatgctggaa tttatgctgt agcagccaca 540
gttttcaaca gtttaggaga tctgaatca 569

<210> SEQ ID NO 215
<211> LENGTH: 630
<212> TYPE: DNA
<213> ORGANISM: Diabrotica virgifera virgifera

<400> SEQUENCE: 215
gggataatat agagataatt tcttcaccca gtgtgtactc tatactcagg tttttgactt 60
tatcaataat ttcatccatg atgaggtgaa actgtagcag gcttgacgta tgcctctttc 120
cacttgtatc ggcagcttct tattaataat ttcggcctgc atattatttc tcctgtatat 180
gttttcggta gtcttgataa tatctgatgg tatgttttga ttacgtgaca ggtgaattac 240
gtcattcagc tctacgcggt cgaatgactt ttgtagatct atgaagcaac agtaaggcgg 300
gacgttgtat tcagtgccgg atttaccact aggccgacta ggccgcggcc tagtgccgca 360
agcaaaaggg ggccgcagcg ctttgtaaaa aaaactttat tggtaaaaaa attgtcacaa 420
cattgtcaaa aatagcaata acgataagaa actccttcca aaaagagtaa acgttacaag 480
acgggctgcc aaatggcatg ctgtaaaagc tattttactt aactactggg agctactacg 540
atgcaattaa aaaaaatatc agccgataca ggggaaacaa atgtgagccg agctgaagct 600
aatggaatca gtaaacaatt tttaaaatta 630

<210> SEQ ID NO 216
<211> LENGTH: 624
<212> TYPE: DNA
<213> ORGANISM: Diabrotica virgifera virgifera

<400> SEQUENCE: 216
ggggacagca atcgcagctg ttttaaaaga aagaaaattg ttccccttct tcgactgtgc 60
ctaccaaggt ttcgcctctg gtaacttggt caaagatgct gctgtggtaa gaaaattcgc 120
cgccgaaggc taggagttct tctgtgccca gagttttgcc aagaacttcg gtctctacaa 180
tgaacgtgtt ggaaacctaa cagtagcggt tagcaaacca gaccttatgg cacctgtaaa 240
atcgcagctt actctcatcg tcagaggaat gtactcaaac ccacctagtc acggagccag 300
gatagtatct tttgtgctca ataacccaga tttggcaaag cagtggcaag ataatatcac 360
tacgatgtct tcaagaataa ttgaaatgag gaccctgttg agaaacgcat tagaggagtt 420
gggcactcca ggagactgga gccatttaac taaacacatc ggaatgttct cttacacagg 480
tctaaatgaa atccagtcag agcacttggt gaagaaacat catgtctacc tgctgcgttc 540
tggaagaatt agtataagtg gtttgaacaa tgacaacgtg aactatgttg ctaaagccat 600
ccatgaaaca gtaaccaccc tacc 624

<210> SEQ ID NO 217
<211> LENGTH: 362
<212> TYPE: DNA
<213> ORGANISM: Diabrotica virgifera virgifera

<400> SEQUENCE: 217
ggggacagtc gacatctgac agtttctaca gtatagttac agtgttcagt ggaaaatatt 60
caattaagac tgcgattata cgacacactt tcactgtcaa ggccgtcttt cttgcatccc 120

```
taaaacgtac atttgcgaca aaaaaattga ctgctgggac ggcagcgatg aagaaaactg    180

ctactacgaa catatctgcc aagaggggga ataccattgt aataatggtt attgtataaa    240

atcggagcaa ttgtgtgatg gctttccgga ttgttctgat aactcagacg aaccatctgg    300

gtgtttagag tattatttgt caacaactac tgatgttaca agtccggaaa atgattatga    360

gc                                                                   362
```

<210> SEQ ID NO 218
<211> LENGTH: 644
<212> TYPE: DNA
<213> ORGANISM: Diabrotica virgifera virgifera

<400> SEQUENCE: 218

```
ggggttcgtg ggtagaatt tcagactttt gacaaattaa aattttgaac aatttatttt     60

attaatttca atcacattgc agttttaaaa agaattaaaa atggtatccc taaatcccgt    120

aagaattctc aagcaagaag ccgaggaaga aagggcagag attgcccgac tcagtagttt    180

tgtaggtgct atagctatag gagatttggt tagaagcacc ttgggaccaa aaggaatgga    240

taaaatttta gtatccagtg gtagatctgc aggatcagtt gaagttacta acgacggagc    300

aactatccta aaatcggtgg gtgttgataa tcctgctgct aaaattttgg tggatatgtc    360

aaaagtccag gatgatgaag taggagatgg caccacatca gtgacagtat tagcatctga    420

actacttaaa gaagcagaaa aacttgtaga acagaaaatt cacccacaaa caatcattgc    480

cggttggagg aaagcagtag atattgccag aaaagctctt ctagaaactg ccaaagacaa    540

cagctctgat tcggaaaagt tcagagaaga tctgatgaac attgccagaa ctacactcag    600

ctcaaagatt ctttcacaac ataaagaata ttttgccaaa ctgg                     644
```

<210> SEQ ID NO 219
<211> LENGTH: 637
<212> TYPE: DNA
<213> ORGANISM: Diabrotica virgifera virgifera

<400> SEQUENCE: 219

```
ggggagtgac agatgacaat aagaaagaat gaatgaaggg caaaatagct tttcatttta     60

atattatgtt caaaaataaa tttacttaga caatccataa aattaaggca actccgtaat    120

tatgacagaa acattagcag ccgaagaaaa acctttaaca aacaatggac gagcagcttt    180

tagtcccgta ccaactaaaa gaacatctgg aggactgatg aaactatcca gttatgtgct    240

agctcttcga ccatggtctc ttagtgcaag tttaattcca actctattag gatcgacaat    300

agcttacaaa tatccagggt cttcggattt taattatata actctatttt ttacgatatt    360

aacaattata tcagtgcatg ggctggtaa tgtagtgaat acatactttg actatgtaaa    420

gggcatagac aatcgaaaat cagacgatag aattcttgta gatcatatat tatcgaagga    480

tgaagttgta tcgttgggtg ctatcttata tttcgcagga tgtattggat ttattatatt    540

agcgaacata tctccagcaa aaatggaaca tttagcttta gtgtattttg gggcttatc     600

gtcaagtttt ttatacaccg ggggcattgg ttttaaa                             637
```

<210> SEQ ID NO 220
<211> LENGTH: 271
<212> TYPE: DNA
<213> ORGANISM: Diabrotica virgifera virgifera

<400> SEQUENCE: 220

```
ggggactcca acgaaattaa tacgtacttt aaacggttta tttatatttt atttaatatt     60

aaactaattt taatacttac tactttccaa aaatttttat taaaacaata ccaaaaatta    120

aaaaaataaa agaataaaac acacacaaac acattgaaaa atgccacaaa taaatgattt    180

ctgaacaata attgttggca aaaatctaac caaatacgca ttttctgaaa aaaaattata    240

taacaaatat acttacaatc ataaaatgta c                                   271
```

<210> SEQ ID NO 221
<211> LENGTH: 80
<212> TYPE: DNA
<213> ORGANISM: Diabrotica virgifera virgifera

<400> SEQUENCE: 221

```
taaagctttg gataaaagac aagccgtact ttgtgtgctc gctgaaaact gtgacgagcc     60

tatgtataag aaactagtct                                                 80
```

<210> SEQ ID NO 222
<211> LENGTH: 657
<212> TYPE: DNA
<213> ORGANISM: Diabrotica virgifera virgifera

<400> SEQUENCE: 222

```
gggggctctt taaattgtgg ttatgttgat ttatttataa agaaataaat ttattttaaa     60

tatgttaaag aattggaatg atttagatgt agaacttcac tcagaggtaa aatgtggaat    120

tgaatcacta aaatttccta ctatgacacc agtgcaagcg tacactatac ctcagctttt    180

aaagaagaaa gatgttgcag ctgaagcagt tactggttct ggaaagactc tggcattcct    240

aataccaata ttacaaataa tgaagcaaag agaaactgaa gaaaaatggg ggaaacatca    300

agtaggggca gttgtcttat ctccaacaag agaattagcc ttgcaaacaa gagatgtact    360

tgataaactg ttagtcgatg ttaaaaatat atccaatatt ttattggttg gaggaaatag    420

tgttgaagaa gatgtaaata atttcaaatc acatggagga aatattataa tttgtactcc    480

tggcagacta gaagatttgt taactaggaa atatgattta aaccttccaa aatcattaaa    540

gagtttggaa atccttattt tagatgaggc tgatagactt ttagatttag gctttcaaaa    600

gtccattgac acaattttaa gttatttgcc taggcaacga aggacaggct tattctc       657
```

<210> SEQ ID NO 223
<211> LENGTH: 541
<212> TYPE: DNA
<213> ORGANISM: Diabrotica virgifera virgifera

<400> SEQUENCE: 223

```
atatataact cggattacca cagtcaaagt gcataaaact taacaatacg caaaaaccgt     60

agcagtccgt ttatttcttt cctgcggcct tggctggagc cttcttggcc ttcttaggtt    120

ttgatttctt atctttcaag atttgtgccc ttctcctttc ttgcaatttt ctggatctaa    180

tcacgacgtt gtcggcactc acggtaatac cacgtttctt ggccaaaagt tcttccctgt    240

ttaactgtct cttttgattc ttcaaaatgg cttcacgttt gagtacagca gcatatggat    300

tcaacttaag catggcctta gcgttggtca atggattgag acgacgtaca cgacgtacaa    360

ccttcttttg aggagcacgt aatacagctt tgatttcatc agccttcaac aatctagata    420

gatcagtgtt ggccatttta ggctggggta gattgtaacc cttcttttcc aatgatgctg    480

ttttccatgt gccgaacaat ttatctaaac gttggaaagc tgattcagtc caaataacaa    540

a                                                                    541
```

<210> SEQ ID NO 224
<211> LENGTH: 650
<212> TYPE: DNA
<213> ORGANISM: Diabrotica virgifera virgifera

<400> SEQUENCE: 224
ggggacattt acgactgatg tgttgatatc ttcactgagg gttacctata atggatatca 60
tagagaaaac cttatcgtat aataacaaac taatagaacc cccacctgat aacattgtgg 120
tccaaaatga agataacgaa gaagttcact atgtaaatat tcatgaggtg cacgtcaaca 180
aagtcatcga gaaaaaactg ggcaccaatc atttcgttct acttaattat gagcttaaac 240
ctataactga ccgtcttggt cttcttggag accacagtat tttgttcgta acattcctca 300
ataatattgg atccaaagaa catttgcaat ttttcgttaa gtattttcct tttactgaat 360
ctcaagcaca attcgctgat ggcatcggag catttgaaaa agaagcactg gtttataaat 420
tgttcaaaga gttttataag caaggtatca ctcaagccag taatgttgtc ccctactgct 480
atgtagtagc tcccaaaaaa tattttatat taaatgatct tactctcgag agttatcaaa 540
ttttaaataa acatatttgc ttagaatacg atgtcgttgt agttgtttta caagctttag 600
cccagttaca ttccggtagt atagcgtacg aagaaaaatt aaagaagaat 650

<210> SEQ ID NO 225
<211> LENGTH: 655
<212> TYPE: DNA
<213> ORGANISM: Diabrotica virgifera virgifera

<400> SEQUENCE: 225
gggcattgag ctcctgcata acaaaaacac tggaaagaat gataaaactt aggctcgaaa 60
gttggctaga aaaaaaacaa taaattatca caaacacaat ttggatttcg aaaaaaatca 120
ttctactgtg gaagctgtga gtcatttggt aacagatata aatttagcgt ttacgaaaaa 180
ttcttcagta atcgctcttt tattagatgt tgaagcagca tacgacaacg ttaatttaaa 240
tatactatat aacaaaatga tacaaatagg tctgccagaa tgcttctgtc aaaaaataat 300
aaaattgtat gactgtagaa aaatttatat atcggtaaat aataacacat ttggtccaag 360
agtagcgatg ggtggtttac ctcaaggagg aatattaagc cctttgttat atttaattta 420
cacttctgat atagaaaaaa atttaaactc aacaaaaatt ttacaatttg cagatgatgt 480
agttatttat caagaaaaca ttaaaataga aaatgcagtc aaatccattg aagaaggaga 540
caaacatatt aaaatatgga gtgaattaca tggactaaat atatctgatt ccaaaaccaa 600
attatgtatt tttacaagaa aacgaaaaga aatacccaat cacatcttaa taaac 655

<210> SEQ ID NO 226
<211> LENGTH: 521
<212> TYPE: DNA
<213> ORGANISM: Diabrotica virgifera virgifera

<400> SEQUENCE: 226
gggggaaacg atgacagttt tgaaagaagt aaaaaagcaa agagaacaca acagaaaaat 60
gaagcagaca aagatacaaa tgcagtcatg attagaatga tgaaagaact tatggagaaa 120
aatgaagaaa tgatgaatga aataaaacag gtcaggaagg aacaagccga aaacaataag 180
caattaatgg aaatgaggca agagaatcag aacttgaaaa gagaagtaaa gcaactacag 240
gaaagaatcg aatacataga aaaatacagt aagaagaaaa gcctgataat atcaggatta 300
aaaatggaca caaacgacga tagaaacatt agagaagaaa tggaaaattt cctagtcaga 360
gaactgcaag ttaaagtgaa attaaggaac gccacaaaaa ttggagagaa tctctgtgtt 420
atagaaacgg aaacaacgac tgaaaaaatg gagatattga aaaacaagag aaagttaaaa 480
aaccacaacg aacgcattta cataaacagt gacctaacga c 521

<210> SEQ ID NO 227
<211> LENGTH: 627
<212> TYPE: DNA
<213> ORGANISM: Diabrotica virgifera virgifera

<400> SEQUENCE: 227
ggggagttcg ttcctgtacg tctgtctgtt cgttcgtgcg tgaccatttt tgatttctac 60
aattattgcc accgccatca ggagagtagc taaactcgga taacttaaat agtgttgtgc 120
ggattgtgat tttcgacatg ggagataaca agaataacga ttctcgaaga aaggtaaaga 180
aagtaaggaa agcggaagat ttagacgatt taaaacagga attagacatc gactatcata 240
agatctcacc agaagaacta tatcaaaggt ttcaaacaca cccagaaaac ggtcttagtc 300
atgcaaaagc gaaagaaaat ttggacaggg acggacccaa tgccctcaca ccaccaaaaa 360
caactcccga atgggtgaaa ttctgtaaaa atctcttcgg gggtttcgca ctcttacttt 420
ggattggtgc aatcatttgt ttcatcgcct actccataca ggctagtact gtagaagaac 480
cagcagatga taatctatat cttggcatcg tattagctgc cgttgttatc gttacaggta 540
tattttctta ttatcaagaa agcaaaagtt caaaaaattat ggaatctttc aagaacatgg 600
tgccccagtt cgcgaccgtt cttaggg 627

<210> SEQ ID NO 228
<211> LENGTH: 643
<212> TYPE: DNA
<213> ORGANISM: Diabrotica virgifera virgifera

<400> SEQUENCE: 228
aggggtgaca acagaaaaat atagaaaatc atcctctgtg tttccgtttt gaacttaact 60
tgtatttagt ttaaaaaata atcatgtcta gaggaagcag tgcaggtttt gaccgacaca 120
taacaatttt ctcgcccgaa ggccgactct atcaagtaga gtatgctttt aaagccatta 180
accaagccgg ccccacttcg gtagcagtcc gaggagtaga tgctgcggcg tgtgtgaccc 240
agagaaagat cccggataag ctgattgatc ccaacacaat tacacatctg ttccagttaa 300
cagaacacac tggatgtgtg atgactggca tgattgctga cagcaagtcc caggtgcaga 360
gagctagata tgaggctgcc gagttcaaat ataagtttgg atatgagatg ccaatcgatg 420
ccttgtgtag gagagtatcg gatatttccc aggtttatac gcagaatgct gagatgagac 480
ctttgggttg ctccatgctt ctgataggat atgaccaaga aatgggacca tgtgtccaca 540
aagctgaccc tgctggctat tactgtggct acagagcagt aagtgtagga tccaaacaaa 600
ctgaagccaa cagctaccta gagaagaagc taaagaagaa aac 643

<210> SEQ ID NO 229
<211> LENGTH: 639
<212> TYPE: DNA
<213> ORGANISM: Diabrotica virgifera virgifera

<400> SEQUENCE: 229
gataacgatc acaaggcaat aaataatcat tagcaatttc aactgttaca ttttcattat 60
cattagcaaa aaccaggtca agtaaaactc cgttacaatt tgtgatgtga ttaagctgaa 120
ataggttgta aaatgcaaaa gtatcaacta aagtatcagt agcagtgtta ctattattac 180
taaagacacc tcttttatca tggtaccatt cgctatttgg cagattgtag tctcctgtta 240
gaatgaactt gtgttcagga aaattgttac agacagattc tatactaata caatgattct 300
cataggatat taaggctgaa ttaggaggaa gatagactgt accaaatata taacattcat 360
tcagagtgca aacttcaaca aacagttcct ccaacttaca cgaacataag gcaatacaat 420
taaaattgaa aaatgtatcc attaatatat tataacaccc tgtaaattta gataataagt 480
attcttagat attaatttaa aattgttatt gtaataccat acaaaaaaaa acaaatagtc 540
tggctaattg gctatgtcaa agccattaat aaaaaaaatc cttatgggag tttttagcgt 600
ggcgatgccg attttcttca aaataatttt caatcggac 639

<210> SEQ ID NO 230
<211> LENGTH: 238
<212> TYPE: DNA
<213> ORGANISM: Diabrotica virgifera virgifera
<220> FEATURE:
<221> NAME/KEY: misc_feature
<222> LOCATION: 139
<223> OTHER INFORMATION: n = A,T,C or G

<400> SEQUENCE: 230
gggtattaac ttttattatt aatttgtata tcgtcgtaat taaatatttt tttagaatta 60
aaatatttaa aatttttata aaaaaattaa tcagatcaag gtgcagtgag agccaaattc 120
aataggaatt taccagccna ggctatggga catcgtattc gtattatgct gtacccatct 180
aagatatagt tgtttttata aatataaata agaaataaaa aatacgtttt ccaacccg 238

<210> SEQ ID NO 231
<211> LENGTH: 116
<212> TYPE: DNA
<213> ORGANISM: Diabrotica virgifera virgifera

<400> SEQUENCE: 231
gaaagttgtg tcttgaaaag tagaaatgac gtctaaagta tctcgtgata ctctatacga 60
gtgtgtgaat ggagtcttgg aaaatgccaa ggagaagaaa aggaactttt tggaaa 116

<210> SEQ ID NO 232
<211> LENGTH: 491
<212> TYPE: DNA
<213> ORGANISM: Diabrotica virgifera virgifera

<400> SEQUENCE: 232
cttatgtatt tagttatggt agtgtagtca tcttaacacc ccttcacccc tccctaacga 60
atctacgacc tagctcccgc acaacaaatg agctgccgtc ccgcaacgag gctttatgtg 120
tctgcttctt cttctttagc cccattctta ccccccagta tctctataga tagtctttcc 180
ttgttcccat atgagcagac atgtaaaacg catcaaactt tgggactcac ccatttcctt 240
acgccccgct caaatcgtca gatttttgaa atatacactc ctttccatgt acttaactta 300
ccttatctta atctgacaat ttcgagtttt ttttaaggat agagtttttt tttcgagccc 360
cccttaacga actcccctgt gttaagagcc aatatatggt agaggtacat ctgcagggta 420
ccaggtttct ccccatatga taatctgacg cgctcgagta actgcaaaaa tccccgcttg 480
ggctccccta c 491

<210> SEQ ID NO 233

<211> LENGTH: 645
<212> TYPE: DNA
<213> ORGANISM: Diabrotica virgifera virgifera

<400> SEQUENCE: 233

```
ggggatgttg tgatggattt tttgagatgt caattttata aatttaaaat ttaattaaaa     60
atcaaaaggg attttatttt atgtctgata gttactggta tattaaaact ataaaaaata    120
ttttaagttt gaaatgaata atgtatttat gttctatatt aaaaggaaga ccaaaacact    180
tacagagaag tttttactca gtgaaaaaat taattaaaga tgaagataac ttaggccgaa    240
gactttatca acaaattaaa gtcaaaggtc ctataactgt agctgattat atgaaggaag    300
tacttactaa ttctacaatg ggatattaca tgcataaaga tgtttttgga gtctcgggtg    360
attttatcac atctccagaa atcactcaga tgtttggaga aattgtagct gtttggttaa    420
taaatgagtg acaaaaaatg ggtctccaa agccgctaca gatagttgaa ctgggaccag    480
gaagaggaac tttggccagt gatatcctga gagtgtttaa tcattttaaa gtactagagc    540
aaacacgctt acagcttgtt gagattagta caacgttaag tgaaattcaa gctaaaaagt    600
tgtgtaatca aaataatgta atcgatgaga atcagcctat ctaca                    645
```

<210> SEQ ID NO 234
<211> LENGTH: 662
<212> TYPE: DNA
<213> ORGANISM: Diabrotica virgifera virgifera

<400> SEQUENCE: 234

```
ggggataata agttcgattt tttacgaaaa tgacaagtat cgagactgtg gggaccattg     60
tcctgaaatt gctgaagttg gtgatcaatt tgatatgtct catcttgtac cgaaccggat    120
atcaaggcta cttcttggga gtaggaggaa cctggaatct aaacgaagaa aaaaatcccg    180
atgcagaaat tgtggcttcc ggcgtattcg taggatttat gatttacaca ttcgtctcgc    240
tgatcagcct ttgcttcgct agtggagatc acaaaaacgac attcactgat attctgatga    300
atatagtagg gatttttatg tggatagctg ctggagctac agctcttcat tattggcttg    360
ggtacttgtc cgaatacaaa tacacgacaa tagattctga acgacaagtt ggtttggcgt    420
taggagcgat gtgtataata aatggagcgg tctatcttgt agacggagta ctttccgcaa    480
tctttatcct caaagccaaa atgcaataac tttcatcgta atataaatat atttatttag    540
gttatatact ttactttaag cagctcaagt ataccgtgac atcccactca tacatcaatg    600
tctataattg tttcatgaca aatcatttaa tagtatttta aagcattcat tcgttcaaca    660
cc                                                                   662
```

<210> SEQ ID NO 235
<211> LENGTH: 677
<212> TYPE: DNA
<213> ORGANISM: Diabrotica virgifera virgifera

<400> SEQUENCE: 235

```
ggggaggttg gtgtggtttt gtcaacaaat aggttgatct atttttgtgt tctttaataa     60
taattgagaa ataattcgat aaaatgggta aaaaggcaga agtaggtact cccaagtacc    120
tggcaaataa aatgaaagcc aaaggtctgc aaaagcttcg atggtattgt caaatgtgtc    180
agaaacagtg cagagatgaa aatggtttca agtgccatac aacctctgaa tctcaccaaa    240
gacaactact gttgtttgca gacaactcca aaaagtatat agatgacttc tcatttgatt    300
tcgcgaaggg atatatggag atccttcgaa gacaatttgg tacaaaaaga gtcaatgcta    360
```

acagagtcta tcaagaatac atacatgaca gggatcatgt ccacatgaat ggtactagat 420
gggtgacact tactggattt gttaaatggt taggtaaaac tggacaagct gttgttgacg 480
aaacagagaa aggttggtac atcacttaca tagatagaag tcccgagacg gtagaaaagg 540
cagaatcgaa aaagaaaaaa gagaaaatgg ataagaacga tgaagagaag caaatagagt 600
ttgtagagaa gcaggctaga ttagcacaag agaaggcagg gccatcagtg gaaccaatct 660
atacagaatt agtgagg 677

<210> SEQ ID NO 236
<211> LENGTH: 600
<212> TYPE: DNA
<213> ORGANISM: Diabrotica virgifera virgifera

<400> SEQUENCE: 236
ggggtacacg ctgggacccg aaagatggtg aactatgcct ggtcaggacg aagtcagggg 60
aaaccctgat ggaggtccgt agcgattctg acgtgcaaat cgatcgtcgg aactgggtat 120
aggggcgaaa gactaatcga accatctagt agctggttcc ctccgaagtt tccttcagga 180
tagctggcgc tcgttccgta cgagtttcat ccggtaaagc gaatgattag aggcattggg 240
gtcgaaacga cctcaaccta ttctcaaact ttaaatgggt gagatcttcg gcttgctcga 300
acttatgaag ccgtgagaaa cgaatcagag tgccaagtgg gccatttttg gtaagcagaa 360
ctggcgctgt gggatgaacc aaacgttgag ttaaagcgcc aaaatcgacg cttatgggat 420
accatgaaag gcgttggtaa cttaagacag caggacggtg gccatggaag tcggaatccg 480
ccaaggagtg tgtaacaact cacctgccga agttactagc cctgaaaatg gatggcgcta 540
aagcgtcgtg cttatactca accgtcagcg gcatgtgcgg ttcgttaata gcgactatga 600

<210> SEQ ID NO 237
<211> LENGTH: 3928
<212> TYPE: DNA
<213> ORGANISM: Diabrotica virgifera virgifera

<400> SEQUENCE: 237
tgcagcgtga cccggtcgtg cccctctcta gagataatga gcattgcatg tctaagttat 60
aaaaaattac cacatatttt ttttgtcaca cttgtttgaa gtgcagttta tctatcttta 120
tacatatatt taaactttac tctacgaata atataatcta tagtactaca ataatatcag 180
tgttttagag aatcatataa atgaacagtt agacatggtc taaaggacaa ttgagtattt 240
tgacaacagg actctacagt tttatctttt tagtgtgcat gtgttctcct tttttttgc 300 aaatagcttc acctatataa tacttcatcc attttattag tacatccatt tagggtttag 360
ggttaatggt ttttatagac taattttttt agtacatcta ttttattcta ttttagcctc 420
taaattaaga aaactaaaac tctattttag tttttttatt taataattta gatataaaat 480
agaataaaat aaagtgacta aaaattaaac aaatacctt taagaaatta aaaaaactaa 540
ggaaacattt ttcttgtttc gagtagataa tgccagcctg ttaaacgccg tcgacgagtc 600
taacggacac caaccagcga accagcagcg tcgcgtcggg ccaagcgaag cagacggcac 660
ggcatctctg tcgctgcctc tggacccctc tcgagagttc cgctccaccg ttggacttgc 720
tccgctgtcg gcatccagaa attgcgtggc ggagcggcag acgtgagccg gcacggcagg 780
cggcctcctc ctcctctcac ggcaccggca gctacggggg attcctttcc caccgctcct 840
tcgctttccc ttcctcgccc gccgtaataa atagacaccc cctccacacc ctctttcccc 900

-continued

```
aacctcgtgt tgttcggagc gcacacacac acaaccagat ctcccccaaa tccacccgtc    960
ggcacctccg cttcaaggta cgccgctcgt cctccccccc cccctctct accttctcta    1020
gatcggcgtt ccggtccatg catggttagg gcccggtagt tctacttctg ttcatgtttg   1080
tgttagatcc gtgtttgtgt tagatccgtg ctgctagcgt tcgtacacgg atgcgacctg   1140
tacgtcagac acgttctgat tgctaacttg ccagtgtttc tctttgggga atcctgggat   1200
ggctctagcc gttccgcaga cgggatcgat ttcatgattt tttttgtttc gttgcatagg   1260
gtttggtttg cccttttcct ttatttcaat atatgccgtg cacttgtttg tcgggtcatc   1320
ttttcatgct ttttttgtc ttggttgtga tgatgtggtc tggttgggcg gtcgttctag    1380
atcggagtag aattctgttt caaactacct ggtggattta ttaattttgg atctgtatgt   1440
gtgtgccata catattcata gttacgaatt gaagatgatg gatggaaata tcgatctagg   1500
ataggtatac atgttgatgc gggttttact gatgcatata cagagatgct ttttgttcgc   1560
ttggttgtga tgatgtggtg tggttgggcg gtcgttcatt cgttctagat cggagtagaa   1620
tactgtttca aactacctgg tgtatttatt aattttggaa ctgtatgtgt gtgtcataca   1680
tcttcatagt tacgagttta agatggatgg aaatatcgat ctaggatagg tatacatgtt   1740
gatgtgggtt ttactgatgc atatacatga tggcatatgc agcatctatt catatgctct   1800
aaccttgagt acctatctat tataataaac aagtatgttt tataattatt ttgatcttga   1860
tatacttgga tgatggcata tgcagcagct atatgtggat ttttttagcc ctgccttcat   1920
acgctattta tttgcttggt actgtttctt ttgtcgatgc tcaccctgtt gtttggtgtt   1980
acttctgcag accggtctct acgtacagtc cggactggcg ccttggcgcg gtaccacatg   2040
gttcgatatc aacaagtttg tacaaaaaag caggggggctt tctgattttt gacagcttct  2100
atagaagttt atcaagatgt tgatgccaaa aaagaataga gtatgtattt acgaatacct   2160
cttcaaagag ggagtcatgg tagctaaaaa agattaccat gccccaaaac acctcgaact   2220
agaaactatc cctaaccttc aagtaattaa ggctttacaa tcacttaaat caaaaggtta   2280
cgtaaaggaa caattcgcct ggaggcatta ttattggtat ttgactaact ctggcatcga   2340
atacctccgc acattcttac acttacctgg agaaattgtc ccatctacct tgaaacgccc   2400
agcaaggaca gaaaccaccc gtcctagacc agctgctctc agatctgaga catctaaacc   2460
ttcagaagac cgtgcaggat acagaaggac tcctggaggc cctggagctg acaagaaagc   2520
tgatgttggt ccaggaactg gagatgttga gttcaggcaa ggattcggac gtggacgggc   2580
accacaataa atttattgat aagttaattt ttataaattg atcagccaat aaaaagtttg   2640
gttaaaaaaa aaaaaaaaaa aaaaaaaaaa aaacagcttt cttgtacaaa gtggtcgata   2700
tcaggtccgc cttgtttctc ctctgtctct tgatctgact aatcttggtt tatgattcgt   2760
tgagtaattt tggggaaagc ttcgtccaca gtttttttc gatgaacagt gccgcagtgg    2820
cgctgatctt gtatgctatc ctgcaatcgt ggtgaactta tttcttttat atcctttact   2880
cccatgaaaa ggctagtaat ctttctcgat gtaacatcgt ccagcactgc tattaccgtg   2940
tggtccatcc gacagtctgg ctgaacacat catacgatct atggagcaaa aatctatctt   3000
ccctgttctt taatgaagga cgtcattttc attagtatga tctaggaatg ttgcaacttg   3060
caaggaggcg tttctttctt tgaatttaac taactcgttg agtggccctg tttctcggac   3120
gtaaggcctt tgctgctcca cacatgtcca ttcgaatttt accgtgttta gcaagggcga   3180
aaagtttgca tcttgatgat ttagcttgac tatgcgattg ctttcctgga cccgtgcagc   3240
tgcccatcga ccactttgta caagaaagct gttttttttt tttttttttt tttttttttt   3300
```

```
taaccaaact ttttattggc tgatcaattt ataaaaatta acttatcaat aaatttattg   3360
tggtgcccgt ccacgtccga atccttgcct gaactcaaca tctccagttc ctggaccaac   3420
atcagctttc ttgtcagctc cagggcctcc aggagtcctt ctgtatcctg cacggtcttc   3480
tgaaggttta gatgtctcag atctgagagc agctggtcta ggacgggtgg tttctgtcct   3540
tgctgggcgt ttcaaggtag atgggacaat ttctccaggt aagtgtaaga atgtgcggag   3600
gtattcgatg ccagagttag tcaaatacca ataataatgc ctccaggcga attgttcctt   3660
tacgtaacct tttgatttaa gtgattgtaa agccttaatt acttgaaggt tagggatagt   3720
ttctagttcg aggtgttttg gggcatggta atctttttta gctaccatga ctccctcttt   3780
gaagaggtat tcgtaaatac atactctatt ctttttggc atcaacatct tgataaactt   3840
ctatagaagc tgtcaaaaat cagaaagccc cctgcttttt tgtacaaact tgttgatggg   3900
gttaggccgc caccgcggtg gagctcga                                     3928
```

<210> SEQ ID NO 238
<211> LENGTH: 4181
<212> TYPE: DNA
<213> ORGANISM: Diabrotica virgifera virgifera

<400> SEQUENCE: 238

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg tttttataga ctaatttttt tagtacatct attttattct attttagcct    420
ctaaattaag aaaactaaaa ctctatttta gttttttat ttaataattt agatataaaa    480
tagaataaaa taaagtgact aaaaattaaa caaataccct ttaagaaatt aaaaaaaacta   540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttttcc tttatttcaa tatatgccgt gcacttgttt gtcgggtcat  1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
```

-continued

```
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga tttttttagc cctgccttca   1920
tacgctattt atttgcttgg tactgtttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcagggggct ttttcacaat gcaggcacca   2100
acgacaaagc caaaaagaga tccaatccac tctgtccaag tttttggcag aaagaaatca   2160
gctacagccg tagcttattg caaaagaggt agaggagtct tgagggtaaa tggcagacct   2220
ctcagccaag tggagcctaa aatgctccaa gacaaacttc aagaacccat tcttcttctt   2280
ggaaaggaca aattctctgc tgttgacatc agagttagag taaatggtgg tggacatgtt   2340
tcccaaattt atgctattag acaagctatc tcaaaggctt tggtagctta ttaccaaaaa   2400
tatgttgatg aagcatcaaa gaaggaattg aaggatatcc ttatccaata tgaccgtacc   2460
ttgttggtag ccgatcccag acgctgcgaa cccaagaaat tcggtggtcc aggtgctcgt   2520
gcccgctacc aaaaatctta ccgttaagtt ctttttaga tttaatgttg tgtttcttgt   2580
atgtattaag atatcaacaa taaacacaat tttttcccgc aaaaaaaaaa aaaaaaaaaa   2640
aaaaaaaaaa cagctttctt gtacaaagtg gtcgatatca ggtccgcctt gtttctcctc   2700
tgtctcttga tctgactaat cttggtttat gattcgttga gtaattttgg ggaaagcttc   2760
gtccacagtt ttttttcgat gaacagtgcc gcagtggcgc tgatcttgta tgctatcctg   2820
caatcgtggt gaacttattt cttttatatc ctttactccc atgaaaaggc tagtaatctt   2880
tctcgatgta acatcgtcca gcactgctat taccgtgtgg tccatccgac agtctggctg   2940
aacacatcat acgatctatg gagcaaaaat ctatcttccc tgttctttaa tgaaggacgt   3000
cattttcatt agtatgatct aggaatgttg caacttgcaa ggaggcgttt ctttctttga   3060
atttaactaa ctcgttgagt ggccctgttt ctcggacgta aggcctttgc tgctccacac   3120
atgtccattc gaattttacc gtgtttagca agggcgaaaa gtttgcatct tgatgattta   3180
gcttgactat gcgattgctt tcctggaccc gtgcagctgc ccatcgacca ctttgtacaa   3240
gaaagctgtt tttttttttt tttttttttt ttttttttgc gggaaaaaat tgtgtttatt   3300
gttgatatct taatacatac aagaaacaca acattaaatc taaaaaagaa cttaacggta   3360
agatttttgg tagcgggcac gagcacctgg accaccgaat ttcttgggtt cgcagcgtct   3420
gggatcggct accaacaagg tacggtcata ttggataagg atatccttca attccttctt   3480
tgatgcttca tcaacatatt tttggtaata agctaccaaa gcctttgaga tagcttgtct   3540
aatagcataa atttgggaaa catgtccacc accatttact ctaactctga tgtcaacagc   3600
agagaatttg tcctttccaa gaagaagaat gggttcttga agtttgtctt ggagcatttt   3660
aggctccact tggctgagag gtctgccatt taccctcaag actcctctac ctcttttgca   3720
ataagctacg gctgtagctg atttctttct gccaaaaact tggacagagt ggattggatc   3780
tctttttggc tttgtcgttg gtgcctgcat tgtgaaaaag ccccctgctt ttttgtacaa   3840
```

```
acttgttgat ggggttaggc cgccaccgcg gtggagctcg aattccggtc cgggtcacct   3900

ttgtccacca agatggaact gcggccgctc attaattaag tcaggcgcgc ctctagttga   3960

agacacgttc atgtcttcat cgtaagaaga cactcagtag tcttcggcca gaatggccat   4020

ctggattcag caggcctaga aggccattta aatcctgagg atctggtctt cctaaggacc   4080

cgggatatcg gaccgattaa actttaattc ggtccgaagc ttgaagttcc tattccgaag   4140

ttcctattct ccagaaagta taggaacttc gcatgcctgc a                       4181
```

<210> SEQ ID NO 239
<211> LENGTH: 5247
<212> TYPE: DNA
<213> ORGANISM: Diabrotica virgifera virgifera

<400> SEQUENCE: 239

```
gtgcagcgtg acccggtcgt gcccctctct agagataatg agcattgcat gtctaagtta     60

taaaaaatta ccacatattt tttttgtcac acttgtttga agtgcagttt atctatcttt    120

atacatatat ttaaacttta ctctacgaat aatataatct atagtactac aataaatatca    180

gtgttttaga gaatcatata aatgaacagt tagacatggt ctaaaggaca attgagtatt    240

ttgacaacag gactctacag ttttatcttt ttagtgtgca tgtgttctcc ttttttttg    300

caaatagctt cacctatata atacttcatc cattttatta gtacatccat ttagggttta    360

gggttaatgg tttttataga ctaatttttt tagtacatct attttattct attttagcct    420

ctaaattaag aaaactaaaa ctctatttta gttttttat ttaataattt agatataaaa    480

tagaataaaa taaagtgact aaaaattaaa caaataccct ttaagaaatt aaaaaaaacta    540

aggaaacatt tttcttgttt cgagtagata atgccagcct gttaaacgcc gtcgacgagt    600

ctaacggaca ccaaccagcg aaccagcagc gtcgcgtcgg gccaagcgaa gcagacggca    660

cggcatctct gtcgctgcct ctggacccct ctcgagagtt ccgctccacc gttggacttg    720

ctccgctgtc ggcatccaga aattgcgtgg cggagcggca gacgtgagcc ggcacggcag    780

gcggcctcct cctcctctca cggcaccggc agctacgggg gattcctttc ccaccgctcc    840

ttcgctttcc cttcctcgcc cgccgtaata aatagacacc ccctccacac cctctttccc    900

caacctcgtg ttgttcggag cgcacacaca cacaaccaga tctcccccaa atccacccgt    960

cggcacctcc gcttcaaggt acgccgctcg tcctcccccc ccccctctc tacctctct   1020

agatcggcgt tccggtccat gcatggttag ggcccggtag ttctacttct gttcatgttt   1080

gtgttagatc cgtgtttgtg ttagatccgt gctgctagcg ttcgtacacg gatgcgacct   1140

gtacgtcaga cacgttctga ttgctaactt gccagtgttt ctctttgggg aatcctggga   1200

tggctctagc cgttccgcag acgggatcga tttcatgatt ttttttgttt cgttgcatag   1260

ggtttggttt gccctttcc tttatttcaa tatatgccgt gcacttgttt gtcgggtcat   1320

cttttcatgc tttttttgt cttggttgtg atgatgtggt ctggttgggc ggtcgttcta   1380

gatcggagta gaattctgtt tcaaactacc tggtggattt attaattttg gatctgtatg   1440

tgtgtgccat acatattcat agttacgaat tgaagatgat ggatggaaat atcgatctag   1500

gataggtata catgttgatg cgggttttac tgatgcatat acagagatgc tttttgttcg   1560

cttggttgtg atgatgtggt gtggttgggc ggtcgttcat tcgttctaga tcggagtaga   1620

atactgtttc aaactacctg gtgtatttat taattttgga actgtatgtg tgtgtcatac   1680

atcttcatag ttacgagttt aagatggatg gaaatatcga tctaggatag gtatacatgt   1740
```

tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgga tttttttagc cctgccttca 1920
tacgctattt atttgcttgg tactgtttct tttgtcgatg ctcaccctgt tgtttggtgt 1980
tacttctgca gaccggtctc tacgtacagt ccggactggc gccttggcgc ggtaccacat 2040
ggttcgatat caacaagttt gtacaaaaaa gcagggggga gtagttgttt ttattgtgag 2100
atgatttcga agttcaccct ggttttcttg gtttgcattg tcgcaccagc gataggtgat 2160
ccaccagttc cagaatggag tgacacttat agcgtagaag gaactatcca tttgccttat 2220
gcagaaatag tagagccttt ccatgcttgg tatgatggaa aatctaaaaa ttcgcgcatt 2280
gattactaca atgggacggc taagacatac caacttggag gaaatggaaa tggtgtccaa 2340
ctgaaagtag ttccattcac tacagaggag gtcctaaacc aaataacgtg cttccagatc 2400
aatggaactg aagacgatcc agtgactcct caatcgattt tgccagattt agaaggattt 2460
gaatatcaag gcatacagga gtatggagat agagaactag aggtatggtt tctaaaaact 2520
gtccagttag aaaaagaaaa cgaatacact ctatgggttg tccgagatga gcatggtaaa 2580
gctattccag ttaaatatga tatgagagga tacaattcgt tattgggaag ccactacgat 2640
cattactatt tgctatacac atcgaagtct tacaggactc acaagattga tccctccgtt 2700
tttgaagtag aaactaatag tgaatgcaga agttttcctg gacccggaaa tcaacatgtt 2760
cacatcatga accccatggc cgaatacatt cgtcccgaaa aaagtgagca cgtggactca 2820
agctttggcg attttataaa taaccacaac aaaaaattacg cagacacaaa agaacacgtt 2880
tttagaaaag aggttttccg tcaaaacgtc aggttcatcg aatctgtcaa ccgacaaaat 2940
aaaggtaagt gttatagtag gggagcaaag taggtgtgct aaatttgcag tcactcgaga 3000
gttatggcga cctattgggt tgtgattatt aggtcctaaa accaaaaaaa gttaagtaaa 3060
attttccatt tccaacaatc gtttttttccg attatagcgt catctatcca taattcgaaa 3120
aaatgtctct aataaaagtt gcttattttt acgaaaaaaa aaaaaaaaaa aaaaaaaaaa 3180
aaacagcttt cttgtacaaa gtggtcgata tcaggtccgc cttgtttctc ctctgtctct 3240
tgatctgact aatcttggtt tatgattcgt tgagtaattt tggggaaagc ttcgtccaca 3300 gtttttttttc gatgaacagt gccgcagtgg cgctgatctt gtatgctatc ctgcaatcgt 3360
ggtgaactta tttcttttat atcctttact cccatgaaaa ggctagtaat ctttctcgat 3420
gtaacatcgt ccagcactgc tattaccgtg tggtccatcc gacagtctgg ctgaacacat 3480
catacgatct atggagcaaa aatctatctt ccctgttctt taatgaagga cgtcattttc 3540
attagtatga tctaggaatg ttgcaacttg caaggaggcg tttctttctt tgaatttaac 3600
taactcgttg agtggccctg tttctcggac gtaaggcctt tgctgctcca cacatgtcca 3660
ttcgaatttt accgtgttta gcaagggcga aaagtttgca tcttgatgat ttagcttgac 3720
tatgcgattg ctttcctgga cccgtgcagc tgcccatcga ccactttgta caagaaagct 3780
gttttttttt ttttttttt ttttttttt tcgtaaaaat aagcaacttt tattagagac 3840
attttttcga attatggata gatgacgcta taatcggaaa aaacgattgt tggaaatgga 3900
aaattttact taactttttt tggttttagg acctaataat cacaacccaa taggtcgcca 3960
taactctcga gtgactgcaa atttagcaca cctactttgc tcccctacta taacacttac 4020
ctttattttg tcggttgaca gattcgatga acctgacgtt ttgacggaaa acctcttttc 4080
taaaaacgtg ttcttttgtg tctgcgtaat ttttgttgtg gttatttata aaatcgccaa 4140
agcttgagtc cacgtgctca ctttttttcgg gacgaatgta ttcggccatg gggttcatga 4200
tgtgaacatg ttgatttccg ggtccaggaa aacttctgca ttcactatta gtttctactt 4260
caaaaacgga gggatcaatc ttgtgagtcc tgtaagactt cgatgtgtat agcaaatagt 4320
aatgatcgta gtggcttccc aataacgaat tgtatcctct catatcatat ttaactggaa 4380
tagctttacc atgctcatct cggacaaccc atagagtgta ttcgttttct ttttctaact 4440
ggacagtttt tagaaaccat acctctagtt ctctatctcc atactcctgt atgccttgat 4500
attcaaatcc ttctaaatct ggcaaaatcg attgaggagt cactggatcg tcttcagttc 4560
cattgatctg gaagcacgtt atttggttta ggacctcctc tgtagtgaat ggaactactt 4620
tcagttggac accatttcca tttcctccaa gttggtatgt cttagccgtc ccattgtagt 4680
aatcaatgcg cgaattttta gattttccat cataccaagc atggaaaggc tctactattt 4740
ctgcataagg caaatggata gttccttcta cgctataagt gtcactccat tctggaactg 4800
gtggatcacc tatcgctggt gcgacaatgc aaaccaagaa aaccagggtg aacttcgaaa 4860
tcatctcaca ataaaaacaa ctactccccc ctgctttttt gtacaaactt gttgatgggg 4920
ttaggccgcc accgcggtgg agctcgaatt ccggtccggg tcacctttgt ccaccaagat 4980
ggaactgcgg ccgctcatta attaagtcag gcgcgcctct agttgaagac acgttcatgt 5040
cttcatcgta agaagacact cagtagtctt cggccagaat ggccatctgg attcagcagg 5100
cctagaaggc catttaaatc ctgaggatct ggtcttccta aggacccggg atatcggacc 5160
gattaaactt taattcggtc cgaagcttga agttcctatt ccgaagttcc tattctccag 5220
aaagtatagg aacttcgcat gcctgca 5247

<210> SEQ ID NO 240
<211> LENGTH: 4939
<212> TYPE: DNA
<213> ORGANISM: Diabrotica virgifera virgifera

<400> SEQUENCE: 240
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gtttttttat ttaataattt agatataaaa 480
tagaataaaa taaagtgact aaaaattaaa caaataccct ttaagaaatt aaaaaaaacta 540 aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960

-continued

```
cggcacctcc gcttcaaggt acgccgctcg tcctcccccc ccccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttttcc tttatttcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttagc cctgccttca   1920
tacgctattt atttgcttgg tactgtttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcagggggat tacaaactga actcaacaac   2100
ctcttttcat cttcgacccg tttgccggcg ttagcttgta aaacatttct gttaaaatca   2160
cgaaccatcc gttaaaagaa atggcagatg aatatttttt tgctttaacc ctcaaaggta   2220
aaaacagtga aatctgggat ccagaagcga agggagcaga ggattaccaa gggggacaca   2280
aattgatcat taaacaagct ttgttgggac ccgaagccca agaaggtgaa gtaaatgttg   2340
tacaagtaga agctatgacg tggaaagact cagttaaaat cccaattgcc acactaaaag   2400
ccggaggccc aaataaccaa gtattgttag atctgtcatt cccagaccca ccagtcacat   2460
tttcacttat acaaggtaat ggaccagttc acattgtagg ccatcattta attggtagtc   2520
cgatggaaga attcgatgaa atggatgaat tagaagagga aatgttggat gatgaagaag   2580
gggaagaagg agccgaggaa gatgaggatg aagatgaacc caaagccaaa aaagcaaaat   2640
cagcgactaa cgccaagggc aaaactcccg taaaaaacaa ttcaaaggct gcaaagaaat   2700
aaacaagttc atctaatccc caaaccacct cctttgtaat gttaagttag ttttttaatg   2760
tatctcggga gttgttatac atccattaac agatcaaccg taacaatttc tcttaaatat   2820
aagtataata ttttatgttt cttgacgtca taagattttg tgaaagtttc ttttattcca   2880
ggtgtaactc ttagttttaa tgtgatcaat atttttaagc tggaaacgta tttatttcct   2940
ttgaaatcat ccaattttgt tgtaaatatg cagccctcat taaaccattt tttgtagcaa   3000
aaaaaaaaaa aaaaaaaaaa aaaaaaaaac agctttcttg tacaaagtgg tcgatatcag   3060
gtccgccttg tttctcctct gtctcttgat ctgactaatc ttggtttatg attcgttgag   3120
taattttggg gaaagcttcg tccacagttt tttttcgatg aacagtgccg cagtggcgct   3180
gatcttgtat gctatcctgc aatcgtggtg aacttatttc ttttatatcc tttactccca   3240
tgaaaaggct agtaatcttt ctcgatgtaa catcgtccag cactgctatt accgtgtggt   3300
ccatccgaca gtctggctga acacatcata cgatctatgg agcaaaaatc tatcttccct   3360
```

gttctttaat gaaggacgtc attttcatta gtatgatcta ggaatgttgc aacttgcaag 3420
gaggcgtttc tttctttgaa tttaactaac tcgttgagtg gccctgtttc tcggacgtaa 3480
ggcctttgct gctccacaca tgtccattcg aattttaccg tgtttagcaa gggcgaaaag 3540
tttgcatctt gatgatttag cttgactatg cgattgcttt cctggacccg tgcagctgcc 3600
catcgaccac tttgtacaag aaagctgttt tttttttttt tttttttttt tttttttgc 3660 tacaaaaaat ggtttaatga gggctgcata tttacaacaa aattggatga tttcaaagga 3720
aataaatacg tttccagctt aaaaatattg atcacattaa aactaagagt tacacctgga 3780
ataaaagaaa ctttcacaaa atcttatgac gtcaagaaac ataaaatatt atacttatat 3840
ttaagagaaa ttgttacggt tgatctgtta atggatgtat aacaactccc gagatacatt 3900
aaaaaactaa cttaacatta caaaggaggt ggtttgggga ttagatgaac ttgtttattt 3960
ctttgcagcc tttgaattgt tttttacggg agttttgccc ttggcgttag tcgctgattt 4020 tgctttttttg gctttgggtt catcttcatc ctcatcttcc tcggctcctt cttccccttc 4080
ttcatcatcc aacatttcct cttctaattc atccatttca tcgaattctt ccatcggact 4140
accaattaaa tgatggccta caatgtgaac tggtccatta ccttgtataa gtgaaaatgt 4200
gactggtggg tctgggaatg acagatctaa caatacttgg ttatttgggc ctccggcttt 4260
tagtgtggca attgggattt taactgagtc tttccacgtc atagcttcta cttgtacaac 4320
atttacttca ccttcttggg cttcgggtcc caacaaagct tgtttaatga tcaatttgtg 4380 tccccccttgg taatcctctg ctcccttcgc ttctggatcc cagatttcac tgtttttacc 4440
tttgagggtt aaagcaaaaa aatattcatc tgccatttct tttaacggat ggttcgtgat 4500
tttaacagaa atgttttaca agctaacgcc ggcaaacggg tcgaagatga aaagaggttg 4560
ttgagttcag tttgtaatcc ccctgctttt ttgtacaaac ttgttgatgg ggttaggccg 4620
ccaccgcggt ggagctcgaa ttccggtccg ggtcaccttt gtccaccaag atggaactgc 4680
ggccgctcat taattaagtc aggcgcgcct ctagttgaag acacgttcat gtcttcatcg 4740
taagaagaca ctcagtagtc ttcggccaga atggccatct ggattcagca ggcctagaag 4800
gccatttaaa tcctgaggat ctggtcttcc taaggacccg ggatatcgga ccgattaaac 4860
tttaattcgg tccgaagctt gaagttccta ttccgaagtt cctattctcc agaaagtata 4920
ggaacttcgc atgcctgca 4939

<210> SEQ ID NO 241
<211> LENGTH: 4661
<212> TYPE: DNA
<213> ORGANISM: Diabrotica virgifera virgifera

<400> SEQUENCE: 241
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttat ttaataattt agatataaaa 480

-continued

```
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc ccccctctc tacttctct    1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttcc tttatttcaa tatatgccgt gcacttgttt gtcgggtcat    1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttagc cctgccttca    1920
tacgctattt atttgcttgg tactgtttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcaggggggtc taattctaat agcccgtatc  2100
tgccaagaga tttgtcaagt aggtttttc tgttttttt ttcttatcaa gtctaaagat     2160
attcagttac gaggtattag atgactggta ttagaggttc ctagaatttt ttgtttagat   2220
cagagttttg tgtatagatg gataactgtt ttgttagtcg tttgccacga aaattggaaa   2280
ttaagttttt ttgcagatac ggggtataga attagactgt caatatggaa acaatgagtt   2340
ttgtaaacat attgatgacg acaatgtatg ttcatgtcat atttcatatg catctataga   2400
tgtagtttga atatgcacaa ttcgttattt taaaaatgtc atctagacgt ttcaatggaa   2460
attagacatc tatagatgtt atgtctgtca acatgttaat atttgaggct atcagcaaca   2520
gtggcataag ctcaaaaact aagttttgag ataaatgcaa tctttgcatt catattttca   2580
ttatgtttat gagataaagc tacaaattat gtagcatcat ctagccaaat atagaggtag   2640
gttgtgtagg tccctgttaa tcggaagatt taattttgct gcttttattg atatattaat   2700
ctaaaaatgc tgaatttgtg acttagtcca ctgttgttct gagggcccca tttaaatgtt   2760
ttcaaaatat gtatagtcaa aactcctttt acatgatgat aagaacgtag ggacatgtga   2820
ataaataccc tgattattta cgttgatggg aatctctctg aaaaaaaaaa aaaaaaaaaa   2880
```

```
aaaaaaaaaa cagctttctt gtacaaagtg gtcgatatca ggtccgcctt gtttctcctc   2940
tgtctcttga tctgactaat cttggtttat gattcgttga gtaattttgg ggaaagcttc   3000
gtccacagtt ttttttcgat gaacagtgcc gcagtggcgc tgatcttgta tgctatcctg   3060
caatcgtggt gaacttattt cttttatatc ctttactccc atgaaaaggc tagtaatctt   3120
tctcgatgta acatcgtcca gcactgctat taccgtgtgg tccatccgac agtctggctg   3180
aacacatcat acgatctatg gagcaaaaat ctatcttccc tgttctttaa tgaaggacgt   3240
cattttcatt agtatgatct aggaatgttg caacttgcaa ggaggcgttt ctttctttga   3300
atttaactaa ctcgttgagt ggccctgttt ctcggacgta aggcctttgc tgctccacac   3360
atgtccattc gaattttacc gtgtttagca agggcgaaaa gtttgcatct tgatgattta   3420
gcttgactat gcgattgctt tcctggaccc gtgcagctgc ccatcgacca ctttgtacaa   3480
gaaagctgtt tttttttttt tttttttttt tttttttca gagagattcc catcaacgta   3540
aataatcagg gtatttattc acatgtccct acgttcttat catcatgtaa aaggagtttt   3600
gactatacat attttgaaaa catttaaatg gggccctcag aacaacagtg gactaagtca   3660
caaattcagc atttttagat taatatatca ataaaagcag caaaattaaa tcttccgatt   3720
aacagggacc tacacaacct acctctatat ttggctagat gatgctacat aatttgtagc   3780
tttatctcat aaacataatg aaaatatgaa tgcaaagatt gcatttatct caaaacttag   3840
tttttgagct tatgccactg ttgctgatag cctcaaatat taacatgttg acagacataa   3900
catctataga tgtctaattt ccattgaaac gtctagatga catttttaaa ataacgaatt   3960
gtgcatattc aaactacatc tatagatgca tatgaaatat gacatgaaca tacattgtcg   4020
tcatcaatat gtttacaaaa ctcattgttt ccatattgac agtctaattc tataccccgt   4080
atctgcaaaa aaacttaatt tccaattttc gtggcaaacg actaacaaaa cagttatcca   4140
tctatacaca aaactctgat ctaaacaaaa aattctagga acctctaata ccagtcatct   4200
aatacctcgt aactgaatat ctttagactt gataagaaaa aaaaaacaga aaaaacctac   4260
ttgacaaatc tcttggcaga tacgggctat tagaattaga ccccctgctt ttttgtacaa   4320
acttgttgat ggggttaggc cgccaccgcg gtggagctcg aattccggtc cgggtcacct   4380
ttgtccacca agatggaact gcggccgctc attaattaag tcaggcgcgc ctctagttga   4440
agacacgttc atgtcttcat cgtaagaaga cactcagtag tcttcggcca gaatggccat   4500
ctggattcag caggcctaga aggccattta aatcctgagg atctggtctt cctaaggacc   4560
cgggatatcg gaccgattaa actttaattc ggtccgaagc ttgaagttcc tattccgaag   4620
ttcctattct ccagaaagta taggaacttc gcatgcctgc a                       4661
```

<210> SEQ ID NO 242
<211> LENGTH: 5116
<212> TYPE: DNA
<213> ORGANISM: Diabrotica virgifera virgifera

<400> SEQUENCE: 242

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg     300
```

-continued caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttttat ttaataattt agatataaaa 480
tagaataaaa taaagtgact aaaaattaaa caaatacct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc ccccctctc taccttctct 1020
agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttcc tttatttcaa tatatgccgt gcacttgttt gtcgggtcat 1320
cttttcatgc tttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680
atcttcatag ttacgagttt aagatggatg gaaatatcga tctaggatag gtatacatgt 1740
tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgga tttttttagc cctgccttca 1920
tacgctattt atttgcttgg tactgtttct tttgtcgatg ctcaccctgt tgtttggtgt 1980
tacttctgca gaccggtctc tacgtacagt ccggactggc gccttggcgc ggtaccacat 2040
ggttcgatat caacaagttt gtacaaaaaa gcagggggag tcgtcaacat caatttcaag 2100
tttcaagaaa aagcaaatca ctacgacttg ccggattttg tagtagtgtt aattttgtat 2160
taaaaaatca aaatgagttc tattggaact gggtacgatt tatcagcttc ccaattctct 2220
cctgatggaa gagtatttca agttgaatat gcaatgaaag cagttgaaaa tagtggcacc 2280
gtaataggcc tccgaggtac agatggcatt gtattggctg ctgaaaagct cattatgtca 2340
aaattgcatg aaccaagtac aaataaacga attttcaaca ttgataaaca cataggaatg 2400
gcattttcag gcttaatagc tgatgcaagg caaatcgttg agattgctag aaaagaagca 2460
tcaaattata gacatcaata tggttcaaat attcctctta aatacctaaa tgatagagta 2520
agcatgtaca tgcatgcata cactttatac agtgctgtta gaccatttgg ttgcagtgtc 2580
atcttggcca gttatgaaga tagtgaccca tctatgtatc tgattgatcc atctggagtt 2640
agctatggat actttggatg tgctacaggt aaagcaaaac agtctgcaaa gactgaaata 2700

```
gaaaaattga agatggggaa tctaacatgc aaagaacttg ttaaagaagc agccaaaatc   2760
atttatttgg tccatgatga gctgaaggat aagaattttg aactggaact ttcatgggta   2820
tgcaaagata cgaatggttt acataccaaa gtgcctgaat cagtgtttgc tgatgcagaa   2880
aaagctgcca aacaagcaat ggaagcagat tcagaatcag atacagaaga tatgtaataa   2940
ctacatttag tttttaatat ttcgctgatg gtggctgttc ttacaatatt tcgtgtgtta   3000
tgttcatata ttatgtaata ctgtgagaat ttccatttca aggataggtt tataactttt   3060
ttttctaata aatacataac tttatgtcaa aaaaaaaaaa aaaaaaaaaa aaaaaaacag   3120
ctttcttgta caaagtggtc gatatcaggt ccgccttgtt tctcctctgt ctcttgatct   3180
gactaatctt ggtttatgat tcgttgagta attttgggga aagcttcgtc cacagttttt   3240
tttcgatgaa cagtgccgca gtggcgctga tcttgtatgc tatcctgcaa tcgtggtgaa   3300
cttatttctt ttatatcctt tactcccatg aaaaggctag taatctttct cgatgtaaca   3360
tcgtccagca ctgctattac cgtgtggtcc atccgacagt ctggctgaac acatcatacg   3420
atctatggag caaaaatcta tcttccctgt tctttaatga aggacgtcat tttcattagt   3480
atgatctagg aatgttgcaa cttgcaagga ggcgtttctt tctttgaatt taactaactc   3540
gttgagtggc cctgtttctc ggacgtaagg cctttgctgc tccacacatg tccattcgaa   3600
ttttaccgtg tttagcaagg gcgaaaagtt tgcatcttga tgatttagct tgactatgcg   3660
attgctttcc tggacccgtg cagctgccca tcgaccactt tgtacaagaa agctgttttt   3720
tttttttttt tttttttttt ttttgacata aagttatgta tttattagaa aaaaaagtta   3780
taaacctatc cttgaaatgg aaattctcac agtattacat aatatatgaa cataacacac   3840
gaaatattgt aagaacagcc accatcagcg aaatattaaa aactaaatgt agttattaca   3900
tatcttctgt atctgattct gaatctgctt ccattgcttg tttggcagct tttctgcat    3960
cagcaaacac tgattcaggc actttggtat gtaaaccatt cgtatctttg catacccatg   4020
aaagttccag ttcaaaattc ttatccttca gctcatcatg gaccaaataa atgattttgg   4080
ctgcttcttt aacaagttct ttgcatgtta gattccccat cttcaatttt tctatttcag   4140
tctttgcaga ctgttttgct ttacctgtag cacatccaaa gtatccatag ctaactccag   4200
atggatcaat cagatacata gatgggtcac tatcttcata actggccaag atgacactgc   4260
aaccaaatgg tctaacagca ctgtataaag tgtatgcatg catgtacatg cttactctat   4320
catttaggta tttaagagga atatttgaac catattgatg tctataattt gatgcttctt   4380
ttctagcaat ctcaacgatt tgccttgcat cagctattaa gcctgaaaat gccattccta   4440
tgtgtttatc aatgttgaaa attcgtttat ttgtacttgg ttcatgcaat tttgacataa   4500
tgagcttttc agcagccaat acaatgccat ctgtacctcg gaggcctatt acggtgccac   4560
tattttcaac tgctttcatt gcatattcaa cttgaaatac tcttccatca ggagagaatt   4620
gggaagctga taaatcgtac ccagttccaa tagaactcat tttgattttt taatacaaaa   4680
ttaacactac tacaaaatcc ggcaagtcgt agtgatttgc tttttcttga aacttgaaat   4740
tgatgttgac gactccccct gctttttttgt acaaacttgt tgatggggtt aggccgccac   4800
cgcggtggag ctcgaattcc ggtccgggtc acctttgtcc accaagatgg aactgcggcc   4860
gctcattaat taagtcaggc gcgcctctag ttgaagacac gttcatgtct tcatcgtaag   4920
aagacactca gtagtcttcg gccagaatgg ccatctggat tcagcaggcc tagaaggcca   4980
tttaaatcct gaggatctgg tcttcctaag gacccgggat atcggaccga ttaaacttta   5040
```

attcggtccg aagcttgaag ttcctattcc gaagttccta ttctccagaa agtataggaa 5100
cttcgcatgc ctgcag 5116

<210> SEQ ID NO 243
<211> LENGTH: 4995
<212> TYPE: DNA
<213> ORGANISM: Diabrotica virgifera virgifera

<400> SEQUENCE: 243
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc ttttttttttg 300 caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttttat ttaataattt agatataaaa 480
tagaataaaa taaagtgact aaaaattaaa caaataccct ttaagaaatt aaaaaaaacta 540 aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc ccccctctc taccttctct 1020 agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttttcc tttatttcaa tatatgccgt gcacttgttt gtcgggtcat 1320
cttttcatgc ttttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680
atcttcatag ttacgagttt aagatggatg gaaatatcga tctaggatag gtatacatgt 1740
tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgga tttttttagc cctgccttca 1920
tacgctattt atttgcttgg tactgtttct tttgtcgatg ctcaccctgt tgtttggtgt 1980
tacttctgca gaccggtctc tacgtacagt ccggactggc gccttggcgc ggtaccacat 2040

-continued

```
ggttcgatat caacaagttt gtacaaaaaa gcagggggct ttttcagcag ttgtcaaagc   2100
actgccacaa tgggtaaaat aatgaaatca ggaaaagtcg tattggtcct cgggggccga   2160
tacgccggca gaaaagccgt agtcgtcaaa acctacgatg aaggtacatc agataaacaa   2220
tacggacatg ccttagtagc tggaattgat aggtacccaa ggaaaatcca caaacgcatg   2280
ggcaaaggca aaatgcacaa gaggtccaag atcaagcctt ttatcaaagt attgaactac   2340
aaccatctca tgcccactag atactctgta gatttggcat cagacttgaa agttgtaccc   2400
aaggacctca aagatgccat gaagaggaag aaggctagat tccagacccg tgtcaaattt   2460
gaggaaaggt ataagcaagg aaagaacaaa tggttcttcc aaaaattgag gttctaggct   2520
gtagatttaa ttttataatt gtacactttt tattttgaga ataaaatgtg gataaatgca   2580
aaaaaaaaaa aaaaaaaaaa aaaaaaaaac agctttcttg tacaaagtgg tcgatatcag   2640
gtccgccttg tttctcctct gtctcttgat ctgactaatc ttggtttatg attcgttgag   2700
taattttggg gaaagcttcg tccacagttt tttttcgatg aacagtgccg cagtggcgct   2760
gatcttgtat gctatcctgc aatcgtggtg aacttatttc ttttatatcc tttactccca   2820
tgaaaaggct agtaatcttt ctcgatgtaa catcgtccag cactgctatt accgtgtggt   2880
ccatccgaca gtctggctga acacatcata cgatctatgg agcaaaaatc tatcttccct   2940
gttctttaat gaaggacgtc attttcatta gtatgatcta ggaatgttgc aacttgcaag   3000
gaggcgtttc tttctttgaa tttaactaac tcgttgagtg gccctgtttc tcggacgtaa   3060
ggcctttgct gctccacaca tgtccattcg aattttaccg tgtttagcaa gggcgaaaag   3120
tttgcatctt gatgatttag cttgactatg cgattgcttt cctggacccg tgcagctgcc   3180
catcgaccac tttgtacaag aaagctgttt tttttttttt tttttttttt tttttttgca   3240
tttatccaca ttttattctc aaaataaaaa gtgtacaatt ataaaattaa atctacagcc   3300
tagaacctca atttttggaa gaaccatttg ttctttcctt gcttatacct ttcctcaaat   3360
ttgacacggg tctggaatct agccttcttc ctcttcatgg catctttgag gtccttgggt   3420
acaactttca agtctgatgc caaatctaca gagtatctag tgggcatgag atggttgtag   3480
ttcaatactt tgataaaagg cttgatcttg gacctcttgt gcattttgcc tttgcccatg   3540
cgtttgtgga ttttccttgg gtacctatca attccagcta ctaaggcatg tccgtattgt   3600
ttatctgatg taccttcatc gtaggttttg acgactacgg cttttctgcc ggcgtatcgg   3660
cccccgagga ccaatacgac ttttcctgat ttcattattt tacccattgt ggcagtgctt   3720
tgacaactgc tgaaaaagcc ccctgctttt ttgtacaaac ttgttgatgg ggttaggccg   3780
ccaccgcggt ggagctcgaa ttccggtccg ggtcaccttt gtccaccaag atggaactgc   3840
ggccgctcat taattaagtc aggcgcgcct ctagttgaag acacgttcat gtcttcatcg   3900
taagaagaca ctcagtagtc ttcggccaga atggccatct ggattcagca ggcctagaag   3960
gccatttaaa tcctgaggat ctggtcttcc taaggacccg ggatatcgga ccgattaaac   4020
tttaattcgg tccgaagctt gaagttccta ttccgaagtt cctattctcc agaaagtata   4080
ggaacttcgc atgcctgcag tgcagcgtga cccggtcgtg cccctctcta gagataatga   4140
gcattgcatg tctaagttat aaaaaattac cacatatttt ttttgtcaca cttgtttgaa   4200
gtgcagttta tctatcttta tacatatatt taaactttac tctacgaata atataatcta   4260
tagtactaca ataatatcag tgttttagag aatcatataa atgaacagtt agacatggtc   4320
taaaggacaa ttgagtattt tgacaacagg actctacagt tttatctttt tagtgtgcat   4380
```

```
gtgttctcct tttttttgc aaatagcttc acctatataa tacttcatcc attttattag   4440
tacatccatt tagggtttag ggttaatggt ttttatagac taattttttt agtacatcta   4500
ttttattcta ttttagcctc taaattaaga aaactaaaac tctattttag tttttttatt   4560
taataattta gatataaaat agaataaaat aaagtgacta aaaattaaac aaataccctt   4620
taagaaatta aaaaaactaa ggaaacattt ttcttgtttc gagtagataa tgccagcctg   4680
ttaaacgccg tcgacgagtc taacggacac caaccagcga accagcagcg tcgcgtcggg   4740
ccaagcgaag cagacggcac ggcatctctg tcgctgcctc tggacccctc tcgagagttc   4800
cgctccaccg ttggacttgc tccgctgtcg gcatccagaa attgcgtggc ggagcggcag   4860
acgtgagccg gcacggcagg cggcctcctc ctcctctcac ggcaccggca gctacggggg   4920
attcctttcc caccgctcct tcgctttccc ttcctcgccc gccgtaataa atagacaccc   4980
cctccacacc ctctt                                                     4995
```

<210> SEQ ID NO 244
<211> LENGTH: 7112
<212> TYPE: DNA
<213> ORGANISM: Diabrotica virgifera virgifera

<400> SEQUENCE: 244

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataaatatca   180
gtgttttaga gaatcatata aatgaacagt tagacatggt ctaaaggaca attgagtatt    240
ttgacaacag gactctacag ttttatcttt ttagtgtgca tgtgttctcc ttttttttg     300
caaatagctt cacctatata atacttcatc cattttatta gtacatccat ttagggttta    360
gggttaatgg tttttataga ctaatttttt tagtacatct attttattct attttagcct    420
ctaaattaag aaaactaaaa ctctatttta gtttttttat ttaataattt agatataaaa    480
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc ccccctctc tacttctct    1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttcc tttatttcaa tatatgccgt gcacttgttt gtcgggtcat    1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
```

-continued

```
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttttagc cctgccttca   1920
tacgctattt atttgcttgg tactgtttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcagggggag ataaaacgaa gaatggcact   2100
agaacaagac ataatcaact acatcgaaga aaaacgttca atttggtatg gacatgtgag   2160
aagagcagat catacaaggt ggatatcaaa gattacggat tggagcccaa taggaaagag   2220
aagaagaggt agaccccgaa tatcgtggag ggatgaagtg tacgaagcca tggaaagacg   2280
agacgttaaa gatggagaat ggtagaacag gaaggactgc agacgttggc tgaaaaaagg   2340
atagatagat agatatagaa atagaaatat ataggtgttt attagcgcgc tatggttatt   2400
atatggggaa tatataatga gaaaagcact cgacaaatgg aatggcggta tttctatcgc   2460
aggaaagaag atctcaaatc tcagatatgc agatgataca ccattaataa ctgcatccga   2520
agaagaaatg tccagtctgc tgcagctagt ggaagccgaa agcaatagat gtggtctcaa   2580
gatcaataaa caaaaaacaa aaattatgat agtagaatat ttaaattcat agtcccagga   2640
acgcaactca tcaatattgg caatatcatt ttaaagtcgt ctactttaaa atgtataata   2700
cgtgtctgaa ttgccgatat aaatgagtca gattaaataa attattggaa gaatttttta   2760
ctaggcaaca ccatttttgt ttatttagta ttattttgta ttttgagaac gacacccgac   2820
ttgggcgtcg aaacgttaat aaaatcattt ttaggtaaaa ttgtggctta tttcccattt   2880
gaatatactt aataacaata tttaaattca cttcagacaa cacgggcctt agaccagttt   2940
gaagtggtta acgagttcga ttatctagga tcctacatca gtaatacagg atgttgtgaa   3000
acagaaatac gtaggagaat aggcattgcc aaaaacgcta tgagtcgatt atcgaaaatc   3060
tggaaagatc gctccttgtc gaagaacacc aaaataagat tagtacgtgc attaattttt   3120
cccatattta attagggatc cgaaacatgg acaatgaaat cggacgacag aaaaaggatt   3180
gacgcctttg aaatgtggtg ctggagaaga atgcttcgga tctcatggac ggaacagaga   3240
acaaatcact caatcttcca agagcttaat attcagactc gactttcctc tacttgcctc   3300
tccaccgcct taaaattttt cggccatatt gcaagaagtg atgataatct ggagagactt   3360
ataatttcgg aaaaggttga agagcgcaga agtagaggtc gctcacctgc tcgatggacg   3420
gaccaagtac aggaagccag tggaaaaaca ttctctgaat ccatgaggga agctcaggac   3480
agaagccgac ggaaagagat agttgatcgt attataggga atcacgacac tcagaaatga   3540
ggaaacgact gaggaggaga aggaggagga gcgtgctcat cactgtatat tattatacaa   3600
tttaattatt actatttaaa taatgtatga aacaaatttt tcaatactgt gtttaagcaa   3660
tggtaatatc gacctcagtc atcccatcga taatgttatt gctgaataac attagcaact   3720
atttagcata gctctgtgat gtatcaaagc atcttgttaa taattggttt ccaatattcc   3780
gtaattcggg attacgagct ttacccacca aacgacacgt atttggtcaa gtagcggttt   3840
```

-continued

```
cgagcatttc aatcatcgcc acatccatca gcatttgtgt agtgaagtaa tctcctttaa   3900
tggagaaggt ggtaaaagac tctatttttt ttgttagtgg tttatttttg gtttgattga   3960
atacaaaaac attacaaaat tatatacaca atgaaattta ctgtttttta tttggaatga   4020
gccataactt tactttgaaa ttaagttttt ttgacatttc gatttccact ttagaaatcg   4080
ttatcaaaaa aaaaaaaaaa aaaaaaaaaa aaaaacagct ttcttgtaca aagtggtcga   4140
tatcaggtcc gccttgtttc tcctctgtct cttgatctga ctaatcttgg tttatgattc   4200
gttgagtaat tttggggaaa gcttcgtcca cagttttttt tcgatgaaca gtgccgcagt   4260
ggcgctgatc ttgtatgcta tcctgcaatc gtggtgaact tatttctttt atatccttta   4320
ctcccatgaa aaggctagta atctttctcg atgtaacatc gtccagcact gctattaccg   4380
tgtggtccat ccgacagtct ggctgaacac atcatacgat ctatggagca aaaatctatc   4440
ttccctgttc tttaatgaag gacgtcattt tcattagtat gatctaggaa tgttgcaact   4500
tgcaaggagg cgtttctttc tttgaattta actaactcgt tgagtggccc tgtttctcgg   4560
acgtaaggcc tttgctgctc cacacatgtc cattcgaatt ttaccgtgtt tagcaagggc   4620
gaaaagtttg catcttgatg atttagcttg actatgcgat tgctttcctg gacccgtgca   4680
gctgcccatc gaccactttg tacaagaaag ctgttttttt tttttttttt tttttttttt   4740
tttgataacg atttctaaag tggaaatcga aatgtcaaaa aaacttaatt tcaaagtaaa   4800
gttatggctc attccaaata aaaaacagta aatttcattg tgtatataat tttgtaatgt   4860
ttttgtattc aatcaaacca aaaataaacc actaacaaaa aaaatagagt cttttaccac   4920
cttctccatt aaaggagatt acttcactac acaaatgctg atggatgtgg cgatgattga   4980
aatgctcgaa accgctactt gaccaaatac gtgtcgtttg gtgggtaaag ctcgtaatcc   5040
cgaattacgg aatattggaa accaattatt aacaagatgc tttgatacat cacagagcta   5100
tgctaaatag ttgctaatgt tattcagcaa taacattatc gatgggatga ctgaggtcga   5160
tattaccatt gcttaaacac agtattgaaa aatttgtttc atacattatt taaatagtaa   5220
taattaaatt gtataataat atacagtgat gagcacgctc ctcctccttc tcctcctcag   5280
tcgtttcctc atttctgagt gtcgtgattc cctataatac gatcaactat ctctttccgt   5340
cggcttctgt cctgagcttc cctcatggat tcagagaatg tttttccact ggcttcctgt   5400
acttggtccg tccatcgagc aggtgagcga cctctacttc tgcgctcttc aacctttttcc   5460
gaaattataa gtctctccag attatcatca cttcttgcaa tatggccgaa aaattttaag   5520
gcggtggaga ggcaagtaga ggaaagtcga gtctgaatat taagctcttg gaagattgag   5580
tgatttgttc tctgttccgt ccatgagatc cgaagcattc ttctccagca ccacatttca   5640
aaggcgtcaa tcctttttct gtcgtccgat ttcattgtcc atgtttcgga tccctaatta   5700
aatatgggaa aaattaatgc acgtactaat cttattttgg tgttcttcga caaggagcga   5760
tctttccaga ttttcgataa tcgactcata gcgtttttgg caatgcctat tctcctacgt   5820
atttctgttt cacaacatcc tgtattactg atgtaggatc ctagataatc gaactcgtta   5880
accacttcaa actggtctaa ggcccgtgtt gtctgaagtg aatttaaata ttgttattaa   5940
gtatattcaa atgggaaata agccacaatt ttacctaaaa atgattttat taacgtttcg   6000
acgcccaagt cgggtgtcgt tctcaaaata caaaataata ctaaataaac aaaaatggtg   6060
ttgcctagta aaaaattctt ccaataattt atttaatctg actcatttat atcggcaatt   6120
cagacacgta ttatacattt taaagtagac gactttaaaa tgatattgcc aatattgatg   6180
agttgcgttc ctgggactat gaatttaaat attctactat cataattttt gtttttttgtt   6240
```

tattgatctt gagaccacat ctattgcttt cggcttccac tagctgcagc agactggaca 6300
tttcttcttc ggatgcagtt attaatggtg tatcatctgc atatctgaga tttgagatct 6360
tctttcctgc gatagaaata ccgccattcc atttgtcgag tgcttttctc attatatatt 6420
ccccatataa taaccatagc gcgctaataa acacctatat atttctattt ctatatctat 6480
ctatctatcc ttttttcagc caacgtctgc agtccttcct gttctaccat tctccatctt 6540
taacgtctcg tctttccatg gcttcgtaca cttcatccct ccacgatatt cggggtctac 6600
ctcttcttct ctttcctatt gggctccaat ccgtaatctt tgatatccac cttgtatgat 6660
ctgctcttct cacatgtcca taccaaattg aacgtttttc ttcgatgtag ttgattatgt 6720
cttgttctag tgccattctt cgttttatct ccccctgctt ttttgtacaa acttgttgat 6780
ggggttaggc cgccaccgcg gtggagctcg aattccggtc cgggtcacct ttgtccacca 6840
agatggaact gcggccgctc attaattaag tcaggcgcgc ctctagttga agacacgttc 6900
atgtcttcat cgtaagaaga cactcagtag tcttcggcca gaatggccat ctggattcag 6960
caggcctaga aggccattta aatcctgagg atctggtctt cctaaggacc cgggatatcg 7020
gaccgattaa actttaattc ggtccgaagc ttgaagttcc tattccgaag ttcctattct 7080
ccagaaagta taggaacttc gcatgcctgc ag 7112

<210> SEQ ID NO 245
<211> LENGTH: 4076
<212> TYPE: DNA
<213> ORGANISM: Diabrotica virgifera virgifera

<400> SEQUENCE: 245
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttttat ttaataattt agatataaaa 480
tagaataaaa taaagtgact aaaaattaaa caaatacccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc ccccccctctc taccttctct 1020 agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200

-continued

```
tggctctagc cgttccgcag acgggatcga tttcatgatt ttttttgttt cgttgcatag   1260
ggtttggttt gccctttcc tttatttcaa tatatgccgt gcacttgttt gtcgggtcat   1320
cttttcatgc tttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttagc cctgccttca   1920
tacgctattt atttgcttgg tactgtttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcaggggggt gtagctttcc gcagcaaaaa   2100
gataggtggt taggcattat tttctaaaaa ccacatggat gaattgttgg caaattcagc   2160
cctagaggct gaaaaattta agccaaccgt agtaaataag cttattgatc taaattatga   2220
cttaggaagc cttttagcac aagacacaaa tgaatttgat acaaatttat taaggaggca   2280
gaaggaagat tatttgctta atttagctag agataacacc caattactat taaatcaaat   2340
atgggactta actacagaac gcctagaaga agctattgta gtgaaattac cacttcaaat   2400
aactttatta cctaggatga aaccactacc taagcccaaa cctttaacaa agtgggaaca   2460
gtttgccaaa acgaaaggta tacagaaaaa gaaaaaatcc aagttatcat gggaccagca   2520
actcaaaaag tgggtaccct tatatggatt taagcgagca caagctgaaa aaaaaaaaaa   2580
aaaaaaaaaa aaaaaaacag ctttcttgta caaagtggtc gatatcaggt ccgccttgtt   2640
tctcctctgt ctcttgatct gactaatctt ggtttatgat tcgttgagta attttgggga   2700
aagcttcgtc cacagttttt tttcgatgaa cagtgccgca gtggcgctga tcttgtatgc   2760
tatcctgcaa tcgtggtgaa cttatttctt ttatatcctt tactcccatg aaaaggctag   2820
taatctttct cgatgtaaca tcgtccagca ctgctattac cgtgtggtcc atccgacagt   2880
ctggctgaac acatcatacg atctatggag caaaaatcta tcttccctgt tctttaatga   2940
aggacgtcat tttcattagt atgatctagg aatgttgcaa cttgcaagga ggcgtttctt   3000
tctttgaatt taactaactc gttgagtggc cctgtttctc ggacgtaagg cctttgctgc   3060
tccacacatg tccattcgaa ttttaccgtg tttagcaagg gcgaaaagtt tgcatcttga   3120
tgatttagct tgactatgcg attgctttcc tggacccgtg cagctgccca tcgaccactt   3180
tgtacaagaa agctgttttt tttttttttt tttttttttt tttttcagct tgtgctcgct   3240
taaatccata taagggtacc cactttttga gttgctggtc ccatgataac ttggattttt   3300
tctttttctg tataccttttc gttttggcaa actgttccca ctttgttaaa ggtttgggct   3360
taggtagtgg tttcatccta ggtaataaag ttatttgaag tggtaatttc actacaatag   3420
cttcttctag gcgttctgta gttaagtccc atatttgatt taatagtaat tgggtgttat   3480
ctctagctaa attaagcaaa taatcttcct tctgcctcct taataaattt gtatcaaatt   3540
catttgtgtc ttgtgctaaa aggcttccta agtcataatt tagatcaata agcttattta   3600
```

ctacggttgg cttaaatttt tcagcctcta gggctgaatt tgccaacaat tcatccatgt 3660
ggtttttaga aaataatgcc taaccaccta tctttttgct gcggaaagct acacccccct 3720 gctttttgt acaaacttgt tgatggggtt aggccgccac cgcggtggag ctcgaattcc 3780
ggtccgggtc acctttgtcc accaagatgg aactgcggcc gctcattaat taagtcaggc 3840
gcgcctctag ttgaagacac gttcatgtct tcatcgtaag aagacactca gtagtcttcg 3900
gccagaatgg ccatctggat tcagcaggcc tagaaggcca tttaaatcct gaggatctgg 3960
tcttcctaag gacccgggat atcggaccga ttaaacttta attcggtccg aagcttgaag 4020
ttcctattcc gaagttccta ttctccagaa agtataggaa cttcgcatgc ctgcag 4076

<210> SEQ ID NO 246
<211> LENGTH: 4415
<212> TYPE: DNA
<213> ORGANISM: Diabrotica virgifera virgifera

<400> SEQUENCE: 246
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttttat ttaataattt agatataaaa 480
tagaataaaa taaagtgact aaaaattaaa caaatacct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc cccccctctc taccttctct 1020
agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gcccttttcc tttatttcaa tatatgccgt gcacttgttt gtcgggtcat 1320
cttttcatgc ttttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680
atcttcatag ttacgagttt aagatggatg gaaatatcga tctaggatag gtatacatgt 1740
tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgga tttttttagc cctgccttca 1920
tacgctattt atttgcttgg tactgtttct tttgtcgatg ctcaccctgt tgtttggtgt 1980
tacttctgca ggggggcagt tatttcgact tttcatgctt gtcataaaat aaaattaaaa 2040
tatatccggc gaggtgttga ctagcggatt tttttagatt caacaatctt attttataaa 2100
ataattagtt aaaatgatgc aaacagctaa taatgcatat tatcccgatt attccactgc 2160
tccaatgcaa cgtcaaatta acccctatgc agataatgga gggagtgtag tagcaatagc 2220
aggtgaagac tttgtaataa ttggtgcaga tacacgtttg agtactggat tttccattta 2280
taccagagaa caaaacaaac ttttcccact atcaggcact actgttttgg gttgtgcagg 2340
atgttggtgt gacactctaa cattaaccag aatccttaaa tctcgcatgc agatgtacca 2400
acaagagcat aacaaaacaa tgtctacaac tgcatgtgcc cagatgttgt caaccatgct 2460
ctactacaag agattctttc cttattatat atcaaacatt ctagtaggtt tagataatga 2520
aggaaagggc tgtgtttaca gctatgatcc tattggacat tgtgaaaaag ctacgtatag 2580
agcaggtggt tcagctggag ctcttcttca gcctctgttg gacaatcaaa ttggacagaa 2640
gaacatgctt aaaacatctg ggaacctctt tagtcaggag aaagctctgt ctacccttaa 2700
agatgtattt atttctgctg ctgaaagaga catctacact ggagatagcg tacttataaa 2760
tattattact aaagatggag taaaggaaga gtccttccag ttgagacggg attagaagca 2820
agtggttttg tttatatttt cttatgtgta attcaaatat actttctaaa taaacaaaaa 2880
aaaaaaaaaa aaaaaaaaaa aaaacagctt tcttgtacaa agtggtcgat atcaggtccg 2940
ccttgtttct cctctgtctc ttgatctgac taatcttggt ttatgattcg ttgagtaatt 3000
ttggggaaag cttcgtccac agtttttttt cgatgaacag tgccgcagtg gcgctgatct 3060
tgtatgctat cctgcaatcg tggtgaactt atttctttta tatcctttac tcccatgaaa 3120
aggctagtaa tctttctcga tgtaacatcg tccagcactg ctattaccgt gtggtccatc 3180
cgacagtctg gctgaacaca tcatacgatc tatggagcaa aaatctatct tccctgttct 3240
ttaatgaagg acgtcatttt cattagtatg atctaggaat gttgcaactt gcaaggaggc 3300
gtttctttct ttgaatttaa ctaactcgtt gagtggccct gtttctcgga cgtaaggcct 3360
ttgctgctcc acacatgtcc attcgaattt taccgtgttt agcaagggcg aaaagtttgc 3420
atcttgatga tttagcttga ctatgcgatt gctttcctgg acccgtgcag ctgcccatcg 3480
accactttgt acaagaaagc tgtttttttt tttttttttt tttttttttt tgtttattta 3540
gaaagtatat ttgaattaca cataagaaaa tataaacaaa accacttgct tctaatcccg 3600
tctcaactgg aaggactctt cctttactcc atctttagta ataatattta taagtacgct 3660
atctccagtg tagatgtctc tttcagcagc agaaataaat acatctttaa gggtagacag 3720
agctttctcc tgactaagag gttccccaga tgttttaagc atgttcttct gtccaatttg 3780
attgtccaac agaggctgaa gaagagctcc agctgaacca cctgctctat acgtagcttt 3840
ttcacaatgt ccaataggat catagctgta aacacagccc tttccttcat tatctaaacc 3900
tactagaatg tttgatatat aataaggaaa gaatctcttg tagtagagca tggttgacaa 3960
catctgggca catgcagttg tagacattgt tttgttatgc tcttgttggt acatctgcat 4020
gcgagattta aggattctgg ttaatgttag agtgtcacac caacatcctg cacaacccaa 4080
aacagtagtg cctgatagtg ggaaaagttt gttttgttct ctggtataaa tggaaaatcc 4140
agtactcaaa cgtgtatctg caccaattat tacaaagtct tcacctgcta ttgctactac 4200
actccctcca ttatctgcat aggggttaat ttgacgttgc attggagcag tggaataatc 4260
gggataatat gcattattag ctgtttgcat cattttaact aattatttta taaaataaga 4320
ttgttgaatc taaaaaaatc cgctagtcaa cacctcgccg gatatatttt aattttattt 4380
tatgacaagc atgaaaagtc gaaataactg ccccc 4415

<210> SEQ ID NO 247
<211> LENGTH: 3389
<212> TYPE: DNA
<213> ORGANISM: Diabrotica virgifera virgifera

<400> SEQUENCE: 247
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc ttttttttg 300 caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttat ttaataattt agatataaaa 480
tagaataaaa taaagtgact aaaaattaaa caaataccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc ccccctctc taccttctct 1020 agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttcc tttatttcaa tatatgccgt gcacttgttt gtcgggtcat 1320
cttttcatgc ttttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680

-continued

```
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga tttttttagc cctgccttca   1920
tacgctattt atttgcttgg tactgtttct tttgtcgatg ctcaccctgt tgtttggtgt   1980
tacttctgca ggggggattt tctctagttt gcaggaagca ggaatttcag taaagaaata   2040
agattaaaat ggcagacaaa gtagaaaagg ttgccagacc aatgaaattc ccttacacat   2100
tcagtgcaaa aattgcacaa ttcccaatca agcactactt gaagaaccaa tggatctgga   2160
aatactatgc tatttctctt gtagtatgtc ttccagtctt caactcgatt agtaaactgg   2220
ccaactctcc tggaaacgtt gctaaatggg cagagattcg cagaagagaa gctgctgaac   2280
atcatcacta agaaaatttt ttttatagta attagtctgc caattgtttt gttctaattt   2340
aatttctatt aaatacatgt agaaaaaaaa aaaaaaaaaa aaaaaaaaaa acagctttct   2400
tgtacaaagt ggtcgatatc aggtccgcct tgtttctcct ctgtctcttg atctgactaa   2460
tcttggttta tgattcgttg agtaattttg gggaaagctt cgtccacagt tttttttcga   2520
tgaacagtgc cgcagtggcg ctgatcttgt atgctatcct gcaatcgtgg tgaacttatt   2580
tcttttatat cctttactcc catgaaaagg ctagtaatct ttctcgatgt aacatcgtcc   2640
agcactgcta ttaccgtgtg gtccatccga cagtctggct gaacacatca tacgatctat   2700
ggagcaaaaa tctatcttcc ctgttcttta atgaaggacg tcattttcat tagtatgatc   2760
taggaatgtt gcaacttgca aggaggcgtt tctttctttg aatttaacta actcgttgag   2820
tggccctgtt tctcggacgt aaggcctttg ctgctccaca catgtccatt cgaattttac   2880
cgtgtttagc aagggcgaaa agtttgcatc ttgatgattt agcttgacta tgcgattgct   2940
ttcctggacc cgtgcagctg cccatcgacc actttgtaca agaaagctgt tttttttttt   3000
tttttttttt ttttttttct acatgtattt aatagaaatt aaattagaac aaaacaattg   3060
gcagactaat tactataaaa aaaattttct tagtgatgat gttcagcagc ttctcttctg   3120
cgaatctctg cccatttagc aacgtttcca ggagagttgg ccagtttact aatcgagttg   3180
aagactggaa gacatactac aagagaaata gcatagtatt tccagatcca ttggttcttc   3240
aagtagtgct tgattgggaa ttgtgcaatt tttgcactga atgtgtaagg gaatttcatt   3300
ggtctggcaa ccttttctac tttgtctgcc attttaatct tatttcttta ctgaaattcc   3360
tgcttcctgc aaactagaga aaatccccc                                     3389
```

<210> SEQ ID NO 248
<211> LENGTH: 3349
<212> TYPE: DNA
<213> ORGANISM: Diabrotica virgifera virgifera

<400> SEQUENCE: 248

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg    300
caaatagctt cacctatata atacttcatc cattttatta gtacatccat ttagggttta    360
gggttaatgg tttttataga ctaatttttt tagtacatct attttattct attttagcct    420
```

```
ctaaattaag aaaactaaaa ctctatttta gtttttttat ttaataattt agatataaaa    480
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttcc tttatttcaa tatatgccgt gcacttgttt gtcgggtcat    1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga tttttttagc cctgccttca   1920
tacgctattt atttgcttgg tactgtttct tttgtcgatg ctcaccctgt tgtttggtgt   1980
tacttctgca gggggggggg ggaggttaag ggaataaagc ccctataaaa tttttatcgg   2040
ctgtgaaaat ttcactacta tttttttaaa gatttcccta ccataataat gtcaaatgcc   2100
cattttaacc tctaatattt ttcgatattc tcgattttta ttttataagc tcaaagagtt   2160
ataacttttt ttatgtgcac ctttgtacta aggtaactta ggttcaatgg aactattttt   2220
attcccagaa tattttattt tattcatgac ccaccttttt actacacctt gtgcaattgt   2280
tatttatttt caaatagata tttaataatg aaaattgtaa ttcttcctcc aatccaaagg   2340
agtgtaaaat ttttagcaga attacttccc ccagctttct tgtacaaagt ggtcgatatc   2400
aggtccgcct tgtttctcct ctgtctcttg atctgactaa tcttggttta tgattcgttg   2460
agtaattttg gggaaagctt cgtccacagt ttttttttcga tgaacagtgc cgcagtggcg   2520
ctgatcttgt atgctatcct gcaatcgtgg tgaacttatt tcttttatat cctttactcc   2580
catgaaaagg ctagtaatct ttctcgatgt aacatcgtcc agcactgcta ttaccgtgtg   2640
gtccatccga cagtctggct gaacacatca tacgatctat ggagcaaaaa tctatcttcc   2700
ctgttcttta atgaaggacg tcattttcat tagtatgatc taggaatgtt gcaacttgca   2760
```

aggaggcgtt tctttctttg aatttaacta actcgttgag tggccctgtt tctcggacgt 2820
aaggcctttg ctgctccaca catgtccatt cgaattttac cgtgtttagc aagggcgaaa 2880
agtttgcatc ttgatgattt agcttgacta tgcgattgct ttcctggacc cgtgcagctg 2940
cccatcgacc actttgtaca agaaagctgg gggaagtaat tctgctaaaa attttacact 3000
cctttggatt ggaggaagaa ttacaatttt cattattaaa tatctatttg aaaataaata 3060
acaattgcac aaggtgtagt aaaaaggtgg gtcatgaata aaataaaata ttctgggaat 3120
aaaaatagtt ccattgaacc taagttacct tagtacaaag gtgcacataa aaaaagttat 3180
aactctttga gcttataaaa taaaaatcga gaatatcgaa aaatattaga ggttaaaatg 3240
ggcatttgac attattatgg taggaaaatc tttaaaaaaa tagtagtgaa attttcacag 3300
ccgataaaaa ttttataggg gctttattcc cttaacctcc ccccccccc 3349

<210> SEQ ID NO 249
<211> LENGTH: 3953
<212> TYPE: DNA
<213> ORGANISM: Diabrotica virgifera virgifera

<400> SEQUENCE: 249
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttttat ttaataattt agatataaaa 480
tagaataaaa taaagtgact aaaaattaaa caaataccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc ccccccctctc taccttctct 1020 agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttttcc tttatttcaa tatatgccgt gcacttgttt gtcgggtcat 1320
cttttcatgc ttttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680
atcttcatag ttacgagttt aagatggatg gaaatatcga tctaggatag gtatacatgt 1740
tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgga tttttttagc cctgccttca 1920
tacgctattt atttgcttgg tactgtttct tttgtcgatg ctcaccctgt tgtttggtgt 1980
tacttctgca gcacgaacta acttggtttt taatacttca ataataaagc tttcaacttc 2040
gtctggtttc atctgtaact ccttttcgat gacatcaaaa gatatttcag gattactctc 2100
agcaagctgc atgaaggaaa gcagtctcat tttttgcata ttctgttcat gatttaaacc 2160
ttgtgcactc acaaattcct tatgttcatt gtaaaacttg aggtaggtgg acaaattttc 2220
actaacaaag atgtttaaaa ggtcatgtat taaatcaccc tccaaaaatc tgacaggttt 2280
tagtgataac aatggatcaa gaaggaatgt gttgggatca gctagtgctg atacaatgca 2340
acggatggcg tcttctctgg catgagaagc atttttgtca gtgtatgtac caagaagttc 2400
aatcatcact aaagcagcct gctcactttg atttgattta accagtactt catgtaaaag 2460
cctataaagc ttttgaagct gttcattaga cggaaggcaa ttggcaaact gttgctttag 2520
atggttgata tcttgaaaca ctaattttac agattctgtc tgtttcgcaa tttgtattaa 2580
gtggtaatat acaggatacc gcattggaga acgatcatcc aatgattgga agagtaacca 2640
taatgctcta agacatacta aaccccagct ttcttgtaca aagtggtcga tatcaggtcc 2700
gccttgtttc tcctctgtct cttgatctga ctaatcttgg tttatgattc gttgagtaat 2760
tttggggaaa gcttcgtcca cagttttttt tcgatgaaca gtgccgcagt ggcgctgatc 2820
ttgtatgcta tcctgcaatc gtggtgaact tatttctttt atatccttta ctcccatgaa 2880
aaggctagta atctttctcg atgtaacatc gtccagcact gctattaccg tgtggtccat 2940
ccgacagtct ggctgaacac atcatacgat ctatggagca aaaatctatc ttccctgttc 3000
tttaatgaag gacgtcattt tcattagtat gatctaggaa tgttgcaact tgcaaggagg 3060
cgtttctttc tttgaattta actaactcgt tgagtggccc tgtttctcgg acgtaaggcc 3120
tttgctgctc cacacatgtc cattcgaatt ttaccgtgtt tagcaagggc gaaaagtttg 3180
catcttgatg atttagcttg actatgcgat tgctttcctg gacccgtgca gctgcccatc 3240
gaccactttg tacaagaaag ctggggacgg ttttacgtgg ggtttagtat gtcttagagc 3300
attatggtta ctcttccaat cattggatga tcgttctcca atgcggtatc ctgtatatta 3360
ccacttaata caaattgcga aacagacaga atctgtaaaa ttagtgtttc aagatatcaa 3420
ccatctaaag caacagtttg ccaattgcct tccgtctaat gaacagcttc aaaagcttta 3480
taggctttta catgaagtac tggttaaatc aaatcaaagt gagcaggctg ctttagtgat 3540
gattgaactt cttggtacat acactgacaa aaatgcttct catgccagag aagacgccat 3600
ccgttgcatt gtatcagcac tagctgatcc caacacattc cttcttgatc cattgttatc 3660
actaaaacct gtcagatttt tggagggtga tttaatacat gaccttttaa acatctttgt 3720
tagtgaaaat ttgtccacct acctcaagtt ttacaatgaa cataaggaat ttgtgagtgc 3780
acaaggttta aatcatgaac agaatatgca aaaaatgaga ctgctttcct tcatgcagct 3840
tgctgagagt aatcctgaaa tatcttttga tgtcatcgaa aaggagttac agatgaaacc 3900
agacgaagtt gaaagcttta ttattgaagt attaaaaacc aagttagttc gtg 3953

<210> SEQ ID NO 250
<211> LENGTH: 3433
<212> TYPE: DNA
<213> ORGANISM: Diabrotica virgifera virgifera

<400> SEQUENCE: 250
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttttat ttaataattt agatataaaa 480
tagaataaaa taaagtgact aaaaattaaa caaataccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc cccccctctc taccttctct 1020
agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttttcc tttatttcaa tatatgccgt gcacttgttt gtcgggtcat 1320
cttttcatgc ttttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680
atcttcatag ttacgagttt aagatggatg gaaatatcga tctaggatag gtatacatgt 1740
tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgga tttttttagc cctgccttca 1920
tacgctattt atttgcttgg tactgtttct tttgtcgatg ctcaccctgt tgtttggtgt 1980
tacttctgca ggggggaaat atatactaca atgaagtttt taagatcgac agtgtgctac 2040
attgccatct tggcaattct ctttaccctc tgtgccgatg aggttgaagg aaggagaaaa 2100

```
atttttgatgg ggcgaaaaag cattaccagg acatatcttc gtggaaatgc tgttcctgcg   2160
tatgtgataa taatccttgt aggaattggt caactcatcc tgggagggat attgtacgtt   2220
gcattgagga agaagatcat tgctgcacct gtaacggcat catatgcagt ggctagacaa   2280
gaaccataaa ttttatttgt ctagaatatt attttctaaa tatgcatctt ttttaaatta   2340
ttgtctacgt aaataataag tctagaaata tataaaaatt gtcaaaaaaa aaaaaaaaaa   2400
aaaaaaaaaa aaacagcttt cttgtacaaa gtggtcgata tcaggtccgc cttgtttctc   2460
ctctgtctct tgatctgact aatcttggtt tatgattcgt tgagtaattt tggggaaagc   2520
ttcgtccaca gtttttttttc gatgaacagt gccgcagtgg cgctgatctt gtatgctatc   2580
ctgcaatcgt ggtgaactta tttcttttat atcctttact cccatgaaaa ggctagtaat   2640
ctttctcgat gtaacatcgt ccagcactgc tattaccgtg tggtccatcc gacagtctgg   2700
ctgaacacat catacgatct atggagcaaa aatctatctt ccctgttctt taatgaagga   2760
cgtcattttc attagtatga tctaggaatg ttgcaacttg caaggaggcg tttctttctt   2820
tgaatttaac taactcgttg agtggccctg tttctcggac gtaaggcctt tgctgctcca   2880
cacatgtcca ttcgaatttt accgtgttta gcaagggcga aaagtttgca tcttgatgat   2940
ttagcttgac tatgcgattg ctttcctgga cccgtgcagc tgcccatcga ccactttgta   3000
caagaaagct gttttttttt tttttttttt tttttttttt tgacaatttt tatatatttc   3060
tagacttatt atttacgtag acaataattt aaaaaagatg catatttaga aaataatatt   3120
ctagacaaat aaaatttatg gttcttgtct agccactgca tatgatgccg ttacaggtgc   3180
agcaatgatc ttcttcctca atgcaacgta caatatccct cccaggatga gttgaccaat   3240
tcctacaagg attattatca catacgcagg aacagcattt ccacgaagat atgtcctggt   3300
aatgcttttt cgccccatca aaatttttct ccttccttca acctcatcgg cacagagggt   3360
aaagagaatt gccaagatgg caatgtagca cactgtcgat cttaaaaact tcattgtagt   3420
atatatttcc ccc                                                        3433
```

```
<210> SEQ ID NO 251
<211> LENGTH: 3121
<212> TYPE: DNA
<213> ORGANISM: Diabrotica virgifera virgifera

<400> SEQUENCE: 251

gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc catttttatta gtacatccat ttagggttta    360
gggttaatgg tttttataga ctaatttttt tagtacatct attttattct attttagcct    420
ctaaattaag aaaactaaaa ctctatttta gtttttttat ttaataattt agatataaaa    480
tagaataaaa taaagtgact aaaaattaaa caaatacccct ttaagaaatt aaaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
```

-continued

```
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttcc tttatttcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga tttttttagc cctgccttca   1920
tacgctattt atttgcttgg tactgtttct tttgtcgatg ctcaccctgt tgtttggtgt   1980
tacttctgca gctgttagtt tcatcgtatt atttttaaaa tctaccacta catgtttttc   2040
tgccaattcg tccactccta ctatcatgtc atgtgacatg tttggcatta ttacacattg   2100
tagtgcatac atattcttgc ccagtcgtac cattactcgt atgccttcat ttatagttgc   2160
caatgtccgt ttgtttgcgc ccactaaatt taccctaggt attttataaa ttaaatttgt   2220
taagttatct tcttctatta gttttctgtt gaccaatcag ctttcttgta caaagtggtc   2280
gatatcaggt ccgccttgtt tctcctctgt ctcttgatct gactaatctt ggtttatgat   2340
tcgttgagta attttgggga aagcttcgtc cacagttttt tttcgatgaa cagtgccgca   2400
gtggcgctga tcttgtatgc tatcctgcaa tcgtggtgaa cttatttctt ttatatcctt   2460
tactcccatg aaaaggctag taatctttct cgatgtaaca tcgtccagca ctgctattac   2520
cgtgtggtcc atccgacagt ctggctgaac acatcatacg atctatggag caaaaatcta   2580
tcttccctgt tctttaatga aggacgtcat tttcattagt atgatctagg aatgttgcaa   2640
cttgcaagga ggcgtttctt tctttgaatt taactaactc gttgagtggc cctgtttctc   2700
ggacgtaagg cctttgctgc tccacacatg tccattcgaa ttttaccgtg tttagcaagg   2760
gcgaaaagtt tgcatcttga tgatttagct tgactatgcg attgctttcc tggacccgtg   2820
cagctgccca tcgaccactt tgtacaagaa agctgattgg tcaacagaaa actaatagaa   2880
gaagataact taacaaattt aatttataaa atacctaggg taaatttagt gggcgcaaac   2940
aaacggacat tggcaactat aaatgaaggc atacgagtaa tggtacgact gggcaagaat   3000
atgtatgcac tacaatgtgt aataatgcca aacatgtcac atgacatgat agtaggagtg   3060
gacgaattgg cagaaaaaca tgtagtggta gattttaaaa ataatacgat gaaactaaca   3120
```

g 3121

<210> SEQ ID NO 252
<211> LENGTH: 3758
<212> TYPE: DNA
<213> ORGANISM: Diabrotica virgifera virgifera

<400> SEQUENCE: 252
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc ttttttttg 300 caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gtttttttat ttaataattt agatataaaa 480
tagaataaaa taaagtgact aaaaattaaa caaataccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc ccccctctc taccttctct 1020 agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttcc tttatttcaa tatatgccgt gcacttgttt gtcgggtcat 1320
cttttcatgc tttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680
atcttcatag ttacgagttt aagatggatg gaaatatcga tctaggatag gtatacatgt 1740
tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgga tttttttagc cctgccttca 1920
tacgctattt atttgcttgg tactgtttct tttgtcgatg ctcaccctgt tgtttggtgt 1980
tacttctgca ggcaaattct atgttaattt gacgattatt ttaaaataac aaggaatgta 2040

-continued

```
gagttgtagg ttaaaaaatt agaataaaat ataatttaca accagtgaac actgatgagt   2100
tgtataaaat acataatata taaatattgt ttttgcaaga acttttcatg catggatgac   2160
caccattccc aatacagtcc ggagtgttta tagaaatgct cttttccaaa ttattttttc   2220
tcttaaacac aacacaatgt gcgagtaata tctaacttga aactgaacgt ttgactcaca   2280
ctgaattgca gtaacgcttg aaacgccact gtggtctata tcgggaatct gtgggcacgt   2340
tttgcgacag ttacttgtta gtacgcgata ctttgctctg tagaatgttt ccgattcaga   2400
gaggcaaaaa atcgcgtcgg tctcaaggtt cagagcgcca atcacagaag tttttctaa   2460
acttaaaatc tagaaggagg catctagtgc gtcaataaaa gatttctaaa atattgttac   2520
ggaaggttgt cagtttagtt gtagtgtttt gggctgttcc cacgtaaaac cgtcccagct   2580
ttcttgtaca aagtggtcga tatcaggtcc gccttgtttc tcctctgtct cttgatctga   2640
ctaatcttgg tttatgattc gttgagtaat tttggggaaa gcttcgtcca cagttttttt   2700
tcgatgaaca gtgccgcagt ggcgctgatc ttgtatgcta tcctgcaatc gtggtgaact   2760
tatttctttt atatccttta ctcccatgaa aaggctagta atctttctcg atgtaacatc   2820
gtccagcact gctattaccg tgtggtccat ccgacagtct ggctgaacac atcatacgat   2880
ctatggagca aaaatctatc ttccctgttc tttaatgaag gacgtcattt tcattagtat   2940
gatctaggaa tgttgcaact tgcaaggagg cgtttctttc tttgaattta actaactcgt   3000
tgagtggccc tgtttctcgg acgtaaggcc tttgctgctc cacacatgtc cattcgaatt   3060
ttaccgtgtt tagcaagggc gaaaagtttg catcttgatg atttagcttg actatgcgat   3120
tgctttcctg gacccgtgca gctgcccatc gaccactttg tacaagaaag ctggggacgg   3180
ttttacgtgg gaacagccca aaacactaca actaaactga caaccttccg taacaatatt   3240
ttagaaatct tttattgacg cactagatgc ctccttctag attttaagtt tagaaaaaac   3300
ttctgtgatt ggcgctctga accttgagac cgacgcgatt ttttgcctct ctgaatcgga   3360
aacattctac agagcaaagt atcgcgtact aacaagtaac tgtcgcaaaa cgtgcccaca   3420
gattcccgat atagaccaca gtggcgtttc aagcgttact gcaattcagt gtgagtcaaa   3480
cgttcagttt caagttagat attactcgca cattgtgttg tgtttaagag aaaaaataat   3540
ttggaaaaga gcatttctat aaacactccg gactgtattg ggaatggtgg tcatccatgc   3600
atgaaaagtt cttgcaaaaa caatatttat atattatgta ttttatacaa ctcatcagtg   3660
ttcactggtt gtaaattata ttttattcta attttttaac ctacaactct acattccttg   3720
ttattttaaa ataatcgtca aattaacata gaatttgc                           3758
```